US012516145B2

(12) United States Patent
Gianneschi et al.

(10) Patent No.: US 12,516,145 B2
(45) Date of Patent: Jan. 6, 2026

(54) BIOACTIVE PEPTIDE BRUSH POLYMERS VIA PHOTOINDUCED REVERSIBLE-DEACTIVATION RADICAL POLYMERIZATION

(71) Applicant: Northwestern University, Evanston, IL (US)

(72) Inventors: Nathan C. Gianneschi, Evanston, IL (US); Hao Sun, Evanston, IL (US)

(73) Assignee: Northwestern University, Evanston, IL (US)

( * ) Notice: Subject to any disclaimer, the term of this patent is extended or adjusted under 35 U.S.C. 154(b) by 954 days.

(21) Appl. No.: 17/764,746

(22) PCT Filed: Sep. 29, 2020

(86) PCT No.: PCT/US2020/053308
§ 371 (c)(1),
(2) Date: Mar. 29, 2022

(87) PCT Pub. No.: WO2021/067293
PCT Pub. Date: Apr. 8, 2021

(65) Prior Publication Data

US 2022/0372200 A1 Nov. 24, 2022

Related U.S. Application Data

(60) Provisional application No. 63/050,277, filed on Jul. 10, 2020, provisional application No. 62/907,993, filed on Sep. 30, 2019.

(51) Int. Cl.
*C07K 19/00* (2006.01)
*A61K 38/00* (2006.01)
(Continued)

(52) U.S. Cl.
CPC ........ *C08F 299/022* (2013.01); *C07K 1/1077* (2013.01); *C08F 2/06* (2013.01);
(Continued)

(58) Field of Classification Search
None
See application file for complete search history.

(56) References Cited

U.S. PATENT DOCUMENTS 4,861,760 A 8/1989 Mazuel et al.
4,911,920 A 3/1990 Jani et al.
(Continued)

FOREIGN PATENT DOCUMENTS

EP 1081163 A1 * 3/2001 ............. C08L 51/10
GB 1586614 3/1981
(Continued)

OTHER PUBLICATIONS

Abderrazak et al. (2015) "NLRP3 inflammasome: from a danger signal sensor to a regulatory node of oxidative stress and inflammatory diseases," Redox Biol, 4, 296-307.
(Continued)

*Primary Examiner* — Catherine S Branch
(74) *Attorney, Agent, or Firm* — Leydig, Voit & Mayer, Ltd.

(57) ABSTRACT

Aspects of the invention include a method for synthesizing a peptide brush polymer, the method comprising: exposing a mixture comprising peptide-containing monomers, one or more photoinitiators, and one or more chain transfer agents to a light sufficient to induce photopolymerization, and photopolymerizing the peptide-containing monomers in the mixture; wherein: the resulting peptide brush polymer comprises at least one peptide-containing polymer block; the at least one peptide-containing polymer block is characterized by a degree of polymerization of at least 10 and a peptide
(Continued)

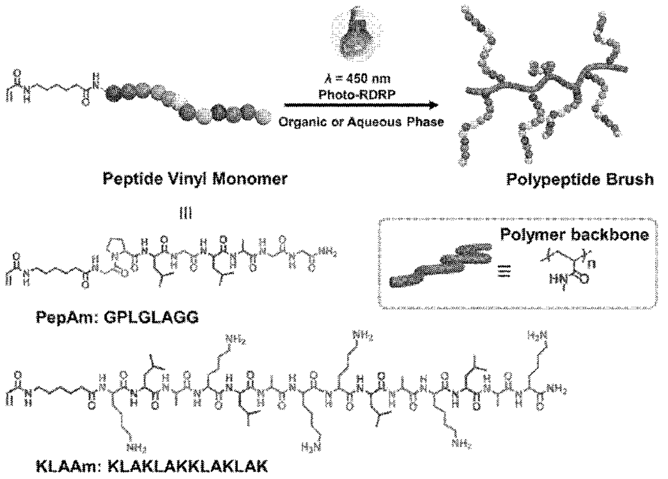

Peptide Vinyl Monomer
Polypeptide Brush
PepAm: GPLGLAGG
KLAAm: KLAKLAKKLAKLAK graft density of 50% to 100%; and at least one peptide moiety of the at least one peptide-containing polymer block has 5 or more amino acid groups.

11 Claims, 90 Drawing Sheets

Specification includes a Sequence Listing.

(51) Int. Cl.

| | |
|---|---|
| ***A61K 38/095*** | (2019.01) |
| ***A61K 47/64*** | (2017.01) |
| ***C07K 1/107*** | (2006.01) |
| ***C08F 2/06*** | (2006.01) |
| ***C08F 2/10*** | (2006.01) |
| ***C08F 2/50*** | (2006.01) |
| ***C08F 220/56*** | (2006.01) |
| ***C08F 299/02*** | (2006.01) |

(52) U.S. Cl.

CPC .................. *C08F 2/10* (2013.01); *C08F 2/50* (2013.01); *C08F 220/56* (2013.01); *C08F 2438/03* (2013.01)

(56) References Cited

U.S. PATENT DOCUMENTS

| | | | |
|---|---|---|---|
| 5,034,506 | A | 7/1991 | Summerton et al. |
| 5,212,162 | A | 5/1993 | Missel et al. |
| 5,235,033 | A | 8/1993 | Summerton et al. |
| 5,403,841 | A | 4/1995 | Lang et al. |
| 5,830,658 | A | 11/1998 | Gryaznov |
| 6,306,993 | B1 | 10/2001 | Rothbard et al. |
| 8,232,360 | B2 | 7/2012 | Sampson et al. |
| 9,040,626 | B2 | 5/2015 | Chien et al. |
| 10,266,631 | B2 | 4/2019 | Lim et al. |
| 10,980,744 | B2 | 4/2021 | Blum et al. |
| 11,072,681 | B2 | 7/2021 | Rush et al. |
| 2003/0113740 | A1 | 6/2003 | Mirkin et al. |
| 2011/0166063 | A1 | 7/2011 | Bossard et al. |
| 2011/0251363 | A1 | 10/2011 | Sampson et al. |
| 2012/0149843 | A1 | 6/2012 | Chien et al. |
| 2014/0105896 | A1 | 4/2014 | Cload et al. |
| 2017/0072062 | A1 | 3/2017 | Benoit et al. |
| 2018/0042843 | A1 | 2/2018 | Blum et al. |
| 2018/0303945 | A1 | 10/2018 | Adams et al. |
| 2019/0070251 | A1 | 3/2019 | Bossard et al. |
| 2021/0283054 | A1 | 9/2021 | Blum et al. |
| 2022/0280625 | A1 | 9/2022 | Gianneschi et al. |

FOREIGN PATENT DOCUMENTS

| | | |
|---|---|---|
| WO | WO 2016/018917 | 2/2016 |
| WO | WO 2016/023036 | 2/2016 |
| WO | WO 2018/156617 | 8/2018 |
| WO | WO 2021/030326 | 2/2021 |
| WO | WO 2021/222523 | 11/2021 |
| WO | WO 2022/006387 | 1/2022 |
| WO | WO 2022/216588 | 10/2022 |

OTHER PUBLICATIONS

Adamiak et al. (2017) "Peptide Brush Polymers and Nanoparticles with Enzyme-Regulated Structure and Charge for Inducing or Evading Macrophage Cell Uptake," ACS Nano, 11(10): 9877-9888. https://doi.org/10.1021/acsnano.7b03686.

Agemy et al. (2011) "Targeted nanoparticle enhanced proapoptotic peptide as potential therapy for glioblastoma," Proc. Natl. Acad. Sci. USA, 108, 17450-17455.

Allegrezza et al. (2016) "Trametinib drives T cell-dependent control of k-Ras-mutated tumors by inhibiting pathological myelopoiesis," Cancer Res. 76: 6253-6265. PMC5094194.

Al-Muhammed et al. (1996) "In-vivo studies on dexamethasone sodium phosphate liposomes," J. Microencapsul. 13(3): 293-306.

Artigas et al. (1981) "Serum trypsin levels in acute pancreatic and non-pancreatic abdominal conditions," Postgrad. Med. J. 57, 219-222.

Arunachalam et al. (2000) "Enzymatic reduction of disulfide bonds in lysosomes: characterization of a gamma-interferon-inducible lysosomal thiol reductase (GILT)," Proc Natl AcadSci U S A, 97 (2), 745-50.

Ayres et al. (2003) "Elastin-Based Side-Chain Polymers Synthesized by ATRP," Macromolecules, 36, 5967-5973.

Ayyoub et al. (1998) "Analysis of the degradation mechanisms of MHC class I-presented tumor antigenic peptides by high performance liquid chromatography/electrospray ionization mass spectrometry: application to the design of peptidase-resistant analogs," Rapid Commun Mass Spectrom, 12 (9), 557-64.

Barbieri et al. (2013) "Peptide Receptor Targeting in Cancer: The Somatostatin Paradigm," Int. J. Pept. 2013, 926295: 20 pp.

Battistella et al. (Dec. 2019) "Delivery of Immunotherapeutic Nanoparticles to Tumors via Enzyme-Directed Assembly," Adv Healthc Mater, 8 (23), e1901105.

Belitsky et al. (2002) "Cellular uptake of N-methylpyrrole/N-methylimidazole polyamide-dye conjugates," Bioorg. Med. Chem. 10(10): 3313-3318.

Berge et al. (1977) "Pharmaceutical Salts," Journal of Pharmaceutical Science 66(1): 1-19.

Bertin et al. (2005) "High-density doxorubicin-conjugated polymeric nanoparticles via ring-opening metathesis polymerization," Chem. Commun., issue 30: 3793-3795.

Biron et al. (2008) "Improving Oral Bioavailability of Peptides by Multiple N-Methylation: Somatostatin Analogues," Angew. Chem., Int. Ed. 47(14): 2595-2599.

Bitler et al. (2015) "Targeting EZH2 methyltransferase activity in ARID1A mutated cells as a synthetic lethal therapeutic strategy," Nature Med.; 21: 231-238. PMC4352133.

Blackman et al. (Jun. 2018) "Confinement of Therapeutic Enzymes in Selectively Permeable Polymer Vesicles by Polymerization-Induced Self-Assembly (PISA) Reduces Antibody Binding and Proteolytic Susceptibility," ACS Cent. Sci. 4 (6), 718-723.

Blackwell et al. (1998) "Highly Efficient Synthesis of Covalently Cross-Linked Peptide Helices by Ring-Closing Metathesis," Angew. Chem., Int. Ed. 37(23): 3281-3284.

Blanchet et al. (2001) "A new generation of Melan-A/MART-1 peptides that fulfill both increased immunogenicity and high resistance to biodegradation: implication for molecular anti-melanoma immunotherapy," J Immunol, 167 (10), 5852-61.

Blum et al. (2014) "Peptides Displayed as High Density Brush Polymers Resist Proteolysis and Retain Bioactivity," Journal of the American Chemical Society. vol. 136, No. 43; pp. 15422-15437; DOI: 10.1021/ja5088216.

Blum et al. (2016) "Activating peptides for cellular uptake via polymerization into high density brushes," Chem. Sci. 7 (2), 989-994.

Blum et al. (Oct. 2019) "Peptide Brush Polymers for Efficient Delivery of a Gene Editing Protein to Stem Cells," Angew. Chem. Int. Ed. 58: 15646-15649.

Blum et al. (Jan. 2022) "Stimuli Induced Uptake of Protein-Like Peptide Brush Polymers," Chem. Eur. J. 28, e202103438.

Bolli et al. (1994) "a-Bicyclo-DNA: Synthesis, Characterization, and Pairing Properties of a-DNA-Analogues with Restricted Conformational Flexibility in the Sugar-Phosphate Backbone," Chapter 7 in Carbohydrate Modifications in Antisense Research, Sanghvi and Cook, eds. pp. 100-117.

Brinckerhoff et al. (1999) "Terminal modifications inhibit proteolytic degradation of an immunogenic mart-127-35 peptide: Implications for peptide vaccines," Int. J. Cancer 83(3): 326-334.

Broos et al. (2010) "Immunomodulatory nanoparticles as adjuvants and allergen-delivery system to human dendritic cells: Implications for specific immunotherapy," Vaccine, 28 (31), 5075-5085.

Bulte et al. (2004) "Iron oxide MR contrast agents for molecular and cellular imaging," NMR Biomed. 17(7): 484-499.

(56) References Cited

OTHER PUBLICATIONS

Burke et al. (2010) "Synthesis and Characterization of Biodegradable HPMA-Oligolysine Copolymers for Improved Gene Delivery," Bioconjugate Chem. 21(1): 140-150.
Busseron et al. (May 2013) "Supramolecular self-assemblies as functional nanomaterials," Nanoscale 5: 7098-7140.
Callmann et al. (2015) "Therapeutic Enzyme-Responsive Nanoparticles for Targeted Delivery and Accumulation in Tumors," Adv Mater., 27(31):4611-4615. PMCID: PMC4699560.
Callmann et al. (Jan. 2020) "Poly(peptide): Synthesis, Structure, and Functionof Peptide-Polymer Amphiphiles and Protein-like Polymers," Accounts Chem Res, 53 (2), 400-413.
Callmann et al. (Jul. 2019) "Antitumor Activity of 1,18-Octadecanedioic Acid- Paclitaxel Complexed with Human Serum Albumin," J Am Chem Soc., 141(30):11765-1769. DOI: 10.1021/jacs.9b04272. PMCID: PMC6676409.
Canning et al. (2016) "A Critical Appraisal of RAFT-Mediated Polymerization- Induced SelfAssembly," Macromolecules, 49, 1985-2001.
Carbone et al. (2017) "First-line nivolumab in stage IV or recurrent non-small-cell lung cancer," New England Journal of Medicine, 376(25), 2415-2426. PMCID: PMC6487310.
Cardarelli (2011) "Quantitative Analysis of Tat Peptide Binding to Import Carriers Reveals Unconventional Nuclear Transport Properties," The Journal of Biological Chemistry 286(14): 12292-12299.
Carmean et al. (2017) "Ultra-High Molecular Weights via Aqueous Reversible-Deactivation Radical Polymerization," Chem, 2, 93-101.
Carreno et al. (2015) "A dendritic cell vaccine increases the breadth and diversity of melanoma neoantigen-specific T cells," Science, 348 (6236), 803-8.
Cartier et al. (2002) "Utilization of synthetic peptides containing nuclear localization signals for nonviral gene transfer systems," Gene Ther. 9: 157-167.
Chang et al. (2015) "Blocking of the PD-1/PD-L1 Interaction by a D-Peptide Antagonist for Cancer Immunotherapy," Angew Chem Int Ed Engl, 54 (40), 11760-4.
Chatterjee et al. (2008) "N-Methylation of Peptides: A New Perspective in Medicinal Chemistry," Acc. Chem. Res. 41(10): 1331-1342.
Chee et al. (Jul. 2018) "Biocompatible Peptide-Coated Ultrasmall Superparamagnetic Iron Oxide Nanoparticles for In Vivo Contrast-Enhanced Magnetic Resonance Imaging," ACS Nano, 12, 6480-6491.
Chen et al. (2016) "Light-Controlled Radical Polymerization: Mechanisms, Methods, and Applications," Chem. Rev. 116, 10167-10211.
Chen et al. (Feb. 2018) "RAFT polymerization of a RGD peptide-based methacrylamide monomer for cell adhesion," Polym. Chem., 9, 1780-1786.
Cheng et al. (May 2019) "Endogenous Reactive Oxygen Species-Triggered Morphology Transformation for Enhanced Cooperative Interaction with Mitochondria," J. Am. Chem. Soc. 141, 7235-7239.
Chiappori et al. (Dec. 2018) "Randomized-controlled phase II trial of salvage chemotherapy after immunization with a TP53-transfected dendritic cell-based vaccine (Ad.p53-DC) in patients with recurrent small cell lung cancer," Cancer Immunol Immunother. PMID: 30591959.
Chien et al. (2010) "Programmable Shape-Shifting Micelles," Angew. Chem., Int. Ed. 122: 5202-5206.
Chien et al. (2012) "Fluorogenic enzyme-responsive micellar nanoparticles," Chem. Sci. 3(9): 2690-2694.
Chien et al. (Dec. 2013) "Enzyme-Directed Assembly of Nanoparticles in Tumors Monitored by in Vivo Whole Animal Imaging and ex Vivo Super-Resolution Fluorescence Imaging," J. Am. Chem. Soc. 135(50): 18710-18713.
Chien et al. (publicly available May 2013) "Enzyme-Directed Assembly of a Nanoparticle Probe in Tumor Tissue," Adv. Mater. (Jul. 2013), 25(26): 3599-3604.
Choi et al. (2003) "Controlled living ring-opening-metathesis polymerization by a fast-initiating ruthenium catalyst," Angew Chem Int Ed Engl, 42 (15), 1743-6.
Chonn et al. (1995) "Recent advances in liposomal drug-delivery systems," Curr. Opin. Biotechnol. 6:698-708.
Chu et al. (2012) "Cathepsin B-sensitive polymers for compartment-specific degradation and nucleic acid release," J. Controlled Release 157(3): 445-454.
Chu et al. (2015) "Multivalent display of pendant pro-apoptotic peptides increases cytotoxic activity," J. Control. Release., 205, 155-161.
Cieslewicz et al. (2013) "Targeted delivery of proapoptotic peptides to tumor- associated macrophages improves survival," Proc. Nat.I. Acad. Sci. USA, 110, 15919-15924.
Clarke et al. (2000) "Characterization ofthe ovalbumin-specific TCR transgenic line OT-I: MHC elements for positive and negative selection," ImmunolCell Biol, 78 (2), 110-7.
Cogan et al. (2017) "Topical Delivery of Anti-VEGF Drugs to the Ocular Posterior Segment Using Cell-Penetrating Peptides," IVOS., 58, 2578-2590.
Conejo-Garcia et al. (2004) "Tumor infiltrating dendritic cell precursors recruited by a b-defensin contribute to vasculogenesis under the influence of Vegf-A," Nat Med; 10:950-958.
Conlon et al. (2013) "Mouse, but not human STING, binds and signals in response to the vascular disrupting agent 5,6-dimethylxanthenone-4-acetic acid," J Immunol, 190(10), 5216-25.
Conrad et al. (2009) "Tunable, Temperature-Responsive Polynorbornenes with Side Chains Based on an Elastin Peptide Sequence," Angew. Chem. Int. Edit. 48(44): 8328-8330.
Corrales et al. (2015) "Direct Activation of STING in the Tumor Microenvironment Leads to Potent and Systemic Tumor Regression and Immunity," CellRep, 11 (7), 1018-30.
Corrigan et al. (Apr. 2019) "Seeing the Light: Advancing Materials Chemistry through Photopolymerization," Chem. Int. Ed. 58, 5170-5189.
Craik et al. (publicly available Dec. 2012) "The Future of Peptide-based Drugs," Chem. Biol. Drug Des. (Jan. 2013), 81(1): 136-147.
Creelan et al. (2015) "Safety and tolerability results from a phase I study of MEDI4736, a human IgG1 anti-programmed cell death-ligand-1 (PD-L1) antibody, combined with gefitinib in patients with non-small-cell lung cancer," Journal of Clinical Oncology 33, 15S: 3047.
Creelan et al. (Aug. 2020) "Abstract CT056: Durable complete responses to adoptive cell transfer using tumor infiltrating lymphocytes (TIL) in nonsmall cell lung cancer (NSCLC): a phase I trial," AACR Annual meeting. Late Breaking and Clinical Trials. Cancer Res (2020) 80 (16_Supplement): CT056.
Creelan et al. (Aug. 2013) "Phase II trial of a GM-CSF-producing and CD40L expressing bystander cell line combined with an allogeneic tumor cell-based vaccine for refractory lung adenocarcinoma." Journal of Immunotherapy. 36(8); 442-450. PMCID: PMC3846277.
Creelan et al. (Aug. 2017) "Safety, pharmacokinetics, and pharmacodynamics of oral omaveloxolone, a synthetic triterpenoid, in a first-in-human trial of patients with advanced solid tumors," Onco Targets Ther. 10:4239-50. PMCID: PMC5587199.
Creelan et al. (Mar. 2013) "Indoleamine 2,3-dioxygenase activity and clinical outcome following induction chemotherapy and concurrent chemoradiation in stage III non-small cell lung cancer," OncoImmunology. 1;2(3). PMCID: PMC3661168.
Creelan et al. (May 2017) "Two phase I/II open label clinical trials evaluating the safety and efficacy of autologous T cells expressing enhanced TCRs specific for NY-ESO-1 or MAGE-A10 in subjects with stage IIIb or stage IV non-small cell lung cancer (NCT02588612/NCT02592577)," TPS3096 Journal of Clinical Oncology 35, No. 15_suppl.
Creelan et al. (Sep. 2018) "OA05. 03 Safety and Clinical Activity of Adoptive Cell Transfer Using Tumor Infiltrating Lymphocytes (TIL) Combined with Nivolumab in NSCLC," Journal of Thoracic Oncology, 13(10), pp. S330-S331.
Cubillos-Ruiz et al. (2009) "Polyethylenimine-based siRNA nanocomplexes reprogram tumor-associated dendritic cells via TLR5 to elicit therapeutic antitumor immunity," J Clin Invest; 119:2231-2244. PMC2719935.
Cubillos-Ruiz et al. (2015) "ER Stress Sensor XBP1 Controls Anti-tumor Immunity by Disrupting Dendritic Cell Homeostasis," Cell: 1527-1538. PMC4580135.

(56) References Cited

OTHER PUBLICATIONS

Curiel et al. (2004) "Specific recruitment of regulatory T cells in ovarian carcinoma fosters immune privilege and predicts reduced survival," Nat Med; 10:942-949.
Darden et al. (1993) "Particle mesh Ewald: An N.log(N) method for Ewald sums in large systems," J. Chem. Phys. 98(12): 10089-10092.
De Gregorio et al. (2009) "Immunology of TLR-independent vaccine adjuvants," Curr OpinImmunol, 21 (3), 339-45.
Demaria et al. (2015) "STING activation of tumorendothelial cells initiates spontaneous and therapeutic antitumor immunity," Proc Natl Acad Sci U S A, 112(50), 15408-13.
Doherty et al. (2009) "Mechanisms of Endocytosis," Annu. Rev. Biochem. 78: 31.1-31.46 and Supplementary Information (69 pp. total).
Dominguez et al. (2017) "Exogenous IL-33 Restores Dendritic Cell Activation and Maturation in Established Cancer," J Immunol, 198 (3), 1365-1375.
Doncom et al. (2017) "Dispersity effects in polymer self-assemblies: a matter of hierarchical control," Chem. Soc. Rev. 46, 4119-4134.
Drucker (Apr. 2020) "Advances in oral peptide therapeutics," Nat. Rev. Drug Discov. 19, 277-289.
Eisenreich et al. (Jul. 2018) "A photoswitchable catalyst system for remote- controlled (co)polymerization in situ," Nat. Catal. 1, 516-522.
Escriou et al. (2003) "NLS bioconjugates for targeting therapeutic genes to the nucleus," Adv. Drug Delivery Rev. 55(2): 295-306.
Essmann et al. (1995) "A smooth particle mesh Ewald method," J. Chem. Phys. 103(19): 8577-8593.
Evans et al. (Jul. 2018) "Seeded Growth of Single-Crystal Two-Dimensional Covalent Organic Frameworks," Science, 361(6397):52-57. PMID: 29930093. DOI: 10.1126/science.aar7883.
Eyles et al. (1997) "Oral Delivery and Fate of Poly(lactic acid) Microsphere- encapsulated Interferon in Rats," J. Pharm. Pharmacol. 49: 669-674.
Fairbanks et al.(2015) "Biomedical applications of polymers derived by reversible addition—fragmentation chain-transfer (RAFT)," Adv. Drug Deliver. Rev. 91, 141-152.
Falciani et al. (2007) "Molecular Basis of Branched Peptides Resistance to Enzyme Proteolysis," Chem. Biol. Drug Des. 69(3): 216-221.
Falo et al. (1992) "Serum proteases alter the antigenicity of peptides presented by class I major histocompatibility complex molecules," Proc Natl Acad Sci U S A, 89(17), 8347-50.
Fantin et al. (2005) "A Bifunctional Targeted Peptide that Blocks HER-2 Tyrosine Kinase and Disables Mitochondrial Function in HER-2-Positive Carcinoma Cells," Cancer Res. 65, 6891-6900.
Fernández-Trillo et al. (2007) "Elastin-Based Side-Chain Polymers: Improved Synthesis via RAFT and Stimulus Responsive Behavior," Macromolecules, 40, 17, 6094-6099.
Ferrara et al. (2016) "Ten years of anti-vascular endothelial growth factor therapy," Nat Rev Drug Discov. 15(6), 385-403.
Figenschau et al. (Aug. 2018) "ICAM1 Expression is Induced by Proinflammatory Cytokines and Associated with TLS Formation in Aggressive Breast Cancer Subtypes," Sci Rep 8, 11720.
Figg et al. (2015) "Polymerization-induced thermal self-assembly (PITSA)," Chem. Sci. 6, 1230-1236.
Figg et al. (2017) "Tuning Hydrophobicity To Program Block Copolymer Assemblies from the Inside Out," Macromolecules, 50 (3), 935-943.
Flanders et al. (Apr. 2018) "Reversible-addition fragmentation chain transfer (RAFT) mediated depolymerization of brush polymers," Polym. Chem. 9, 2328-2335.
Foster et al. (Aug. 2018) "Ring-Opening Metathesis Polymerization in Aqueous Media Using a Macroinitiator Approach," Angew. Chem. Int. Ed. 57, 10672-10676.
Frankel et al. (1988) "Cellular uptake of the tat protein from human immunodeficiency virus," Cell 55(6): 1189-1193.
Fu et al. (2015) "STING agonist formulated cancer vaccines can cure established tumors resistant to PD-1 blockade," Sci Transl Med, 7 (283), 283ra52.
Fu et al. (2016) "Photoacid-mediated ring opening polymerization driven by visible light," Chem. Commun. 52, 7126-7129.
Futaki et al. (2001) "Arginine-rich Peptides: An Abundant Source of Membrane-Permeable Peptides Having Potential as Carriers for Intracellular Protein Delivery," J. Biol. Chem. 276(8): 5836-5840.
Gao et al. (1995) "Controlled Release of a Contraceptive Steroid from Biodegradable and Injectable Gel Formulations: In Vitro Evaluation," Pharm. Res. 12(6): 857-863.
Gentilucci et al. (2010) "Chemical Modifications Designed to Improve Peptide Stability: Incorporation of Non-Natural Amino Acids, Pseudo-Peptide Bonds, and Cyclization," Curr. Pharm. Design, 16, 3185-3203.
Giacomello et al. (Apr. 2020) "The cell biology of mitochondrial membrane dynamics," Nat. Rev. Mol. Cell Bio. 21, 204-224.
Gordon et al. (2001) "Inhibition of β-Amyloid(40) Fibrillogenesis and Disassembly of β-Amyloid(40) Fibrils by Short B-Amyloid Congeners Containing N-Methyl Amino Acids at Alternate Residues," Biochemistry 40(28): 8237-8245.
Gray et al. (Sep. 2018) "A phase I/randomized phase II study of GM.CD40L vaccine in combination with CCL21 in patients with advanced lung adenocarcinoma," Cancer Immunol Immunother. 67:1853-1862.
Grazon et al. (Oct. 2020) "Aqueous Ring-Opening Polymerization-Induced Self-Assembly (ROPISA) of N-Carboxyanhydrides," Angew. Chem. Int. Ed. 59, 622-626.
Green et al. (1988) "Autonomous functional domains of chemically synthesized human immunodeficiency virus tat trans-activator protein," Cell 55(6): 1179-1188.
Gubin et al. (2014) "Checkpoint blockade cancer immunotherapy targets tumour-specific mutant antigens," Nature, 515 (7528), 577-81.
Guidotti et al. (2017) "Cell-Penetrating Peptides: From Basic Research to Clinics," Trends Pharmacol. Sci. 38, 406-424.
Guo et al. (2013) "Therapeutic cancer vaccines: past, present, and future," Adv Cancer Res, 119, 421-75.
Guo et al. (Jul. 2018) Neoantigen Vaccine Delivery for Personalized Anticancer Immunotherapy, Front Immunol. 9:1499.
Hahn et al. (Apr. 2013) "Polymerization of a peptide-based enzyme substrate," Chem Commun (Camb) 49(28): 2873-2875 (8 pp.).
Hamamoto et al. (2002) "Antimicrobial Activity and Stability to Proteolysis of Small Linear Cationic Peptides with D-Amino Acid Substitutions," Microbiol. Immunol. 46(11): 741-749.
Hanahan et al. (2011) "Hallmarks of cancer: the next generation," Cell, 144(5), 646-674.
Hanover et al. (1984) "Kinetics of transit of transferrin and epidermal growth factor through clathrin-coated membranes," Cell 39(2): 283-293.
Hastings et al. (2011) "Disulfide reduction in the endocytic pathway: immunological functions of gamma-interferon-inducible lysosomal thiol reductase," Antioxid Redox Signal, 15 (3), 657-68.
Heitz et al. (2009) "Twenty years of cell-penetrating peptides: from molecular mechanisms to therapeutics," Br. J. Pharmacol. 157(2): 195-206.
Hellmann et al. (2014) "Smoking History and Response to Nivolumab in Patients with Advanced NSCLC," Annals of Oncology 25, S4 426-70, 1229PD.
Hellmann et al. (Apr. 2018) "Genomic Features of Response to Combination Immunotherapy in Patients with Advanced Non-Small-Cell Lung Cancer," Cancer Cell. pii: S1535-6108(18)30123-5. PMCID: PMC5953836.
Henikoff et al. (1992) "Amino acid substitution matrices from protein blocks," Proc. Nat'l Acad. Sci. USA 89(22):10915-10919.
Henninot et al. (Feb. 2018) "The Current State of Peptide Drug Discovery: Back to the Future?," J. Med. Chem. 61, 1382-1414.
Herdewijn et al. (1994) "Hexopyranosyl-Like Oligonucleotides," Chapter 6 in Carbohydrate Modifications in Antisense Research, Sanghvi and Cook, eds. pp. 80-99.
Hill et al. (2015) "Expanding the Scope of RAFT Polymerization: Recent Advances and New Horizons," Macromolecules, 48, 5459-5469.

(56) References Cited

OTHER PUBLICATIONS

Hua et al. (Jul. 2018) "Current Trends and Challenges in the Clinical Translation of Nanoparticulate Nanomedicines: Pathways for Translational Development and Commercialization," Front Pharmacol. 9, 790.
Huang et al. (2017) "Mimicking Melanosomes: Polydopamine Nanoparticles as Artificial Microparasols," ACS Cent Sci., 3(6):564-569. https://doi.org/10.1021/acscentsci.6b00230.
Huh et al. (2005) "In Vivo Magnetic Resonance Detection of Cancer by Using Multifunctional Magnetic Nanocrystals," J. Am. Chem. Soc. 127(35): 12387-12391.
Humphrey et al. (1996) "VMD: Visual Molecular Dynamics," J. Malec. Graphics 14: 33-38.
Hundal et al. (2016) "pVAC-Seq: A genome-guided in silico approach to identifying tumor neoantigens," Genome Med, 8 (1), 11.
International Search Report and Written Opinion, dated Apr. 5, 2021, corresponding to International Application No. PCT/US2020/053308, (from which the present application claims priority,) 11 pp.
Isenberg et al. (2007) "Thrombospondin-1 Inhibits Nitric Oxide Signaling via CD36 by Inhibiting Myristic Acid Uptake," J. Bio. Chem. 282(21), 15404-15415.
Itoh et al. (Jan. 2020) "Solid-Phase Total Synthesis of Yaku'amide B Enabled by Traceless Staudinger Ligation," Angew. Chem. Int. Ed. 59, 4564-4571.
Ivin et al. (2000) "Thermodynamics of Addition Polymerization," J. Polym. Sci., Part A: Polym. Chem. 38 (12), 2137-2146.
Jakalian et al. (2000) "Fast, efficient generation of high-quality atomic charges. AM1-BCC model: I. Method," J. Comput. Chem. 21(2): 132-146.
Jakalian et al. (2002) "Fast, efficient generation of high-quality atomic charges. AM1-BCC model: II. Parameterization and validation," J. Comput. Chem. 23(16): 1623-1641.
James et al. (Jul. 2014) "Poly(oligonucleotides)," Journal of the American Chemical Society 136: 11216-11219.
Ji et al. (2011) "Digesting New Information About the Role of Trypsin in Pancreatitis," Gastroenterology, 141, 1972-1975.
Jia et al. (Jan. 2017) "Effect of PEG Architecture on the Hybridization Thermodynamics and Protein Accessibility of PEGylated Oligonucleotides," Angew. Chem. Int. Ed. 56, 1239-1243.
Jia et al. (Jul. 2017) "Depth-Profiling the Nuclease Stability and the Gene Silencing Efficacy of Brush-Architectured Poly(ethylene glycol)-DNA Conjugates," J. Am. Chem. Soc. 139, 10605-10608.
Johnson et al. (2010) "Drug-Loaded, Bivalent-Bottle-Brush Polymers by Graft-through ROMP," Macromolecules 43(24): 10326-10335.
Johnson et al. (2010) "Synthesis of Statistical Copolymers Containing Multiple Functional Peptides for Nucleic Acid Delivery," Biomacromolecules 11(11): 3007-3013.
Johnson et al. (2011) "Core-Clickable PEG-Branch-Azide Bivalent-Bottle-Brush Polymers by ROMP: Grafting-Through and Clicking-To," J. Am. Chem. Soc. 133(3): 559-566.
Jun et al. (2005) "Nanoscale Size Effect of Magnetic Nanocrystals and Their Utilization for Cancer Diagnosis via Magnetic Resonance Imaging," J. Am. Chem. Soc. 127(16): 5732-5733.
Kammeyer et al. (May 2013) "Polymerization of protecting-group-free peptides via ROMP," Polymer Chemistry 4(14): 3929-3933.
Kaplan et al. (2005) "Cationic TAT peptide transduction domain enters cells by macropinocytosis," J. Controlled Release 102(1): 247-253.
Kaspar et al. (Sep. 2013) "Future directions for peptide therapeutics development," Drug Discovery Today 18(17-18): 807-817.
Kasper et al. (May 2019) "Vinylphosphonites for Staudinger-induced chemoselective peptide cyclization and functionalization," Chem Sci, 10, 6322-6329.
Kawai et al. (2010) "The role of pattern-recognition receptors in innate immunity: update on Toll-like receptors," Nature Immunology, 11 (5), 373-384.
Kebriaei et al. (Jun. 2018) "A phase 1 multicenter study evaluating the safety and efficacy of MHC class II-restricted MAGE-A3/A6 T-cell receptor engineered T cells (KITE-718) in patients with advanced cancer," Journal of Clinical Oncology 2018 36:15_suppl, TPS3104.
Keskin et al. (Jan. 2019) "Neoantigen vaccine generates intratumoral T cell responsesin phase Ib glioblastoma trial," Nature, 565 (7738), 234-239.
Khalil et al. (2016) "The future of cancer treatment:immunomodulation, CARs and combination immunotherapy," Nat Rev Clin Oncol, 13(5): 273-290.
Kim et al. (2011) "Synthesis of all-hydrocarbon stapled a-helical peptides by ring-closing olefin metathesis," Nat. Protoc. 6(6): 761-771.
Kinkead et al. (Oct. 2018) "Combining STING-based neoantigen-targeted vaccine with checkpoint modulators enhances antitumorimmunity in murine pancreatic cancer," Jci Insight, 3 (20).
Kirkin et al. (1999) "Establishment of gp100 and MART-1/Melan-A-specific cytotoxic T lymphocyte clones using in vitro immunization against preselected highly immunogenic melanoma cell clones," Cancer Immunol Immunother, 48 (5), 239-46.
Knutson et al. (2005) "Tumor antigen-specific T helper cells in cancer immunity and immunotherapy," Cancer Immunol Immunother. 54(8):721-8.
Kolonko et al. (2008) "A Polymeric Domain That Promotes Cellular Internalization," J. Am. Chem. Soc. 130(17): 5626-5627.
Kolonko et al. (2009) "General Synthetic Route to Cell-Permeable Block Copolymers via Romp," J. Am. Chem. Soc. 131(21): 7327-7333.
Koren et al. (2012) "Cell-penetrating peptides: breaking through to the other side," Trends Mol. Med. 18(7): 385-393.
Kottisch et al. (2016) "Cationic Polymerization of Vinyl Ethers Controlled by Visible Light," J. Am. Chem. Soc. 138, 15535-15538.
Kottisch et al. (May 2018) "Enhancing Temporal Control and Enabling Chain-End Modification in Photoregulated Cationic Polymerizations by Using Iridium-Based Catalysts," Angew. Chem. Int. Ed. 130, 8392-8396.
Kreiter et al. (2015) "Mutant MHC class II epitopes drive therapeutic immune responses to cancer," Nature, 520 (7549), 692-U269.
Ku et al. (2011) "Controlling and Switching the Morphology of Micellar Nanoparticles with Enzymes," J. Am. Chem. Soc. 133: 8392-8395.
Kuykendall et al. (2015) "Distribution of Immune Markers and Their Association with Overall Survival and Time to Progression in Non-Small-Cell Lung Cancer," Journal of Thoracic Oncology. 10, S2, 9, S268, Mini oral session, Sep. 7, 2015, Abstract.
Lam et al. (Oct. 2018) "LBA38 Safety and anti-tumor effects of MAGE-A10c796 TCR T-cells in two clinical trials," Annals of Oncology, vol. 29, Issue suppl_8, 1.
Lange et al. (2007) "Classical Nuclear Localization Signals: Definition, Function, and Interaction with Importin α," J. Biol. Chem. 282(8): 5101-5105.
Le et al. (Feb. 2019) "Straightforward access to biocompatible poly(2-oxazoline)-coated nanomaterials by polymerization-induced self-assembly," Chem. Commun, 55, 3741-3744.
Le et al. (Mar. 2019) "Ultra-Fast Synthesis of Multivalent Radical Nanoparticles by Ring-Opening Metathesis Polymerization-Induced Self-Assembly," Angew. Chem. In. Ed. 58, 4725-4731.
Lee et al. (2003) "N-Terminal Site-Specific Mono-PEGylation of Epidermal Growth Factor," Pharm. Res. 20(5): 818-825.
Lee et al. (Jan. 2020) "Stimuli-Responsive Conformational Transformation of Peptides for Tunable Cytotoxicity," Bioconjug. Chem. 31, 43-50.
Lei et al. (1995) "Structure-Function Analysis of Human Glucose-6-phosphatase, the Enzyme Deficient in Glycogen Storage Disease Type 1a," J. Biol. Chem. 270(20): 11882-11886.
Leicher et al. (1998) "Coexpression of the KCNA3B Gene Product with Kv1.5 Leads to a Novel A-type Potassium Channel," J. Biol. Chem. 273(52):35095- 35101.
Li et al. (2002) "Preparation and characterization of PEGylated adducts of recombinant human tumor necrosis factor-a from *Escherichia coli*," Biotechnol. 92(3): 251-258.
Li et al. (2016) "Structure and Function of Iron-Loaded Synthetic Melanin," ACS Nano, 10(11): 10186-10194. PMCID: PMC5295137.

(56) References Cited

OTHER PUBLICATIONS

Li et al. (2017) "CD54-NOTCH1 Axis Controls Tumor Initiation and Cancer Stem Cell Functions in Human Prostate Cancer," Theranostics. 7(1):67-8.
Li et al. (Jun. 2018) "A facile approach to enhance antigen response for personalized cancer vaccination," Nat Mater, 17 (6), 528-534.
Lindorff-Larsen et al. (2010) "Improved side-chain torsion potentials for the Amber ff99SB protein force field," Proteins 78(8): 1950-1958.
Liu et al. (Aug. 2018) "Polymerization Induced Self-Assembly of a Site-Specific Interferon α-Block Copolymer Conjugate into Micelles with Remarkably Enhanced Pharmacology," J. Am. Chem. Soc. 140(33), 10435-10438.
Liu et al. (Oct. 2019) "Discovery of low-molecular weight anti-PD-L1 peptides for cancer immunotherapy," J Immunother Cancer, 7 (1), 270.
Livant et al. (2000) "The PHSRN sequence induces extracellular matrix invasion and accelerates wound healing in obese diabetic mice," J. Clin. Invest. 105(11):1537-1545.
Lopez et al. (2011) "Molecular Mechanism of Cyclodextrin Mediated Cholesterol Extraction," PLoS Comp. Biol. 7(3): e1002020, pp. 1-11.
Lu et al. (2009) "One-Pot Synthesis of Brush-Like Polymers via Integrated Ring-Opening Metathesis Polymerization and Polymerization of Amino Acid N-Carboxyanhydrides," JACS 131(38): 13582-13583.
Luckerath et al. (Apr. 2020) "DNA-Polymer Nanostructures by RAFT Polymerization and Polymerization-Induced Self-Assembly," Angew. Chem. Int. Ed. doi: 10.1002/anie.201916177.
Lynn et al. (Mar. 2020) "Peptide-TLR-7/8a conjugate vaccines chemically programmed for nanoparticle self-assembly enhanceCD8 T-cell immunity to tumor antigens," Nat Biotechnol, 38 (3), 320-332.
Lytle et al. (Nov. 2018) "Stem cell fate in cancer growth, progression and therapy resistance," Nat Rev Cancer. Nov. 2018; 18(11):669-680.
Macri et al. (2016) "Targeting dendritic cells: a promising strategy to improve vaccine effectiveness," Clin Transl Immunology, 5 (3), e66.
Martinez et al. (Sep. 2020) "A Thermodynamic Roadmap for the Grafting-through Polymerization of PDMS11MA" Acs Macro Lett. 9, 1303-1309.
Matson et al. (2010) "Monotelechelic Poly(oxa)norbornenes by Ring-Opening Metathesis Polymerization using Direct End-Capping and Cross Metathesis," Macromolecules 43(1): 213-221.
Maynard et al. (2000) "Synthesis of Norbornenyl Polymers with Bioactive Oligopeptides by Ring-Opening Metathesis Polymerization," Macromolecules 33(17):6239-6248.
Maynard et al. (2001) "Inhibition of Cell Adhesion to Fibronectin by Oligopeptide-Substituted Polynorbornenes," J. Am. Chem. Soc. 123, 1275-1279.
McGregor (2008) "Discovering and improving novel peptide therapeutics," Curr. Opin. Pharmacol. 8(5): 616-619.
Meeth et al. (2016) "The YUMM lines: a series of congenic mouse melanoma cell lines with defined genetic alterations," Pigm Cell Melanoma R, 29 (5), 590-597.
Mellman et al. (2011) Cancer immunotherapy comes of age. Nature, 480 (7378),480-9.
Menacho-Melgar et al. (Feb. 2019) "A review of lipidation in the development of advanced protein and peptide therapeutics," J. Control Release, 295, 1-12.
Michaudel et al. (2017) "Cationic Polymerization: From Photoinitiation to Photocontrol," Angew. Chem. Int. Ed. 56, 9670-9679.
Millar et al. (Apr. 2020) "Antibody-mediated delivery of viral epitopes to tumors harnesses CMV-specific T cells for cancer therapy," Nat Biotechnol. 38(4):420-425.
Miller et al. (1994) "Proteolytic studies of homologous peptide and N-substituted glycine peptoid oligomers," Bioorg. Med. Chem. Lett. 4(22): 2657-2662.
Mitchell et al. (2000) "Polyarginine enters cells more efficiently than other polycationic homopolymers," J. Pept. Res. 56(5): 318-325.
Molla et al. (Jun. 2018) "Dynamic actuation of glassy polymersomes through isomerization of a single azobenzene unit at the block copolymer interface," Nat. Chem. 10, 659-666.
Monfardini et al. (1995) "A Branched Monomethoxypoly(ethylene glycol) for Protein Modification," Bioconjugate Chem. 6(1): 62-69.
Mougel et al. (Mar. 2019) "Therapeutic Cancer Vaccine and Combinations With Antiangiogenic Therapies and Immune Checkpoint Blockade," Front Immunol, 10.
Moynihan et al. (Sep. 2018) "Enhancement of Peptide Vaccine Immunogenicity by Increasing Lymphatic Drainage and Boosting Serum Stability," Cancer Immunol Res, 6 (9), 1025-1038.
Murata et al. (1997) "Syntheses and Radical Polymerization Behavior of Methacrylamides Having Peptide Moieties: Effect of the Methylene Chain Introduced between the Methacrylamide and Peptide Moieties on the Polymerizability and Polymer Structure," Macromolecules 30(10): 2902-2906.
Naing et al. (Jul. 2018) "Epacadostat plus durvalumab in patients with advanced solid tumors: preliminary results of the ongoing, open-label, phase I/II ECHO-203 study," AACR; Cancer Res 2018 Abstract CT177.
Nakase et al. (2004) "Cellular Uptake of Arginine-Rich Peptides: Roles for Macropinocytosis and Actin Rearrangement," Mol. Ther. 10(6): 1011-1022.
Navaratna et al. (Jan. 2020) "Directed Evolution Using Stabilized Bacterial Peptide Display," J. Am. Chem. Soc. 142, 1882-1894.
Needleman et al. (1970) "A general method applicable to the search for similarities in the amino acid sequence of two proteins," J. Mol. Biol. 48: 443-453.
Newberg et al. (1996) "Importance of MHC class 1 alpha2 and alpha3 domains in the recognition of self and non-self MHC molecules," J Immunol, 156 (7), 2473-80.
Ng et al. (Oct. 2018) "Pushing the Limits of High Throughput PET-RAFT Polymerization," Macromolecules, 51, 7600-7607.
Ngambenjawong et al. (2017) "Multivalent Polymers Displaying M2 Macrophage-Targeting Peptides Improve Target Binding Avidity and Serum Stability, "ACS Biomater. Sci. Eng. 2017, 3, 2050-2053.
Nguyen et al. (2015) "Enzyme-responsive Nanoparticles for Targeted Accumulation and Prolonged Scaffold Retention in Heart Tissue After Myocardial Infarction," Adv Mater., 27(37):5547-5552. PMID: PMC4699559.
Nischan et al. (publicly available Aug. 2013) "Stabilization of Peptides for Intracellular Applications by Phosphoramidate-Linked Polyethylene Glycol Chains," Angew. Chem., Int. Ed. (Nov. 2013), 52(45): 11920-11924.
Niu et al. (2017) "Engineering live cell surfaces with functional polymers via cytocompatible controlled radical polymerization," Nat. Chem. 9, 537-545.
O'Brien-Simpson et al. (1997) "Polymerization of Unprotected Synthetic Peptides: A View toward Synthetic Peptide Vaccines," J. Am. Chem. Soc. 119(6): 1183-1188.
Ogawa, et al. (2015) "Metal-Free Ring-Opening Metathesis Polymerization," J. Am. Chem. Soc. 137, 1400-1403.
Oliver et al. (Dec. 2018) "Scalable Fiber-like Micelles and Block Co-micelles by Polymerization-Induced Crystallization-Driven Self-Assembly," J. Am. Chem. Soc. 140, 18104-18114.
Osapay et al. (1997) "Lanthionine-somatostatin analogs: synthesis, characterization, biological activity, and enzymatic stability studies," J. Med. Chem. 40(14): 2241-2251.
Ostankovitch et al. (1998) "A partially modified retro-inverso pseudopeptide modulates the cytokine profile ofCTL specific for an influenza virus epitope," J Immunol, 161 (1), 200-8.
Ostro (1989) "Use of liposomes as injectable-drug delivery systems ," Am. J. Hosp. Pharm.46:1576-1587.
Ott et al. (2017) "An immunogenic personal neoantigen vaccine for patients with melanoma," Nature, 547 (7662), 217-221.
Ouyang et al. (2010) "Simultaneous Visualization of Protumorigenic Src and MT1-MMP Activities with Fluorescence Resonance Energy Transfer," Cancer Res. 70(6): 2204-2212.

(56) References Cited

OTHER PUBLICATIONS

Overwijk et al. (1998) "gp100/pmel 17 is a murine tumor rejection antigen: induction of "self"-reactive, tumoricidal T cells using high-affinity, altered peptide ligand," J Exp Med, 188 (2), 277-86.
Pan et al. (2016) "Mechanism of Photoinduced Metal-Free Atom Transfer Radical Polymerization: Experimental and Computational Studies," J. Am. Chem. Soc. 138, 2411-2425.
Pan et al. (2017) "Automated Synthesis of Well-Defined Polymers and Biohybrids by Atom Transfer Radical Polymerization Using a DNA Synthesizer," Angew. Chem. Int. Ed. 56, 2740-2743.
Parent et al. (Oct. 2018) "Hierarchical Spidroin Micellar Nanoparticles as the Fundamental Precursors of Spider Silks," Proc Nat Acad Sci U S A, 115(45): 11507-11512. PMCID: PMC6233143.
Patel et al. (2007) "Cell Penetrating Peptides: Intracellular Pathways and Pharmaceutical Perspectives," Pharm. Res. 24(11): 1977-1992.
Patel et al. (2012) "Synthesis and Cell Adhesive Properties of Linear and Cyclic RGD Functionalized Polynorbornene Thin Films," Biomacromolecules 13(8): 2546-2553.
Patterson et al. (2015) "Observing the Growth of Metal-Organic Frameworks by In Situ Liquid Cell Tem," J Am Chem Soc., 137(23):7322-7328. https://doi.org/10.1021/jacs.5b00817.
Payne et al. (Aug. 2020) "BTN3A1 governs antitumor responses by coordinating ab and gd T cells," Science 369, 942-949.
Pazos et al. (2009) "Peptide-based fluorescent biosensors," Chem. Soc. Rev. 38(12): 3348-3359.
Pearson et al. (1988) "Improved tools for biological sequence comparison," Proc. Nat'l. Acad. Sci. USA 85(8):2444-2448.
Penfold et al. (Aug. 2019) "Emerging Trends in Polymerization-Induced Self-Assembly," ACS Macro Lett, 8, 1029-1054.
Peng et al. (2006) "Characterization of HLA-A2-restricted HPV-16 E7-specific CD8(+) T-cell immune responses induced by DNA vaccines in HLA-A2 transgenic mice," Gene Ther, 13 (1), 67-77.
Perales-Puchalt et al. (2016) "Follicle-stimulating hormone receptor is expressed by most ovarian cancer subtypes and is a safe and effective immunotherapeutic target," Clin. Cancer Res. 23:441-53. PMC5241180.
Perrier (2017) "50th Anniversary Perspective: RAFT Polymerization—A User Guide," Macromolecules, 50, 19, 7433-7447.
Peters et al. (2017) "Impact of tumor mutation burden on the efficacy of first-line nivolumab in stage iv or recurrent non-small cell lung cancer: An exploratory analysis ofCheckMate 026," Cancer Res;77(13 Suppl): Abstract nr CT082.
Phillips et al. (2005) "Scalable molecular dynamics with NAMD," Journal of Computational Chemistry 26(16): 1781-1802.
Pini et al. (2008) "Branched Peptides as Therapeutics," Curr. Protein Pept. Sci. 9(5): 468-477.
Poropatich et al. (2017) "Comprehensive T-cell immunophenotyping and next-generation sequencing of human papillomavirus (HPV)-positive and HPV-negative head and neck squamous cell carcinomas," J Pathol, 243 (3), 354-365.
Powell et al. (1993) "Peptide Stability in Drug Development. II. Effect of Single Amino Acid Substitution and Glycosylation on Peptide Reactivity in Human Serum," Pharm. Res. 10(9): 1268-1273.
Price et al. (2004) "A modified TIP3P water potential for simulation with Ewald summation," J. Chem. Phys. 121(20): 10096-10103.
Proetto et al. (2016) "Cellular Delivery of Nanoparticles Revealed with Combined Optical and Isotopic Nanoscopy," ACS Nano, 10 (4),4046-54.
Pronk et al. (publicly available Feb. 2013) "GROMACS 4.5: a high-throughput and highly parallel open source molecular simulation toolkit," Bioinformatics (Apr. 2013) 29(7): 845-854.
Puglisi et al. (1995) "Solution Structure of a Bovine Immunodeficiency Virus Tat-TAR Peptide-RNA Complex," Science 270(5239): 1200-1203, (Machine Generated Copy).
Ramon et al. (2005) "PEGylated Interferon-a2b: A Branched 40K Polyethylene Glycol Derivative, " Pharm. Res. 22(8): 1374-1386.
Rankin et al. (2007) "The controlled homogeneous organic solution polymerization of new hydrophilic cationic exo-7-oxanorbornenes via ROMP with RuCI2(PCy3)2CHPh in a novel 2,2,2-trifluoroethanol/methylenechloride solvent mixture," J. Polym. Sci. A Polym. Chem. 45(11): 2113-2128.
Rao (1995) "Recent developments of collagen-based materials for medical applications and drug delivery systems," Biomater Sci. Polym. Ed. 7:623-645.
Rao et al. (2012) "Norbornene Derived Doxorubicin Copolymers as Drug Carriers with pH Responsive Hydrazone Linker," Biomacromolecules 13(1): 221-230.
Raus et al. (2014) "ATRP of POSS Monomers Revisited: Toward High-Molecular Weight Methacrylate—POSS (Co)Polymers," Macromolecules, 47 (21), 7311-7320.
Regenbrecht et al. (2008) "Stemming cancer: functional genomics of cancer stem cells in solid tumors," Stem Cell Rev. 4(4):319-28.
Reissmann et al. (2000) "The LHRH antagonist Cetrorelix: a review," Human Reproduction Update 6(4): 322-331.
Richard et al. (2003) "Cell-penetrating Peptides: A Reevaluation of the Mechanism of Cellular Uptake," J. Biol. Chem. 278(1): 585-590.
Roberts et al. (2012) "Chemistry for peptide and protein PEGylation," Adv. Drug Deliv. Rev. 64, 116-127.
Rodal et al. (1999) "Extraction of Cholesterol with Methyl-β-Cyclodextrin Perturbs Formation of Clathrin-coated Endocytic Vesicles," Mol. Biol. Cell 10(4): 961-974.
Roloff et al. (2017) "Micellar Thrombin-Binding Aptamers: Reversible Nanoscale Anticoagulants," J Am Chem Soc., 139(46): 16442-16445. PMID: 29135251. DOI: 10.1021/jacs.7b07799.
Roloff et al. (Jan. 2018) "Self-Transfecting Micellar RNA: Modulating Nanoparticle Cell Interactions via High Density Display of Small Molecule Ligands on Micelle Coronas," Bioconjug Chem., 29(1):126-135. PMCID: PMC5993044.
Rozek et al. (2003) "Structure-Based Design of an Indolicidin Peptide Analogue with Increased Protease Stability," Biochemistry 42(48): 14130-14138.
Ruijtenbeek et al. (2001) "Peptoid—Peptide Hybrids That Bind Syk SH2 Domains Involved in Signal Transduction," ChemBioChem 2(3): 171-179.
Rush et al. (2013) "Nuclease-resistant DNA via High Density Packing in Polymeric Micellar Nanoparticle Coronas," ACS Nano, 7(2):1379-1387. PMCID: PMC3608424.
Rush et al. (May 2014) "Intracellular mRNA Regulation with Self-Assembled Locked Nucleic Acid Polymer Nanoparticles," J. Am. Chem. Soc. 136: 7615-7618.
Rutkowski et al. (2015) "Microbially driven TLR-dependent signalling governs distal malignant progression through tumor-promoting inflammation," Cancer Cell; 27: 27-40. PMC4293269.
Ruttekolk et al. (2011) "Coupling to Polymeric Scaffolds Stabilizes Biofunctional Peptides for Intracellular Applications," Mol. Pharmacol. 79(4): 692-700.
Sahin et al. (Mar. 2018) "Personalized vaccines for cancer immunotherapy," Science. 359. 1355-1360.
Samarajeewa et al. (publicly available Dec. 2013) "Programmed hydrolysis of nanoassemblies by electrostatic interaction-mediated enzymatic-degradation," Chem. Commun. (Jan. 2014), 50(8): 968-970.
Sánchez-Paulete et al. (Dec. 2017) "Antigen cross-presentation and T-cell cross-priming in cancer immunology and immunotherapy," Ann Oncol. 28(suppl_12):xii44-xii55.
Sanford et al. (2001) "A Versatile Precursor for the Synthesis of New Ruthenium Olefin Metathesis Catalysts," Organometallics 20(25): 5314-5318.
Scarlett et al. (2012) "Ovarian cancer progression is controlled by phenotypic changes in dendritic cells," J Exp Med; 209:495-506. PMC3302234.
Schabath et al. (2016) "Differential association of STK11 and TP53 with KRAS mutation-associated gene expression, proliferation and immune surveillance in lung adenocarcinoma," Oncogene 35(24): 3209-3216, PMCID: PMC4837098.
Schafmeister et al. (2000) "An All-Hydrocarbon Cross-Linking System for Enhancing the Helicity and Metabolic Stability of Peptides," J. Am. Chem. Soc. 122(24): 5891-5892.

(56) References Cited

OTHER PUBLICATIONS

Schellinger et al. (Jul. 2013) "Block Copolymers Containing a Hydrophobic Domain of Membrane-Lytic Peptides Form Micellar Structures and Are Effective Gene Delivery Agents," ACS Macro Lett. 2(8): 725-730.
Scholl et al. (1999) "Synthesis and Activity of a New Generation of Ruthenium-Based Olefin Metathesis Catalysts Coordinated with 1,3-Dimesityl-4,5-dihydroimidazol-2-ylidene Ligands," Org. Lett. 1(6): 953-956.
Schuster et al. (1997) "Neoglycopolymers produced by aqueous ring-opening metathesis polymerization: decreasing saccharide density increases activity," J. Mol. Catal. 116(1-2): 209-216.
Shae et al. (Mar. 2019) "Endosomolytic polymersomes increase the activity of cyclic dinucleotide STING agonists to enhance cancer immunotherapy," Nat Nanotechnol, 14 (3), 269-278.
Shanmugam (2016) "Aqueous RAFT Photopolymerization with Oxygen Tolerance," Macromolecules, 49, 24, 9345-9357, doi: 10.1021/acs.macromol.6b02060.
Shannon et al. (2001) "Novel cyclic peptide inhibits intercellular adhesion molecule-1-mediated cell aggregation," J Pept Res. 58(2):140-50.
Sharp et al. (2009) "Uptake of particulate vaccine adjuvants by dendritic cells activates the NALP3 inflammasome," P Natl Acad Sci USA, 106 (3), 870-875.
Shi et al. (Oct. 2013) "Engineering biodegradable and multifunctional peptide-based polymers for gene delivery," J. Biol. Eng. 7: 25, pp. 1-10.
Sivick et al. (Dec. 2018) "Magnitude of Therapeutic STING Activation Determines CD8(+) T Cell-Mediated Anti-tumor Immunity," Cell Rep, 25 (11), 3074-3085 e5.
Smith et al. (1981) "Comparison of Biosequences," Adv. Appl. Math. 2:482-489.
Smith et al. (2017) "MET:GRB2 Signaling-Associated Complexes Correlate with Oncogenic MET Signaling and Sensitivity to MET kinase inhibitors," Clin Cancer Res. PMCID: PMC5833309.
Smyth et al. (2016) "Combination cancer immunotherapies tailored to the tumour microenvironment," Nat Rev Clin Oncol, 13 (3), 143-58.
Som et al. (2011) "Self-Activation in De Novo Designed Mimics of Cell-Penetrating Peptides," Angew. Chem., Int. Ed. 123: 6271-6274.
Song et al. (Oct. 2018) "IRE1α-XBP1 controls T cell function in ovarian cancer by regulating mitochondrial activity," Nature. 562:423-8. PMC6237282.
Spicer et al. (Feb. 2018) "Peptide and protein nanoparticle conjugates: versatile platforms for biomedical applications," Chem. Soc. Rev. 47, 3574-3620.
Spring et al. (publicly available May 2014) "The preparation of well-controlled poly(N-cyclohexyl-exo-norbornene-5, 6-dicarboximide) polymers," Polymer Journal (Sep. 2014) 46: 576-583.
Steer et al. (2002) "β-Amino Acids: Versatile Peptidomimetics," Curr. Med. Chem. 9(8): 811-822.
Stephen et al. (2014) "Transforming Growth Factor-beta-Mediated Suppression of Antitumor T Cells Requires FoxP1 Transcription Factor Expression," Immunity; 41:427-39. PMC4174366.
Stephen et al. (2017) "SATB1 expression governs epigenetic repression of PD-1 in tumor-reactive T cells," Immunity; 46: 51-64. PMC5336605.
Stickle et al. (1992) "Hydrogen bonding in globular proteins," J. Mol. Biol. 226(4): 1143-1159.
Su et al. (1991) "In Vitro Stability of Growth Hormone Releasing Factor (GRF) Analogs in Porcine Plasma," Horm. Metab. Res. 23(1): 15-21.
Suma et al. (2017) "Modulated Fragmentation of Proapoptotic Peptide Nanoparticles Regulates Cytotoxicity," J. Am. Chem. Soc. 139, 4009-4018.
Sun et al. (2012) "A novel mouse CD133 binding-peptide screened by phage display inhibits cancer cell motility in vitro," Clin Exp Metastasis, 29, 185-196.
Sun et al. (Feb. 2019) "Architecture-transformable polymers: Reshaping the future of stimuli-responsive polymers," Prog. Polym. Sci.89, 61-75.
Sun et al. (Nov. 2019) "Bioactive Peptide Brush Polymers via Photoinduced Reversible-Deactivation Radical Polymerization," Angewandte Chemie International Edition in English. vol. 58, No. 48; pp. 17359-17364; DOI: 10.1002/anie.201908634.
Sun et al. (Oct. 2020) "Proapoptotic Peptide Brush Polymer Nanoparticles via Photoinitiated Polymerization-Induced Self-Assembly," Angew. Chem. 59, 19136-19142.
Sutthasupa et al. (2010) "Recent advances in ring-opening metathesis polymerization, and application to synthesis of functional materials," Polymer Journal 42: 905-915.
Svoronos et al. (2017) "Tumor cell-independent estrogen signaling drives malignant progression through MDSC mobilization," Cancer Discovery. 7: 72-85. PMC5222699.
Tan et al. (2015) "Photo-PISA: Shedding Light on Polymerization-Induced Self- Assembly," ACS Macro Lett. 4, 1249-1253.
Tesone et al. (2016) "Satb1 Overexpression Drives Tumor-Promoting Activities in Cancer-Associated Dendritic Cells," Cell Reports. 14: 1774-1786. PMC4767618.
Thomas et al. (2003) "Conditions for Facile, Controlled RAFT Polymerization of Acrylamide in Water," Macromolecules, 36, 1436-1439.
Thomas et al. (2004) "Hydrolytic Susceptibility of Dithioester Chain Transfer Agents and Implications in Aqueous RAFT Polymerizations," Macromolecules, 37, 1735-1741.
Thompson et al. (publicly available Dec. 2013) "Labelling Polymers and Micellar Nanoparticles via Initiation, Propagation and Termination with ROMP," Polym Chem, Mar. 2014 5(6):1954-1964.
Thundimadathil (Dec. 2012) "Cancer Treatment Using Peptides: Current Therapies and Future Prospects," Journal of Amino Acids 2012(967347): 1-13.
Tijssen (1993) "Overview of principles of hybridization and the strategy of nucleic acid probe assays," in Techniques in Biochemistry and Molecular Biology—Hybridization with Nucleic Probes, 19-78.
Toft et al. (2012) "Coassembled Cytotoxic and Pegylated Peptide Amphiphiles Form Filamentous Nanostructures with Potent Anti-tumor Activity in Models of Breast Cancer," ACS Nano, 6, 7956-7965.
Toti et al. (2010) "Interfacial Activity Assisted Surface Functionalization: A Novel Approach To Incorporate Maleimide Functional Groups and cRGD Peptide on Polymeric Nanoparticles for Targeted Drug Delivery," Mol Pharm. 7(4): 1108-1117.
Touve et al. (Apr. 2018) "Polymerization-Induced Self-Assembly of Micelles Observed by Liquid Cell Transmission Electron Microscopy," ACS Central Sci. 4, 543-547.
Trabulo et al. (2010) "Cell-Penetrating Peptides—Mechanisms of Cellular Uptake and Generation of Delivery Systems," Pharmaceuticals 3(4): 961-993.
Trnka et al. (2001) "The Development of L2X2RuCHR Olefin Metathesis Catalysts: An Organometallic Success Story," Acc. Chem. Res. 34(1): 18-29.
Tsai et al. (2015) "ICAM1 Is a Potenital Cancer Stem Cell Marker of Esophageal Squamous Cell Carcinoma," PLOS ONE 10(11): e0142834.
Turbant et al. (2009) "Cynomolgus macaques immunized with two HIV-1 Tat stabilized proteins raise strong and long-lasting immune responses with a pattern of Th1/Th2response differing from that in mice," Vaccine, 27 (39), 5349-56.
Tymoczko ed. (2010) Biochemistry: A Short Course, 2nd ed., W.H. Freeman and Company: 13-15.
Ungerleider et al. (2017) "Enzyme-Targeted Nanoparticles for Delivery to Ischemic Skeletal Muscle," Polym Chem., 8(34):5212-5219. PMCID: PMC5662209.
Uto et al. (2009) "Modulation of innate and adaptive immunity by biodegradable nanoparticles," Immunol Lett, 125 (1), 46-52.
Valdebenito et al. (2010) "Effect of solvent on the free radical polymerization of N,N-dimethylacrylamide," Polym. Int. 59, 1246-1251.

(56) References Cited

OTHER PUBLICATIONS

Van Der Burg et al. (2016) "Vaccines for established cancer: overcoming the challenges posed by immune evasion," Nat Rev Cancer. 16(4):219-33.
Vanommeslaeghe et al. (2010) "CHARMM general force field: A force field for drug-like molecules compatible with the CHARMM all-atom additive biological force fields," J. Comput. Chem. 31(4): 671-690.
Vanommeslaeghe et al. (2012) "Automation of the CHARMM General Force Field (CGenFF) I: Bond Perception and Atom Typing," J. Chem. Inf. Model. 52(12): 3144-3154.
Vanommeslaeghe et al. (2012) "Automation of the CHARMM General Force Field (CGenFF) II: Assignment of Bonded Parameters and Partial Atomic Charges," J. Chem. Inf Model. 52(12): 3155-3168.
Varlas et al. (Aug. 2018) "Photoinitiated Polymerization-Induced Self-Assembly in the Presence of Surfactants Enables Membrane Protein Incorporation into Vesicles," Macromolecules, 51, 6190-6201.
Verdine et al. (2012) "Chapter one—Stapled Peptides for Intracellular Drug Targets," Methods Enzymol. 503: 3-33.
Vlieghe et al. (2010) "Synthetic therapeutic peptides: science and market," Drug Discovery Today 15(1-2): 40-56.
Vonderheit et al. (2005) "Rab7 Associates with Early Endosomes to Mediate Sorting and Transport of Semliki Forest Virus to Late Endosomes," PLOS Biol. 3(7): 1225-1238.
Wang et al. (1999) "Phase I trial of a MART-1 peptide vaccine with incomplete Freund's adjuvant for resected high-risk melanoma," ClinCancer Res, 5 (10), 2756-65.
Wang et al. (2004) "Development and testing of a general amber force field," J. Comput. Chem. 25(9): 1157-1174.
Wang et al. (2014) "Recent progress of cell-penetrating peptides as new carriers for intracellular cargo delivery," J. Controlled Release (Jan. 2014) 174: 126-136.
Wang et al. (May 2019) "Rational vaccinology with spherical nucleic acids," Proc Natl Acad Sci U S A, 116(21), 10473-10481.
Webber et al. (2016) "Supramolecular PEGylation of biopharmaceuticals," Proc. Natl. Acad. Sci. USA, 113, 14189-14194.
Weinstock et al. (2012) "Protease-resistant peptide design-empowering nature's fragile warriors against HIV," Pept. Sci. 98(5): 431-442.
Weiss et al. (2017) "The STING agonist DMXAA triggers a cooperation between T lymphocytes and myeloid cells that leads to tumor regression," Oncoimmunology, 6 (10), e1346765.
Wender et al. (2000) "The design, synthesis, and evaluation of molecules that enable or enhance cellular uptake: Peptoid molecular transporters," Proc. Natl. Acad. Sci. U. S. A. 97(24): 13003-13008.
Widmann et al. (1991) "Differential stability of antigenic MHC class I restricted synthetic peptides," J Immunol, 147 (11), 3745-51.
Wolchok et al. (2007) "Safety and immunogenicity of tyrosinase DNA vaccines in patients with melanoma," Mol Ther, 15 (11), 2044-50.
Woodley (1994) "Enzymatic barriers for GI peptide and protein delivery," Crit. Rev. Ther. Drug Carrier Syst. 11(2-3): 61-95.
Wright et al. (Apr. 2019) "Ring-opening metathesis polymerization-induced self-assembly (ROMPISA) of a cisplatin analogue for high drug-loaded nanoparticles," Polym. Chem. 10 (23), 2996-3000.
Wright et al. (Apr. 2018) "Aqueous-Phase Ring-Opening Metathesis Polymerization-Induced Self-Assembly," ACS Macro Lett, 7, 401-405.
Wu et al. (2017) "Targeting the Genome-Stability Hub Ctf4 by Stapled-Peptide Design," Angew. Chem. Int. Ed. 56, 12866-12872.
Xiao et al. (2015) "Bioinspired Structural Colors Produced via Self-Assembly of Synthetic Melanin Nanoparticles," ACS Nano, 9(5):5454-5460. https://doi.org/10.1021/acsnano.5b01298.
Xiao et al. (2017) "Bio-Inspired Bright Non-Iridescent Photonic Melanin Supraballs," Science Advances, 3(9): e1701151. DOI: 10.1126/sciadv.1701151.
Xu at al. (2016) "Selective Photoactivation: From a Single Unit Monomer Insertion Reaction to Controlled Polymer Architectures," J. Am. Chem. Soc. 138 (9), 3094-3106.
Xu et al. (2013) "Cytomegalovirus-based cancer vaccines expressing TRP2 induce rejection of melanoma in mice," Biochem Biophys Res Commun, 437 (2), 287-91.
Xu et al. (2014) "A Robust and Versatile Photoinduced Living Polymerization of Conjugated and Unconjugated Monomers and Its Oxygen Tolerance," J. Am. Chem. Soc. 136, 5508-5519.
Yadav et al. (2014) "Predicting immunogenic tumour mutations by combining mass spectrometry and exome sequencing," Nature, 515(7528), 572-6.
Yamaguchi et al. (2003) "Effect of a,a-Dialkyl Amino Acids on the Protease Resistance of Peptides," Biosci., Biotechnol., Biochem. 67(10): 2269-2272.
Yang et al. (2016) "Development of a Robust Photocatalyzed ATRP Mechanism Exhibiting Good Tolerance to Oxygen and Inhibitors," Macromolecules, 49, 7653-7666.
Yang et al. (Nov. 2018) "Self-Assembled Aptamer-Grafted Hyperbranched Polymer Nanocarrier for Targeted and Photoresponsive Drug Delivery," Angew. Chem. Int. Ed. 57, 17048-17052.
Yeow et al. (2017) "Photoinitiated Polymerization-Induced Self-Assembly (Photo-PISA): New Insights and Opportunities," Adv. Sci. 4, 1700137.
Yu et al. (Feb. 2019) "A Hybrid Platform Based on a Bispecific Peptide-Antibody Complex for Targeted Cancer Therapy," Angew. Chem. Int. Ed. 58, 2005-2010.
Zhang et al. (2003) "Intratumoral T cells, recurrence and survival in epithelial ovarian cancer," N Engl J Med; 348:201-211.
Zhang et al. (2007) "Thrombospondin-based antiangiogenic therapy," Microvasc Res. 74(2-3), 90-99.
Zhang et al. (2015) "Polyelectrolyte Multilayers Assembled Entirely from Immune Signals on Gold Nanoparticle Templates Promote Antigen-Specific T Cell Response," ACS Nano, 9 (6), 6465-77.
Zhao et al. (2016) "Prognostic value of the expression of cancer stem cell-related markers CD133 and CD44 in hepatocellular carcinoma: From patients to patient- derived tumor xenograft models," Oncotarget. 7(30):47431-47443.
Zhao et al. (publicly available Aug. 2013) "Mimicry of High-Density Lipoprotein: Functional Peptide-Lipid Nanoparticles Based on Multivalent Peptide Constructs," J. Am. Chem. Soc. (Sep. 2013) 135(36): 13414-13424.
Zhou et al. (2015) "Aqueous Polymerization-Induced Self-Assembly for the Synthesis of Ketone-Functionalized Nano-Objects with Low Polydispersity," ACS Macro Lett, 4, 495-499.
Zidovetzki et al. (2007) "Use of cyclodextrins to manipulate plasma membrane cholesterol content: Evidence, misconceptions and control strategies," Biochim. Biophys. Acta 1768(6): 1311-1324.

* cited by examiner

DMA

PepAm

Poly(PepAm-co-DMA)

KLAAm

Poly(KLAAm-co-DMA)

Rhodamine | WGA 488 | Merge

Rho-KLA peptide

KLAAm$_{25}$-co-DMA$_{75}$

KLAAm$_{25}$-co-DMA$_{25}$

KLAAm$_{10}$

PMMA MacoCTA

PMMA-b-P(DMA-co-PepAm)

PnBA (P6)

PnBA-b-poly(PepAm-co-DMA) (P9)

Poly(KLAAm$_{10}$-co-DMA$_{30}$) MacroCTA

Poly(KLAAm$_{10}$-co-DMA$_{30}$)-*b*-(DAAm$_m$-co-DMA$_n$)

KLAAm

Poly(KLAAm-co-DMA) MacroCTA

Peptide brush copolymers

Peptide brush homopolymers

Peptide brush copolymers and peptide brush copolymer nanoparticles:

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Synthetic construct

<400> SEQUENCE: 1

Gly Pro Leu Gly Leu Ala Gly Gly Trp Gly Glu Arg Asp Gly Ser
1               5                   10                  15


<210> SEQ ID NO 2
<211> LENGTH: 13
<212> TYPE: PRT
<213> ORGANISM: Artificial sequence
<220> FEATURE:
<223> OTHER INFORMATION: Synthetic construct

<400> SEQUENCE: 2

Gly Ala Leu Thr Pro Arg Gly Ala Asp Ser Gly Ser Gly
1               5                   10


<210> SEQ ID NO 3
<211> LENGTH: 14
```

-continued

<212> TYPE: PRT
<213> ORGANISM: Artificial sequence
<220> FEATURE:
<223> OTHER INFORMATION: Synthetic construct

<400> SEQUENCE: 3

Lys Leu Ala Lys Leu Ala Lys Lys Leu Ala Lys Leu Ala Lys
1 5 10

<210> SEQ ID NO 4
<211> LENGTH: 13
<212> TYPE: PRT
<213> ORGANISM: Artificial sequence
<220> FEATURE:
<223> OTHER INFORMATION: Synthetic construct

<400> SEQUENCE: 4

Gly Ser Gly Lys Glu Phe Gly Ala Asp Ser Gly Ser Gly
1 5 10

<210> SEQ ID NO 5
<211> LENGTH: 8
<212> TYPE: PRT
<213> ORGANISM: Artificial sequence
<220> FEATURE:
<223> OTHER INFORMATION: Synthetic construct

<400> SEQUENCE: 5

Gly Pro Leu Gly Leu Ala Gly Gly
1 5

<210> SEQ ID NO 6
<211> LENGTH: 12
<212> TYPE: PRT
<213> ORGANISM: Artificial sequence
<220> FEATURE:
<223> OTHER INFORMATION: Synthetic construct

<400> SEQUENCE: 6

His Val Leu Val Met Ser Ala Thr Lys Lys Lys Lys
1 5 10

<210> SEQ ID NO 7
<211> LENGTH: 12
<212> TYPE: PRT
<213> ORGANISM: Artificial sequence
<220> FEATURE:
<223> OTHER INFORMATION: Synthetic construct

<400> SEQUENCE: 7

Gly Gly Gly Cys Tyr Phe Gln Asn Cys Pro Lys Gly
1 5 10

<210> SEQ ID NO 8
<211> LENGTH: 8
<212> TYPE: PRT
<213> ORGANISM: Artificial sequence
<220> FEATURE:
<223> OTHER INFORMATION: Synthetic construct

<400> SEQUENCE: 8

Asp Arg Val Tyr Ile His Pro Phe
1 5

<210> SEQ ID NO 9
<211> LENGTH: 9
<212> TYPE: PRT

-continued

<213> ORGANISM: Artificial sequence
<220> FEATURE:
<223> OTHER INFORMATION: Synthetic construct

<400> SEQUENCE: 9

Ala Gln Tyr Gln Asp Lys Leu Ala Arg
1 5

<210> SEQ ID NO 10
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: D-alloisoleucine

<400> SEQUENCE: 10

Gly Val Xaa Ser Gln Ile Arg Pro
1 5

<210> SEQ ID NO 11
<211> LENGTH: 9
<212> TYPE: PRT
<213> ORGANISM: Artificial sequence
<220> FEATURE:
<223> OTHER INFORMATION: Synthetic construct

<400> SEQUENCE: 11

Lys Val Pro Arg Asn Gln Asp Trp Leu
1 5

<210> SEQ ID NO 12
<211> LENGTH: 12
<212> TYPE: PRT
<213> ORGANISM: Artificial sequence
<220> FEATURE:
<223> OTHER INFORMATION: Synthetic construct

<400> SEQUENCE: 12

Gly Pro Leu Gly Leu Ala Gly Gly Trp Gly Glu Arg
1 5 10

BIOACTIVE PEPTIDE BRUSH POLYMERS VIA PHOTOINDUCED REVERSIBLE-DEACTIVATION RADICAL POLYMERIZATION

CROSS-REFERENCE TO RELATED APPLICATIONS

This application is a U.S. National Stage Application under 35 U.S.C. § 371 of International Application No. PCT/US2020/053308, filed Sep. 29, 2020, which claims the benefit of priority to U.S. Provisional Patent Applications No. 62/907,993, filed Sep. 30, 2019, and No. 63/050,277, filed Jul. 10, 2020, each of which is hereby incorporated by reference in its entirety.

STATEMENT REGARDING FEDERALLY SPONSORED RESEARCH OR DEVELOPMENT

This invention was made with government support under award number R01HL139001 awarded by the National Institutes of Health and the National Heart Lung and Blood Institute, under award number DMR-1710105 awarded by the National Science Foundation, and under Grant No. FA9550-16-1-0150 awarded by the Air Force Office of Scientific Research (AFOSR). The government has certain rights in the invention.

REFERENCE TO A SEQUENCE LISTING

A sequence listing containing SEQ ID NOs.: 1-12, created Sep. 29, 2020, 3 kB, is provided herewith in a computer-readable nucleotide/amino acid .txt file and is specifically incorporated by reference.

BACKGROUND OF INVENTION

Brush polymers that include peptides as side chain have the potential to provide enhanced biological activities and cell penetration, leading to new or improved therapies. Such polymers could be made by a variety of techniques, including peptide brush polymers prepared via ring-opening metathesis polymerization (ROMP) and atom transfer radical polymerization. However, such methods involve the use heavy metals such as ruthenium and copper-based catalysts. The possibility of residual heavy metals remaining after synthesis raises concerns for biomedical applications.

Accordingly, there exists a need in the for metal-residue-free brush polymers with bioactive peptides. Additional desirable properties and synthesis parameters would include: the ability to use mild reaction conditions, retain spatiotemporal control over the reaction with minimal if any additional reactive molecules, room temperature reaction, aqueous reactions, the polymerization's high tolerance of oxygen and water, high degree of functionalization or peptide graft density, high bioactivity and cellular uptake efficiency, and a controllable degree of toxicity according to therapeutic needs.

SUMMARY OF THE INVENTION

Provided herein are peptide-containing brush polymers (peptide brush polymers), and methods for synthesizing these, that provide the above mentioned advantages. These synthesis methods describes herein use photo-induced polymerization and can be performed in aqueous solutions, in organic conditions, at room temperature, and with exposure to oxygen. The methods disclosed herein provide for well-controlled peptide graft density and brush architecture, leading to a well-controlled bioactivity, such as to tune cellular uptake and cytotoxicity according to the needs of a biomedical application. For example, certain peptides described herein feature enzyme-responsive and pro-apoptotic amino acid sequences. While copolymerization with comonomers provide advantages in some embodiments, these methods also provide for synthesis of peptide brush polymers with 100% peptide graft density, for example to maximize bioactivity and synthesis efficiency (no need for comonomers and complex array of copolymer architectures, in some embodiments).

Aspects of the invention include a method for synthesizing a peptide brush polymer, the method comprising: exposing a mixture comprising peptide-containing monomers, one or more photoinitiators, and one or more chain transfer agents to a light, and photopolymerizing the peptide-containing monomers in the mixture; wherein: the resulting peptide brush polymer comprises at least one peptide-containing polymer block; the at least one peptide-containing polymer block is characterized by a degree of polymerization of at least 10 and a peptide graft density of 50% to 100%; and at least one peptide moiety of the at least one peptide-containing polymer block has 5 or more amino acid groups. The light, to which the mixture is exposed, should be sufficient or capable of inducing or initiating the photopolymerization of the peptide-containing monomers (and preferably other monomers in the mixture) in the presence of said mixture. Preferably for some applications, in any of the methods and polymers disclosed herein, at least one peptide moiety of the at least one peptide-containing polymer block has at least 6 amino acid groups, preferably for some applications at least 7 amino acid groups, preferably for some applications at least 8 amino acid groups, preferably for some applications at least 9 amino acid groups, preferably for some applications at least 10 amino acid groups, preferably for some applications at least 11 amino acid groups, preferably for some applications at least 12 amino acid groups, preferably for some applications at least 13 amino acid groups, preferably for some applications at least 14 amino acid groups, preferably for some applications at least 15 amino acid groups. Optionally, in any of the methods and polymers disclosed herein, each peptide moiety (or, "Pep" in formulas below) of the peptide brush polymer independently has at least 5 amino acids, preferably for some applications at least 6 amino acid groups, preferably for some applications at least 7 amino acid groups, preferably for some applications at least 8 amino acid groups, preferably for some applications at least 9 amino acid groups, preferably for some applications at least 10 amino acid groups, preferably for some applications at least 11 amino acid groups, preferably for some applications at least 12 amino acid groups, preferably for some applications at least 13 amino acid groups, preferably for some applications at least 14 amino acid groups, preferably for some applications at least 15 amino acid groups.

Preferably, in any of the methods and polymers disclosed herein, the peptide-containing monomers are photopolymerized according a monomer conversion of greater than or equal to 90%, preferably greater than or equal to 95%, more preferably greater than or equal to 98%, more preferably greater than or equal to 99%. Preferably, in any of the methods and polymers disclosed herein, the mixture has a temperature selected from the range of 5° C. to 45° C. during the photopolymerizing step, optionally 5° C. to 40° C., optionally 5° C. to 35° C., optionally 10° C. to 45° C., optionally 10° C. to 40° C., optionally 10° C. to 35° C., optionally 10° C. to 30° C., optionally 15° C. to 30° C., optionally 15° C. to 25° C., more preferably 20° C. to 25° C. Optionally, in any of the methods and polymers disclosed herein, the mixture is exposed to an inert or non-oxygen gas(es) during the photopolymerizing step. Optionally, in any of the methods and polymers disclosed herein, the mixture is exposed to nitrogen gas and/or argon gas during the photopolymerizing step. Optionally, in any of the methods and polymers disclosed herein, the mixture is aqueous. Optionally, in any of the methods and polymers disclosed herein, the light is characterized by wavelength(s) selected from the range of about 320 nm to about 700 nm, during the photopolymerizing step, selected from the range of about 320 nm to about 500 nm, optionally selected from the range of about 345 nm to about 405 nm, optionally selected from the range of about 410 nm to about 500 nm. The light can be coherent, noncoherent, semicoherent, or any combination of these.

Optionally, in any of the methods and polymers disclosed herein, the one or more photoinitiators comprise eosin Y disodium, pentamethyldiethylenetriamine, sodium phenyl-2,4,6-trimethylbenzoylphosphinate, lithium phenyl-2,4,6-trimethylbenzoylphosphinate, Zn(II) meso-Tetra(4-sulfonatophenyl)porphine, or a combination of these. Optionally, in any of the methods and polymers disclosed herein, the one or more photoinitiators comprise eosin Y disodium, pentamethyldiethylenetriamine, sodium phenyl-2,4,6-trimethylbenzoylphosphinate, lithium phenyl-2,4,6-trimethylbenzoylphosphinate, Zn(II) meso-Tetra(4-sulfonatophenyl)porphine, any substituted form of these, any derivative of these, or a combination of these. Optionally, in any of the methods and polymers disclosed herein, each of the one or more chain transfer agents comprises one or more trithiocarbonate groups, one or more carboxylic acids, or any combination of these. Optionally, in any of the methods and polymers disclosed herein, the one or more chain transfer agents comprises a chain transfer agent characterized by formula FX13:

(FX13)

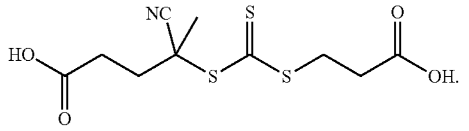

Optionally, in any of the methods and polymers disclosed herein, the one or more chain transfer agents are water-soluble. Optionally, in any of the methods and polymers disclosed herein, the mixture further comprises at least one comonomer, each comonomer being free of a peptide sequence; and wherein the photopolymerizing step comprises copolymerizing the peptide-containing monomers and the at least one comonomer.

Preferably, in any of the methods and polymers disclosed herein, the at least one peptide-containing polymer block is characterized by a peptide graft density of 70% to 100%, more preferably 80% to 100%, more preferably 90% to 100%, further more preferably 92% to 100%, further more preferably 94% to 100%, further more preferably 95% to 100%, further more preferably 96% to 100%, further more preferably 98% to 100%, further more preferably 99% to 100%. The method of any one of the preceding claims, wherein the at least one peptide-containing polymer block is characterized by a peptide graft density of 100%. Preferably, in any of the methods and polymers disclosed herein, the at least one peptide-containing polymer block is bound to a second polymer block, wherein the second polymer block has a peptide graft density of 0% to 100%. Optionally, in any of the methods and polymers disclosed herein, the at least one peptide-containing polymer block is bound to a second polymer block, wherein the second polymer block has a peptide graft density of 0% to 50%, optionally 50% to 100%, optionally 75% to 100%, optionally 0% to 25%, optionally 0% to 10%, optionally 0% to 5%, optionally 0%.

Optionally, in any of the methods and polymers disclosed herein, the method comprises copolymerizing a second polymer block with the at least one peptide-containing polymer. Optionally, in any of the methods and polymers disclosed herein, the second polymer block is hydrophobic. Optionally, in any of the methods and polymers disclosed herein, the step of copolymerizing the second polymer block is performed after the step of photopolymerizing the at least one peptide-containing block. Optionally, in any of the methods and polymers disclosed herein, the step of copolymerizing the second polymer block comprises a photopolymerization. Preferably, in any of the methods and polymers disclosed herein, the method further comprises isolating the peptide brush polymer. Optionally, in any of the methods and polymers disclosed herein, the method comprises removing substantially all unreacted monomers, photoinitiators, and chain transfer agents, after the step of photopolymerizing. Optionally, in any of the methods and polymers disclosed herein, the resulting peptide brush polymer forms a micelle or nanoparticle.

Optionally, in any of the methods and polymers disclosed herein, the method comprises comprising self-assembly of the peptide brush polymer into a micelle or nanoparticle. Optionally, in any of the methods and polymers disclosed herein, the method comprises dispersing the peptide brush polymer in water or an aqueous solution. Optionally, in any of the methods and polymers disclosed herein, each monomer, each chain transfer agent, each photoinitiator, and the resulting peptide brush polymer are metal-free.

Optionally, in any of the methods and polymers disclosed herein, the method comprises metal-free photoinduced reversible-deactivation radical polymerization and/or photoelectron transfer reversible addition-fragmentation transfer polymerization. Optionally, in any of the methods and polymers disclosed herein, the method comprises exposing the peptide brush polymer to an enzyme and causing enzymatic digestion of at least a portion of the peptide brush polymer. Optionally, in any of the methods and polymers disclosed herein, the method comprises administering to a subject an effective amount of the peptide brush polymer to treat or manage a condition.

Optionally, in any of the methods and polymers disclosed herein, each peptide-containing monomer in the mixture has a peptide sequence that is the same. Optionally, in any of the methods and polymers disclosed herein, the peptide brush polymer comprises at least two different peptide sequences. Optionally, in any of the methods and polymers disclosed herein, the peptide brush polymer comprises at least three different peptide sequences. Optionally, in any of the methods and polymers disclosed herein, the peptide brush polymer comprises at least four different peptide sequences, optionally at least 5 different peptide sequences, optionally at least 6 different peptide sequences.

Optionally, in any of the methods and polymers disclosed herein, each peptide-containing monomer is independently characterized by formula FX1: Z-(A-Pep)$_x$ (FX1); wherein: Z is a polymer backbone precursor group; A is a covalent anchor group; Pep is a peptide moiety; and x is an integer selected from the range of 1 to 2. Optionally, in any of the methods and polymers disclosed herein, Z comprises an olefin group, a vinyl group, an acrylate group, an acrylamide group, a styrene group, or any combination of these. Optionally, in any of the methods and polymers disclosed herein, Z comprises an olefin group, a vinyl group, an acrylate group, an acrylamide group, a styrene group, an aryl group, a cycloalkenyl group, a cycloalkenylene group, an alkene group, or any combination of these. Optionally, in any of the methods and polymers disclosed herein, Z comprises an olefin group, a vinyl group, an acrylate group, an acrylamide group, or any combination of these. Optionally, in any of the methods and polymers disclosed herein, Z does not comprise a ROMP-polymerizable group. Optionally, in any of the methods and polymers disclosed herein, Z does not comprise a norbornene group.

Optionally, in any of the methods and polymers disclosed herein, Z is characterized by formula FX2A, FX2B, FX2C, FX2D, FX2E, or FX2F:

(FX2A)

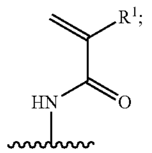

(FX2B)

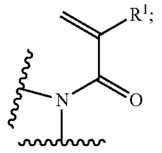

(FX2C)

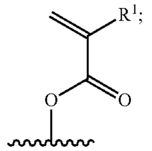

(FX2D)

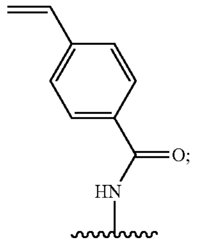

(FX2E)

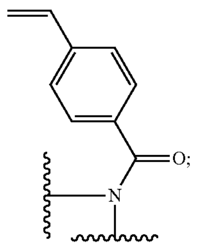

or

-continued (FX2F)

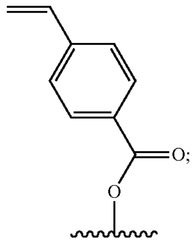

wherein: $R^1$ is a hydrogen or a methyl group. Optionally, in any of the methods and polymers disclosed herein, each A independently selected from the group consisting of single bond, an oxygen, and one or more substituted or substituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof. Optionally, in any of the methods and polymers disclosed herein, each A is independently characterized by formula FX3A, FX3B, or FX3C;

(FX3A)

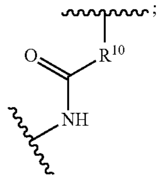

(FX3B)

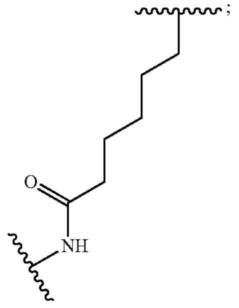

(FX3C)

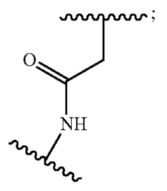

wherein: $R^{10}$ is a substituted or unsubstituted C1-C10 alkyl. Optionally, in any of the methods and polymers disclosed herein, each Pep comprises at least 5 amino acids, preferably for some applications at least 6 amino acids, preferably for some applications at least 7 amino acids, preferably for some applications at least 8 amino acids, preferably for some applications at least 9 amino acids, preferably for some applications at least 10 amino acids, more preferably for some applications at least 11 amino acids, more preferably for some applications at least 12 amino acids, more preferably for some applications at least 15 amino acids.

Optionally, in any of the methods and polymers disclosed herein, each P comprises a sequence having at least 80% sequence homology with SEQ ID NO:1 (GPLGLAGGWGERDGS), SEQ ID NO:2 (GALTPRGADSGSG), SEQ ID NO:3 (KLAKLAKKLAKLAK), SEQ ID NO:4 (GSGKEFGADSGSG), SEQ ID NO:5 (GPLGLAGG), SEQ ID NO:6 (HVLVMSATKKKK), SEQ ID NO:7 (GGGCYFQNCPKG)(Terlipressin), SEQ ID NO:8 (DRVYIHPF)(Angiotensin 2), SEQ ID NO:9 (AQYQDKLAR)(DA1), SEQ ID NO:10 (GVi(allo)SQIRP) (ABT898), SEQ ID NO:11 (KVPRNQDWL)(gp100), SEQ ID NO:12 (GPLGLAGGWGER), or a combination of these.

Optionally, in any of the methods and polymers disclosed herein, each comonomer, if present, in the mixture is independently characterized by formula FX4:

$$Z'-(M)_y \quad \text{(FX4);}$$

wherein: Z' is a polymer backbone precursor group; M is an alkyl group, an alkenylene group, an arylene group, an alkoxy group, an acyl group, a carboxyl group, an aliphatic group, an amide group, an aryl group, an amine group, an ether group, a ketone group, an ester group, or combinations thereof; and y is an integer selected from the range of 1 to 2. Optionally, in any of the methods and polymers disclosed herein, each comonomer, if present, in the mixture is independently characterized by formula FX5A, FX5B, FX5C:

(FX5A)

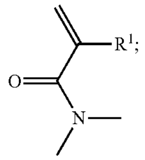

(FX5B)

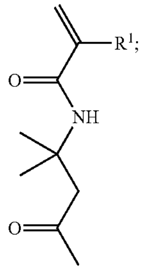

(FX5C)

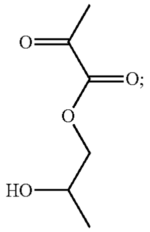

wherein: $R^1$ is a hydrogen or a methyl group.

Optionally, in any of the methods and polymers disclosed herein, the peptide brush polymer is characterized by formula FX6A or FX6B:

$$Q^1\text{-}[B^1]_m\text{-}Q^2 \quad \text{(FX6A);}$$

$$\text{or } Q^1\text{-}[B^1]_m\text{—/—}[B^2]_n\text{-}Q^2 \quad \text{(FX6B);}$$

wherein: each $B^1$ is independently a peptide-containing polymer block; each $B^2$ is independently a peptide-free polymer block; each of m and n is independently an integer greater than or equal to 1; the symbol "/" indicates that the units separated thereby are covalently linked randomly or in any order; and each of $Q^1$ and $Q^2$ is independently a polymer terminating group.

Optionally, in any of the methods and polymers disclosed herein, each $B^1$ is characterized by the formula (FX7):

(FX7)

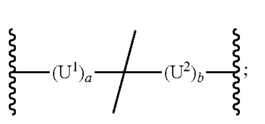

wherein: each $U^1$ is independently a peptide-containing repeating unit; each $U^2$ is independently a peptide-free repeating unit; a is an integer selected from the range of 2 to 500, preferably 2 to 100; b is 0 or an integer selected from the range of 2 to 500, preferably 2 to 100; and the symbol "/" indicates that the units separated thereby are covalently linked randomly or in any order. Optionally, in any of the methods and polymers disclosed herein, each $U^1$ is independently characterized by the formula FX8A or FX8B and each $U^2$, if present, is independently characterized by the formula FX9A or FX9B:

(FX8A)

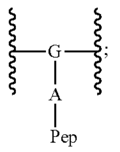

(FX8B)

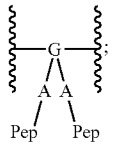

(FX9A)

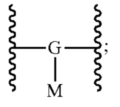

(FX9B)

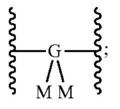

wherein: each G is independently a polymer backbone group; each A is independently a covalent anchor group; each Pep is independently a peptide moiety; and each M is independently an alkyl group, an alkenylene group, an arylene group, an alkoxy group, an acyl group, a carboxyl group, an aliphatic group, an amide group, an aryl group, an amine group, an ether group, a ketone group, an ester group, or combinations thereof. Optionally, in any of the methods and polymers disclosed herein, each G is independently characterized by formula FX10A, FX10B, FX10C, FX10D, FX10E, or FX10F:

(FX10A)

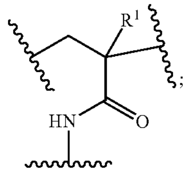

(FX10B)

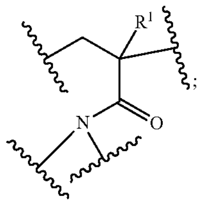

(FX10C)

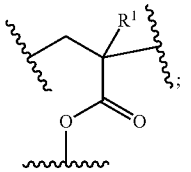

(FX10D)

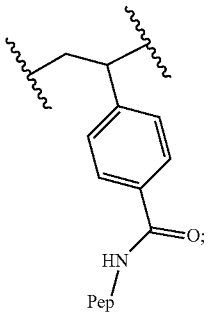

(FX10E)

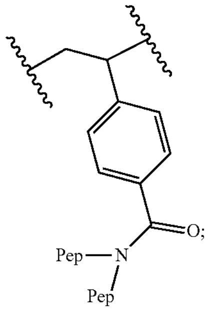

(FX10F)

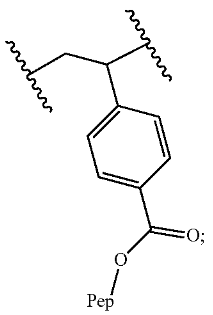

wherein: $R^1$ is a hydrogen or a methyl group. Optionally, in any of the methods and polymers disclosed herein, the peptide brush polymer is characterized by formula FX6A and m is 1. Optionally, in any of the methods and polymers disclosed herein, the peptide brush polymer is characterized by formula FX11A or FX11B:

(FX11A)

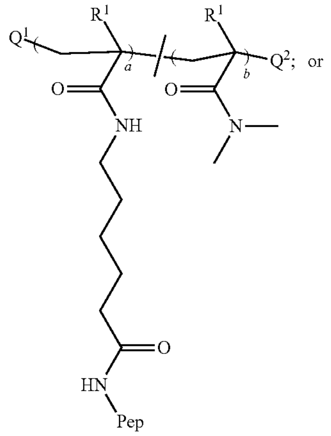

(FX11B)

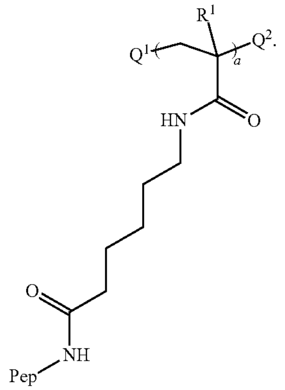

Optionally, in any of the methods and polymers disclosed herein, the peptide brush polymer is characterized by formula FX6A, m is 1, and b is 0. Optionally, in any of the methods and polymers disclosed herein, the peptide brush polymer is characterized by formula FX6A, m is 1, b is 0, and a is an integer selected from the range of 10 to 100. Optionally, in any of the methods and polymers disclosed herein, each of $Q^1$ and $Q^2$ is independently a hydrogen or characterized by formula FX14A or FX14B:

(FX14A)

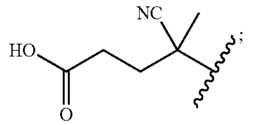

(FX14B)

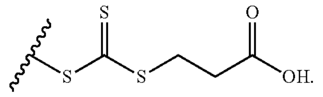

Optionally, in any of the methods and polymers disclosed herein, $Q^1$ is characterized by formula FX14A. Optionally, in any of the methods and polymers disclosed herein, $Q^2$ is hydrogen or characterized by formula FX14B. Optionally, in any of the methods and polymers disclosed herein, the peptide brush polymer is characterized by formula FX12:

(FX12)

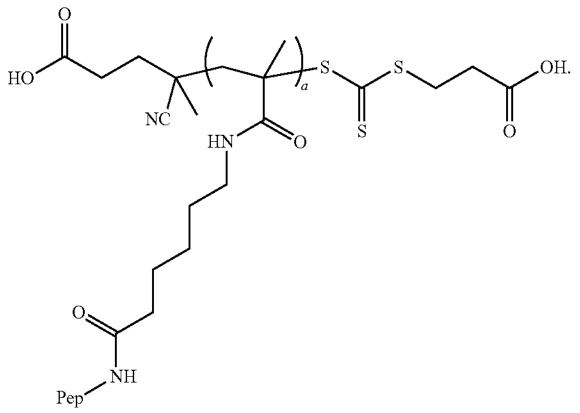

Optionally, in any of the methods and polymers disclosed herein, each peptide moiety (or, "Pep" in formulas) of the peptide brush polymer independently has at least 5 amino acids, preferably for some applications at least 6 amino acid groups, preferably for some applications at least 7 amino acid groups, preferably for some applications at least 8 amino acid groups, preferably for some applications at least 9 amino acid groups, preferably for some applications at least 10 amino acid groups, preferably for some applications at least 11 amino acid groups, preferably for some applications at least 12 amino acid groups, preferably for some applications at least 13 amino acid groups, preferably for some applications at least 14 amino acid groups, preferably for some applications at least 15 amino acid groups.

Optionally, in any of the methods and polymers disclosed herein, the at least one peptide-containing polymer block is hydrophilic. Optionally, in any of the methods and polymers disclosed herein, in the peptide brush polymer comprises a hydrophobic peptide-free polymer block.

Optionally, in any of the methods and polymers disclosed herein, the peptide brush polymer is water-soluble. Optionally, in any of the methods and polymers disclosed herein, the peptide brush polymer is amphiphilic. Optionally, in any of the methods and polymers disclosed herein, the peptide brush polymer is in the form of a micelle or nanoparticle. Optionally, in any of the methods and polymers disclosed herein, the peptide brush polymer is provided in an aqueous solution and wherein the peptide brush polymer is in the form of a micelle or nanoparticle in said aqueous solution. Optionally, in any of the methods and polymers disclosed herein, each peptide moiety or Pep is a branched polypeptide, a linear polypeptide or a cross-linked polypeptide. Optionally, in any of the methods and polymers disclosed herein, each peptide moiety or Pep is a therapeutic peptide. Preferably, in any of the methods and polymers disclosed herein, each of at least 30%, preferably at least 50%, preferably at least 70%, more preferably at least 80%, further more preferably at least 90%, further more preferably all of the peptide moieties is a therapeutic peptide. Preferably, in any of the methods and polymers disclosed herein, any of the peptide sequences of the peptide brush polymer have a higher bioactivity and higher cellular uptake efficiency compared to the same peptide sequence provided in absence of the peptide brush polymer. Preferably, in any of the methods and polymers disclosed herein, each of at least 50% of the peptide sequences of the peptide brush polymer have a higher bioactivity and higher cellular uptake efficiency compared to the same peptide sequences, respectively, provided in absence of the peptide brush polymer.

Preferably, in any of the methods and polymers disclosed herein, the peptide brush polymer is characterized by a solubility in water of at least 50 mg/mL, preferably at least 100 mg/mL, more preferably at least 150 mg/mL, further more preferably at least 200 mg/mL, optionally selected from the range of 50 mg/mL to 200 mg/mL, optionally selected from the range of 100 mg/mL to 200 mg/mL.

Aspects of the invention include a peptide brush polymer formed from any of the embodiments, or combinations thereof, described herein. Aspects of the invention include a peptide brush polymer comprising: at least 5 peptide-containing repeating units; wherein each peptide-containing repeating unit comprises a poly(meth)acrylamide or poly (meth)acrylate polymer backbone group directly or indirectly covalently linked to a polymer side chain group comprising a peptide moiety; wherein: the peptide brush polymer is characterized by a degree of polymerization of at least 10 and a peptide graft density of 50% to 100%; and each peptide moiety has at least 10 amino acid groups. Optionally, in any of the methods and polymers disclosed herein, the polymer is characterized by a degree of polymerization of at least 15. Optionally, in any of the methods and polymers disclosed herein, the polymer has a peptide graft density of 90% to 100%. Optionally, in any of the methods and polymers disclosed herein, the polymer has a peptide graft density of 100%. Optionally, in any of the methods and polymers disclosed herein, each peptide moiety has at least 6 amino acid groups, preferably at least 7 amino acid groups, preferably at least 8 amino acid groups, preferably at least 9 amino acid groups, preferably at least 10 amino acid groups, preferably at least 11 amino acid groups, preferably at least 12 amino acid groups, preferably at least 13 amino acid groups, preferably at least 14 amino acid groups, preferably at least 15 amino acid groups. Optionally, in any of the polymers disclosed herein, the at least one peptide-containing polymer block is hydrophilic. Optionally, in any of the polymers disclosed herein, the peptide brush polymer comprises a hydrophobic peptide-free polymer block. Optionally, in any of the polymers disclosed herein, the peptide brush polymer is water-soluble. Optionally, in any of the polymers disclosed herein, the peptide brush polymer is amphiphilic. Optionally, in any of the polymers disclosed herein, the peptide brush polymer is in the form of a micelle or nanoparticle. Optionally, in any of the polymers disclosed herein, the peptide brush polymer is provided in an aqueous solution and wherein the peptide brush polymer is in the form of a micelle or nanoparticle in said aqueous solution. Optionally, in any of the polymers disclosed herein, each peptide moiety or Pep is a branched polypeptide, a linear polypeptide or a cross-linked polypeptide. Optionally, in any of the polymers disclosed herein, each of at least 50% of the peptide moieties is a therapeutic peptide.

Optionally, in any of the methods and polymers disclosed herein, the peptide brush polymer is characterized by formula FX13A:

$$Q^1\text{-}[U^1]_a\text{—/—}[U^2]_b\text{-}Q^2 \quad \text{(FX13A);}$$

or each of $Q^1$ and $Q^2$ is independently a polymer terminating group; each $U^1$ is independently a peptide-containing repeating unit; each $U^2$ is independently a peptide-free repeating unit; a is an integer selected from the range of 2 to 500, preferably 2 to 100; b is 0 or an integer selected from the range of 2 to 500, preferably 2 to 100; and the symbol "/" indicates that the units separated thereby are linked randomly or in any order. Optionally, in any of the methods and polymers disclosed herein, each $U^1$ is independently characterized by the formula FX8A or FX8B and each $U^2$, if present, is independently characterized by the formula FX9A or FX9B:

(FX8A)

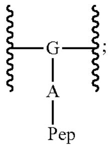

(FX8B)

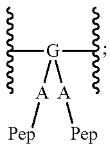

(FX9A)

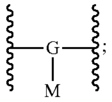

(FX9B)

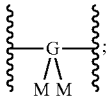

wherein: each G is independently a polymer backbone group; each A is independently a covalent anchor group; each Pep is independently a peptide moiety; and each M is independently an alkyl group, an alkenylene group, an arylene group, an alkoxy group, an acyl group, a carboxyl group, an aliphatic group, an amide group, an aryl group, an amine group, an ether group, a ketone group, an ester group, or combinations thereof. Optionally, in any of the methods and polymers disclosed herein, each G is independently characterized by formula FX10A, FX10B, FX10C, FX10D, FX10E, or FX10F:

(FX10A)

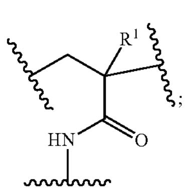

(FX10B)

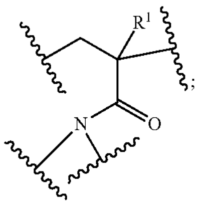

(FX10C)

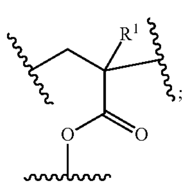

-continued (FX10D)

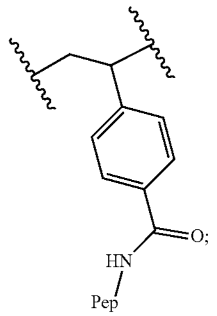

(FX10E)

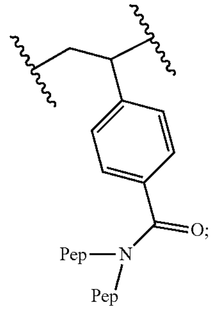

(FX10F)

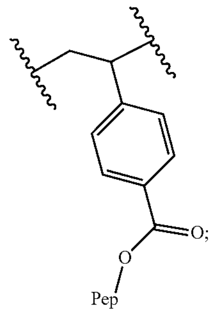

wherein: $R^1$ is a hydrogen or a methyl group. Optionally, in any of the methods and polymers disclosed herein, each A independently selected from the group consisting of single bond, an oxygen, and one or more substituted or substituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof. Optionally, in any of the methods and polymers disclosed herein, each A is independently characterized by formula FX3A, FX3B, or FX3C;

(FX3A)

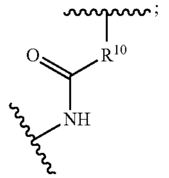

-continued (FX3B)

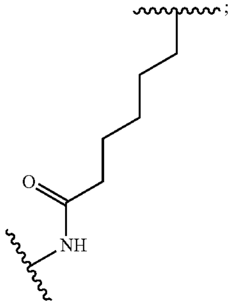

(FX3C)

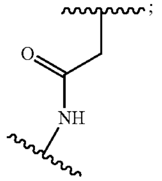

wherein: $R^{10}$ is a substituted or unsubstituted C1-C10 alkyl.

Optionally, in any of the methods and polymers disclosed herein, each peptide moiety comprises a sequence having at least 80% sequence homology with SEQ ID NO:1 (GPLGLAGGWGERDGS), SEQ ID NO:2 (GALTPR-GADSGSG), SEQ ID NO:3 (KLAKLAKKLAKLAK), SEQ ID NO:4 (GSGKEFGADSGSG), SEQ ID NO:5 (GPLGLAGG), SEQ ID NO:6 (HVLVMSATKKKK), SEQ ID NO:7 (GGGCYFQNCPKG)(Terlipressin), SEQ ID NO:8 (DRVYIHPF)(Angiotensin 2), SEQ ID NO:9 (AQYQDKLAR)(DA1), SEQ ID NO:10 (GVi(allo)SQIRP) (ABT898), SEQ ID NO:11 (KVPRNQDWL)(gp100), SEQ ID NO:12 (GPLGLAGGWGER), or a combination of these.

Optionally, in any of the methods and polymers disclosed herein, the peptide brush polymer is characterized by formula FX11A or FX11B:

(FX11A)

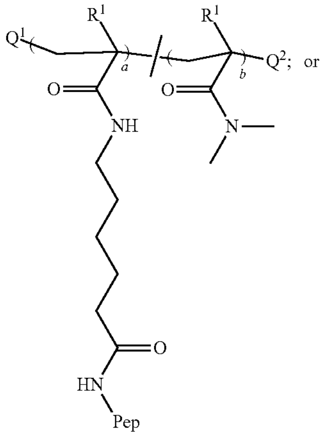

-continued (FX11B)

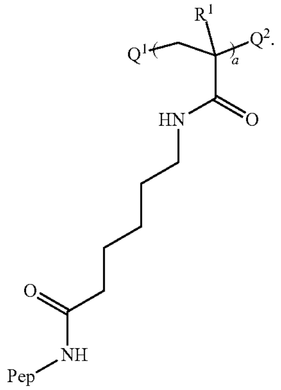

Optionally, in any of the methods and polymers disclosed herein, b is 0 and a is an integer selected from the range of 2 to 100, optionally 10 to 100, optionally 2 to 500, optionally 10 to 500. Preferably, a is an integer selected from the range of 10 to 100. Optionally, in any of the methods and polymers disclosed herein, the peptide brush polymer is characterized by formula FX13B: $Q^1$-$[U^1]_a$-$Q^2$ (FX13B); wherein each of $Q^1$ and $Q^2$ is independently a polymer terminating group; each $U^1$ is independently a peptide-containing repeating unit; and a is an integer selected from the range of 2 to 500, preferably selected from the range of 2 to 100.

Optionally, in any of the methods and polymers disclosed herein, the peptide brush polymer is the peptide brush polymer is characterized by formula FX12:

(FX12)

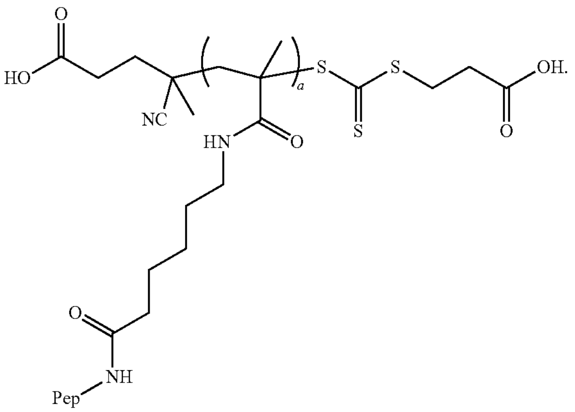

Optionally, in any of the methods and polymers disclosed herein, the peptide brush polymer is the peptide brush polymer is characterized by a degree of polymerization of at least 10 and a peptide graft density of 100%.

Aspects of the invention also include an aqueous solution comprises a peptide brush polymer according to any of the embodiments, or any combination of embodiments, provided herein. Optionally, the peptide brush polymer is in the form of a micelle or nanoparticle in the aqueous solution. Preferably, the aqueous solution is a therapeutic formulation. Preferably, the aqueous solution is a therapeutic formulation acceptable for administering to a human subject to treat or manage a condition in the human subject.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 43A. Synthesis of peptide brush polymer nanoparticles by photo-PISA. FIG. 43B. GPC analysis of peptide brush polymer macroCTA and resulting amphiphilic block copolymers (NP1-NP3). FIG. 43C. DLS traces of peptide brush polymer nanoparticles (NP1-NP3). FIGS. 43D-43H. TEM images of peptide brush polymer nanoparticles (NP1-NP5) with low and high magnifications. (KLAKLAKKLAKLAK is SEQ ID NO:3.)

STATEMENTS REGARDING CHEMICAL COMPOUNDS AND NOMENCLATURE

Figure 1:
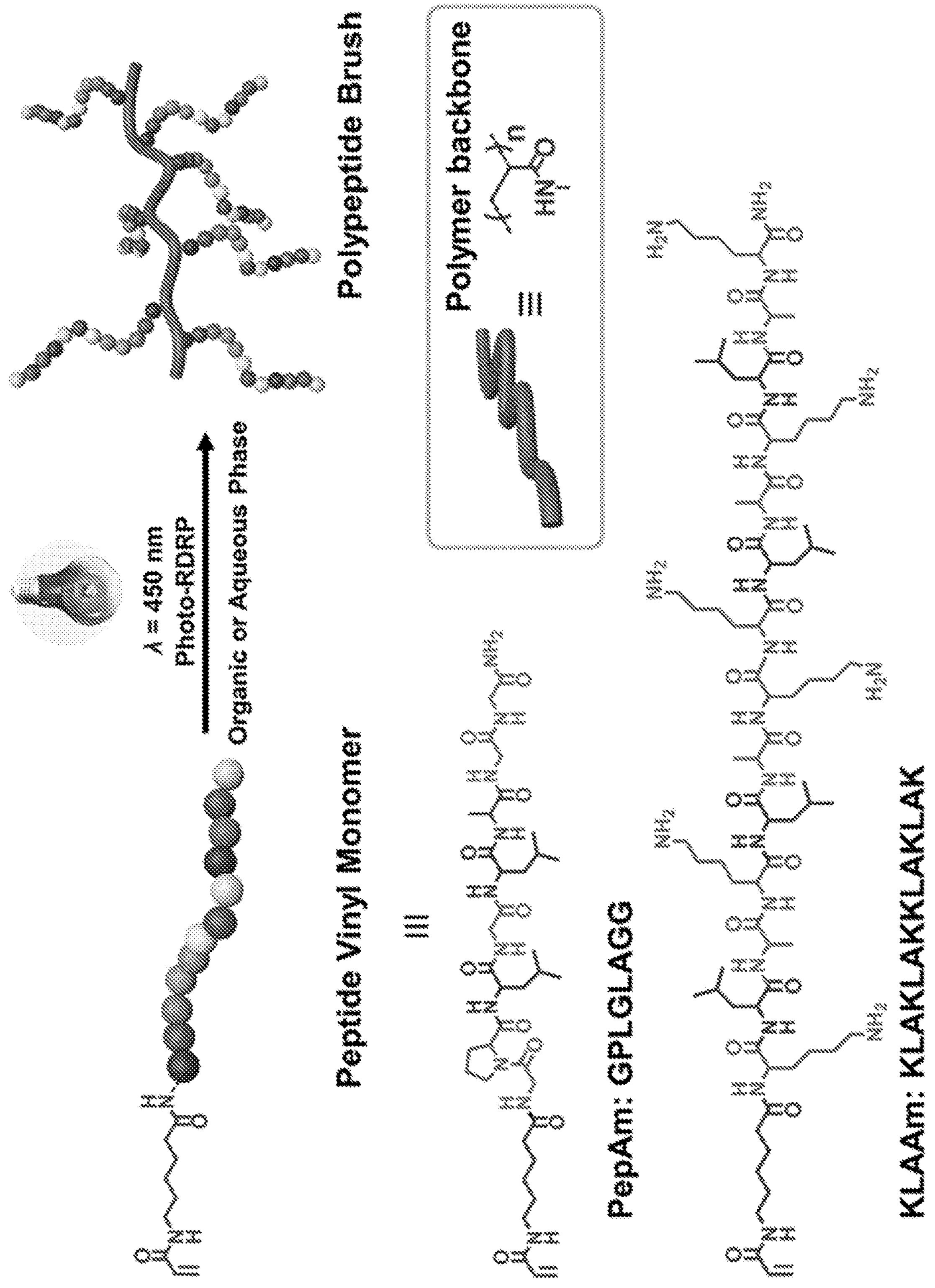
FIG. 1. Synthesis of peptide brush polymers via photo-RDRP. Two bioactive peptide vinyl monomers were designed. A thermolysin-responsive amino acid sequence GPLGLAGG (SEQ ID NO:5), and pro-apoptotic peptide KLAKLAKKLAKLAK (SEQ ID NO:3).

In general, the terms and phrases used herein have their art-recognized meaning, which can be found by reference to standard texts, journal references and contexts known to those skilled in the art. The following definitions are provided to clarify their specific use in the context of the invention.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 5 repeating units, in some embodiments greater or equal to 10 repeating units) and a high number average molecular weight (e.g. greater than or equal to 100 Da, in some embodiments greater than or equal to 10 kDa, in some embodiments greater than or equal to 50 kDa, in some embodiments greater than or equal to 100 kDa). In some embodiments, polymers are commonly the polymerization product of one or more monomer precursors (i.e., polymerizable monomers). Copolymers may comprise two or more different types or compositions of monomer units, and include random, block, brush, brush block, alternating, segmented, grafted, tapered and other architectures. Useful polymers include organic polymers that may be in amorphous, semi-amorphous, crystalline or semi-crystalline states. Cross linked polymers having linked monomer chains are useful for some applications, for example linked by one or more disulfide linkages. The invention includes polymers comprising (poly)peptide side chain. Optionally, the peptide side chains are therapeutic agents or comprise therapeutic agent(s). Preferably, in any of the methods and polymers disclosed herein, each of at least 30%, preferably at least 50%, preferably at least 70%, more preferably at least 80%, further more preferably at least 90%, further more preferably all of the peptide moieties is a therapeutic peptide.

The term polymer includes homopolymers. As used herein, the term "homopolymer" preferably refers to a brush polymer having a 100% peptide density wherein each monomer unit or repeating unit of said brush polymer comprises a side chain group with a peptide moiety, or in other words, each repeating unit of said homopolymer is a peptide-containing repeating unit. As used herein, each peptide sequence of a homopolymer is not necessarily identical, such that a homopolymer optionally includes more than one peptide sequence. Optionally, each peptide sequence of a homopolymer is identical. In some embodiments, the term "homopolymer" is used to describe a single polymer block of a block polymer, in which case each repeating unit of said single polymer block is a peptide-containing repeating unit.

An "oligomer" refers to a molecule composed of repeating structural units connected by covalent chemical bonds often characterized by a number of repeating units less than that of a polymer (e.g., equal to or less than 3 repeating units) and a lower molecular weights (e.g. less than or equal to 1,000 Da) than polymers. Oligomers may be the polymerization product of one or more polymerizable monomers (also referred to as monomer precursors).

A "polypeptide" or "oligopeptide" herein are used interchangeably and refer to a polymer of repeating structural units connected by a peptide bond. Typically, the repeating structural units of the polypeptide are amino acids including naturally occurring amino acids, non-naturally occurring amino acids, analogues of amino acids or any combination of these. The number of repeating structural units of a polypeptide, as understood in the art, are typically less than a "protein", and thus the polypeptide often has a lower molecular weight than a protein. Peptides and peptide moieties, as used and described herein, comprise two or more amino acid groups connected via peptide bonds.

Amino acids and amino acid groups refer to naturally-occurring amino acids, unnatural (non-naturally occurring) amino acids, and/or combinations of these. Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

"Block copolymers" are a type of copolymer comprising blocks or spatially segregated domains, wherein different domains comprise different polymerized monomers, for example, including at least two chemically distinguishable blocks. Block copolymers may further comprise one or more other structural domains, such as hydrophobic groups, hydrophilic groups, etc. In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends or the interior of a polymer (e.g. [A][B]), or may be provided in a selected sequence ([A][B][A][B]). "Diblock copolymer" refers to block copolymer having two different polymer blocks. "Triblock copolymer" refers to a block copolymer having three different polymer blocks, including compositions in which two non-adjacent blocks are the same or similar. "Pentablock" copolymer refers to a copolymer having five different polymer including compositions in which two or more non-adjacent blocks are the same or similar.

"Polymer backbone group" refers to groups that are covalently linked to make up a backbone of a polymer, such as a block copolymer. Polymer backbone groups may be linked to side chain groups, such as polymer side chain groups. Some polymer backbone groups useful in the present compositions are derived from polymerization of a monomer selected from the group consisting of a substituted or unsubstituted, olefin, vinyl, acrylate, acrylamide, cyclic olefin, norbornene, norbornene anhydride, cyclooctene, cyclopentadiene, styrene and acrylate. Some polymer backbone groups useful in the present compositions are obtained from metal-free photoinduced reversible-deactivation radical polymerization (photo-RDRP), photo-electron transfer reversible addition-fragmentation transfer polymerization (PET-RAFT), and/or photoinitiated polymerization-induced self-assembly (photo-PISA). Polymer backbones may terminate (e.g., by coupling, disproportionation, or chain transfer) in a range of backbone terminating groups including, but not limited to, hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, $—CO_2R^{30}$, $—CONR^{31}R^{32}$, $—COR^{33}$, —$SOR^{34}$, —$OSR^{35}$, —$SO_2R^{36}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane, acrylate, catechol, or any combinations thereof; wherein each of $R^{30}$-$R^{42}$ is independently hydrogen, $C_1$-$C_{10}$ alkyl or $C_5$-$C_{10}$ aryl. A polymer backbone may terminate in backbone terminating groups that is a portion or moiety from a chain transfer used during polymerization of the polymer.

As used herein, the term "chain transfer agent" refers to a compound that reacts with a growing polymer chain to interrupt growth and transfer the reactive species to a different compound (e.g., different polymer chain, monomer, or polymerizable monomer). The chain transfer agent can help regulate the average molecular weight of a polymer by terminating polymerization. Exemplary chain transfer agents include, but are not limited to, compounds with one or more trithiocarbonate or dithioester groups, compounds with one or more carboxylic acid groups, and compounds with a combination of these. Useful chain transfer agents for polymerization as used herein include, for example, 4-((((2-carboxyethyl)thio)carbonothioyl)thio)-4-cyanopentanoic acid (CAS Number 2055041-03-5), 4-Cyano-4-(((ethylthio) carbonothioyl)thio)pentanoic acid (CAS Number 1137725-46-2), 4-Cyano-4-(phenylcarbonothioylthio)pentanoic acid (CAS Number 201611-92-9), derivatives thereof, and substituted variations thereof. Useful chain transfer agents for polymerization as used herein include, for example, chain transfer agents with a dithioester group.

"Polymer side chain group" refers to a group covalently linked (directly or indirectly) to a polymer backbone group that comprises a polymer side chain, optionally imparting steric properties to the polymer. In an embodiment, for example, a polymer side chain group is characterized by a plurality of repeating units having the same, or similar, chemical composition. A polymer side chain group may be directly or indirectly linked to the polymer backbone groups. In some embodiments, polymer side chain groups provide steric bulk and/or interactions that result in an extended polymer backbone and/or a rigid polymer backbone. Some polymer side chain groups useful in the present compositions include unsubstituted or substituted polypeptide groups. Some polymers useful in the present compositions comprise repeating units obtained via anionic polymerization, cationic polymerization, free radical polymerization, group transfer polymerization, a photopolymerization, a ring-opening polymerization, metal-free photoinduced reversible-deactivation radical polymerization (photo-RDRP), photo-electron transfer reversible addition-fragmentation transfer polymerization (PET-RAFT), and/or photoinitiated polymerization-induced self-assembly (photo-PISA). A polymer side chain may terminate in a wide range of polymer side chain terminating groups including hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$SOR^{34}$, —$OSR^{35}$, —$SO_2R^{31}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane acrylate, or catechol; wherein each of $R^{30}$-$R^{42}$ is independently hydrogen or $C_1$-$C_5$ alkyl.

As used herein, the term "brush polymer" refers to a polymer comprising repeating units each independently comprising a polymer backbone group directly or indirectly covalently linked to at least one polymer side chain group. A brush polymer may be characterized by brush density, which refers to the percentage of the repeating units in a brush polymer that comprise a polymer side chain group. Brush polymers of certain aspects are characterized by a brush density greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Brush polymers of certain aspects are characterized by a brush density selected from the range 50% to 100%, optionally some embodiments a density selected from the range of 75% to 100%, or optionally for some embodiments a density selected from the range of 90% to 100%.

The terms "monomer" or "polymerizable monomer" can be used interchangeably and refer to a monomer precursor capable of undergoing polymerization as described herein to form a polymer according to embodiments described herein. The term "polymerizable monomer" is also interchangeably referred to herein as a "monomer precursor." Generally, the "monomer" or "polymerizable monomer" comprises an olefin capable of undergoing polymerization as described herein.

The terms "monomer unit," "repeating monomer unit," "repeating unit," and "polymerized monomer" can be used interchangeably and refer to a monomeric portion of a polymer described herein which is derived from or is a product of polymerization of one individual "monomer" or "polymerizable monomer." Each individual monomer unit of a polymer is derived from or is a product of polymerization of one polymerizable monomer. Each individual "monomer unit" or "repeating unit" of a polymer comprises one (polymerized) polymer backbone group. For example, in a polymer that comprises monomer units X and Y arranged as X-Y-X-Y-X-Y-X-Y (where each X is identical to each other X and each Y is identical to each other Y), each X and each Y is independently can be referred to as a repeating unit or monomer unit.

As used herein, the term "degree of polymerization" refers to the average number of monomer units per polymer chain. Since the degree of polymerization can vary from polymer to polymer, the degree of polymerization is generally represented by an average which can be determined by, for example, gel permeation chromatography with a multi-angle light scattering detector (GPC-MALS). The degree of polymerization can be calculated by the number-average molecular weight of polymer (e.g., determined by GPC-MALS) dividing by the molar mass of the monomer.

As used herein, the terms "peptide density" and "peptide graft density" interchangeably refer to the percentage of monomer units in the polymer chain which have a peptide covalently linked thereto. The percentage is based on the overall sum of monomer units in the polymer chain. For example, for certain polymers described herein, each $P^1$ is the polymer side chain comprising the peptide, each $P^2$ is a polymer side chain having a composition different from that of $P^1$, and each S is independently a repeating unit having a composition different from $P^1$ and $P^2$. Thus, the peptide density of $P^1$, or percentage of monomer units comprising the peptide of $P^1$ (i.e., $P^1$ for this particular example) would be represented by the formula:

$$\frac{P^1}{P^1 + P^2 + S} \times 100,$$

where each variable refers to the number of monomer units of that type in the polymer chain.

In an aspect, the polymer side chain groups can have any suitable spacing on the polymer backbone. Typically, the space between adjacent polymer side chain groups is from 3 angstroms to 30 angstroms, and optionally 5 to 20 angstroms and optionally 5 to 10 angstroms. By way of illustration, in certain embodiments having a brush density of 100%, the polymer side chain groups typically are spaced 6±5 angstroms apart on the polymer backbone. In some embodiments the brush polymer has a high a brush density (e.g. greater than 70%), wherein the polymer side chain groups are spaced 5 to 20 angstroms apart on the polymer backbone.

The term "sequence homology" or "sequence identity" means the proportion of amino acid matches between two amino acid sequences. When sequence homology is expressed as a percentage, e.g., 50%, the percentage denotes the fraction of matches over the length of sequence that is compared to some other sequence. Gaps (in either of the two sequences) are permitted to maximize matching; for example, wherein gap lengths of 5 amino acids or less, optionally 3 amino acids or less, are usually used.

The term "fragment" refers to a portion, but not all of, a composition or material, such as a polypeptide composition or material. In an embodiment, a fragment of a polypeptide refers to 50% or more of the sequence of amino acids, optionally 70% or more of the sequence of amino acids and optionally 90% or more of the sequence of amino acids.

"Polymer blend" refers to a mixture comprising at least one polymer, such as a brush polymer, e.g., brush block copolymer, and at least one additional component, and optionally more than one additional component. In some embodiments, for example, a polymer blend of the invention comprises a first brush copolymer and one or more addition brush polymers having a composition different than the first brush copolymer. In some embodiments, for example, a polymer blend of the invention further comprises one or more additional brush block copolymers, homopolymers, copolymers, block copolymers, brush block copolymers, oligomers, solvent, small molecules (e.g., molecular weight less than 500 Da, optionally less than 100 Da), or any combination of these. Polymer blends useful for some applications comprise a first brush polymer, and one or more additional components comprising polymers, block copolymers, brush polymers, linear block copolymers, random copolymers, homopolymers, or any combinations of these. Polymer blends of the invention include mixture of two, three, four, five and more polymer components.

A "peptide-containing monomer" is a monomer species that comprises a peptide moiety. Preferably, a peptide-containing monomer comprises a polymer backbone precursor group, one or more covalent anchor (or, linker) groups covalently attached to the backbone precursor group, and at least one peptide moiety (generally, one or two peptide moieties) each independently covalently attached to an anchor group. The term "polymer backbone precursor group" refers to a polymerizable group of a monomer that forms a polymer backbone group upon polymerization of said monomer.

A "peptide-containing polymer block" is a polymer block that comprises at least one peptide moiety. A peptide-containing polymer block comprises peptide-containing repeating units. A "peptide-containing repeating unit" is a repeating unit of the polymer block that comprises a peptide moiety. Preferably, a peptide-containing repeating unit comprises a polymer backbone group, one or more covalent anchor (or, linker) groups covalently attached to the polymer backbone group, and at least one peptide moiety (generally, one or two peptide moieties) each independently covalently attached to an anchor group. The polymer backbone group of each repeating unit, such as of a peptide-containing repeating unit or a peptide-free repeating unit, is directly or indirectly covalently attached to a polymer backbone group of at least one other repeating unit.

The term "peptide-free polymer block" refers to a polymer block that is free of peptide moieties. A peptide-free polymer block can comprise side chain group that are free of a peptide moiety. A peptide-free-polymer block has peptide-free repeating units. A "peptide-free repeating unit" is a repeating unit of the polymer block that does not have a peptide moiety.

A "peptide brush polymer" is a brush polymer comprising polymer side chain groups each comprising one or more peptide moieties.

A "peptide moiety" is a moiety or group that comprises or consists of a peptide.

The term "monomer conversion" refers to a fraction, typically expressed as a percentage, of monomers provided for polymerization and exposed to polymerization conditions that are polymerized to form a polymer by creating monomer units. Monomer conversion can be calculated by nuclear magnetic resonance spectroscopy which determines the remaining fraction of vinyl protons (5.5-6.5 ppm) after the polymerization, wherein:

Monomer conversion=[initial intensity of vinyl protons−remaining intensity of vinyl protons]/[initial intensity of vinyl protons]

As used herein, the term "photoinitiator" refers to a compound that creates a reactive species (e.g., free radicals, cations or anions) when exposed to light (such as visible and/or ultraviolet light). A photoinitiator is optionally a photocatalyst, and vice versa. Exemplary photoinitiators include but are not limited to eosin Y disodium, pentamethyldiethylenetriamine, sodium phenyl-2,4,6-trimethylbenzoylphosphinate, lithium phenyl-2,4,6-trimethylbenzoylphosphinate, Zn(II) meso-Tetra(4-sulfonatophenyl)porphine (optionally together with ascorbic acid), substituted variations of any of these, derivatives of any of these, and combinations of these. For example, Shanmugam, et al. (S. Shanmugam, 2016, "Aqueous RAFT Photopolymerization with Oxygen Tolerance," Macromolecules 2016, 49, 24, 9345-9357, doi: 10.1021/acs.macromol.6b02060), which is incorporated herein by reference, uses Zn(II) meso-Tetra(4-sulfonatophenyl)porphine with ascorbic acid for RAFT photopolymerization.

The term "photopolymerization" refers to a polymerization process that uses light (such as visible and/or ultraviolet light) to initiate and propagate a polymerization reaction to form a polymer. Preferably, but not necessarily, photopolymerization described herein can be initiated by visible light.

As used herein, visible light refers to any suitable electromagnetic radiation the wavelength(s) of which are about 380 nm to about 740 nm. A particularly preferable range of wavelengths of visible light suitable for photopolymerization is 380 nm to 500 nm. Another particularly preferable range of wavelengths of light suitable for photopolymerization is 500 nm to 700 nm.

As used herein, ultraviolet light refers to any suitable electromagnetic radiation the wavelength(s) of which are about 10 nm to about 380 nm. A particularly preferable range of wavelengths of ultraviolet light suitable for photopolymerization is 300 nm to 380 nm, preferably 320 nm to 380 nm.

When referring to a material, such as a polymer, being aqueous, the term "aqueous" refers to said material being dispersed, dissolved, or otherwise solvated by water. Preferably, an aqueous material, such as an aqueous peptide brush polymer, is water-soluble. An "aqueous solution" refers to a solution that comprises water as solvent and one or more solute species dispersed, dissolved, or otherwise solvated by the water. An aqueous process, such as a polymerization, is a process taking place in an aqueous solution. Optionally, but not necessarily, an aqueous solution or an aqueous solvent includes 20 vol. % or less, optionally 15 vol. % or less, optionally 10 vol. % or less, preferably 5 vol. % or less, of a non-aqueous or organic solvent.

Figure 86A:
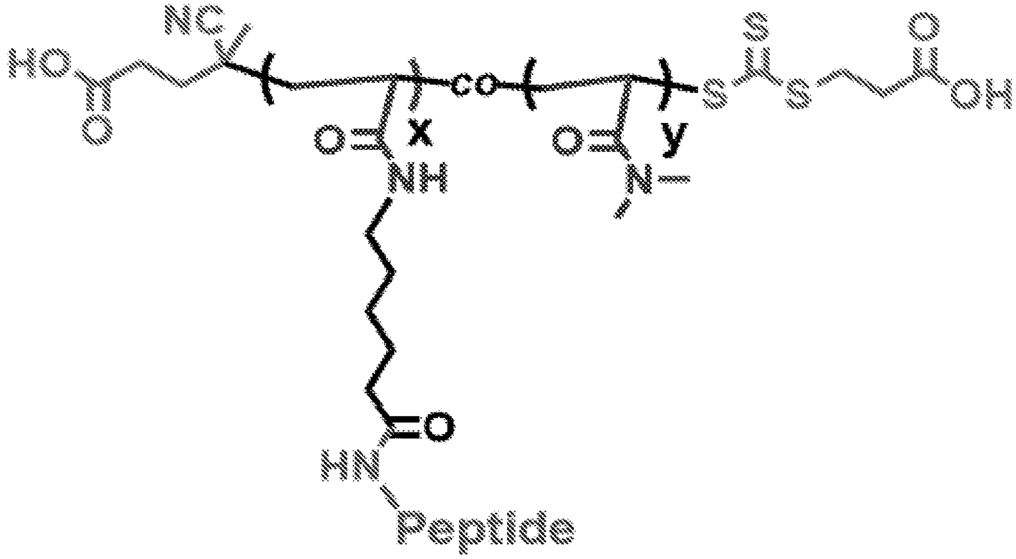
FIGS. 86A-86C. Formulas of exemplary peptide brush polymers according to embodiments disclosed herein. Block copolymers such as that of FIG. 86C, according to embodiments described herein, can form nanoparticles.
Figure 86B:
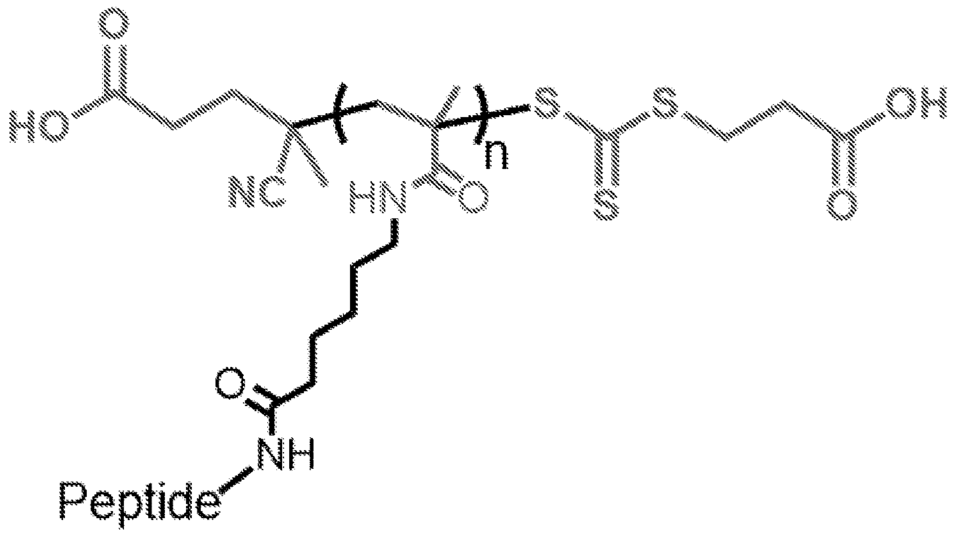
Figure 86C:
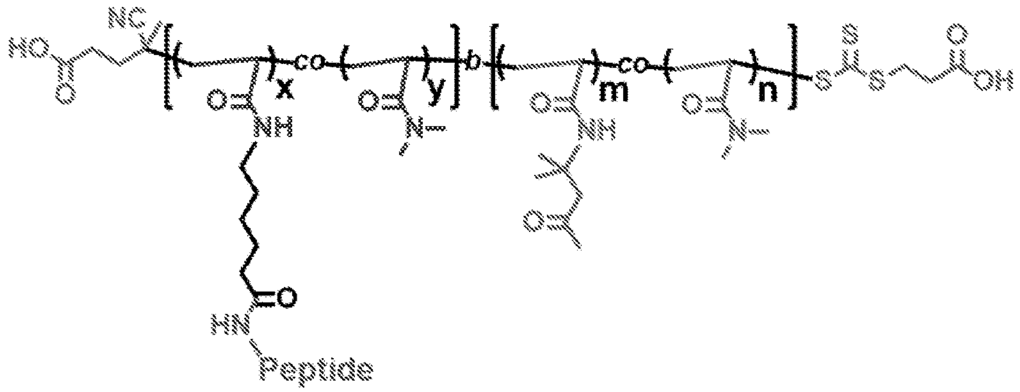

As used herein, the term "-co-" as used in a formula, such as in "poly[(KLAAm10-co-DMA30)-b-(DAAm280-co-DMA120)]" and in FIG. 86A, indicates that the monomer or repeating units on either side of "-co-" together form a copolymer or have been copolymerized. The repeating units separated by "-co-" can be covalently linked randomly or in any order. As used herein, the term "-b-" as used in a formula, such as in "poly[(KLAAm10-co-DMA30)-b-(DAAm280-co-DMA120)]" and in FIG. 86C, indicates that the repeating units or copolymers separated by "-b-" are covalently attached blocks that have been copolymerized to form a block copolymer. The units or blocks separated by "-b-" can be covalently linked randomly or in any order.

The term "metal-free" refers to a chemical species, such as a monomer, a polymer, a chain transfer agent, a photoinitiator, or another molecule or compound, whose chemical formula is free of a metal element. Preferably, a metal-free chemical species provided to a mixture, reaction, or method described herein, comprises less than 5%, preferably less than 1%, preferably less than 0.1%, more preferably less than 0.01%, more preferably less than 0.001%, further more preferably less than 0.0001% by mass of metal or metal-containing impurities. Preferably, a metal-free chemical species provided to a mixture, reaction, or method described herein, is free of a metal or metal-containing impurities. Preferably, all chemical species, including any catalysts, used in polymerization reactions according to methods disclosed herein are metal-free chemical species. The terms metal and metal element are exclusive of B, Si, and Se.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

Unless otherwise specified, the term "average molecular weight," refers to number average molecular weight. Number average molecular weight is the defined as the total weight of a sample volume divided by the number of molecules within the sample. As is customary and well known in the art, peak average molecular weight and weight average molecular weight may also be used to characterize the molecular weight of the distribution of polymers within a sample.

As is customary and well known in the art, hydrogen atoms in formulas presented throughout herein, such as, but not limited to formulas FX2A, FX2B, FX2C, FX2D, FX2E, FX2F, FX3A, FX3B, FX5A, FX5B, FX5C, FX10A, FX10B, FX10C, FX10D, FX10E, FX10F, FX11A, FX11B, and FX12, are not always explicitly shown, for example, hydrogen atoms bonded to the carbon atoms of aromatic, heteroaromatic, and alicyclic rings are not always explicitly shown in formulas presented herein. The structures provided herein, for example in the context of the description of formulas just listed and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^2$).

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups (e.g. $L^1$-$L^2$).

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^2$).

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^2$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^2$).

As used herein, the terms “cycloalkenylene” and “cycloalkenylene group” are used synonymously and refer to a divalent group derived from a cycloalkenyl group as defined herein. The invention includes compounds having one or more cycloalkenylene groups. Cycloalkenylene groups in some compounds function as linking and/or spacer groups. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups, for example, as one or more linking groups (e.g. $L^1$-$L^2$).

As used herein, the terms “alkynylene” and “alkynylene group” are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^2$).

As used herein, the term “halo” refers to a halogen group such as a fluoro (—F), chloro (—Cl), bromo (—Br), iodo (—I) or astato (—At).

The term “heterocyclic” refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term “carbocyclic” refers to ring structures containing only carbon atoms in the ring. Carbon atoms of carbocyclic rings can be bonded to a wide range of other atoms and functional groups, for example, provided as substituents.

The term “alicyclic ring” refers to a ring, or plurality of fused rings, that is not an aromatic ring. Alicyclic rings include both carbocyclic and heterocyclic rings.

The term “aromatic ring” refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term “fused ring” or “fused ring structure” refers to a plurality of alicyclic and/or aromatic rings provided in a fused ring configuration, such as fused rings that share at least two intra ring carbon atoms and/or heteroatoms.

As used herein, the term “alkoxyalkyl” refers to a substituent of the formula alkyl-O-alkyl.

As used herein, the term “polyhydroxyalkyl” refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term “polyalkoxyalkyl” refers to a substituent of the formula alkyl-(alkoxy)$_n$-alkoxy wherein n is an integer from 1 to 10, preferably 1 to 4, and more preferably for some embodiments 1 to 3.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As used herein, the term "substituted" can mean that one or more hydrogens on the designated atom or group (e.g., substituted alkyl group) are replaced with another group provided that the designated atom's normal valence is not exceeded. For example, when the substituent is oxo (i.e., =O), then two hydrogens on the atom are replaced. The substituent group can be any substituent group described herein. For example, substituent groups can include one or more of a hydroxyl, an amino (e.g., primary, secondary, or tertiary), an aldehyde, a carboxylic acid, an ester, an amide, a ketone, nitro, an urea, a guanidine, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

As to any of the groups described herein which contain one or more substituents, it is understood that such groups do not contain any substitution or substitution patterns which are sterically impractical and/or synthetically non-feasible. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or D- or L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms. Isomers include structural isomers and stereoisomers such as enantiomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or 14C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "~~~" denotes the point of attachment of a chemical moiety to the remainder of a molecule or chemical formula.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to a subject, such as a patient in need of treatment; slowing in the rate of degeneration or decline; making the final point of degeneration less debilitating; improving a subject's physical or mental well-being. The treatment or amelioration of symptoms can be based on objective or subjective parameters; including the results of a physical examination, neuropsychiatric exams, and/or a psychiatric evaluation.

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As defined herein, the term "inhibition", "inhibit", "inhibiting" and the like in reference to a protein-inhibitor (e.g. antagonist) interaction means negatively affecting (e.g.

decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein The term "modulator" refers to a composition that increases or decreases the level of a target molecule or the function of a target molecule.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym*. Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

The term "non-peptide therapeutic moiety" refers to a therapeutic moiety that is not a peptide or a polypeptide having at least 2 amino acids. A therapeutic moiety refers to a therapeutic agent covalently attached to compound or molecule, such as a polymer according to any of the embodiments disclosed herein. A therapeutic moiety is optionally a monovalent moiety. The therapeutic moiety is a therapeutic agent that is a therapeutically or pharmaceutically active therapeutic agent when attached to the polymer, when released from the polymer (such as via a chemical reaction), or both. A therapeutic agent is capable of treating or managing a condition, such as a disease, in a living subject, such as a human or animal. A non-peptide therapeutic moiety is optionally a small molecule having a molecular weight below 4500 Da, optionally below 2000 Da, optionally below 1000 Da. Unless otherwise stated, a peptide or polypeptide of the invention can be a therapeutic peptide, which is a therapeutic moiety that is or that comprises a peptide or polypeptide. Optionally the term "peptide" can refer to a polypeptide.

Optionally in any of the polymers, methods, and compositions disclosed herein, at least a fraction of all side chain moieties in the polymer that are side chain moieties comprising a peptide moiety are selected to provide for cellular uptake. The term "cellular uptake" refers to any process or mechanism that results in a molecule, peptide, therapeutic agent, compound, polymer, or portion thereof, or material being transported either actively of passively across the cellular membrane of a biological cell. Optionally, cellular uptake refers to cellular uptake of or penetration of a biological by at least a portion of the polymer, the majority of the polymer, or the entirety of the polymer. Cellular uptake can be measured or quantified, such as via absorbance or fluorescence signal unique to a portion of the polymer (such as the drug) using different cellular assays, UV-Vis absorption spectroscopy, fluorescence spectroscopy, radio labeling, mass-spectroscopy, and/or inductively coupled plasma mass spectrometry. Optionally in any of the polymers, methods, and liquid compositions disclosed herein, at least one of the plurality of peptide moieties is a non-cell-penetrating peptide. Optionally in any of the polymers, methods, and liquid compositions disclosed herein, each peptide moiety of at least a majority of the plurality of peptide moieties is a non-cell-penetrating peptide. Optionally in any of the polymers, methods, and liquid compositions disclosed herein, the polymer has a net positive charge. Preferably, the net positive charge of the polymer is present at least when the polymer is exposed to physiological conditions, including normal physiological conditions. Preferably, any positive charge of the polymer is present at least when the polymer is exposed to physiological conditions, including normal physiological conditions. Preferably in any of the polymers, methods, and liquid compositions disclosed herein, at least one of the plurality of peptide moieties has a positive charge. The presence of a positive charge can increase or otherwise enhance the therapeutic activity or function of the polymer, or portions thereof such as of the non-peptide therapeutic(s) and any therapeutic peptides, if present. In embodiments, the presence of a positive charge on the polymer can increase or otherwise enhance the therapeutic activity or function of the polymer, or portions thereof at least because of the enhanced or improved cellular uptake efficiency of the polymer due to the presence of the positive charge. Preferably, polymers disclosed herein can penetrate or be taken up by a biological cell even when any, a majority, or even when all of the peptide sequences on said polymer do not correspond to cell-penetrating peptides. This is because peptide sequences that are not cell-penetrating peptides but that have at least a single positive charge are able to enter cells (cellular uptake) once polymerized as a high density brush of peptides, wherein, in contrast, the monomeric peptide alone would be unable to enter the cell. See also Blum, et al. ("Activating peptides for cellular uptake via polymerization into high density brushes." A. P. Blum, J. K. Kammeyer and N. C. Gianneschi, Chem. Sci., 2016, 7, 989-994), which is incorporated herein by reference in its entirety to the extent not inconsistent herewith.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value. The term "substantially" refers to a property, condition, or value that is within 20%, 10%, within 5%, within 1%, optionally within 0.1%, or is equivalent to a reference property, condition, or value. The term "substantially equal", "substantially equivalent", or "substantially unchanged", when used in conjunction with a reference value describing a property or condition, refers to a value that is within 20%, within 10%, optionally within 5%, optionally within 1%, optionally within 0.1%, or optionally is equivalent to the provided reference value. The term "substantially greater", when used in conjunction with a reference value describing a property or condition, refers to a value that is at least 1%, optionally at least 5%, optionally at least 10%, or optionally at least 20% greater than the provided reference value. The term "substantially less", when used in conjunction with a reference value describing a property or condition, refers to a value that is at least 1%, optionally at least 5%, optionally at least 10%, or optionally at least 20% less than the provided reference value.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

The invention can be further understood by the following non-limiting examples.

Example 1A: Bioactive Peptide Brush Polymers Via Photoinduced Reversible-Deactivation Radical Polymerization Abstract: Harnessing metal-free photoinduced reversible-deactivation radical polymerization (photo-RDRP) in organic and aqueous phases, we report a synthetic approach to enzyme-responsive and pro-apoptotic peptide brush polymers. Thermolysin-responsive peptide based polymeric amphiphiles assembled into spherical micellar nanoparticles that undergo a morphology transition to worm-like micelles upon enzyme-triggered cleavage of coronal peptide side-chains. Moreover, pro-apoptotic polypeptide brushes show enhanced cell uptake over individual peptide chains of the same sequence, resulting in a significant increase in cytotoxicity to cancer cells. Importantly, increased grafting density of pro-apoptotic peptides on brush polymers correlates with increased uptake efficiency and concurrently, cytotoxicity. The mild synthetic conditions afforded by photo-RDRP, make it possible to access well-defined peptide-based polymer bioconjugate structures with tunable bioactivity.

Introduction: The convergence of photochemistry and controlled polymerization techniques has led to the development of new living polymerization methodologies, post-polymerization modification strategies, and to the production of advanced materials.[1] In comparison with common triggers for polymerization, light has the unique advantage of providing mild reaction conditions, without the need for adding additional reactive molecules, and providing spatiotemporal control over reactions.[2-6] The toolbox of photo-induced controlled polymerization techniques is expanding, giving rise to photo-induced reversible deactivation radical polymerization (photo-RDRP),[1-6] photo-induced ring-opening metathesis polymerization (photo-ROMP),[7] photo-controlled cationic polymerization,[8] and photo-triggered ring opening polymerization (photo-ROP) of cyclic esters or N-carboxyanhydride.[9] Among these photo-induced polymerization methods, photo-RDRP techniques have received the most interest due to their broad vinyl monomer scope and relatively mild reaction conditions conducted at room temperature, in metal-free systems, and with high tolerance to oxygen and water.[10-11] We reasoned that these mild conditions should provide a route for the incorporation of peptide-modified vinyl monomers into bioactive, highly functionalized polymers, and polymeric materials. The mild conditions would minimize side reactions and thus retain the integrity of the biomolecules during polymerization and provide clean materials following polymerization.[6, 12-13]

Photo-electron transfer reversible addition-fragmentation transfer polymerization (PET-RAFT) represents a powerful tool in the arsenal of photo-RDRP approaches.[5] This technique can be performed under visible blue or green light in the presence of a biocompatible organo-photocatalyst such as eosin Y.[2] More generally, RAFT polymerization has demonstrated tolerance towards many functional groups pendent on monomers.[14] Therefore, we postulated that PET-RAFT could serve as an ideal photo-RDRP approach to explore photo polymerization of peptide-modified vinyl monomers.

The multi-valent display of peptides as side chains in brush polymers can lead to materials with enhanced biological activities such as higher binding affinities to targets and increased cell-penetration.[15-17] Examples include peptide brush polymers prepared via ring-opening metathesis polymerization (ROMP) and atom transfer radical polymerization which involve the use of ruthenium and copper-based catalysts.[18-20] The possibility of residual heavy metals remaining after synthesis raises concerns in biomedical applications. Herein we demonstrate a metal-free photo-RDRP approach to peptide brush polymers (FIG. 1). Two bioacitive peptide vinyl monomers featuring enzyme-responsive and pro-apoptotic amino acid sequences were successfully copolymerized with dimethylacrylamide (DMA) via PET-RAFT protocol in both organic and aqueous solutions. Trithiocarbornate based RAFT agents were used because the resultant polymers with terminal trithiocarbonate moeity have been demonstrated nontoxic in vitro and can be easily removed upon the polymerization.[21] Incorporation of the DMA comonomer not only lessened the steric hindrance from the peptide macromonomer, but also facilitated the preparation of peptide brush polymers with different grafting densities. Furthermore, the robust nature of PET-RAFT allowed access to various architectures including brush and linear-brush diblock copolymers consisting of enzyme-responsive peptide side chains. Linear-brush diblock copolymers self-assembled into micelles, capable of further morphing into worm-like structure upon treatment with thermolysin. By variation of the grafting density of pro-apoptotic peptide, the cellular uptake efficiency and cytotoxicity of peptide brush polymers can be controlled, revealing the crucial role of architecture (i.e., grafting density) in governing the bioactivity of polypeptide brushes. These results highlight the potential of photo-RDRP for the preparation of peptide brush polymer materials with well-defined structures and highly tunable properties in biomedical applications.

Results and Discussion: Peptide monomers containing acrylamide moieties, serving as the polymerizable group for radical polymerization were synthesized by addition of acrylic acid to an amino-hexanoic spacer unit on the N-terminus of the peptide chain (FIG. 1).

Two amino acid sequences were chosen to prepare two proof-of-concept systems. The first sequence GPLGLAGG (SEQ ID NO:5), is a known substrate for various proteolytic enzymes including thermolysin.[19] The other is a sequence KLAKLAKKLAKLAK (SEQ ID NO:3), which, when internalized, triggers apoptosis of cells by mitochondrial membrane disruption.[22] The chemical structure and purity of the peptide monomers (PepAm and KLAAm in FIG. 1) were verified by high performance liquid chromatography (HPLC), $^1$H NMR spectroscopy, and electrospray ionization mass spectrometry (ESI-MS) (FIGS. 8-12).

Figure 2A:
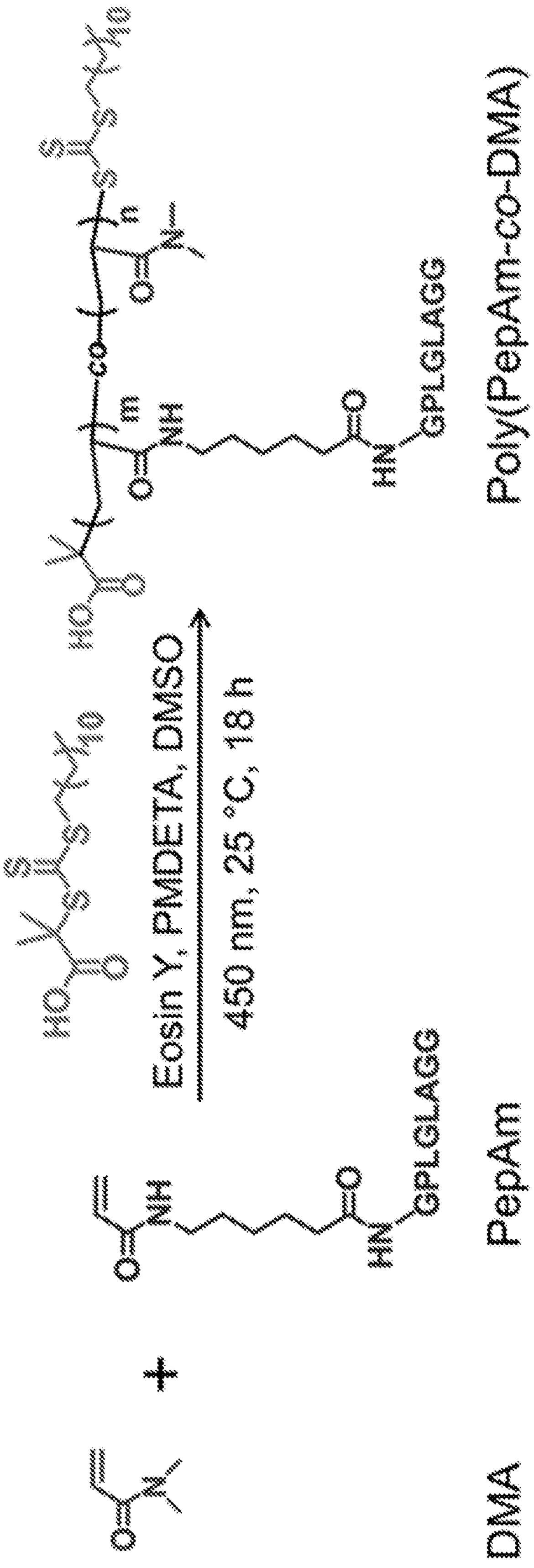
FIG. 2A. Photo-RDRP of PepAm and DMA in DMSO.
Figure 2B:
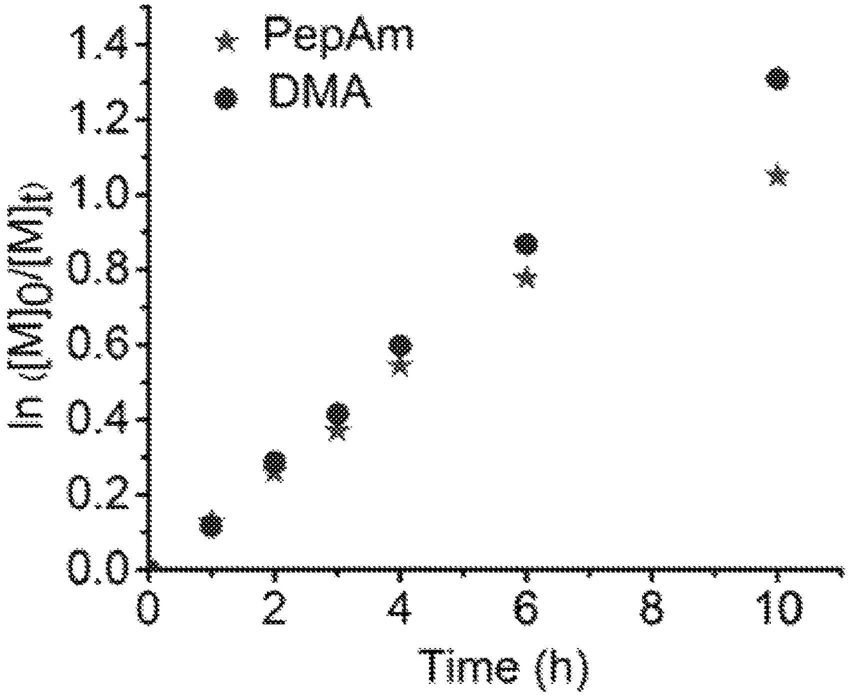
FIG. 2B. Kinetic plot of monomer concentrations versus time for PepAm and DMA over the course of photo-RDRP.
Figure 2C:
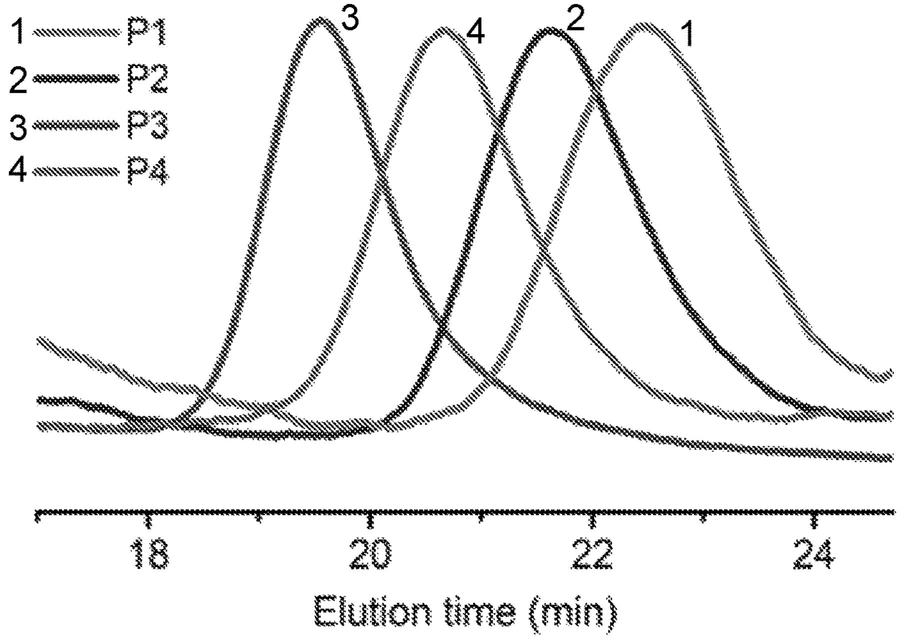
FIG. 2C. GPC traces of enzyme-responsive peptide brush polymers (P1-P4, Table 1) with different grafting densities. P1-P4 represent poly(PepAm$_6$-co-DMA$_7$), poly(PepAm$_{15}$-co-DMA$_{45}$), poly(PepAm$_{34}$-co-DMA$_{117}$), and poly(PepAm$_{21}$-co-DMA$_{71}$), respectively. (GPLGLAGG is SEQ ID NO:5.)

Due to the steric bulk of the peptide macromonomers, we reasoned that random copolymerization with a spacer monomer would enhance overall monomer conversions as well as improve control over the course of photo-RDRP. To examine this, the homopolymerization of PepAm in DMSO was first conducted (Table 1, Entry 1). According to the kinetics, no polymerization was observed after 18 hours, suggesting that steric hindrance stemming from the peptide side chains significantly hampered the photo-RDRP process. In view of this, a comonomer, dimethyl acrylamide was employed in the preparation of enzyme-responsive polypeptide brushes (Table 1, Entries 2-5). DMA was chosen due to its similar vinyl substructure (i.e., acrylamide) in comparison with the peptide monomer (FIGS. 2A-2C).

TABLE 1

| Photo-RDRP of peptide-acrylamide (PepAm) and DMA | | | | | | | | |
|---|---|---|---|---|---|---|---|---|
| | Equiv. to CTA | | | Conv. (%) | | $M_{n,\ theo}$ | $M_{n,\ GPC}$ | |
| Entry | PepAm | DMA | $[M]_0$ | PepAm | DMA | (g/mol) | (g/mol) | Đ |
| [a]P0 | 50 | 0 | 0.18M | 0% | N/A | N/A | N/A | N/A |
| [a]P1 | 50 | 50 | 0.36M | 12% | 15% | 5 600 | 4 900 | 1.08 |
| [a]P2 | 50 | 100 | 0.54M | 30% | 45% | 16 500 | 10 800 | 1.15 |
| [a]P3 | 50 | 150 | 0.72M | 68% | 78% | 39 900 | 46 000 | 1.01 |
| [b]P4 | 50 | 150 | 0.72M | 42% | 47% | 24 200 | 25 000 | 1.02 |

Note:
In each polymerization, 200 μL of DMSO was used.
[M]/[CTA]/[EY]/[PMDETA] = X/1/0.05/1.
[a]The polymerizations were triggered by blue LED (450 nm).
[b]The polymerization was promoted under sunlight in Northwestern University.

Figure 13:
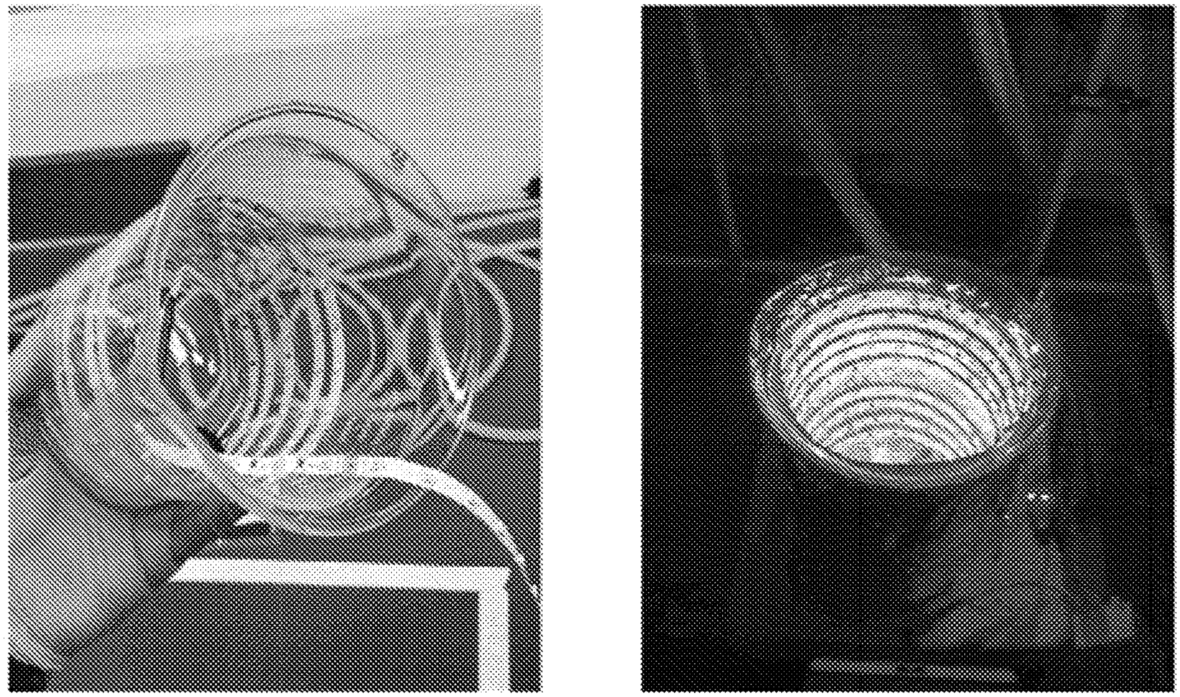
FIG. 13. Assembly of photo-reactor by wrapping the LED strip light inside a beaker.
Figure 14:
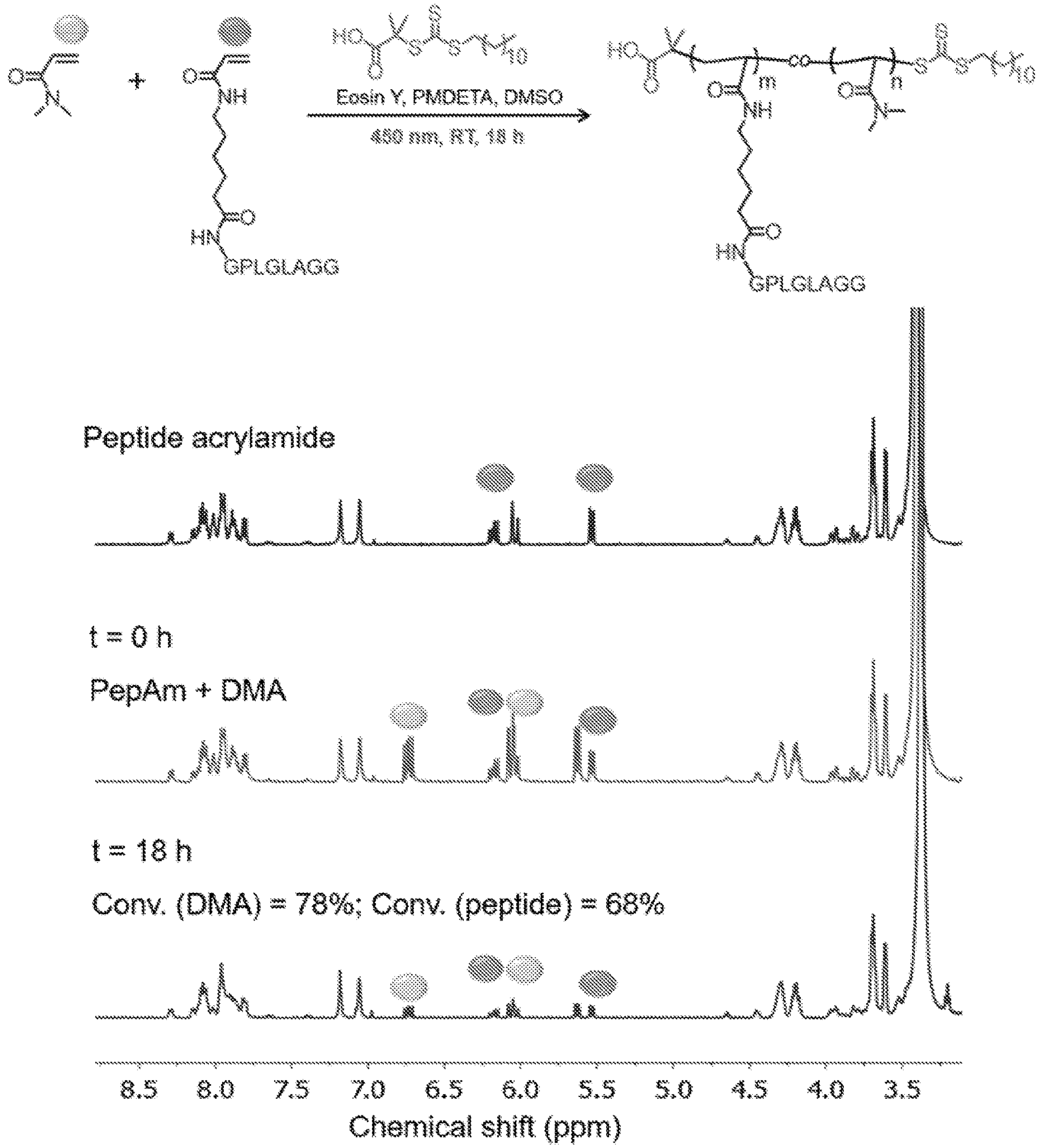
FIG. 14. $^1$H NMR spectra of enzyme-responsive peptide acrylamide (top blue), monomer mixtures before polymerization (middle green), and after polymerization for 18 h (bottom red). (GPLGLAGG is SEQ ID NO:5.)
Figure 15A:
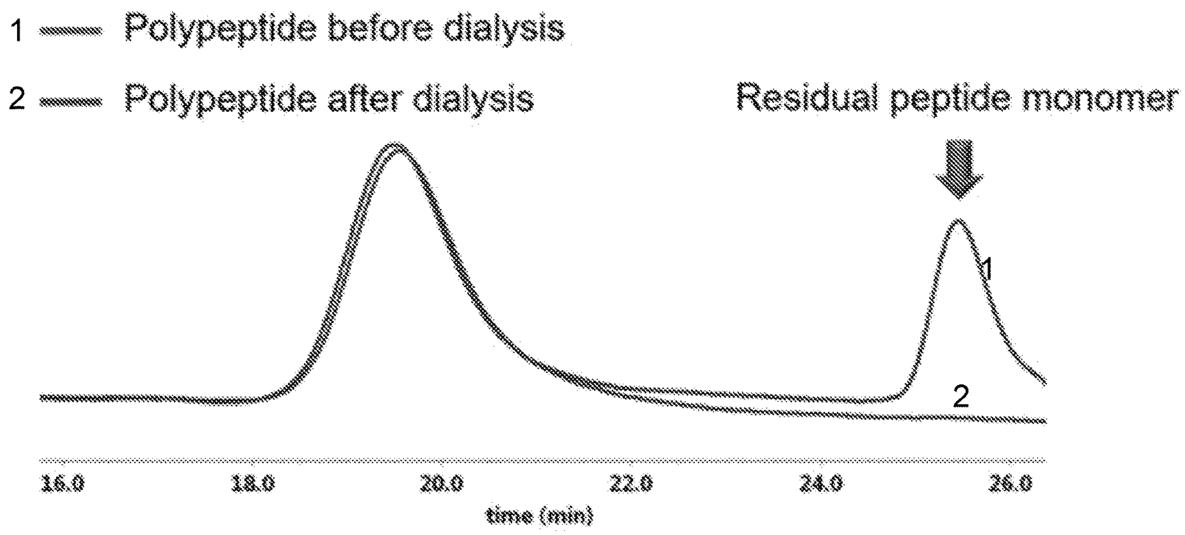
FIG. 15A. GPC traces of P1 before and after dialysis (cut-off: 20,000 Da). The disappearance of peptide monomer peak clearly indicated that polypeptide was pure after dialysis.
Figure 15B:
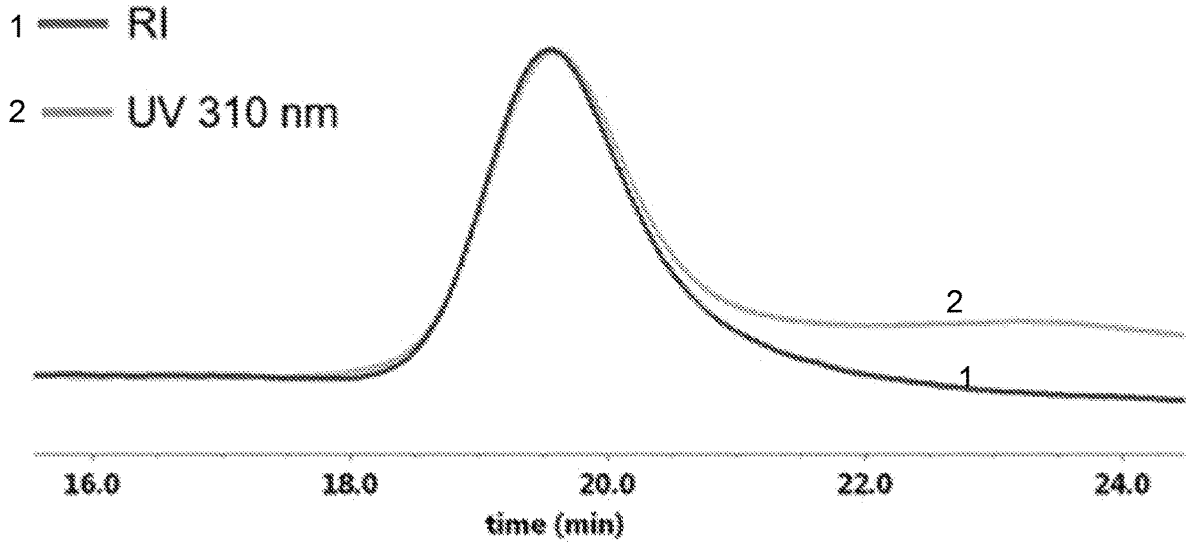
FIG. 15B. GPC traces of P1 from both RI detector and UV detector (310 nm).
Figure 16:
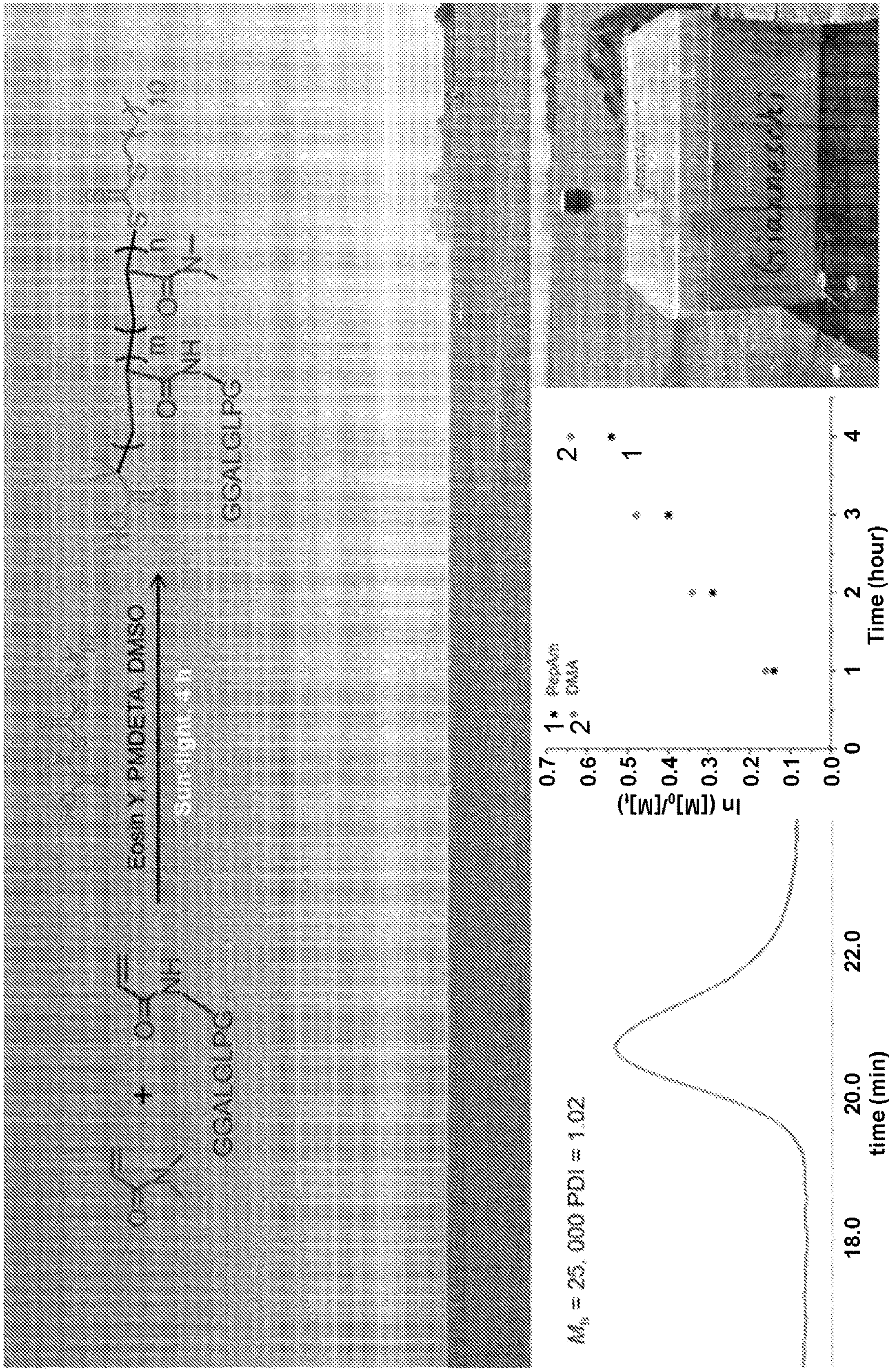
FIG. 16. Sunlight-induced polymerization of peptide acrylamide in lakeshore at Northwestern University (Evanston campus, Aug. 17, 2018). $^1$H NMR based kinetic study of polymerization demonstrated that peptide acrylamide possessed a propagation rate on par with that of the commoner DMA; SEC trace of the final product indicated that the polypeptide product is well-defined with a narrow polydispersity and number-average molecular weight similar to theoretical value (refer to P4 in Table 1). (GPLGLAGG is SEQ ID NO:5.)
Figure 17:
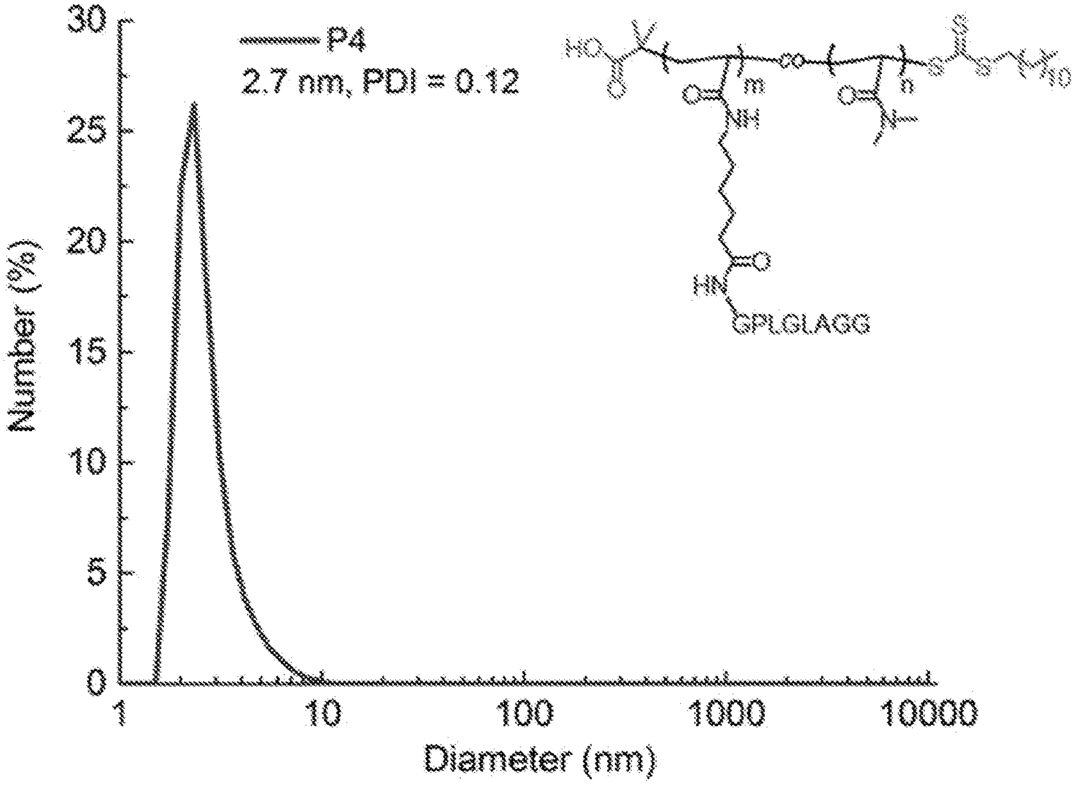
FIG. 17. DLS trace of P4 in DIW. The small size (<10 nm) of the polypeptide indicates that the polymer exists as free unimers in DIW. (GPLGLAGG is SEQ ID NO:5.)

To understand the composition and distribution of PepAm and DMA in the polymers, $^1H$ NMR spectroscopy was used to study the rate of polymerization and conversion of the two monomers in photo-RDRP under blue LED (Table 1, entry 4, FIG. 13). According to $^1H$ NMR analysis (FIG. 2B and FIG. 14), both the peptide monomer and DMA comonomer had similar propagation rates, indicative of a statistical distribution of peptide monomers along the polymer backbone. Gel permeation chromatography (GPC) analysis showed a narrow molecular weight distribution for all polypeptide brushes with different grafting densities (FIG. 2C, Table 1). Moreover, theoretical molecular weights of all polymers are on par with those from GPC results, suggesting good control over the photo polymerizations. While full monomer conversions were not achieved, residual PepAm and DMA monomers were effectively removed by dialysis of the crude polymer mixtures in water, as confirmed by its disappearance in the GPC trace (FIGS. 15A-15B). We note, natural sun-light was also effective in triggering the photopolymerization of PepAm, leading to well-defined polypeptide brushes (FIGS. 16-17).

Figure 18:
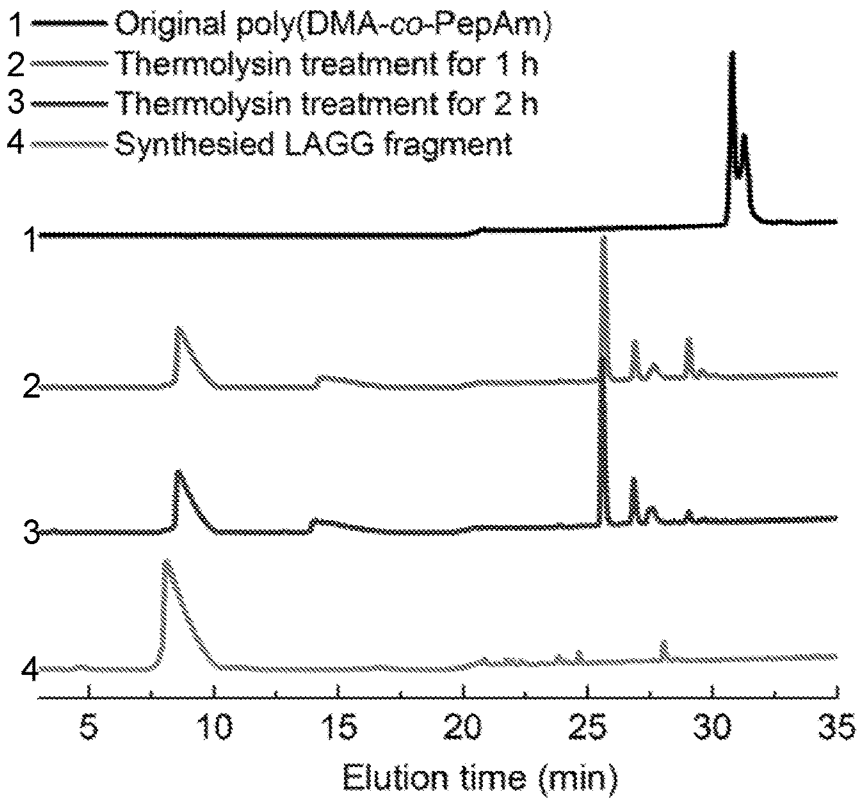
FIG. 18. HPLC traces of P1 before and after being treated with thermolysin (1/300 equiv. to the number of peptides in the polymer). No further increase in the peak of the cleaved LAGG fragment was observed after 1 hour, suggesting that the enzyme-induced peptide cleavage was complete within one hour.
Figure 19A:
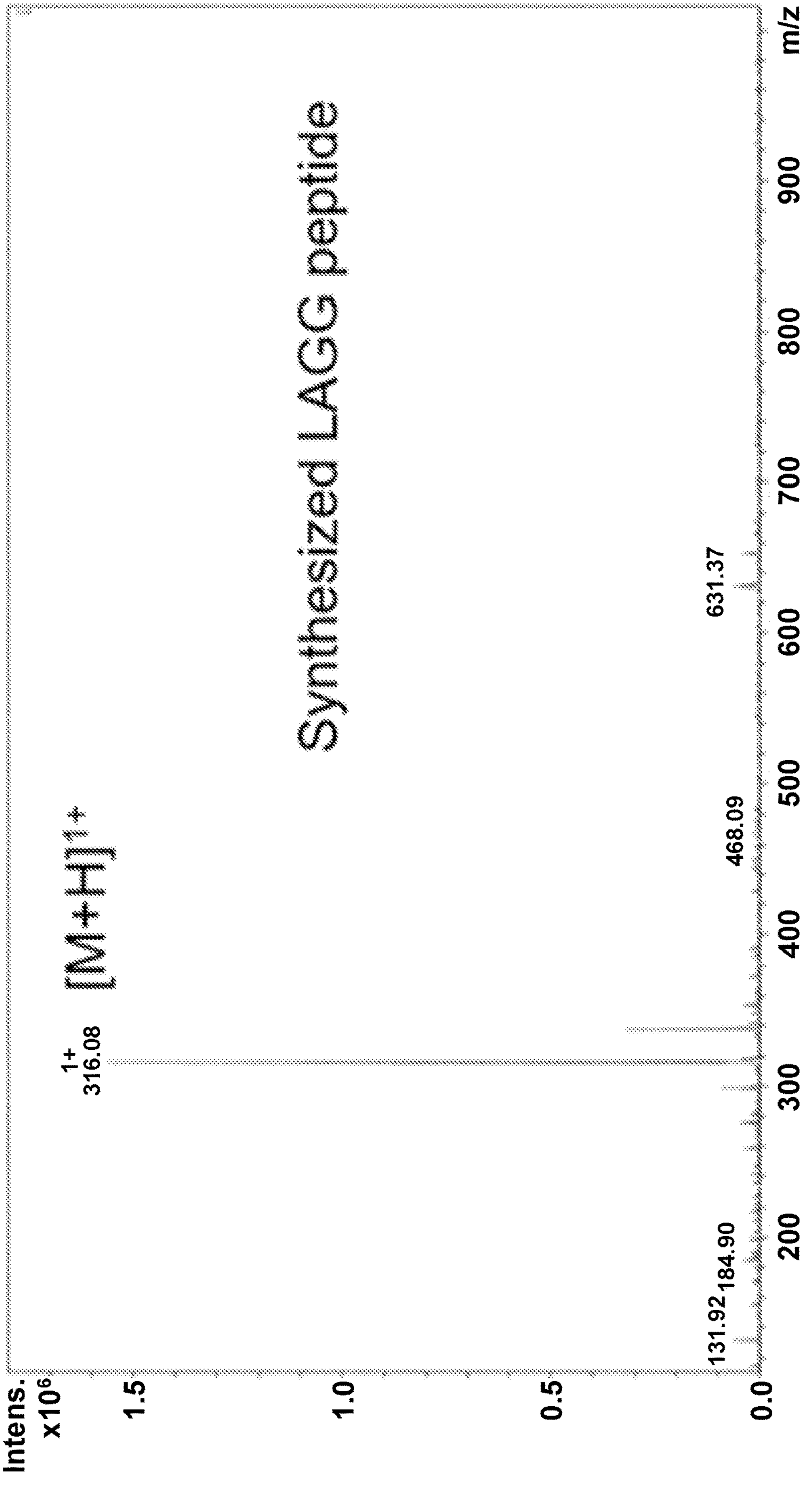
FIGS. 19A-19B. ESI-Mass spectra of synthetic LAGG fragment (FIG. 19A) and cleaved LAGG fragment (FIG. 19B) which was collected from HPLC separation. Notably, the cleaved LAGG was from P1 after treatment with thermolysin.
Figure 19B:
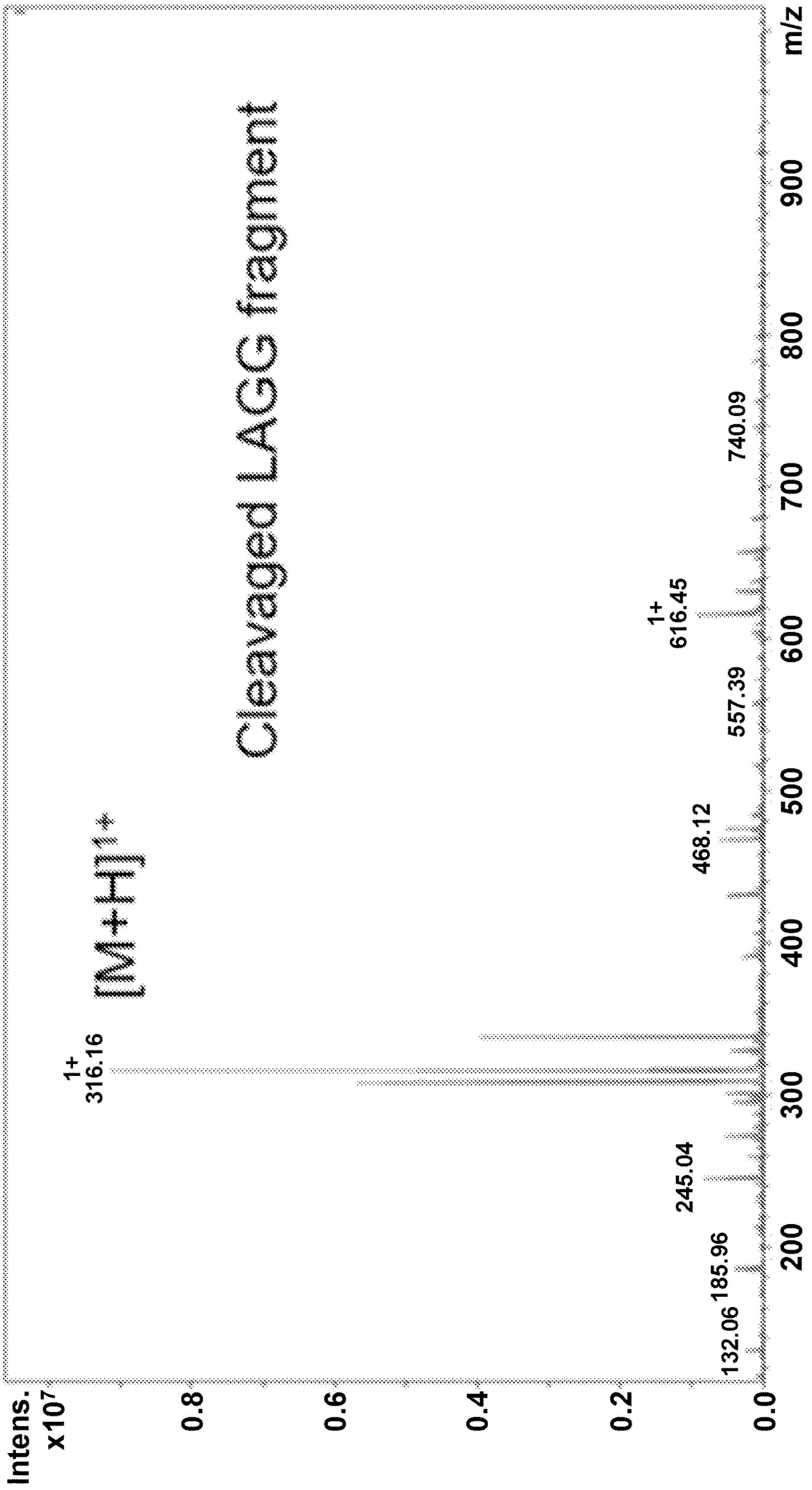
Figure 20:
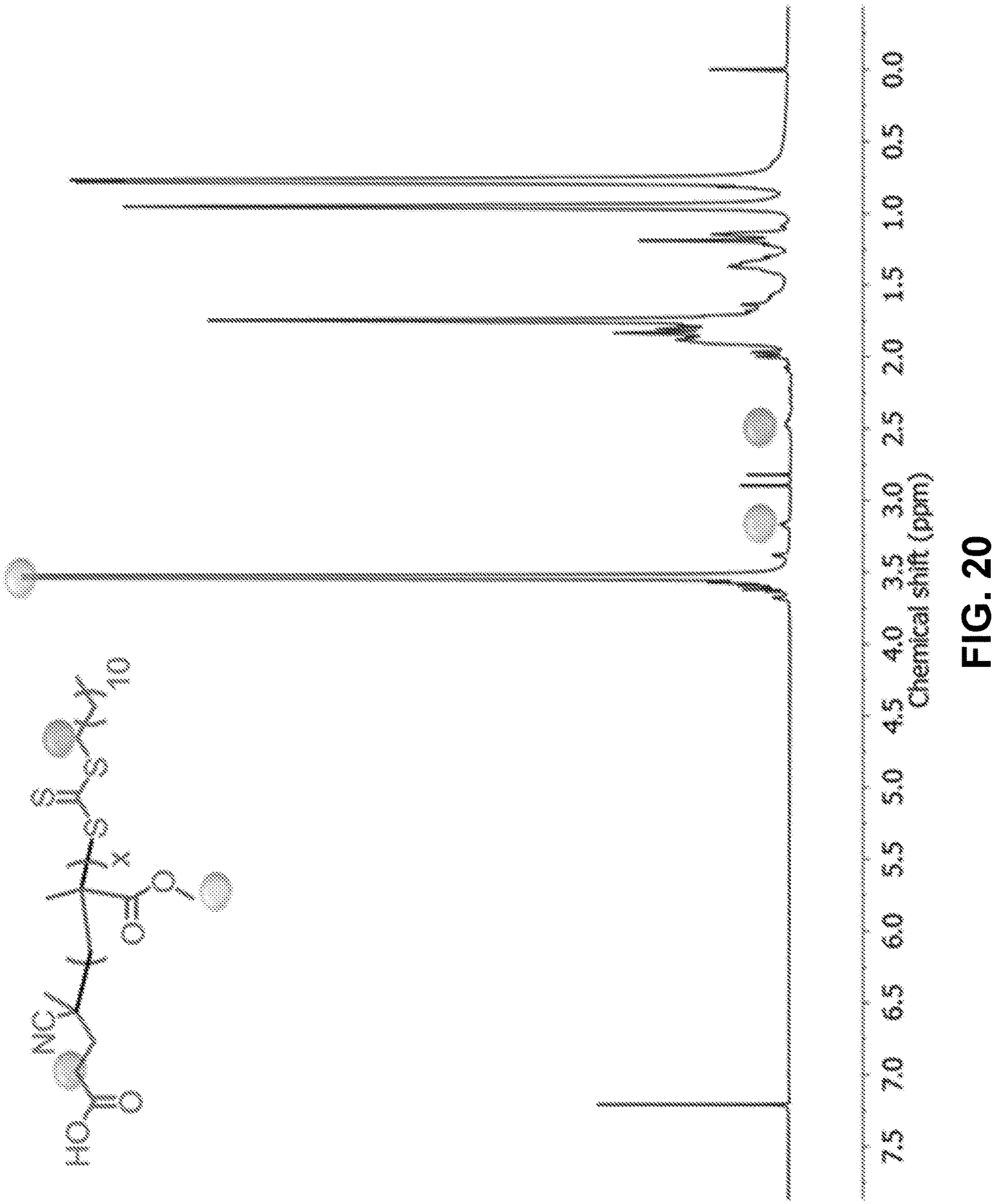
FIG. 20. $^1$H NMR spectrum of PMMA$_{90}$ macroCTA (P5) in CDCl$_3$ at 25° C.
Figure 21:
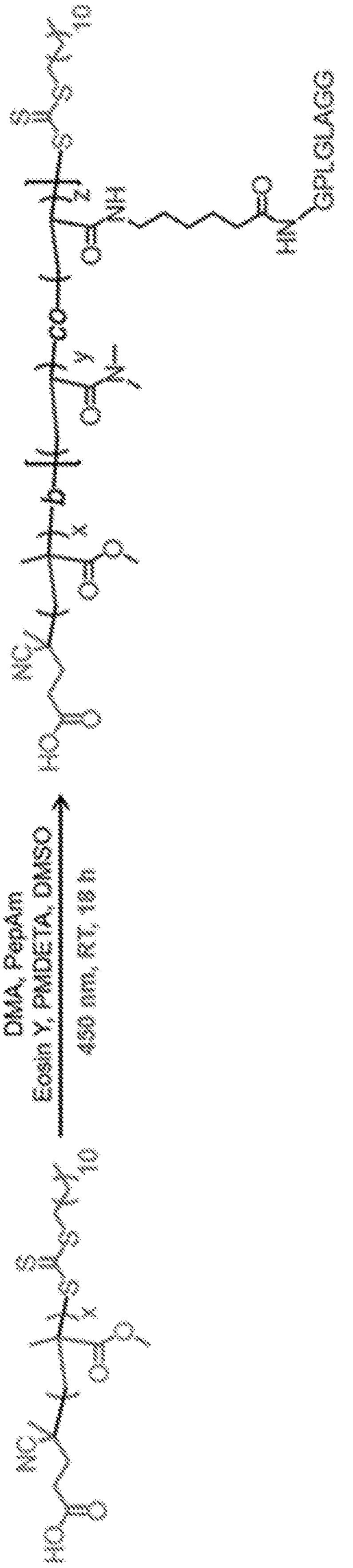
FIG. 21. Chain extension of PMMA macroCTA with DMA and PepAm.
Figure 22:
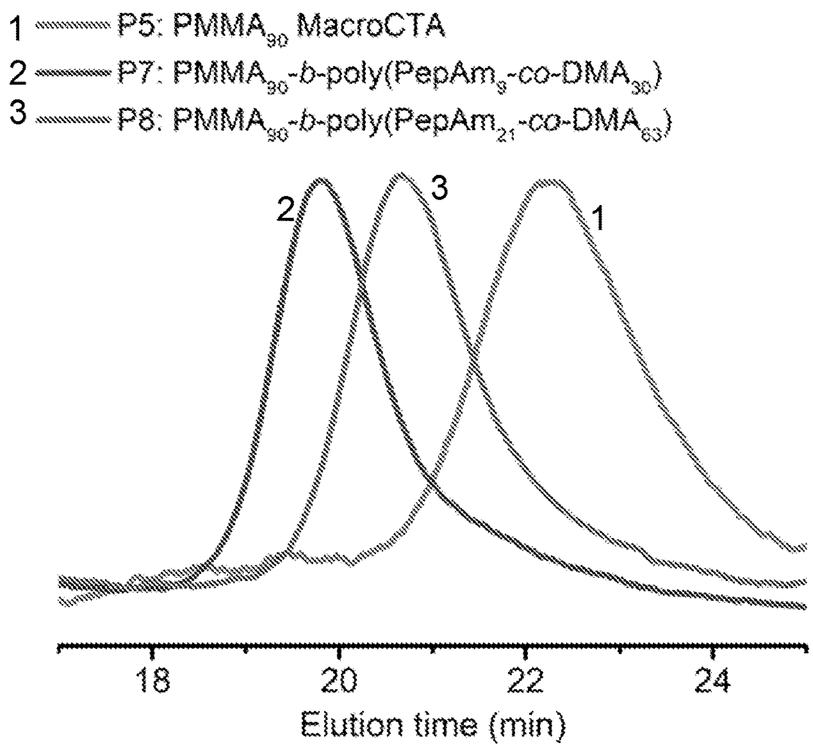
FIG. 22. GPC traces of PMMA$_{90}$ macroCTA (P5), PMMA$_{90}$-b-poly(PepAm$_9$-co-DMA$_{30}$) (P7), and PMMA$_{90}$-b-poly(PepAm$_{21}$-co-DMA$_{63}$) (P8).
Figure 23A:
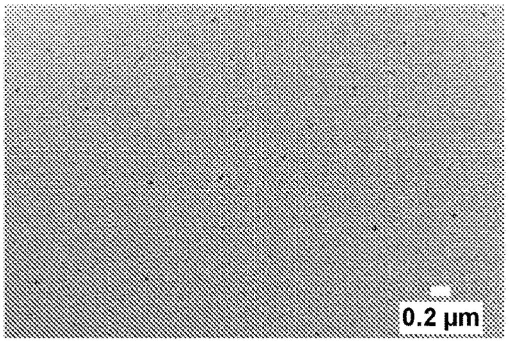
FIG. 23A. TEM image of PMMA$_{90}$-b-poly(PepAm$_9$-co-DMA$_{30}$) in DIW.
Figure 23B:
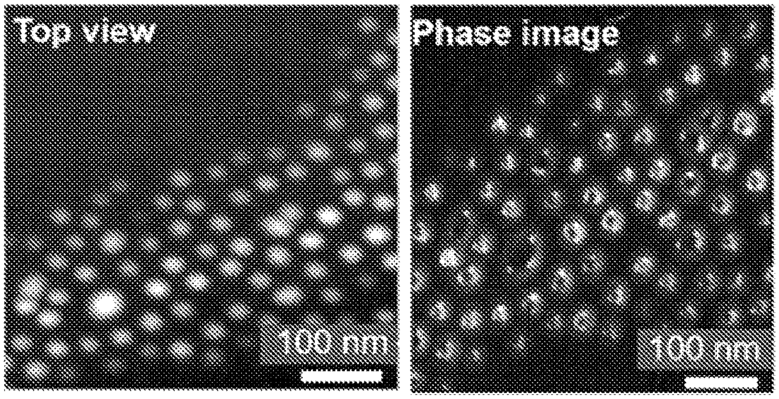
FIG. 23B. AFM micrographs of PMMA$_{90}$-b-poly(PepAm$_9$-co-DMA$_{30}$) in DIW.
Figure 24:
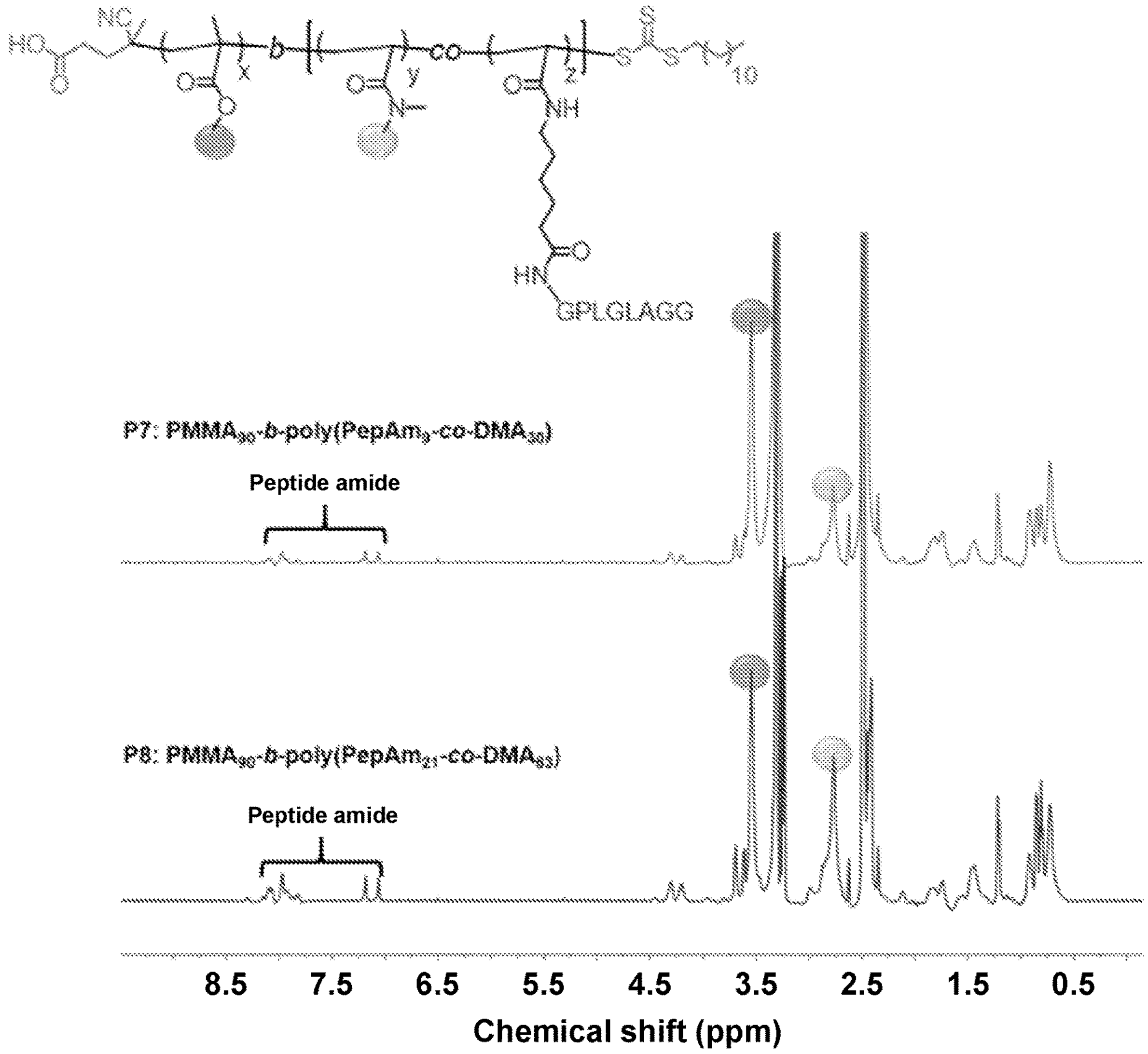
FIG. 24. $^1$H NMR spectrum of PMMA$_{90}$-b-poly(PepAm$_9$-co-DMA$_{30}$) (P7), and PMMA$_{90}$-b-poly(PepAm$_{21}$-co-DMA$_{63}$) (P8) in d$_6$-DMSO at 25° C. (GPLGLAGG is SEQ ID NO:5.)
Figure 25A:
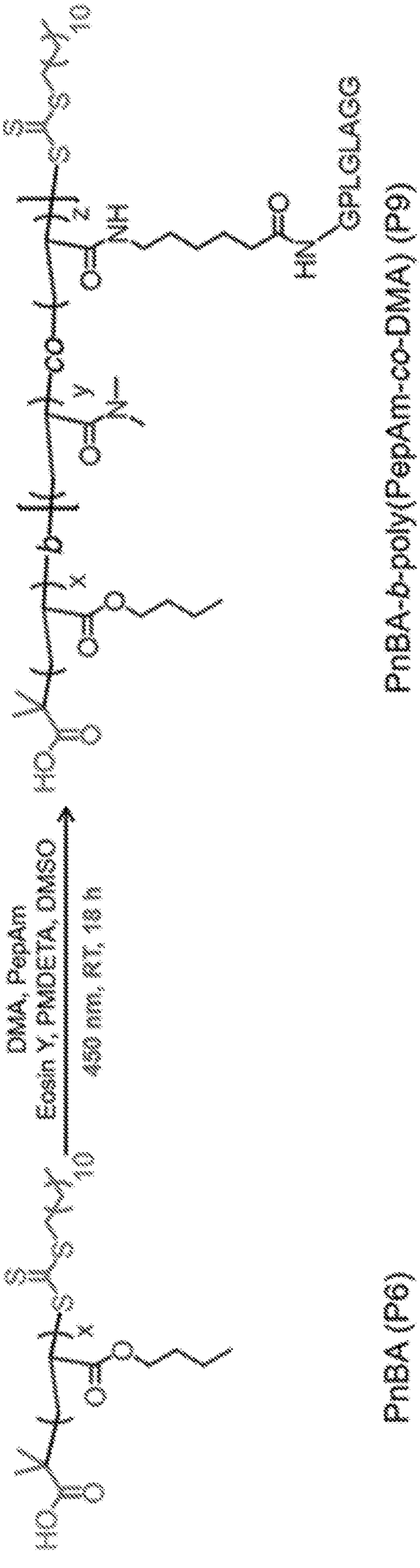
FIG. 25A. Chain extension of PnBA macroCTA with peptide monomers and DMA spacers.
Figure 25B:
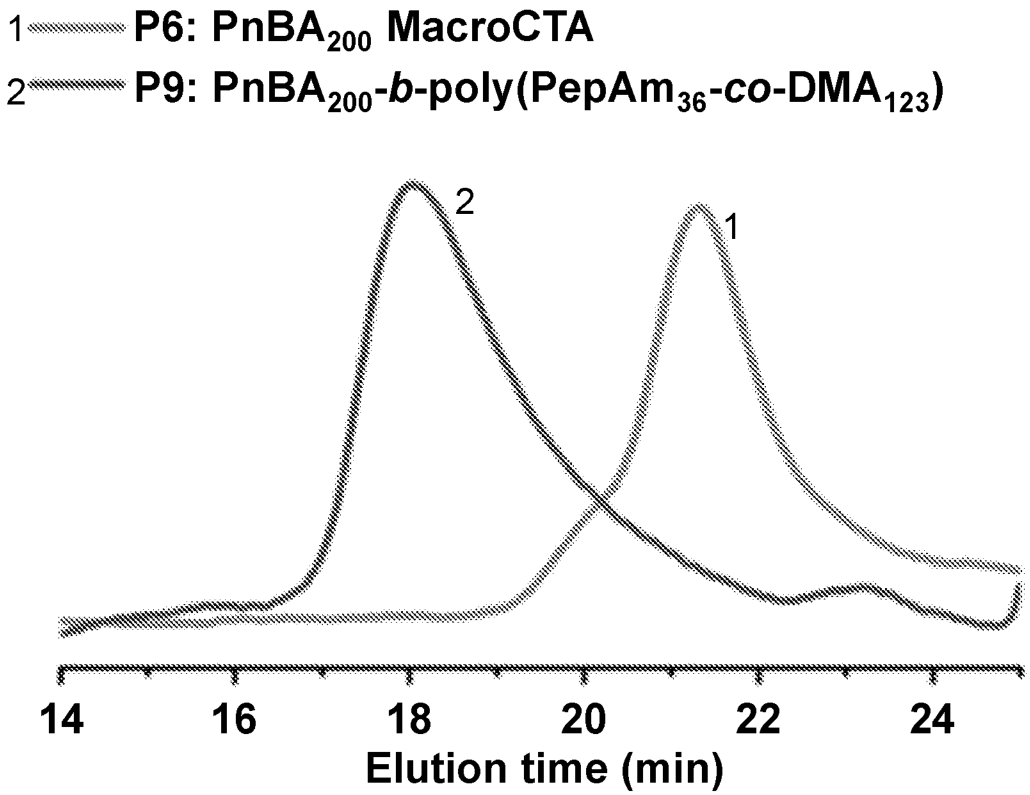
FIG. 25B. GPC traces of PnBA macroCTA (P6) and block copolymer PnBA$_{200}$-b-poly(PepAm$_{36}$-co-DMA$_{123}$) (P9) indicated a successful chain extension.
Figure 25C:
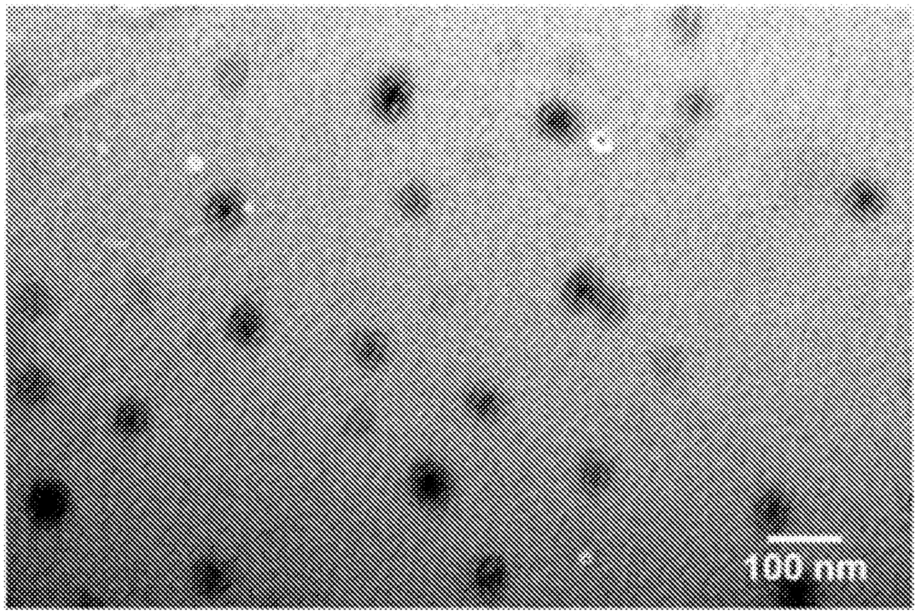
FIG. 25C. TEM image confirmed the micellar structure of P9 in DIW. (GPLGLAGG is SEQ ID NO:5.)
Figure 26:
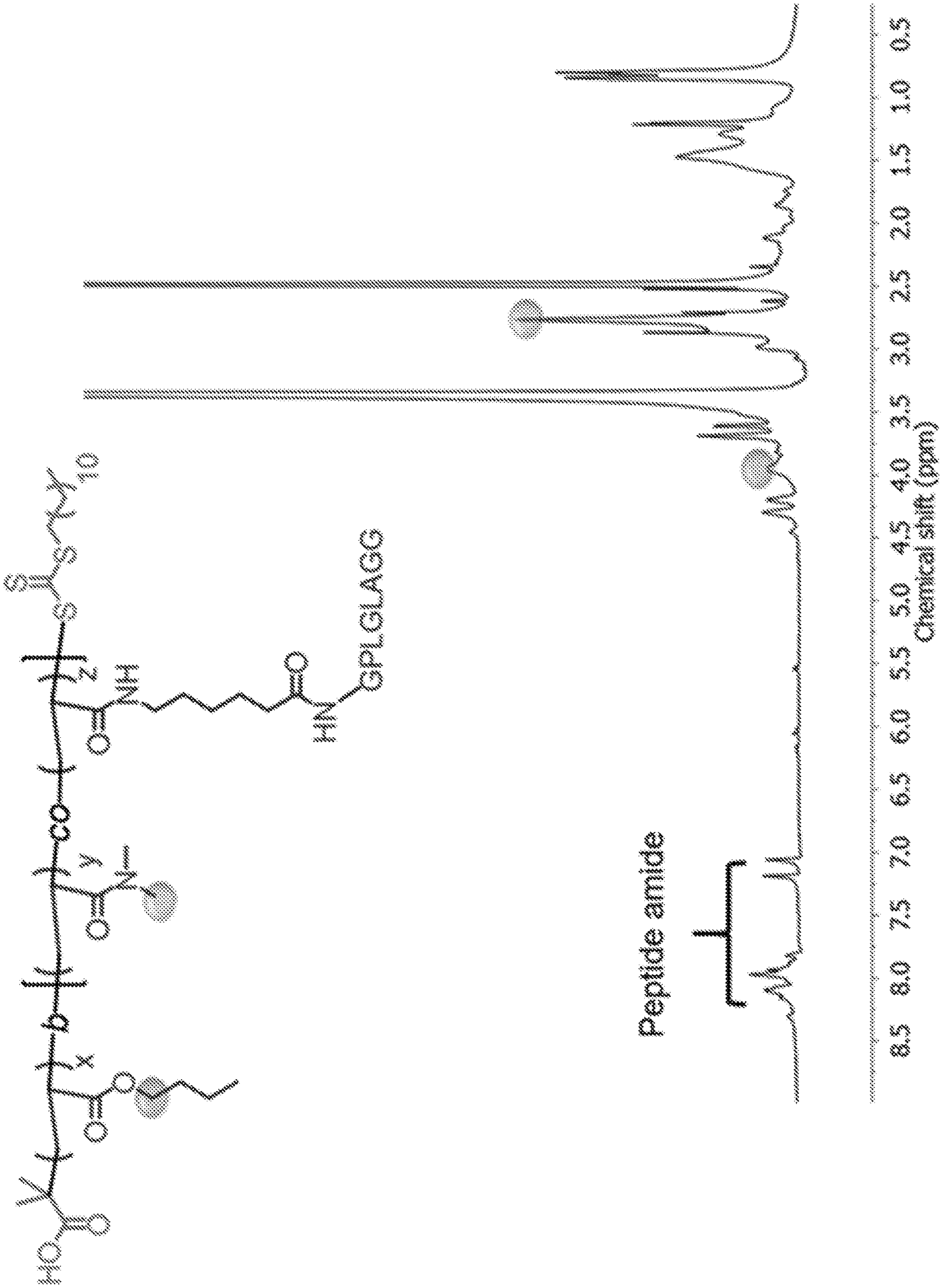
FIG. 26. $^1$H NMR spectrum of $PnBA_{200}$-b-poly($PepAm_{36}$-co-$DMA_{123}$) (P9) in $d_6$-DMSO. (GPLGLAGG is SEQ ID NO:5.)

To examine the bio-activity of polypeptide brushes, polymer poly($PepAm_{21}$-co-$DMA_{71}$) (P4) was treated with thermolysin, an enzyme that can selectively cleave the amide bond between glycine (G) and leucine (L) (FIGS. 3A-3D). HPLC was employed to monitor the cleavage reaction, showing that the polypeptide brushes were rapidly cleaved within 1 hour under the investigated conditions (FIG. 18). The cleaved peptide fragment was further analyzed by ESI-MS and shown to have an identical mass to that of the genuine synthetic cleavage fragment LAGG (FIGS. 19A-19B). These results clearly indicate that the side-chain peptides remain accessible and reactive towards enzyme cleavage following polymerization. This is counter to our previous observations of highly dense peptide brushes generated using ring-opening metathesis polymerization, where peptides can be made entirely resistant to aggressive proteolytic treatments.[15] The different activity of peptide brush polymers to enzyme digestion likely stems from the structural variation in polymer backbones prepared by photo-RDRP and ROMP. In comparison with rigid polynorbornene backbone containing $sp^2$ hybridized carbon-carbon double bonds, vinyl polymer backbone is more flexible and hence increases the accessibility of side chain peptides to surrounding enzymes. Moreover, the radical approach (i.e., photo-RDRP) to peptide brush polymers was achieved via copolymerization of peptide vinyl monomers and spacer monomers, resulting in random copolymers with a lower grafting density than that of polynorbornene-type polymers, which were synthesized by homopolymerization of norbornene modified peptide monomers.

Figure 3A:
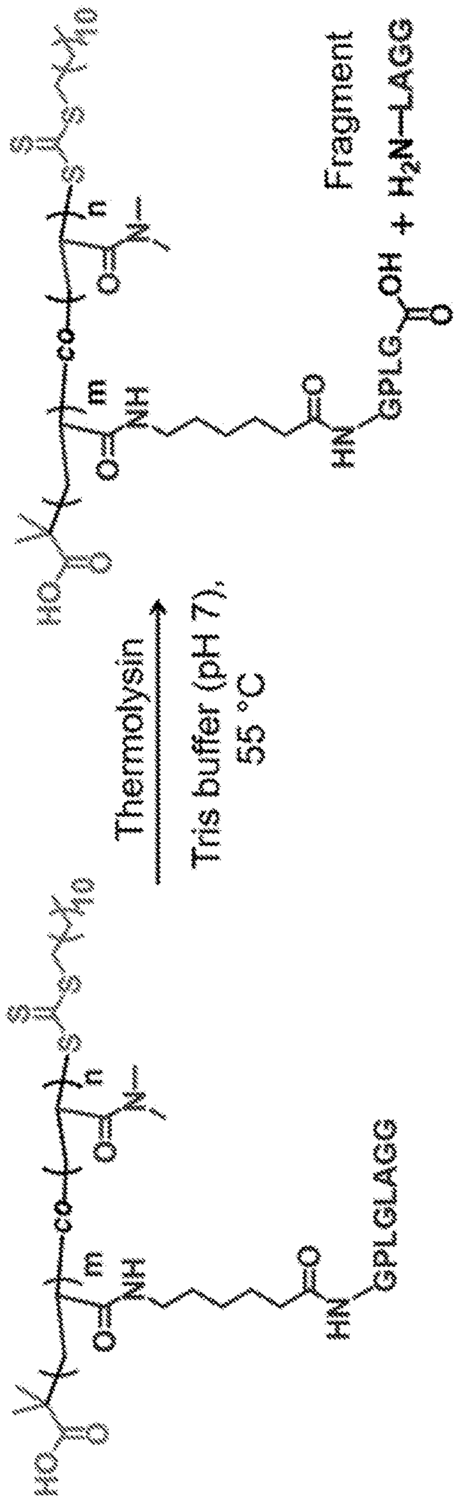
FIG. 3A. Schematic of thermolysin-promoted cleavage of poly(PepAm$_{21}$-co-DMA$_{71}$) (P4).
Figure 3B:
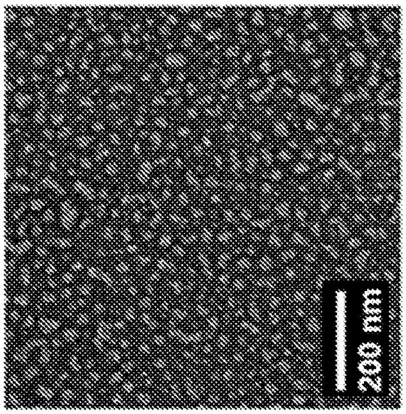
FIG. 3B. TEM micrograph of PMMA$_{90}$-b-poly(PepAm$_{21}$-co-DMA$_{63}$) based micelles (P8) before treatment with thermolysin.
Figure 3C:
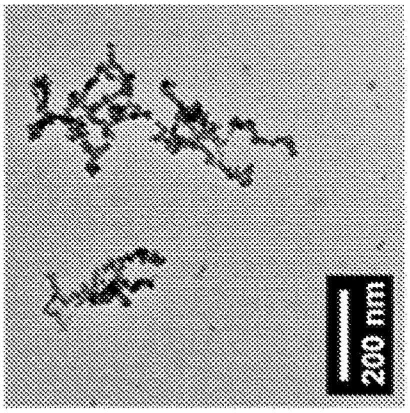
FIG. 3C. TEM micrograph of PMMA$_{90}$-b-poly(PepAm$_{21}$-co-DMA$_{63}$) based micelles (P8) after treatment with thermolysin.
Figure 3D:
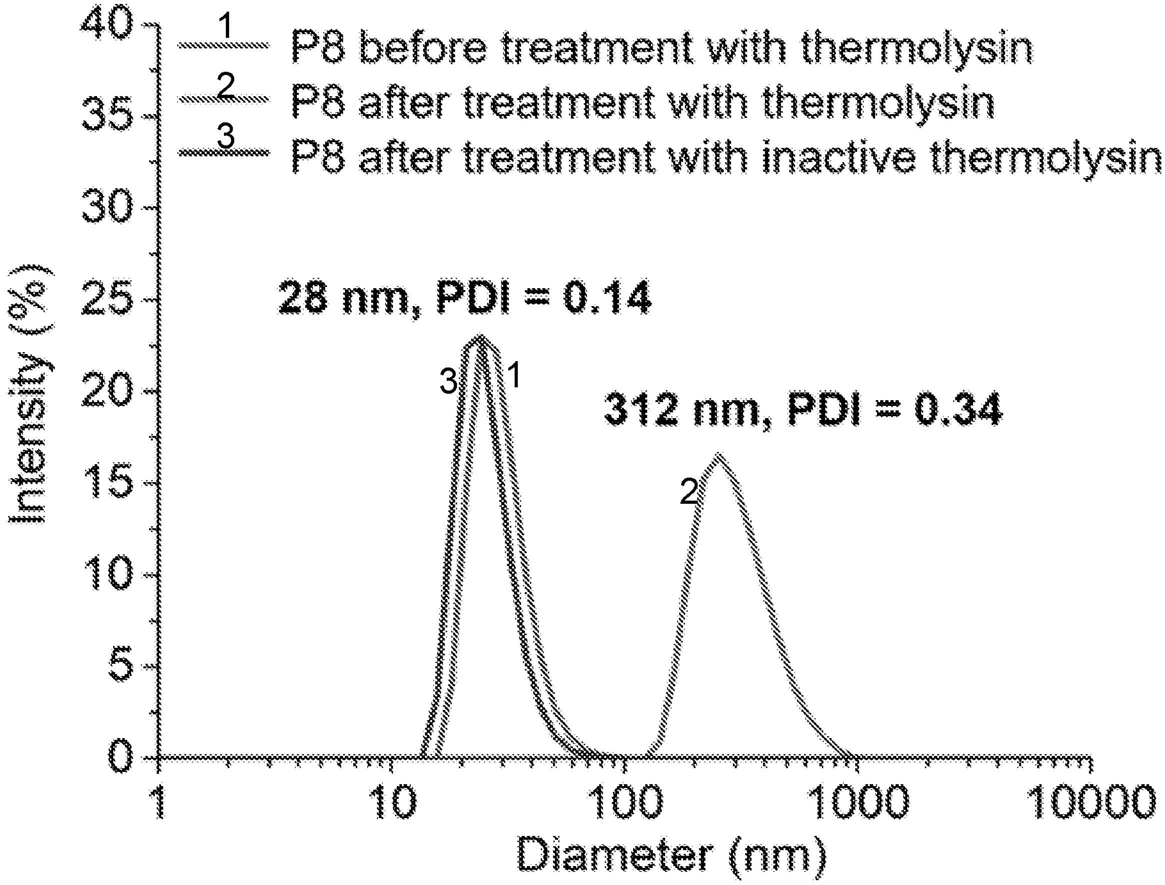
FIG. 3D. DLS traces of P8 based nano-objects before and after thermolysin-induced cleavage. (GPLGLAGG is SEQ ID NO:5.)

To capitalize on this accessibility to substrate, amphiphilic block copolymers were prepared (P7-P9, Table 2) by chain extension of poly(methyl methacrylate) or poly(n-butyl acrylate) based macro chain transfer agents with PepAm and DMA (FIGS. 20-26). The resulting amphiphilic diblock copolymers assembled into micelles in water. For example, $PMMA_{90}$-b-poly($PepAm_{21}$-co-$DMA_{63}$) (P8, Table 2) were spherical micelles, 24 nm in diameter as characterized by transmission electron microscope (TEM), in good agreement with the hydrodynamic diameter (28 nm) determined by dynamic light scattering (DLS) (FIGS. 3B and 3D).

TABLE 2

| Preparation of enzyme-responsive diblock copolymer | | | | | | | | |
|---|---|---|---|---|---|---|---|---|
| | Equiv. to macroCTA | | | Conv. (%) | | $M_{n,\ theo}$ | $M_{n,\ GPC}$ | |
| Entry | PepAm | DMA | $[M]_0$ | PepAm | DMA | (g/mol) | (g/mol) | Đ |
| [a]P7 | 13 | 37 | 0.72M | 72% | 79% | 19 900 | 16 200 | 1.04 |
| [a]P8 | 25 | 75 | 0.72M | 82% | 84% | 31 800 | 27 000 | 1.06 |
| [b]P9 | 50 | 150 | 0.72M | 71% | 82% | 68 000 | 66 400 | 1.17 |

Note:
In each polymerization, 200 μL of DMSO was used.
[M]/[CTA]/[EY]/[PMDETA] = X/1/0.05/1, RXN time = 18 h.
[a]The chain extensions were performed using PMMA macroCTA (P5).
[b]The chain extension was performed using PnBA macroCTA (P6).

Figure 27:
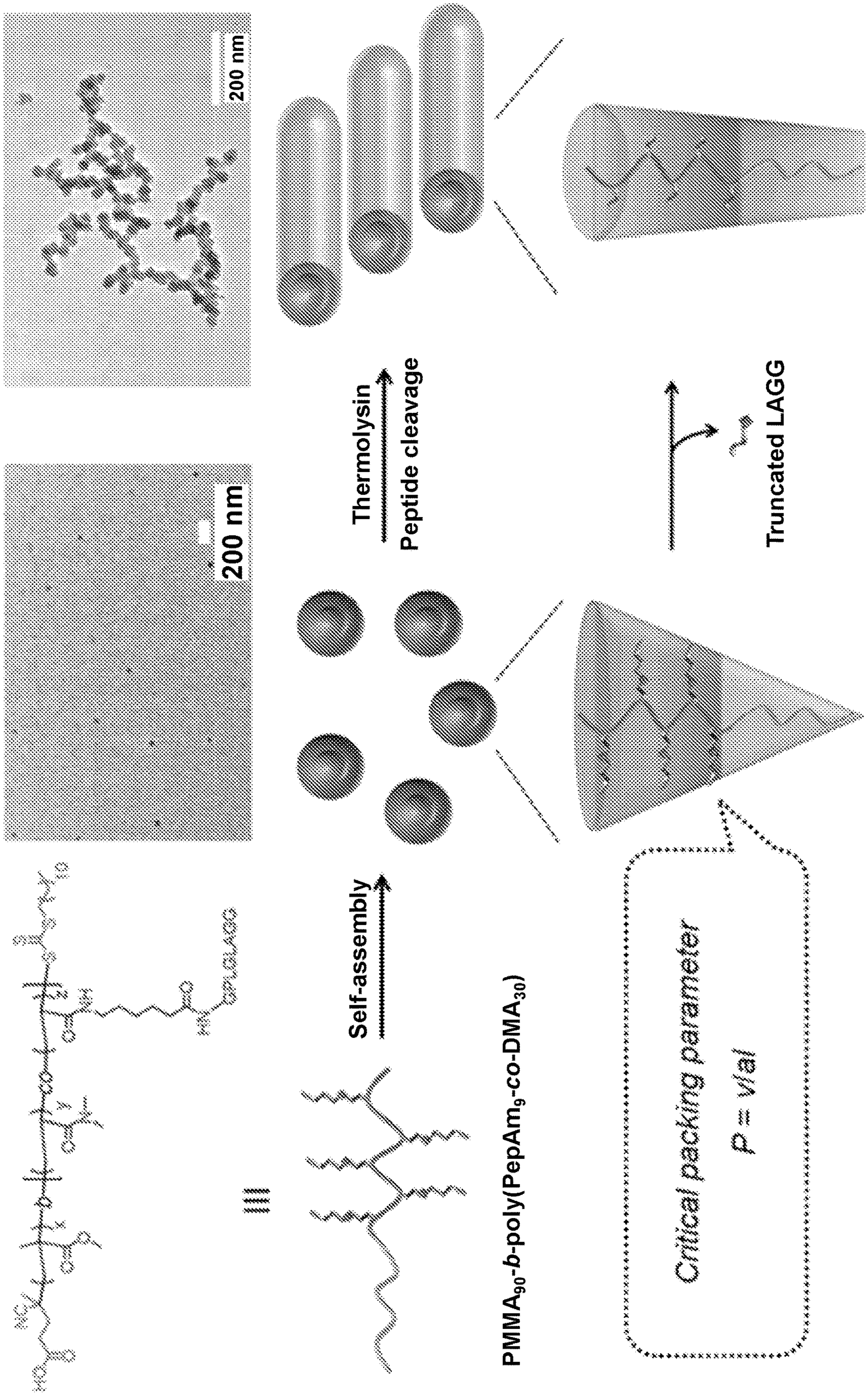
FIG. 27. Enzyme-promoted shape transformation of $PMMA_{90}$-b-poly($PepAm_9$-co-$DMA_{30}$) (P7) based micelles. TEM elucidated a transition from spherical micelle to fused worm micelles after treatment with thermolysin. (GPLGLAGG is SEQ ID NO:5.)
Figure 28:
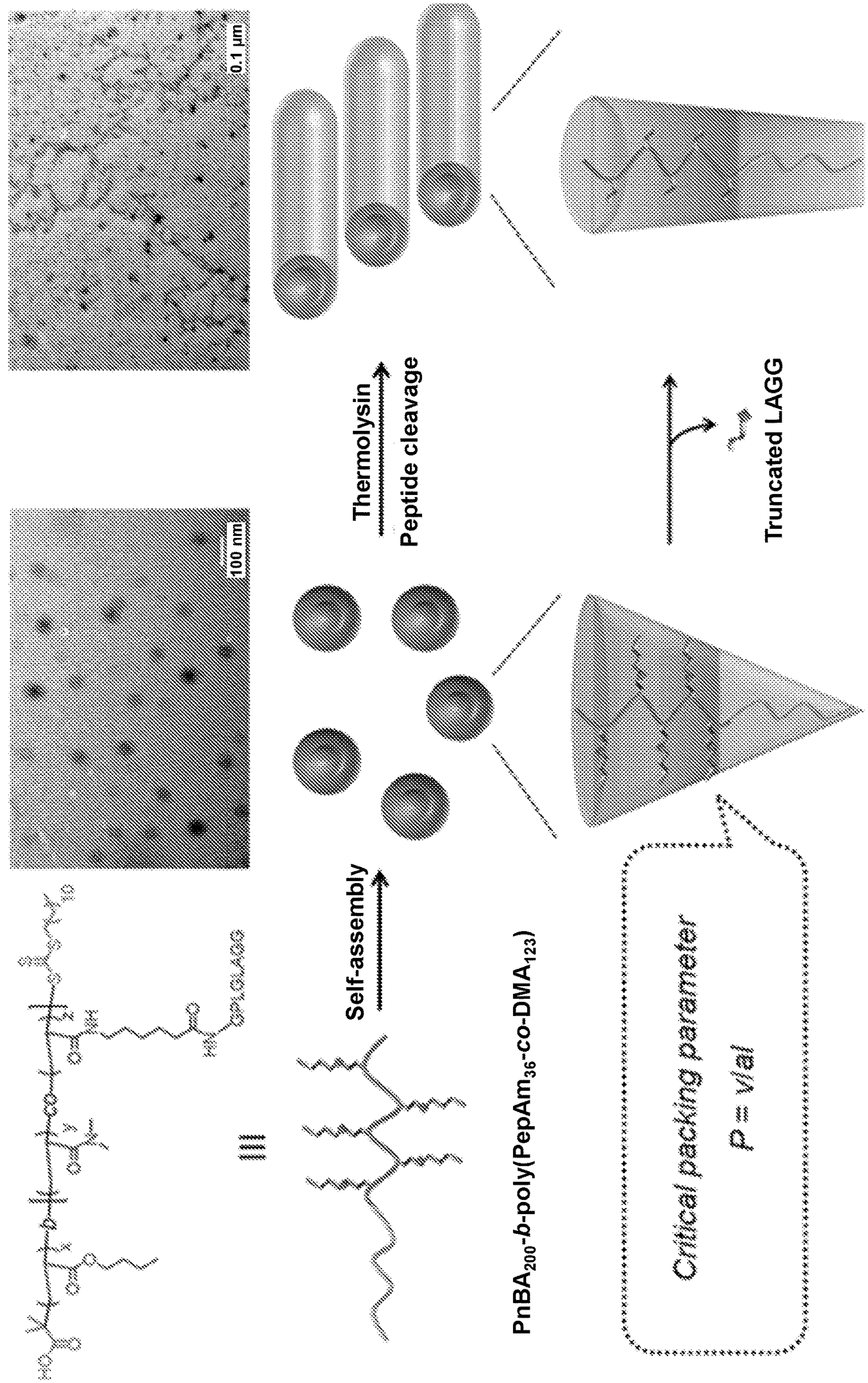
FIG. 28. Enzyme-promoted shape transformation of $PnBA_{200}$-b-poly($PepAm_{36}$-co-$DMA_{123}$) (P9) based micelles. TEM elucidated a transition from spherical micelle to a mixture of micelles and fiber structure after treatment with thermolysin. (GPLGLAGG is SEQ ID NO:5.)
Figure 29:
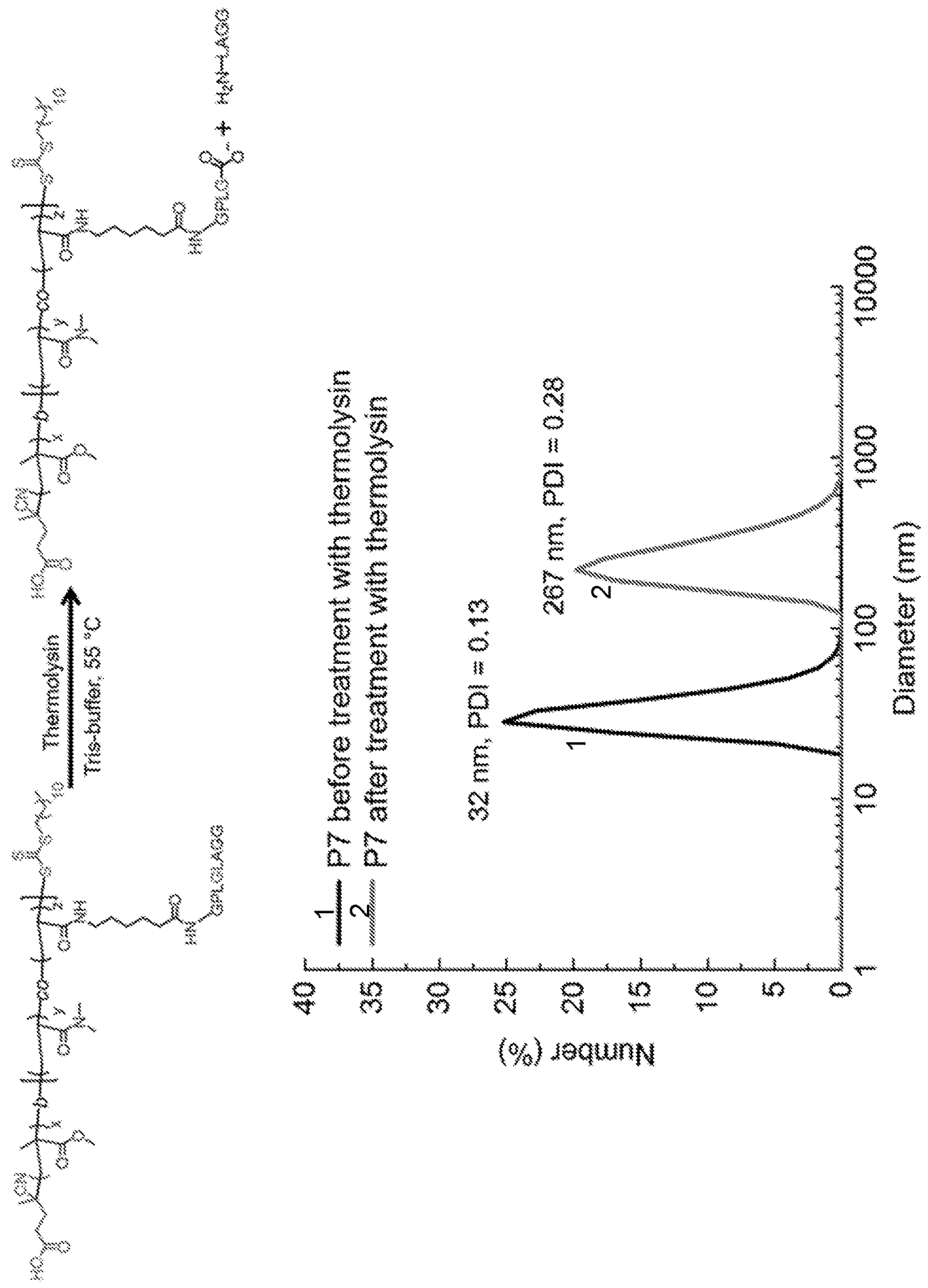
FIG. 29. DLS traces of $PMMA_{90}$-b-poly($PepAm_{21}$-co-$DMA_{63}$) (P7) based nano-objects before and after thermolysin-promoted cleavage. (GPLGLAGG is SEQ ID NO:5.)

The critical packing parameter (CPP) dictates the thermodynamic morphology of amphiphilic block copolymers. In principle, a higher CPP (>⅓) can lead to the formation of higher order morphologies such as cylinders and bilayer vesicles.[23] Since polypeptide brush polymer P4 showed rapid cleavage in the presence of thermolysin (vide supra), we expected that the micelles formed from polypeptide containing diblock polymers could respond to thermolysin, resulting in truncation of the hydrophilic polypeptide corona and thus a reduction in interfacial curvature (i.e., increment in CPP), leading to a change in morphology. Indeed, TEM and DLS showed that the spherical micellar structure of P8 underwent a phase transition into a worm-like phase upon treatment with thermolysin (FIGS. 3C and 3D). By contrast, no change in diameter was observed for particles treated under the same cleavage conditions using deactivated thermolysin which had been pretreated with ethylenediaminetetraacetic acid (FIG. 3D). In addition, similar morphological transformations were observed in other block copolymer micelles including $PMMA_{90}$-b-poly($PepAm_9$-co-$DMA_{30}$) (P7) and $PnBA_{200}$-b-poly($PepAm_{36}$-co-$DMA_{123}$) (P9), demonstrating the versatility of this approach to enzyme-responsive shape-shifting nanoparticles (FIGS. 27-29).

Figure 30:
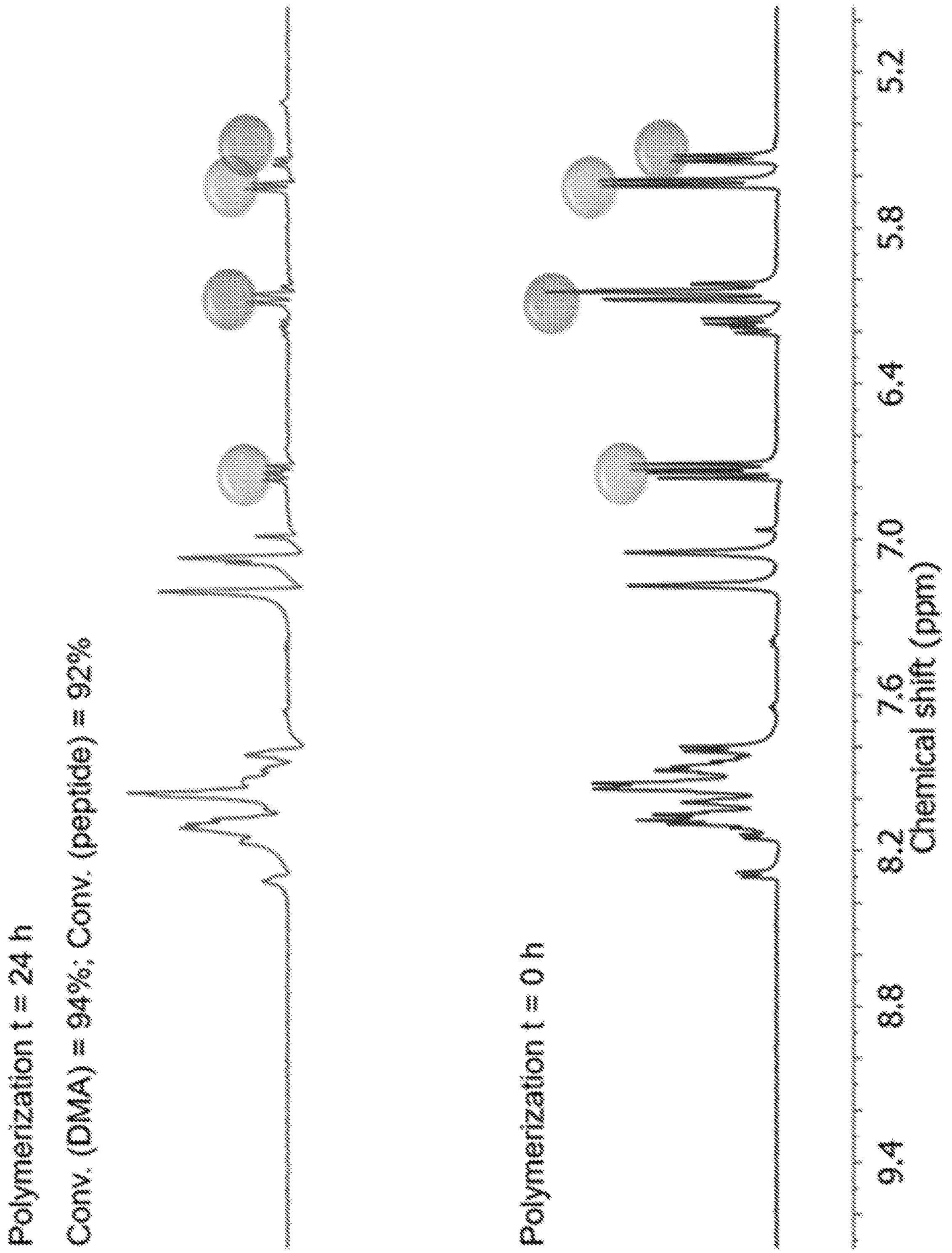
FIG. 30. $^1$H NMR spectra of reaction mixture (P10) before and after photo-polymerization in DIW. The dramatic reduction in vinyl proton signals (5.4 to 6.8 ppm) indicated a high monomer conversion.
Figure 31:
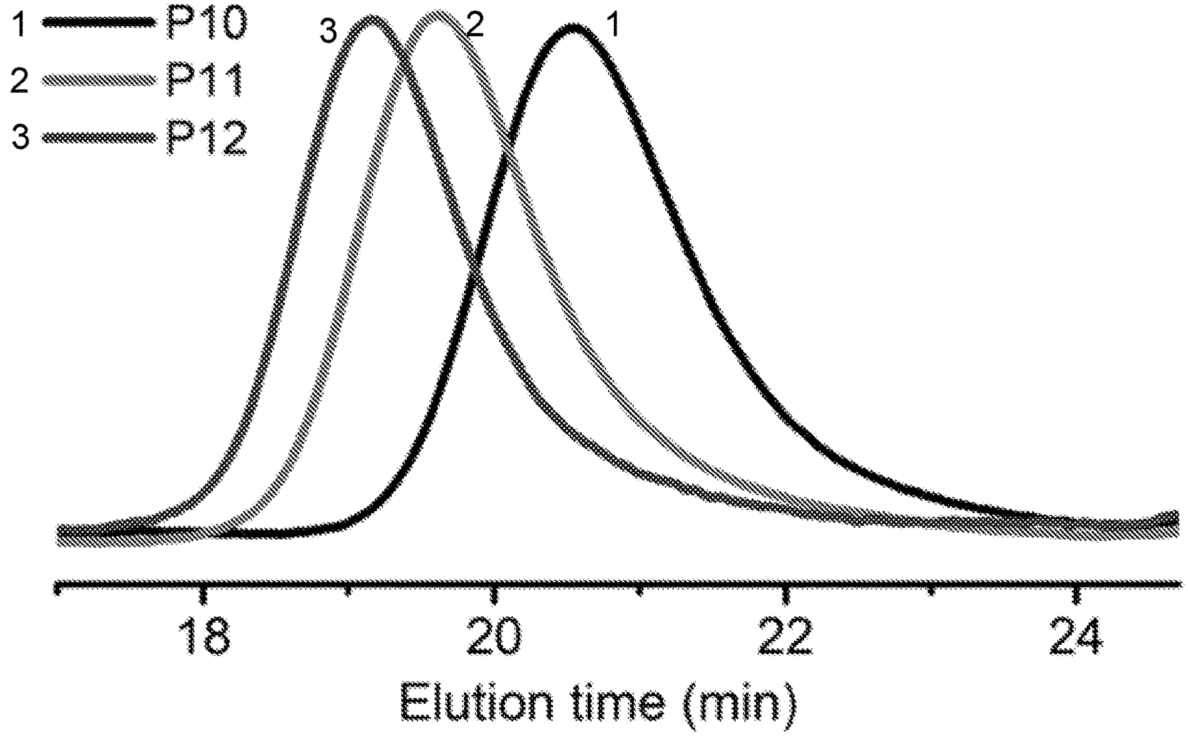
FIG. 31. GPC traces of poly(PepAm-co-DMA) (P10-P12) prepared by aqueous photo-electron transfer RAFT polymerization. Please refer to Table 3 for the information of molecular weights and dispersity of each polymer.
Figure 32:
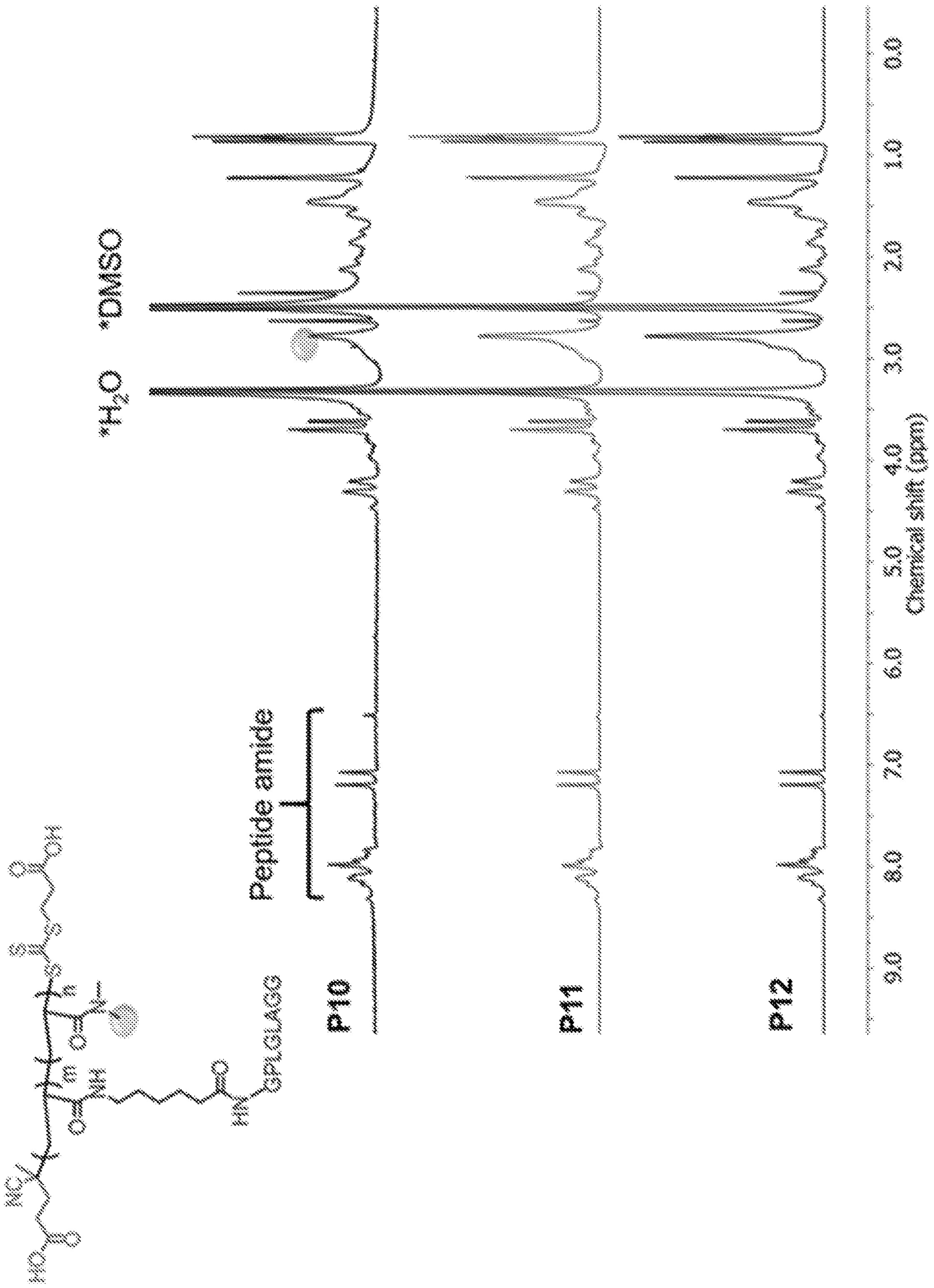
FIG. 32. $^1$H NMR spectra of poly(PepAm-co-DMA) (P10-P12) in $d_6$-DMSO at 25° C. (GPLGLAGG is SEQ ID NO:5.)

The ability to conduct polymerizations directly in water is of significant interest to the field of biomedical polymer materials, as it not only avoids the use of toxic organic solvents but also eliminates the time-consuming step of transferring the polymeric materials from the organic to aqueous phase. To explore the feasibility of aqueous photo-RDRP of peptide monomers, we examined the photo-RDRP of both enzyme-responsive peptide acrylamide (PepAm) and pro-apoptotic KLA peptide acrylamide (KLAAm) in water. Table 3 summarizes the polymerization results for PepAm and DMA, indicating dramatically higher monomer conversions in water compared to those obtained by photo-polymerizations in DMSO (Table 1). We hypothesize that this is due to the hydrogen bonding between the amide carbonyl groups with water molecules, leading to enhanced solubility of PepAm in aqueous solution.[24] Polymers (P10-P12) were analyzed by GPC and NMR (FIGS. 30-32) and showed molecular weights that were in good agreement with theoretical values, confirming that photo-RDRP of PepAm was unaffected under aqueous conditions.

TABLE 3

Aqueous photo-RDRP of PepAm and DMA

| | Equiv. to CTA | | | Conv. (%) | | $M_{n,\ theo}$ | $M_{n,\ GPC}$ | |
|---|---|---|---|---|---|---|---|---|
| Entry | PepAm | DMA | $[M]_0$ | PepAm | DMA | (g/mol) | (g/mol) | Đ |
| $^a$P10 | 50 | 50 | 0.36M | 60% | 64% | 27 685 | 26 100 | 1.06 |
| $^a$P11 | 50 | 100 | 0.54M | 87% | 85% | 44 230 | 48 700 | 1.01 |
| $^a$P12 | 50 | 150 | 0.72M | 92% | 94% | 51 388 | 55 400 | 1.04 |

Note:
In each polymerization, 200 μL of DMSO was used.
[M]/[CTA]/[EY]/[PMDETA] = X/1/0.05/1.
$^a$The polymerizations were triggered by blue LED.

Figure 4A:
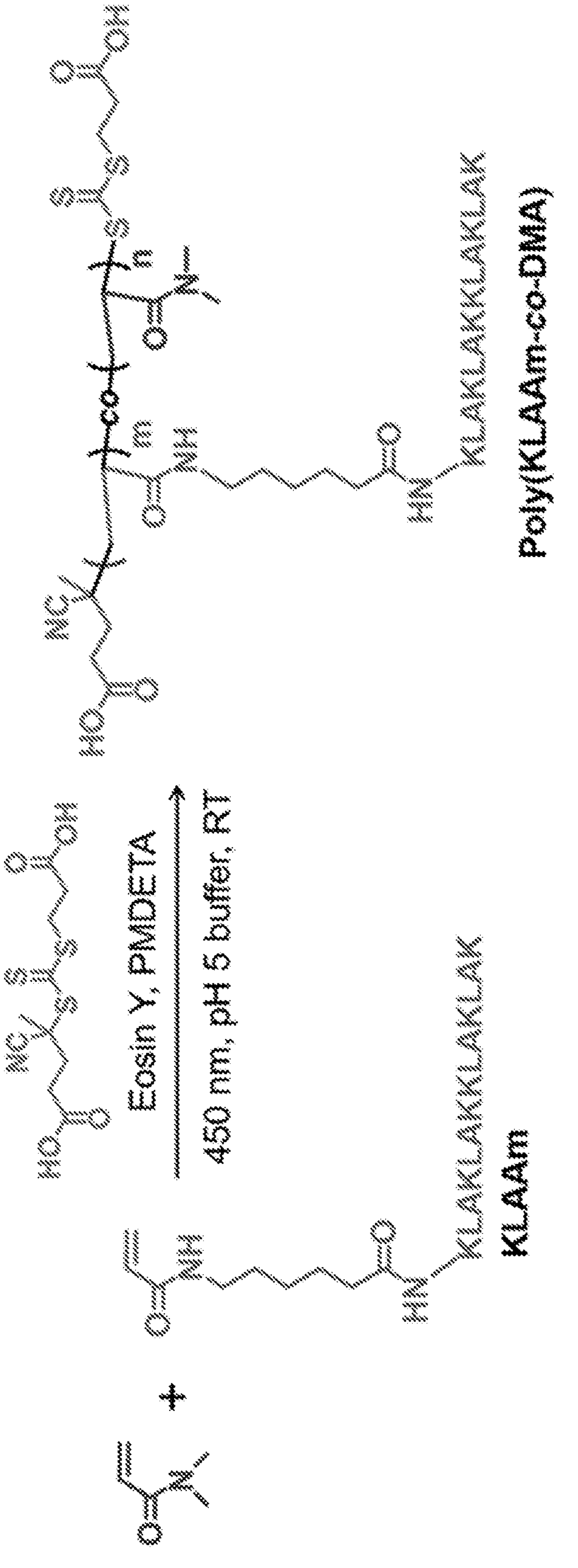
FIG. 4A. Aqueous photo-RDRP of KLAAm and DMA in acidic buffer (pH 5).
Figure 4B:
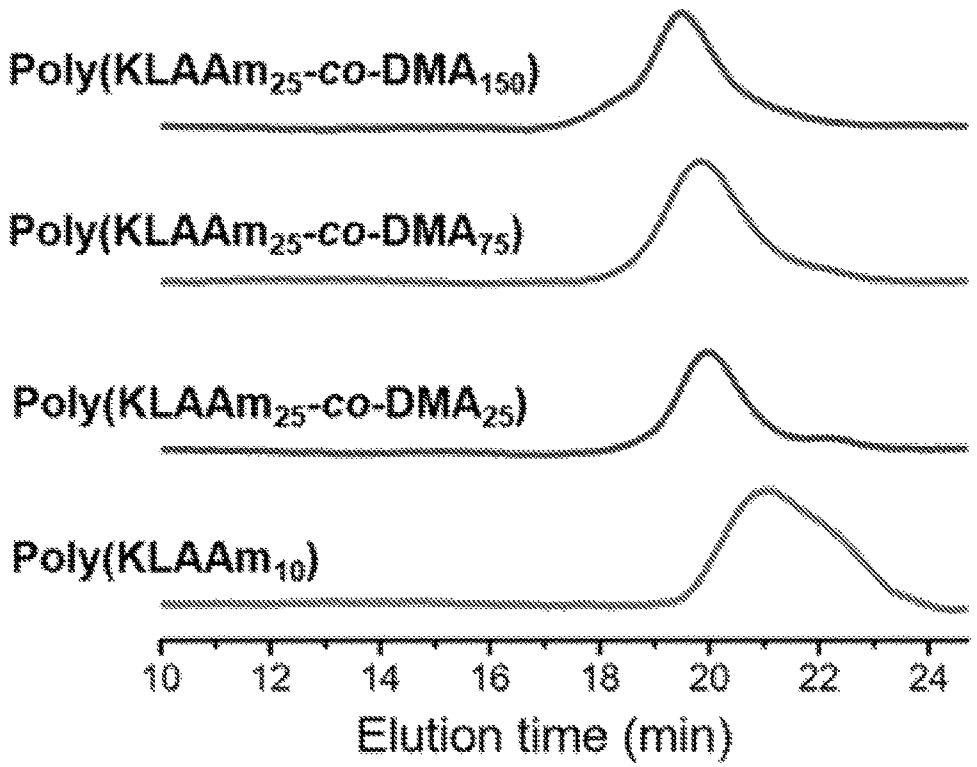
FIG. 4B. GPC traces of KLA based peptide brush polymers with different grafting densities (P13-P16, Table 4).
Figure 4C:
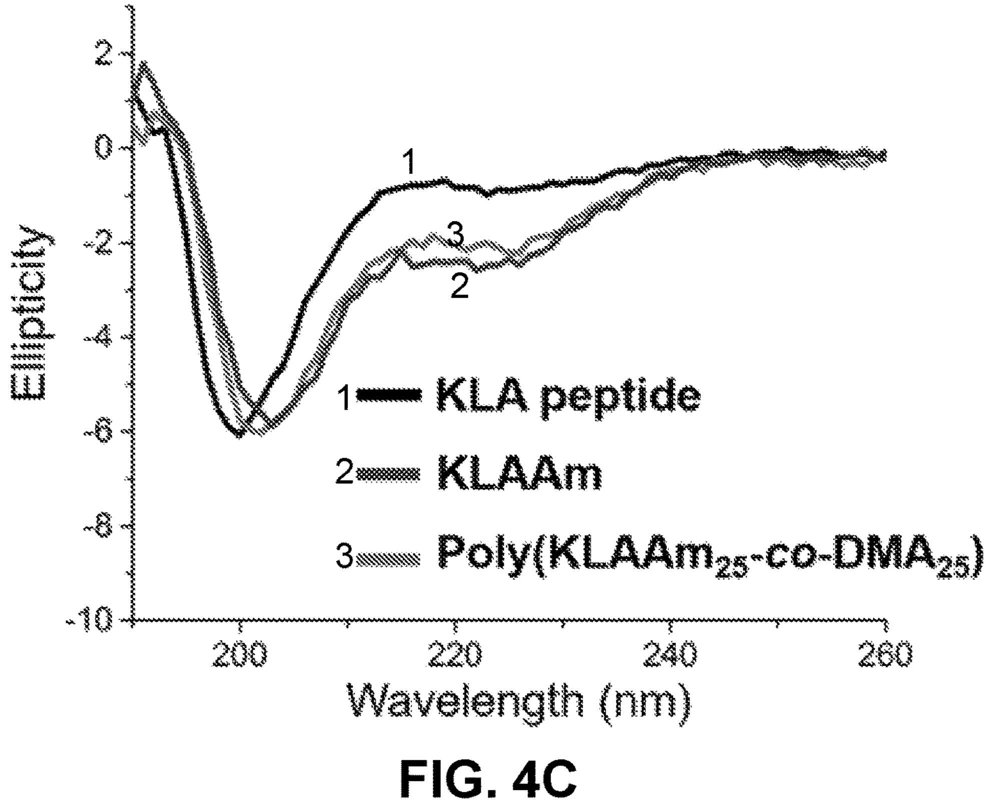
FIG. 4C. Circular dichroism spectra of KLA peptide, KLAAm, and representative polymer: poly (KLAAm$_{25}$-co-DMA$_{25}$). (KLAKLAKKLAKLAK is SEQ ID NO:3.)
Figure 5A:
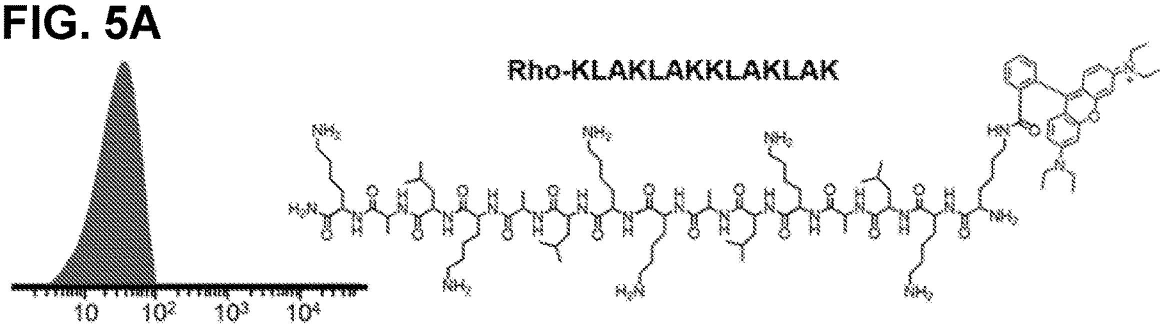
FIGS. 5A-5D. Flow cytometry analysis ($\lambda_{ex/em}$=548/570 nm) of HeLa cells incubated with rhodamine B-labeled KLA peptide (FIG. 5A), poly(KLAAM$_{25}$-co-DMA$_{75}$) (FIG. 5B), poly(KLAAM$_{25}$-co-DMA$_{25}$) (FIG. 5C), and poly (KLAAM$_{10}$) (FIG. 5D) at a concentration of 0.25 μM with respect to the dye. Chemical structures of each dye-labeled materials are shown adjacent to the corresponding histogram. KLA based peptide brush polymers possessed markedly higher cell uptake ability than that of KLA peptide. (KLAKLAKKLAKLAK is SEQ ID NO:3.)
Figure 5B:
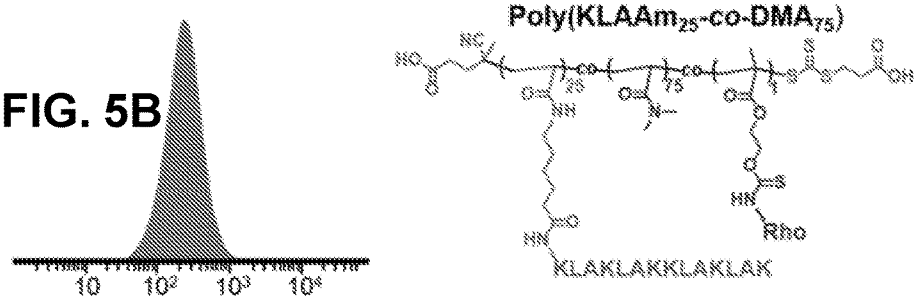
Figure 5C:
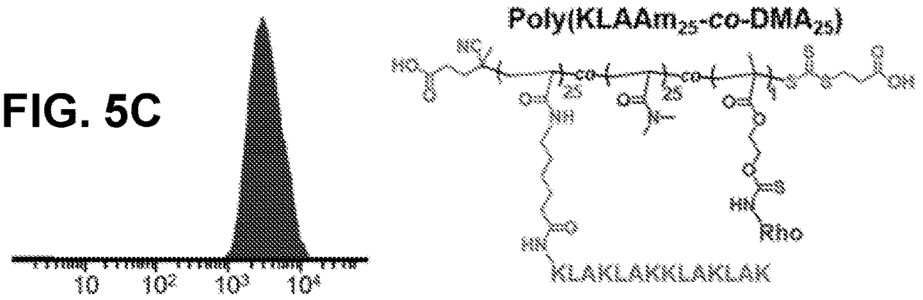
Figure 5D:
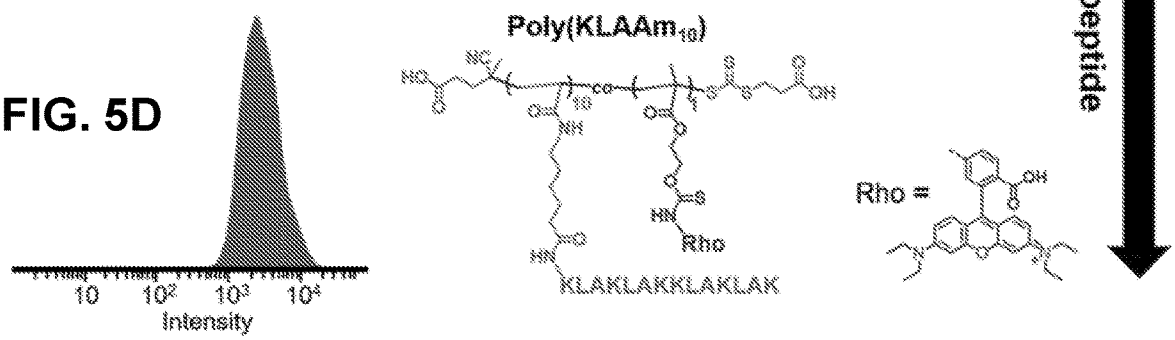
Figure 6A:
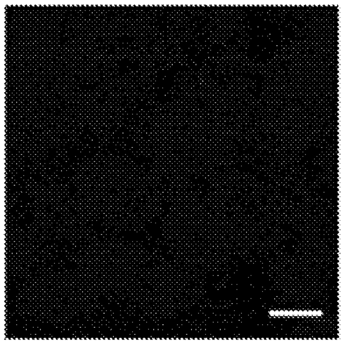
FIGS. 6A-6L. Confocal laser scanning microscopy images of Hela cells treated with rhodamine-labeled peptide based materials at a concentration of 0.25 μM with respect to rhodamine B ($\lambda_{ex/em}$=548/570 nm). From top to bottom: KLA peptide (FIGS. 6A-6C), poly(KLAAm$_{25}$-co-DMA$_{75}$) (FIGS. 6D-6F), poly(KLAAm$_{25}$-co-DMA$_{25}$) (FIGS. 6G-61), and poly(KLAAm$_{10}$) (FIGS. 6J-6L). Cell nuclei were stained with 4', 6-diamidino-2-phenylindole (DAPI, $\lambda_{ex/em}$=360/460 nm). Cell membrane was stained with wheat germ agglutinin, Alexa Fluor 488 conjugate (WGA 488, $\lambda_{ex/em}$=495/519 nm). Scale bar: 20 μm, inset scale bar 10 μm.
Figure 6B:
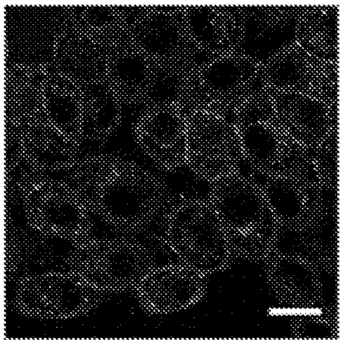
Figure 6C:
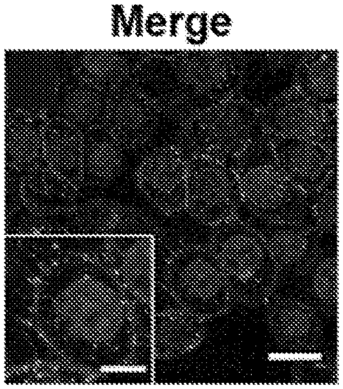
Figure 6D:
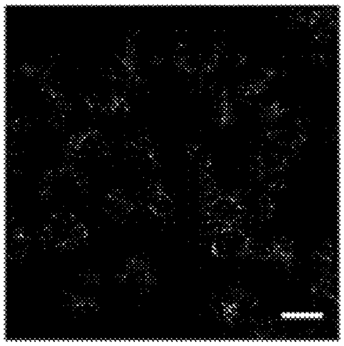
Figure 6E:
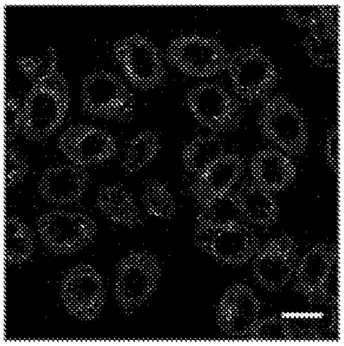
Figure 6F:
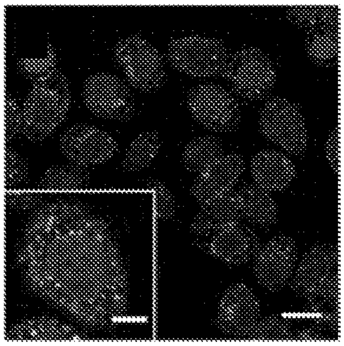
Figure 6G:
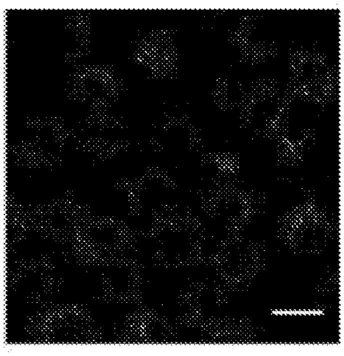
Figure 6H:
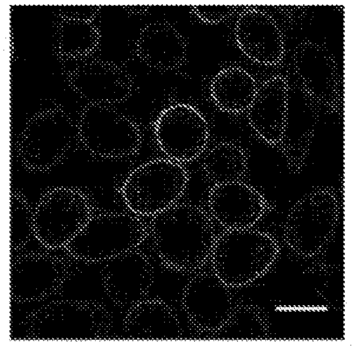
Figure 6I:
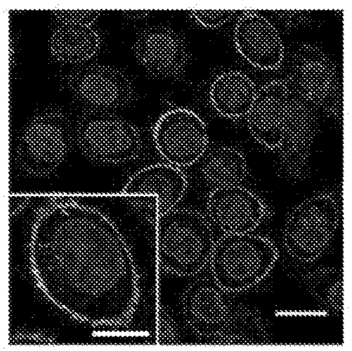
Figure 6J:
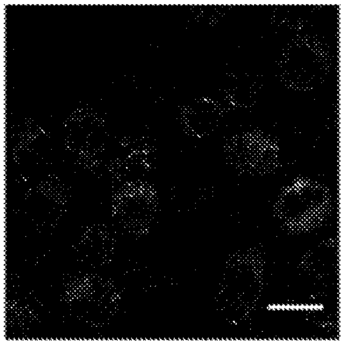
Figure 6K:
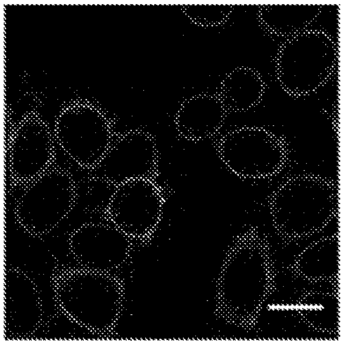
Figure 6L:
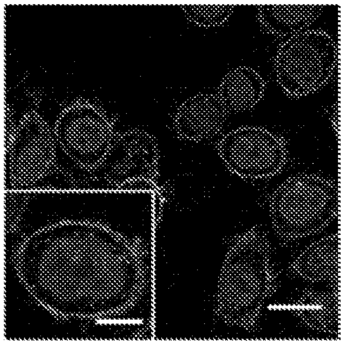
Figure 33:
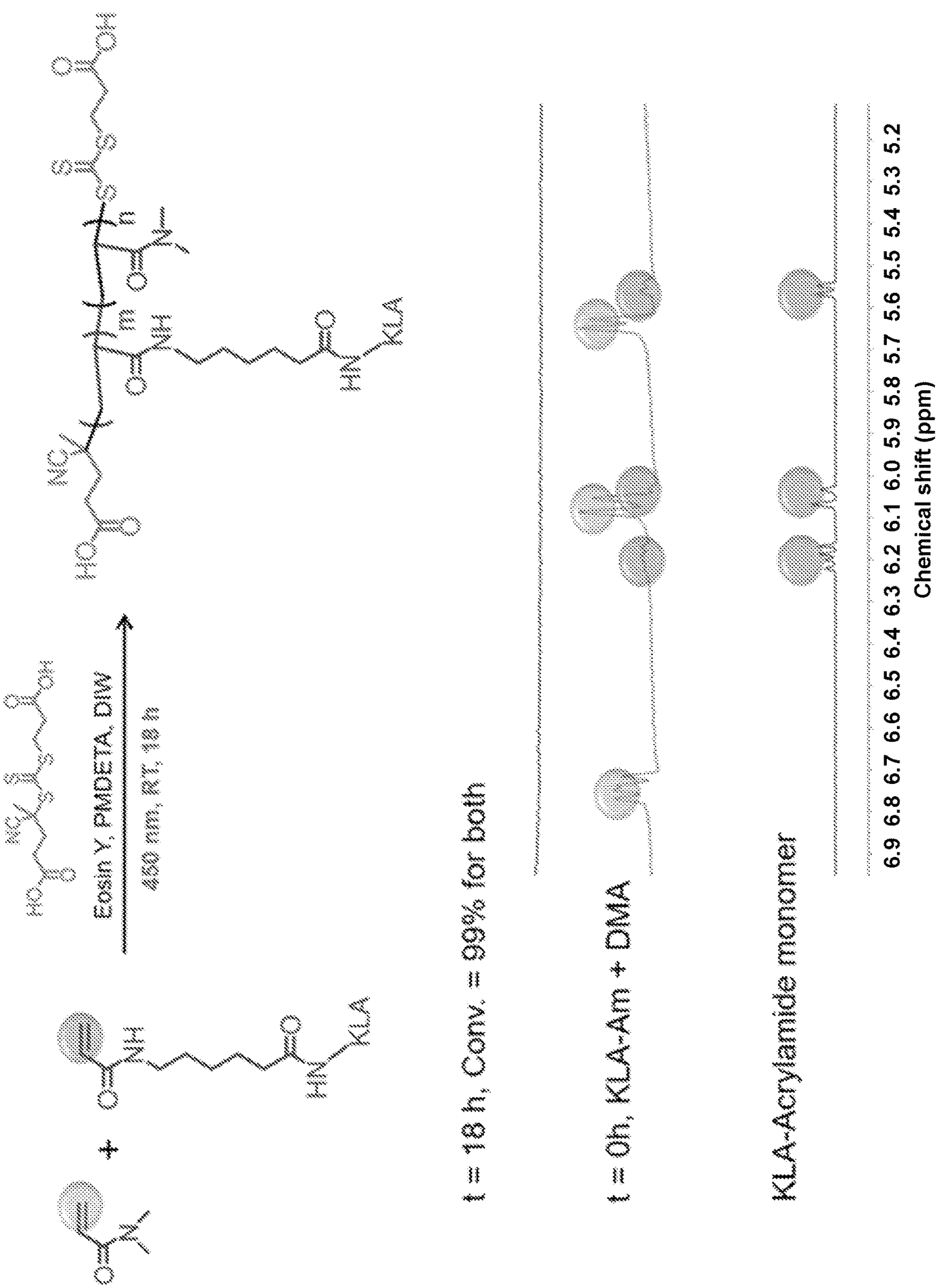
FIG. 33. $^1$H NMR spectra of reaction mixture (P14) before and after photo-polymerization in DIW. The full diminishment in vinyl proton signals (5.4 to 6.8 ppm) indicated quantitative monomer conversions were achieved for both KLA acrylamide and DMA. (KLA is the peptide KLAKLAKKLAKLAK (SEQ ID NO:3).)
Figure 34:
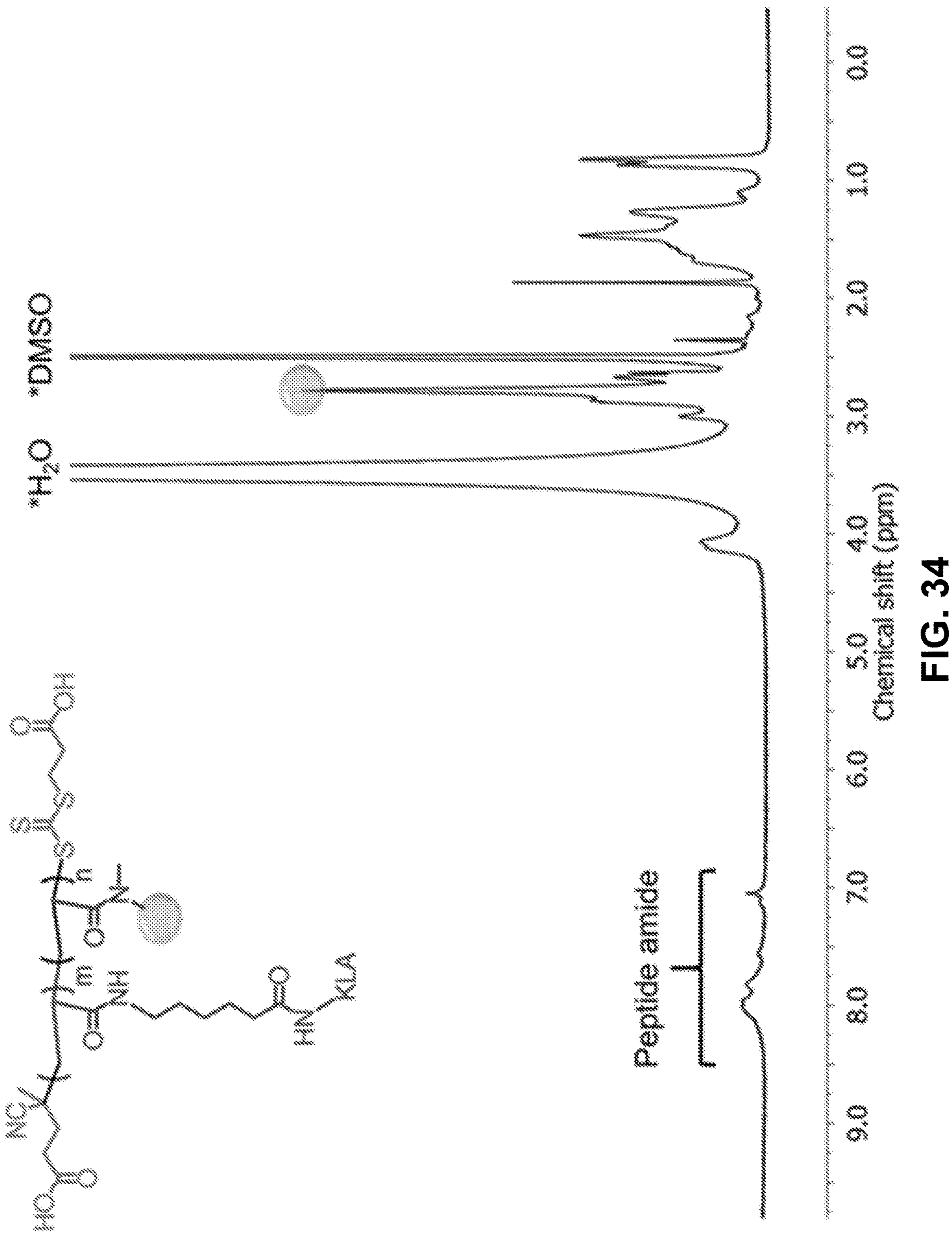
FIG. 34. $^1$H NMR spectrum of poly($KLAAm_{25}$-co-$DMA_{25}$) (P14) in $d_6$-DMSO at 25° C. (KLA is the peptide KLAKLAKKLAKLAK (SEQ ID NO:3).)
Figure 35:
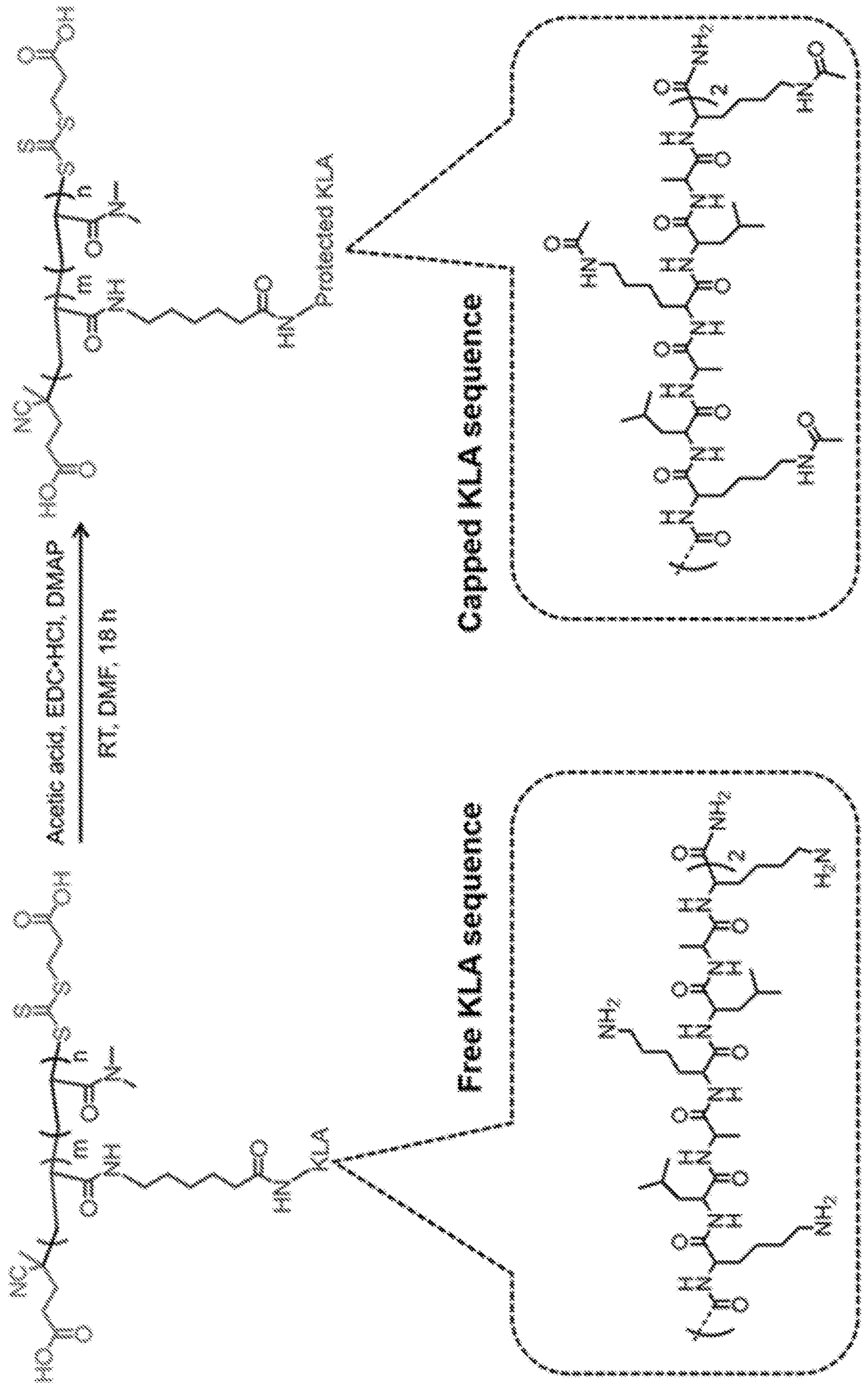
FIG. 35. Schematic of the N-acetylation of KLA based polypeptide brushes. (KLA is the peptide KLAKLAKKLAKLAK (SEQ ID NO:3).)
Figure 36:
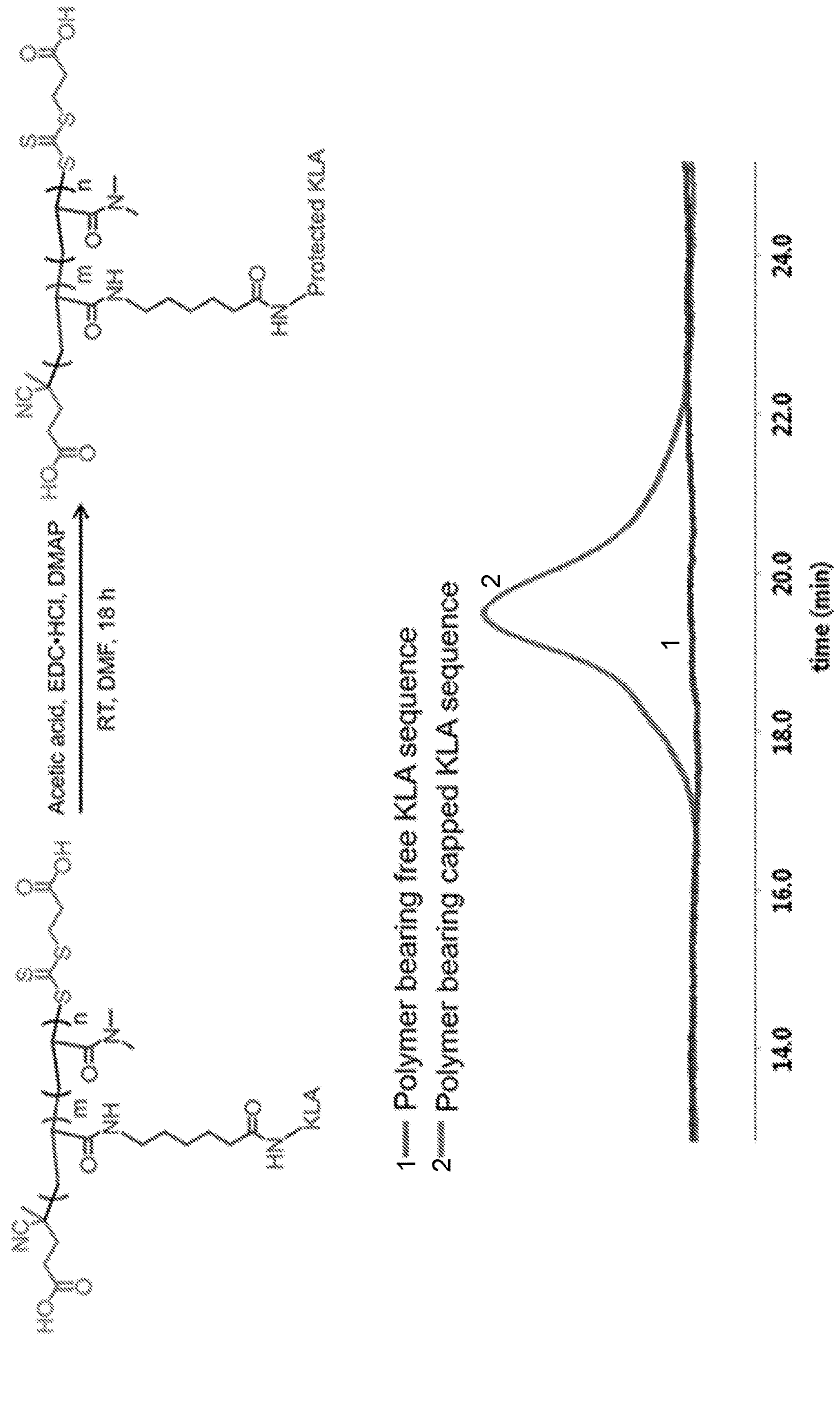
FIG. 36. GPC traces of poly($KLAAm_{25}$-co-$DMA_{150}$) (P16) before and after N-acetylation. The protection of amines eliminated the interactions between polymers and the GPC columns, allowing for accurate evaluation of the number-average molecular weights from these amine-abundant polymers. (KLA is the peptide KLAKLAKKLAKLAK (SEQ ID NO:3).)
Figure 37:
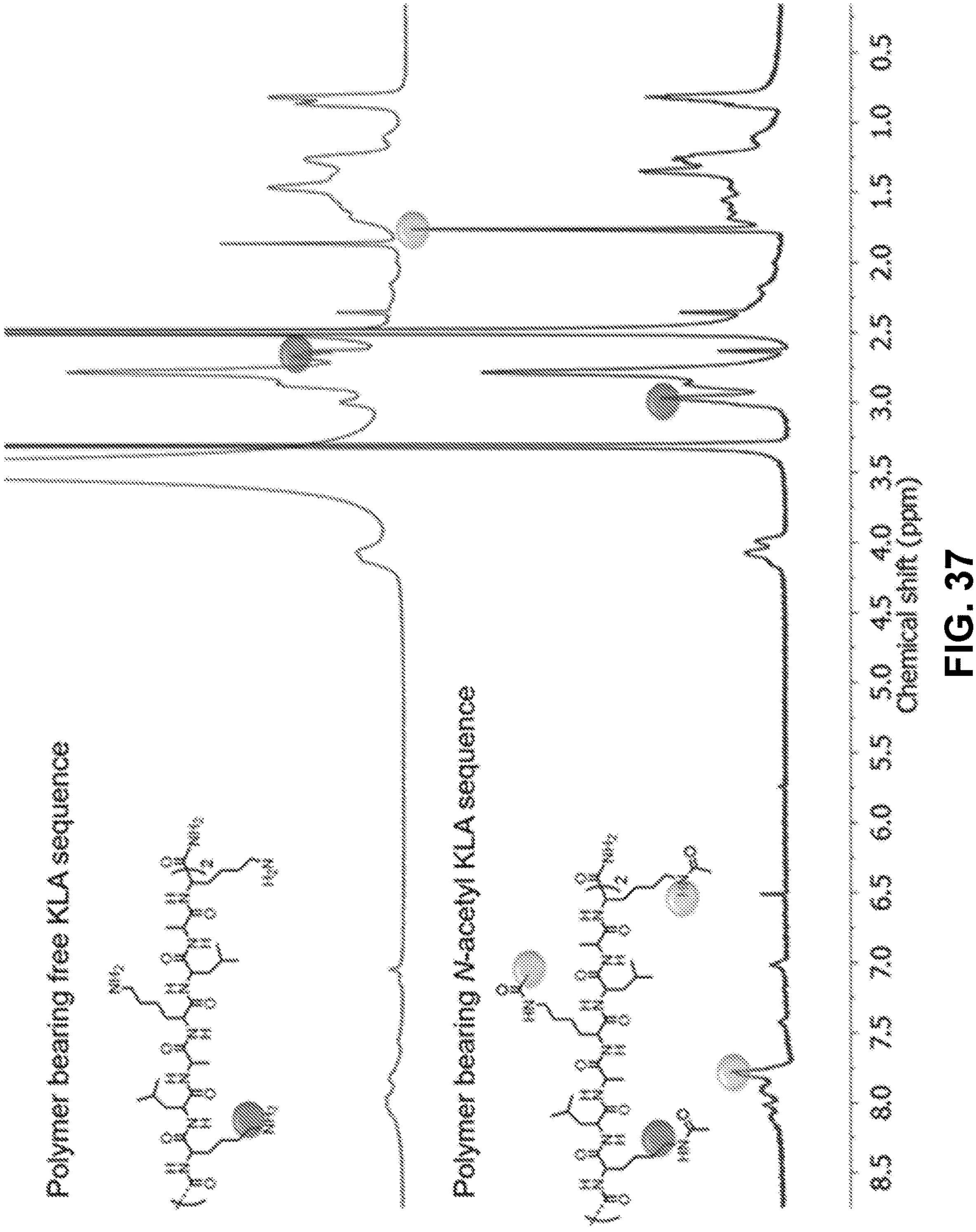
FIG. 37. $^1$H NMR spectra of poly($KLAAm_{25}$-co-$DMA_{150}$) (P16) before and after N-acetylation.
Figure 38:
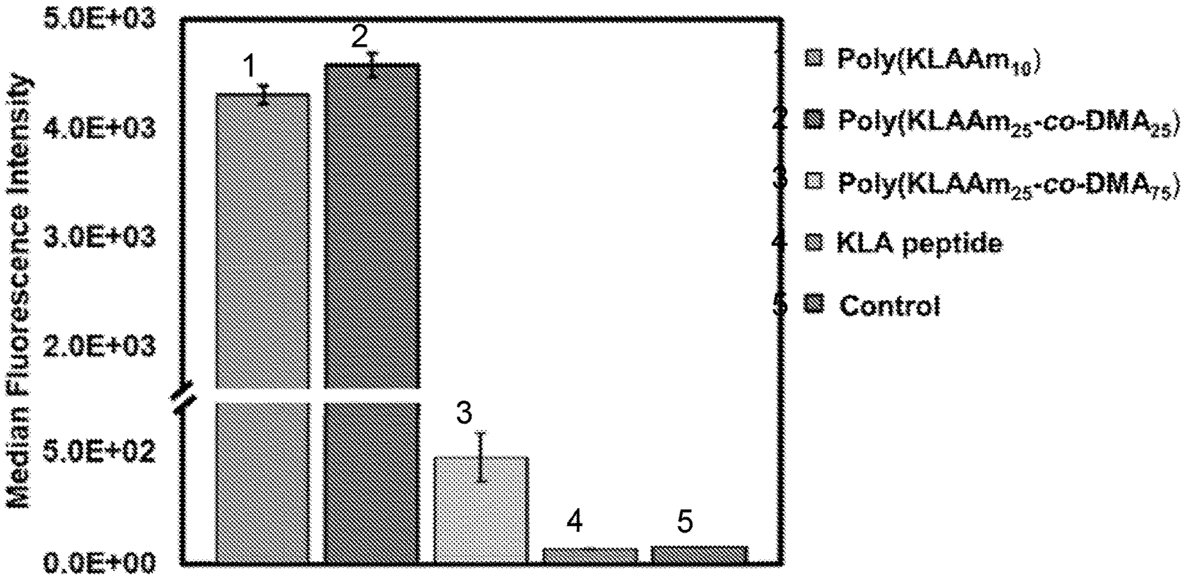
FIG. 38. Evaluating cellular uptake ability of KLA based materials using flow cytometry: quantification of rhodamine fluorescence intensity of KLA based materials in Hela cells. The concentration of each material was set to 0.25 μM with respect to Rhodamine B. (data represent mean±s.d., n=3 independent experiments).
Figure 39:
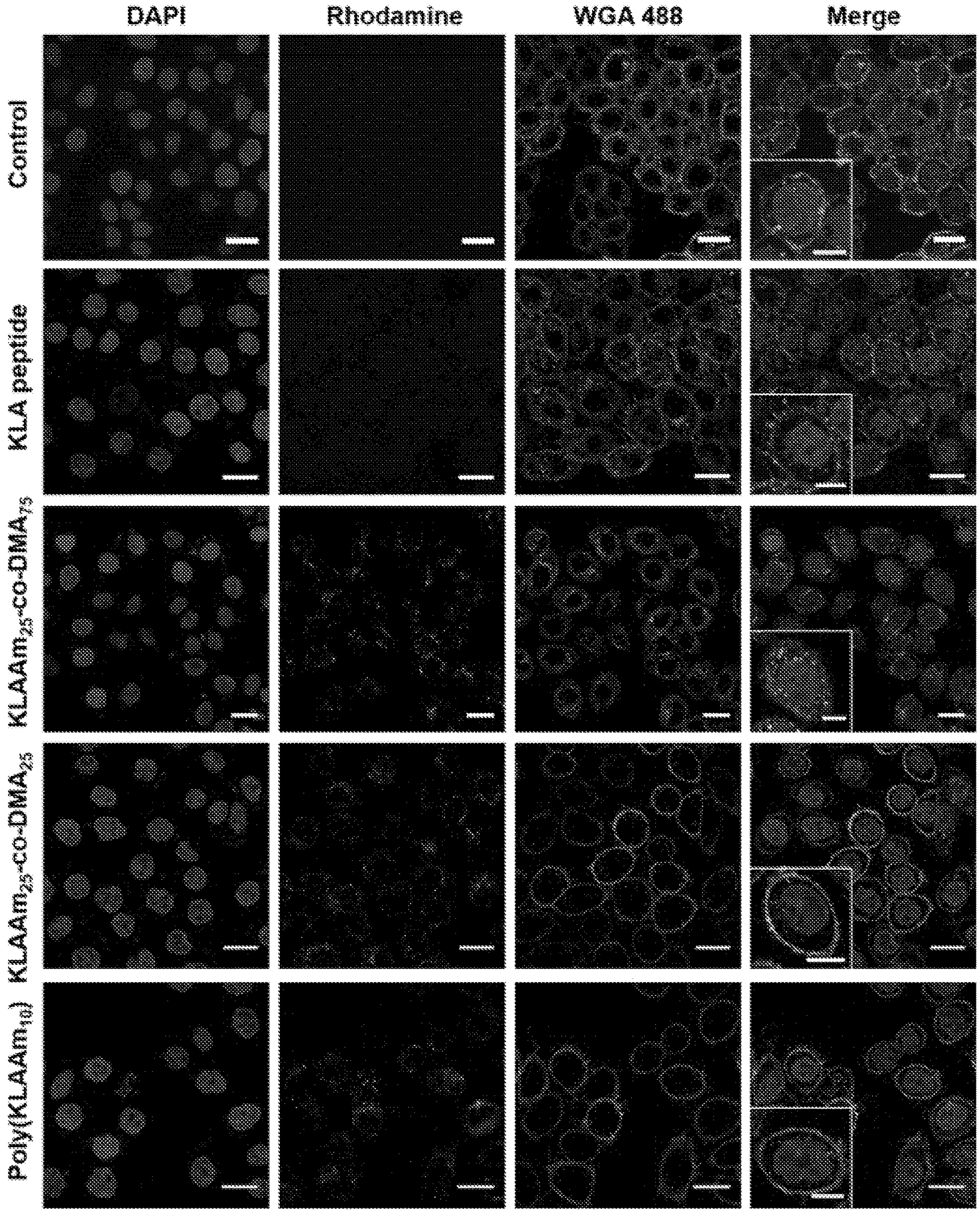
FIG. 39. Confocal microscopy images of Hela cells incubated with rhodamine-labeled KLA peptide, poly($KLAAm_{10}$), poly($KLAAm_{25}$-co-$DMA_{25}$), and poly ($KLAAm_{25}$-co-$DMA_{75}$) at a concentration of 0.25 μM with respect to Rhodamine. Cell nuclei were stained with DAPI. Cell membrane was stained with WGA 488. Scale bar: 20 μm, insert scale bar 10 μm.
Figure 40:
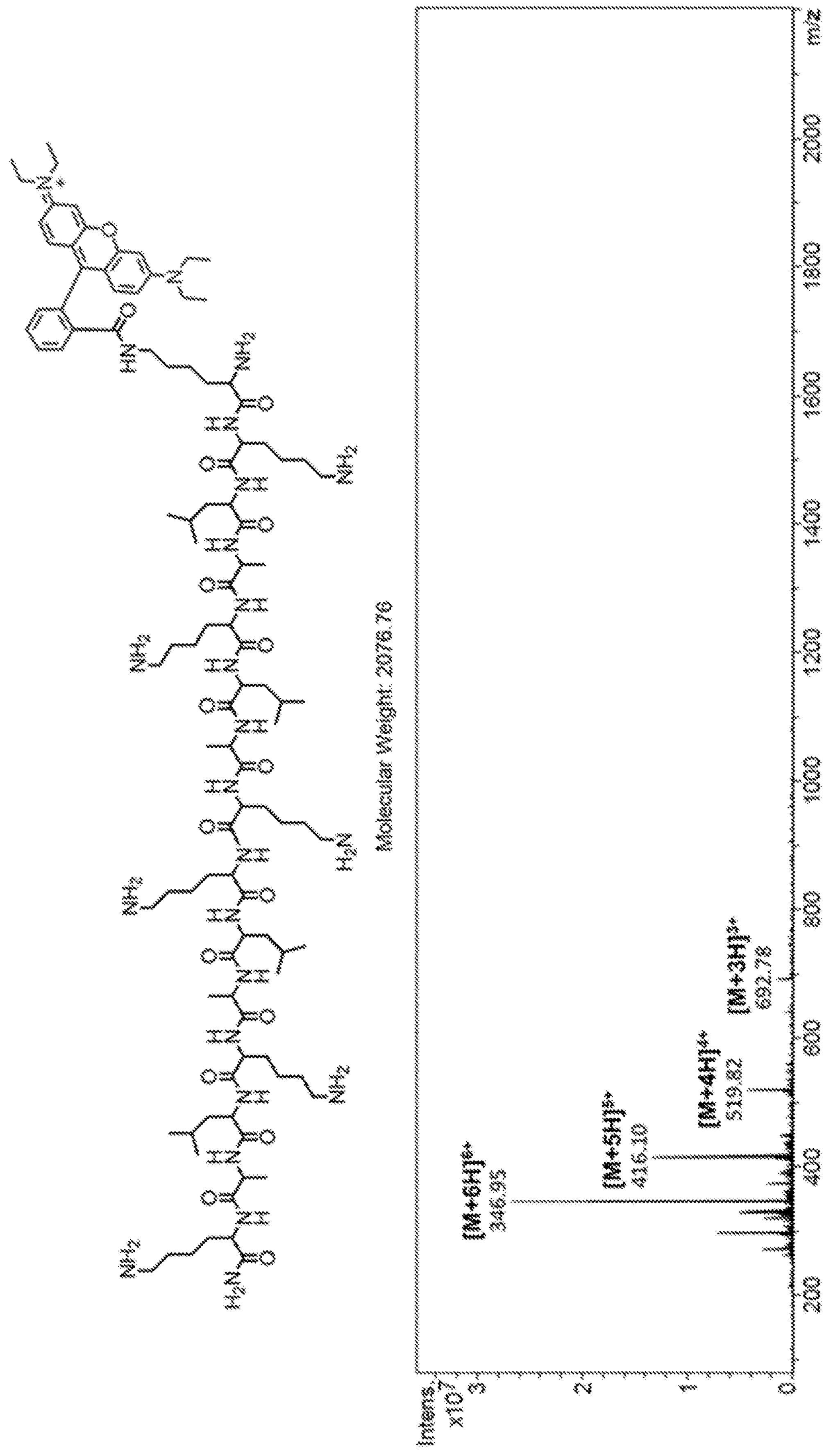
FIG. 40. ESI-Mass spectrum of rhodamine B labeled KLA peptide (Rho-KLA).
Figure 41:
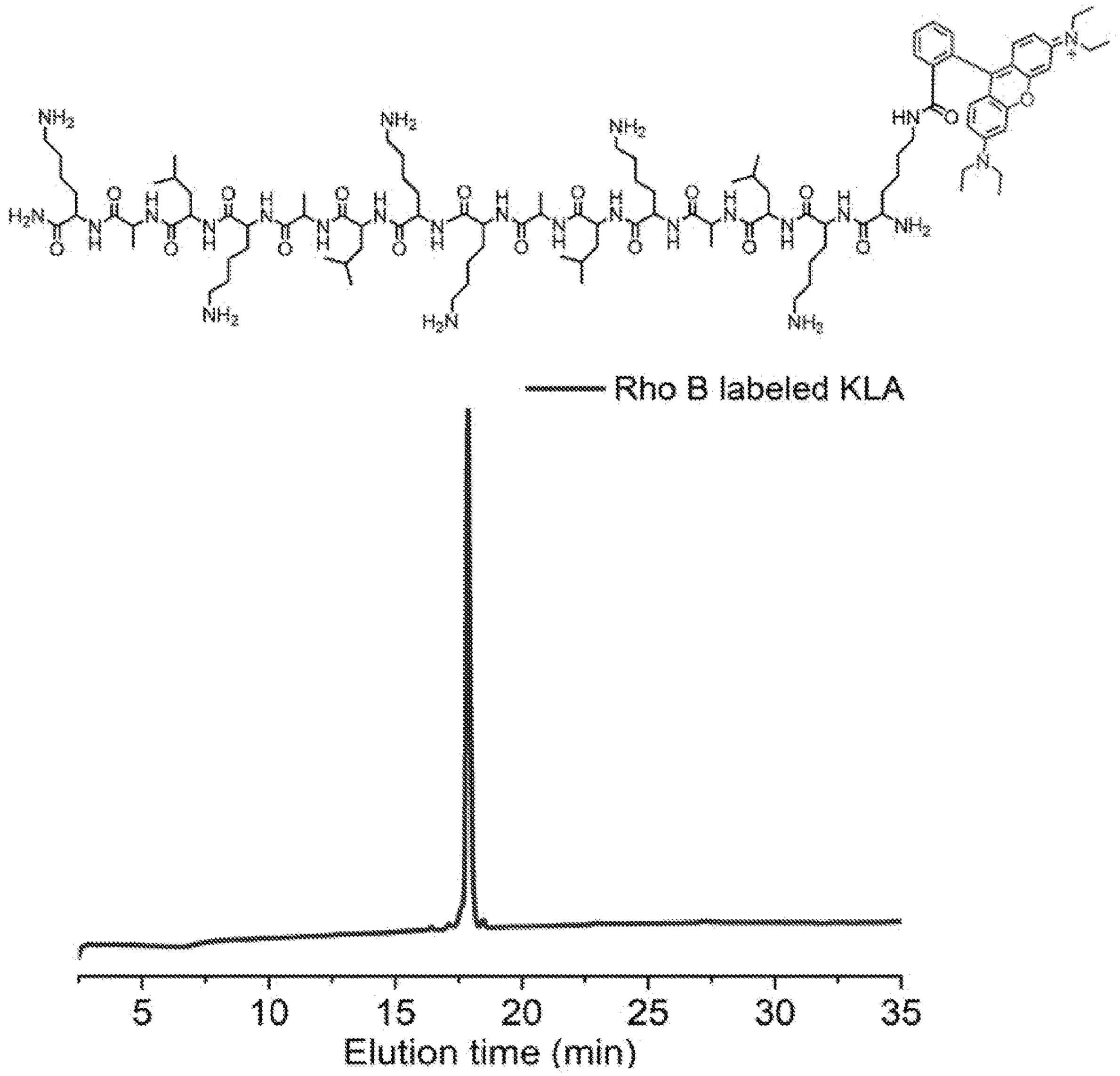
FIG. 41. HPLC trace of rhodamine B labeled KLA peptide.

For the KLAAm monomer, which contains abundant amine groups, acetate buffer (pH 5) was utilized to fully protonate the amine groups, reducing their nucleophilicity (pKa=9) and thus precluding undesired aminolysis of the chain transfer agents (FIGS. 4A-4C). By adjusting the feed ratio of DMA to KLAAm, polypeptide brushes with various grafting densities of KLA side chains were prepared (Table 4, P13-P16). Based on NMR analysis, monomer conversions were quantitative for all random copolymerizations of DMA and KLAAm (FIGS. 33-34). However, the homopolymerization of KLAAm led to a modest monomer conversion (40%) possibly due to the steric bulk of the KLA peptide macromonomer. The narrow and symmetric GPC traces of KLA based polypeptide brushes indicates good control over the aqueous photo-RDRP of KLAAm (FIG. 4B, FIGS. 36-37). Furthermore, the secondary structure of KLA peptides and brush polymers were assessed by circular dichroism (CD) spectroscopy, which showed a mixture of α-helix and random coil. The CD spectra of the KLA monomer and resulting polymers are identical, suggesting the polymerization process does not alter the secondary structure of the peptide (FIG. 4C).

TABLE 4

Aqueous photo-RDRP of KLA-acrylamide (KLAAm) and DMA

| | Equiv. to CTA | | | Conv. (%) | | $M_{n,\ theo}$ | $M_{n,\ GPC}$ | |
|---|---|---|---|---|---|---|---|---|
| Entry | KLAAm | DMA | $[M]_0$ | KLAAm | DMA | (g/mol) | (g/mol) | Đ |
| $^a$P13 | 25 | 0 | 0.09M | 40% | N/A | 17 207 | 24 100 | 1.09 |
| $^a$P14 | 25 | 25 | 0.18M | 98% | 99% | 45 032 | 48 200 | 1.03 |

TABLE 4-continued

| Aqueous photo-RDRP of KLA-acrylamide (KLAAm) and DMA | | | | | | | | |
|---|---|---|---|---|---|---|---|---|
| | Equiv. to CTA | | | Conv. (%) | | $M_{n,\ theo}$ | $M_{n,\ GPC}$ | |
| Entry | KLAAm | DMA | $[M]_0$ | KLAAm | DMA | (g/mol) | (g/mol) | Đ |
| [a]P15 | 25 | 75 | 0.36M | 99% | 99% | 49 982 | 53 600 | 1.08 |
| [a]P16 | 25 | 150 | 0.72M | 99% | 99% | 57 407 | 62 400 | 1.16 |

Note:
In each polymerization, 200 μL of acetate buffer (0.1M, pH 5) was used.
[M]/[CTA]/[EY]/[PMDETA] = X/1/0.05/1.
[a]The polymerizations were triggered by blue LED.

Figure 7:
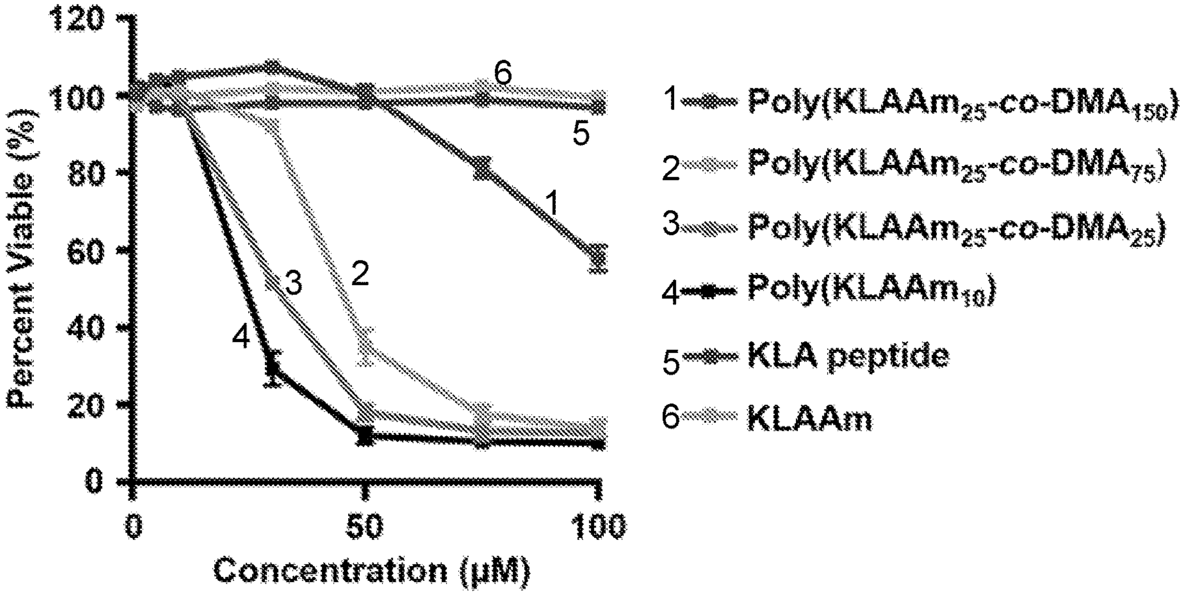
FIG. 7. Cell viability assay of KLA peptide, KLAAm, and a library of KLA based peptide brush polymers with different grafting densities. Hella cells were treated with peptide based materials and incubated for 72 hours at 37° C. (CellTilter-Blue assay, n=3 independent experiments with three independent samples in each). KLA peptide and KLAAm did not exhibit cytotoxicity to Hela Cells even at a concentration of 100 μM. The IC$_{50}$ value of peptide brush polymers decreased as the grafting density of peptide brush polymer increased, indicating a higher cytotoxicity of KLA peptide brush polymers with a more compact brush architecture.
Figure 8:
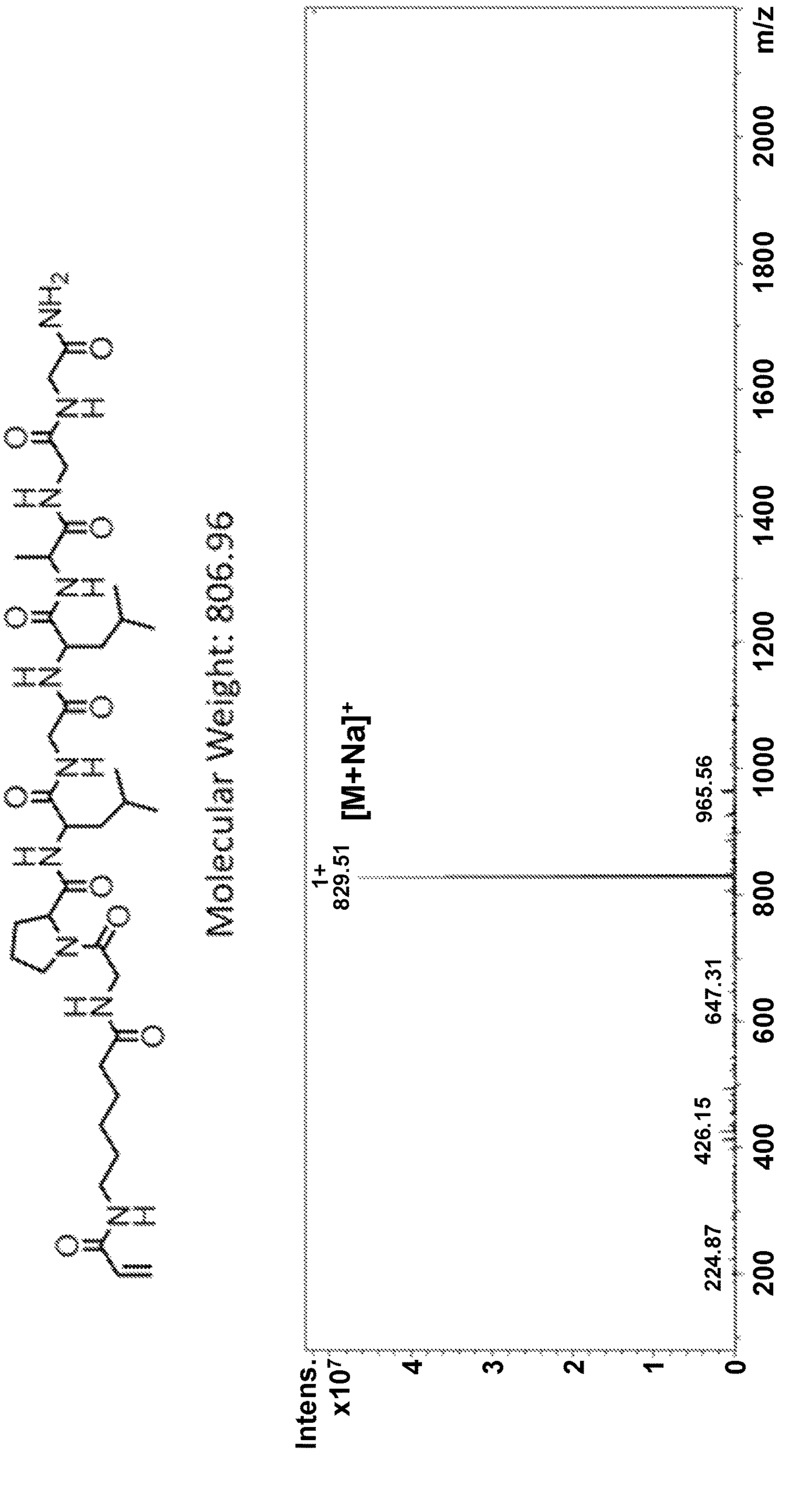
FIG. 8. ESI-Mass spectrum of enzyme-responsive peptide monomer.
Figure 9:
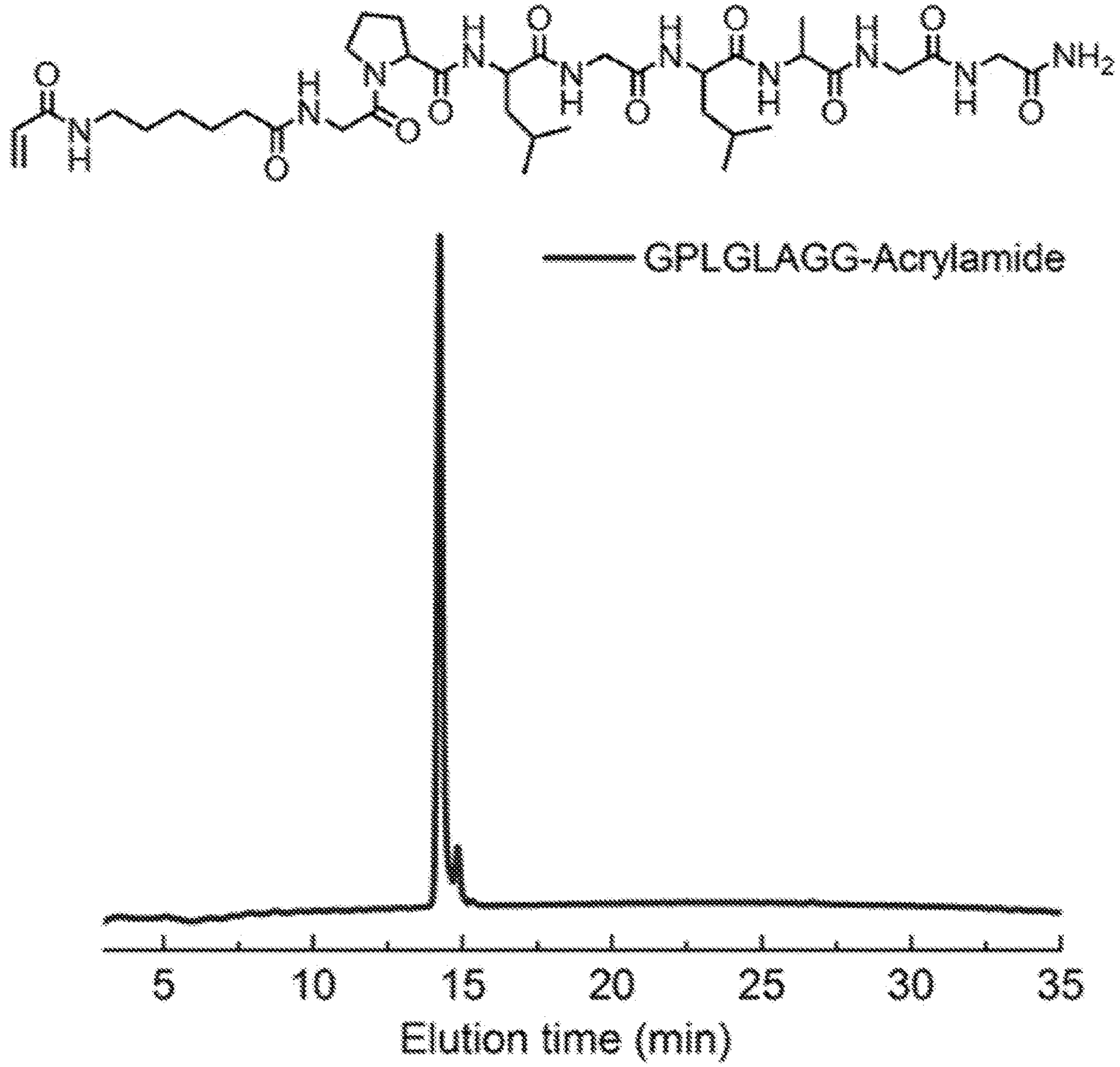
FIG. 9. HPLC trace of enzyme-responsive peptide monomer. (GPLGLAGG is SEQ ID NO:5.)
Figure 10:
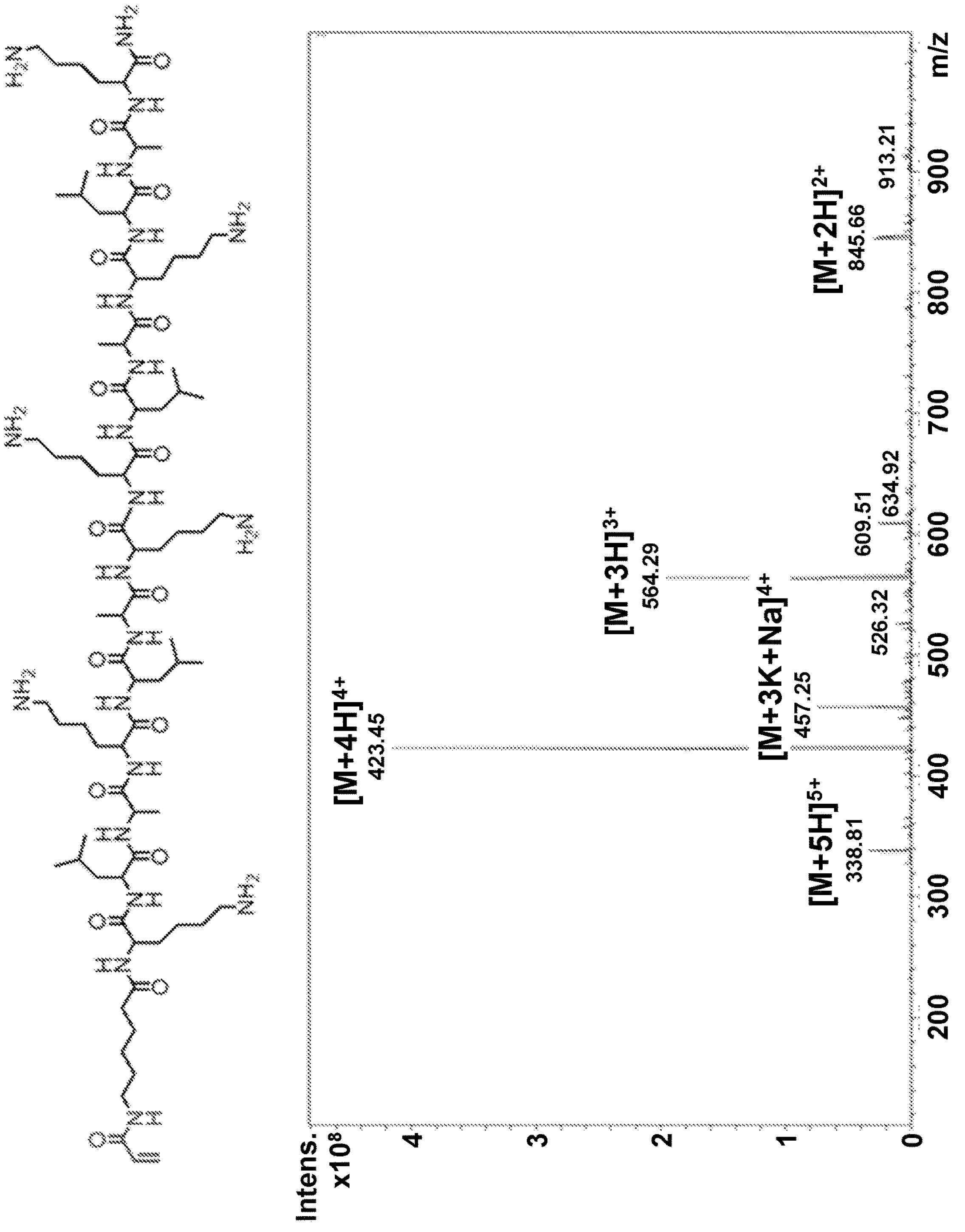
FIG. 10. ESI-Mass spectrum of KLA peptide acrylamide monomer.
Figure 11:
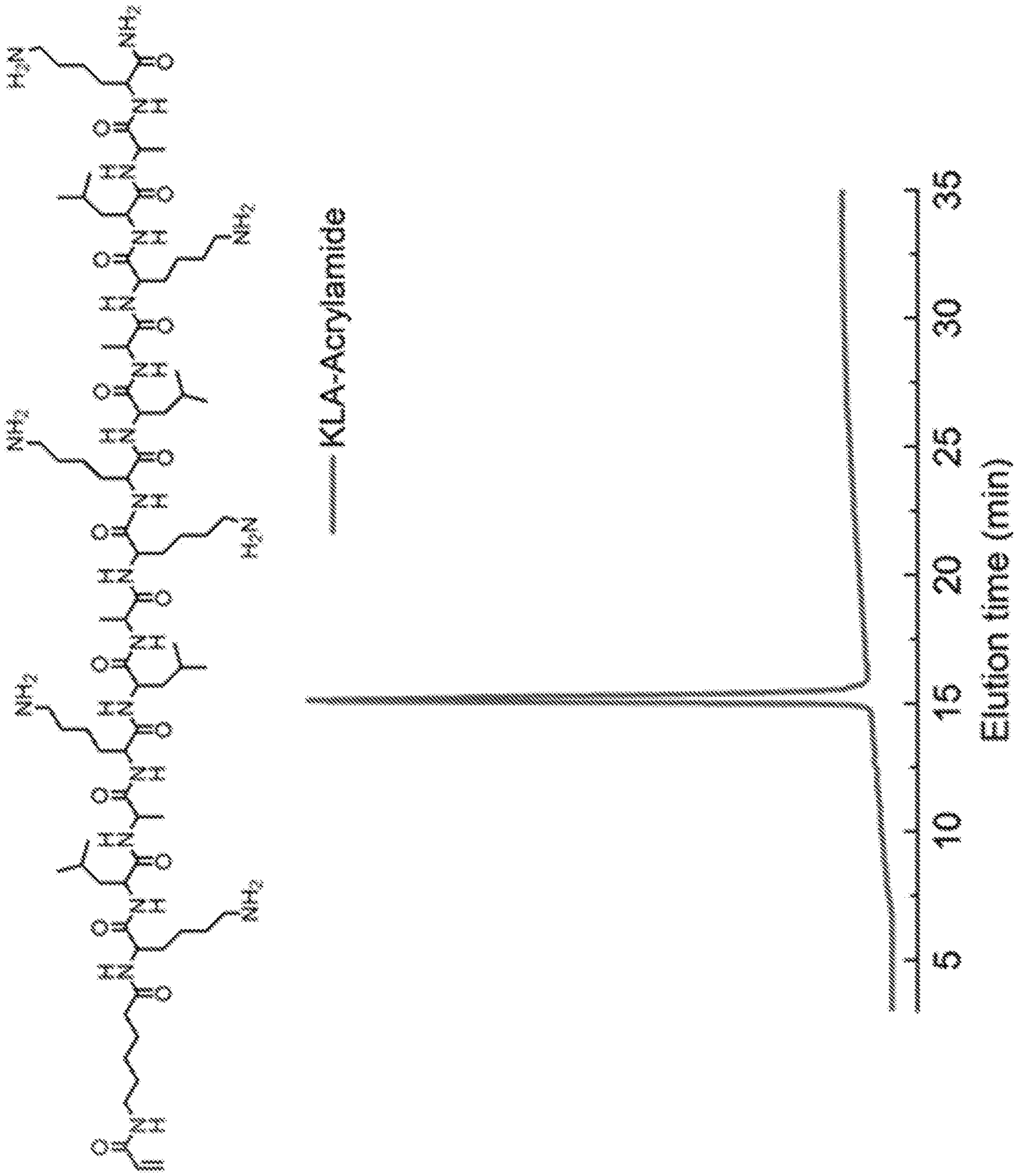
FIG. 11. HPLC trace of KLA peptide acrylamide monomer.
Figure 12:
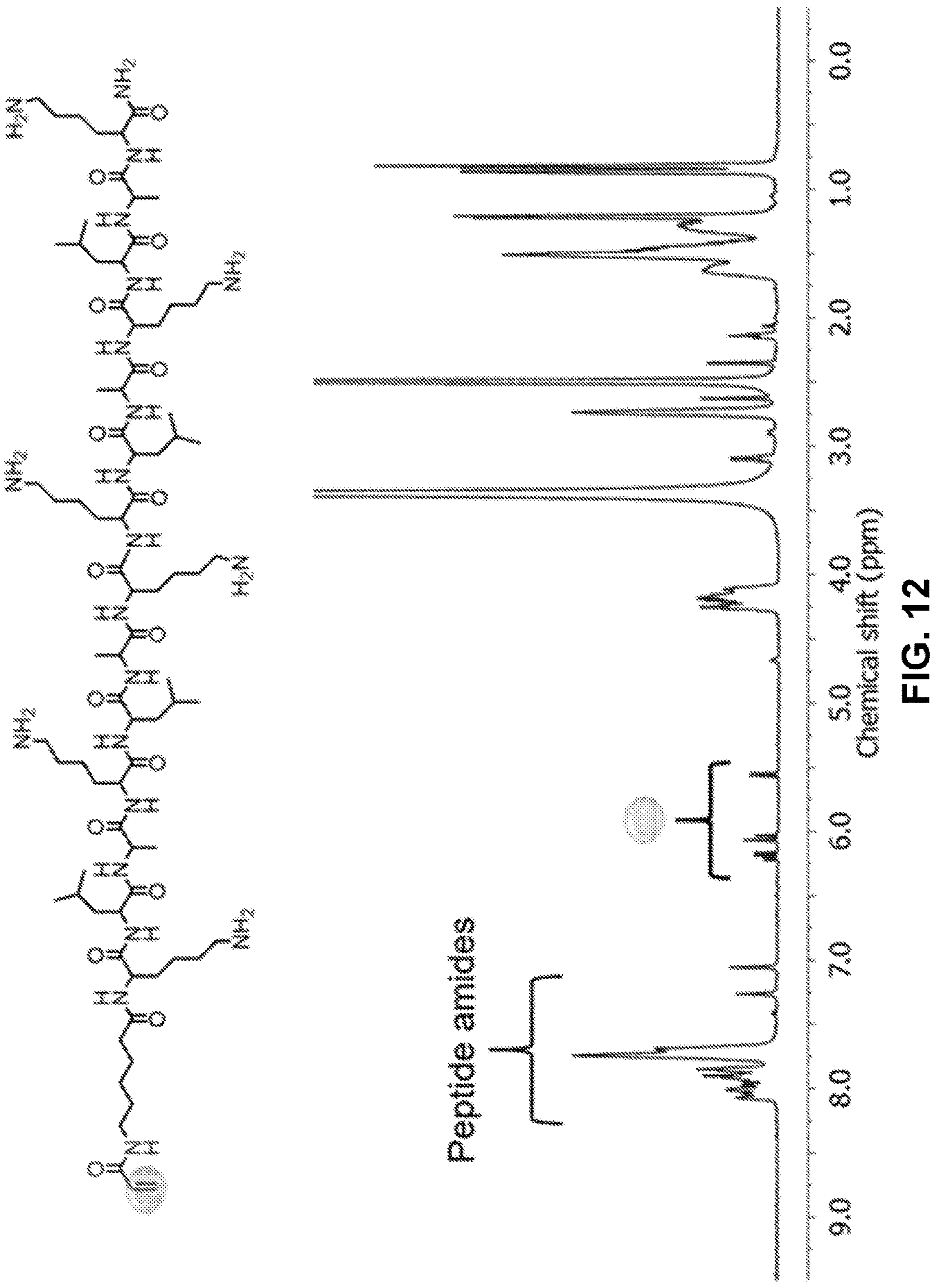
FIG. 12. $^1$H NMR spectrum of KLA peptide acrylamide monomer in d$_6$-DMSO at 25° C.

The KLA peptide sequence used in these studies is a known pro-apoptotic peptide which is capable of inducing cell apoptosis via disruption of mitochondrial membranes.[25] It is typically fused with a cell-penetrating peptide because of its otherwise poor cellular uptake.[26] The KLA based brush polymers, while lacking a cell-penetrating peptide moiety, collectively possess a number of cationic charges when polymerized, which could enhance the affinity to the negatively charged cell membrane and consequently promote delivery of the KLA based polymer brushes into cells.[16] To elucidate the role of KLA grafting densities on the cellular uptake and cytotoxicity of KLA brush polymers, we conducted in vitro cell studies of different brush polymers (P13-P16, Table 4) in HeLa cells (FIGS. 5-7). Flow cytometry was used to quantify the cell uptake efficiency of brush polymers. All KLA peptide brush polymers show significantly more cellular uptake compared to the free peptide (FIGS. 5A-5D). This observation is consistent with the multivalency of KLA peptides organized as polypeptide brushes, which enhanced the affinity and cell uptake of the KLA containing materials. In addition, cell internalization of densely grafted polypeptides including poly($KLAAm_{25}$-co-$DMA_{25}$) and poly($KLAAm_{10}$) clearly outperformed more sparsely grafted polypeptide brushes such as poly ($KLAAm_{25}$-co-$DMA_{75}$) (FIGS. 5A-5D and 38).

The cellular uptake behavior of KLA peptide and polymer brushes were further studied by confocal laser scanning microscopy (CLSM). Cells treated with rhodamine labeled KLA peptide showed no uptake even at a high concentration (50 μM with respect to peptide). On the other hand, the cellular uptake of all KLA peptide brush polymers was clearly visible at the same peptide concentration, as evidenced by the increase in rhodamine fluorescence in HeLa cells (FIGS. 6A-6L and 39). Finally, cytotoxicity assays demonstrated that KLA based polymer brushes had significantly higher cytotoxicity than either the free KLA peptide or the KLAAm monomer (FIG. 7). Notably, the cytotoxicity of polypeptide brushes was dependent on the grafting density of KLA peptides. As the grafting density of KLA peptide increased and the polymer brushes became more compact, the half-maximum inhibitory concentration $IC_{50}$ values decreased. These cytotoxicity results are consistent with the observed cellular uptake behavior of KLA brush polymers, further demonstrating the role of grafting density on the material properties.

Conclusion: In summary, we present examples of photo-RDRP of peptide acrylamide monomers. This is a robust synthetic approach to prepare bioactive polypeptide brushes under mild conditions using visible light, in aqueous solution, and at room temperature. We envision that a wide variety of other functional peptide monomers such as therapeutic and cell-penetrating peptides will be compatible with this technique. Moreover, we demonstrated the important role that the architecture (i.e., grafting density) of peptide brush polymers has on function such as cell penetration and cytotoxicity towards cancer cells. Given the widespread interest in peptides as therapeutics and targeting moieties in biomedicine, we envision these mild synthetic procedures will open the door to entirely new peptide brush polymer biomaterials.

EXPERIMENTAL EXAMPLES

Preparation of Peptide Vinyl Monomers via Solid-Phase Peptide Synthesis (SPPS): peptides were synthesized on Rink resins (0.67 mmol/g) using standard FMOC SPPS procedures on an AAPPTec Focus XC automated synthesizer. A typical SPPS procedure included deprotection of the N-terminal Fmoc group with 20% 4-methyl-piperidine in DMF (1×20 min, followed by 1×5 min), and 30 min amide couplings (twice) using 3.0 equiv. of the Fmoc-protected amino acid, 2.9 equiv. of HBTU and 6.0 equiv. of DIPEA. After that, peptide acrylamide monomers were prepared by amide coupling to Fmoc-6-aminohexanoic acid, followed by Fmoc deprotection and final amidation with acrylic acid (3 equiv.) in the presence of HBTU (2.9 equiv.), and DIPEA (6.0 equiv.). The crude peptide monomers were obtained by cleavage from the resins and further purified by preparative HPLC.

Aqueous photo-RDRP of peptide acrylamide monomers: In a typical aqueous photoinduced polymerization (P14), KLA peptide (KLAKLAKKLAKLAK) (SEQ ID NO:3) acrylamide monomer (30 mg, 25 equiv.) and DMA (1.8 mg, 25 equiv.) were dissolved in 150 μL of acetate buffer (0.1 M, pH 5). Then 10 μL (1.0 equiv.) of water-soluble RAFT agent stock solution (2.2 mg in 100 μL of acetate buffer) was added into the reaction mixture. Following that, 10 μL (0.05 equiv.) of eosin Y disodium salt stock solution (2.5 mg in 1 mL of acetate buffer) and PMDETA (0.12 mg, 1.0 equiv.) were added. The solution was degassed by $N_2$ flow for 30 min and then placed into the photo-reactor (450 nm, 2.8 mW/$cm^2$) for 24 h. Upon the polymerization, the polymer product was purified by dialysis into DIW, followed by lyophilization.

References corresponding to Example 1A

[1] a) N. Corrigan, J. Yeow, P. Judzewitsch, J. T. Xu, C. Boyer, Angew. Chem. Int. Ed. 2019, 58, 5170-5189; Angew. Chem. 2019, 131, 5224-5243; b) J. T. Xu, K. Jung, A. Atme, S. Shanmugam, C. Boyer, J. Am. Chem. Soc. 2014, 136, 5508-5519; c) M. Chen, M. J. Zhong, J. A. Johnson, Chem. Rev. 2016, 116, 10167-10211; d) H. Sun, C. P. Kabb, M. B. Sims, B. S. Sumerlin, Prog. Polym. Sci. 2019, 89, 61-75; e) M. R. Molla, P. Rangadurai, L. Antony, S. Swaminathan, J. J. de Pablo, S. Thayumanavan, Nat. Chem. 2018, 10, 659-666; f) L. Yang, H. Sun, Y. Liu, W. J. Hou, Y. Yang, R. Cai, C. Cui, P. H. Zhang, X. S. Pan, X. W. Li, L. Li, B. S. Sumerlin, W. H. Tan, Angew. Chem. Int. Ed. 2018, 57, 17048-17052; Angew. Chem. 2018, 130, 17294-17298.
[2] J. Niu, D. J. Lunn, A. Pusuluri, J. I. Yoo, M. A. O'Malley, S. Mitragotri, H. T. Soh, C. J. Hawker, Nat. Chem. 2017, 9, 537-545.
[3] a) X. C. Pan, S. Lathwal, S. Mack, J. J. Yan, S. R. Das, K. Matyjaszewski, Angew. Chem. Int. Ed. 2017, 56, 2740-2743; Angew. Chem. 2017, 129, 2784-2787; b) X. C. Pan, C. Fang, M. Fantin, N. Malhotra, W. Y. So, L. A. Peteanu, A. A. Isse, A. Gennaro, P. Liu, K. Matyjaszewskit, J. Am. Chem. Soc. 2016, 138, 2411-2425.
[4] R. N. Carmean, T. E. Becker, M. B. Sims, B. S. Sumerlin, Chem 2017, 2, 93-101.
[5] J. T. Xu, S. Shanmugam, C. K. Fu, K. F. Aguey-Zinsou, C. Boyer, J. Am. Chem. Soc. 2016, 138, 3094-3106.
[6] J. B. Tan, H. Sun, M. G. Yu, B. S. Sumerlin, L. Zhang, ACS Macro Lett. 2015, 4, 1249-1253.
[7] K. A. Ogawa, A. E. Goetz, A. J. Boydston, J. Am. Chem. Soc. 2015, 137, 1400-1403.
[8] a) V. Kottisch, M. J. Supej, B. P. Fors, Angew. Chem. Int. Ed. 2018, 57, 8260-8264; Angew. Chem. 2018, 130, 8392-8396; b) Q. Michaudel, V. Kottisch, B. P. Fors, Angew. Chem. Int. Ed. 2017, 56, 9670-9679; Angew. Chem. 2017, 129, 9798-9808; c) V. Kottisch, Q. Michaudel, B. P. Fors, J. Am. Chem. Soc. 2016, 138, 15535-15538.
[9] a) F. Eisenreich, M. Kat han, A. Dallmann, S. P. Ihrig, T. Schwaar, B. M. Schmidt, S. Hecht, Nat. Catal. 2018, 1, 516-522; b) C. K. Fu, J. T. Xu, C. Boyer, Chem. Commun. 2016, 52, 7126-7129.
[10] G. Ng, J. Yeow, R. Chapman, N. Isahak, E. Wolyetang, J. J. Cooper-White, C. Boyer, Macromolecules 2018, 51, 7600-7607.
[11] Q. Z. Yang, J. Lalevee, J. Poly, Macromolecules 2016, 49, 7653-7666.
[12] S. Varlas, L. D. Blackman, H. E. Findlay, E. Reading, P. J. Booth, M. I. Gibson, R. K. O'Reilly, Macromolecules 2018, 51, 6190-6201.
[13] L. D. Blackman, S. Varlas, M. C. Arno, Z. H. Houston, N. L. Fletcher, K. J. Thurecht, M. Hasan, M. I. Gibson, R. K. O'Reilly, ACS Central Sci. 2018, 4, 718-723.
[14] M. R. Hill, R. N. Carmean, B. S. Sumerlin, Macromolecules 2015, 48, 5459-5469.
[15] A. P. Blum, J. K. Kammeyer, J. Yin, D. T. Crystal, A. M. Rush, M. K. Gilson, N. C. Gianneschi, J. Am. Chem. Soc. 2014, 136, 15422-15437.
[16] A. P. Blum, J. K. Kammeyer, N. C. Gianneschi, Chem. Sci. 2016, 7, 989-994.
[17] H. D. Maynard, S. Y. Okada, R. H. Grubbs, J. Am. Chem. Soc. 2001, 123, 1275-1279.
[18] L. Ayres, M. R. J. Vos, P. J. H. M. Adams, I. O. Shklyarevskiy, J. C. M. van Hest, Macromolecules 2003, 36, 5967-5973.
[19] L. Adamiak, M. A. Touve, C. L. M. LeGuyader, N. C. Gianneschi, ACS Nano 2017, 11, 9877-9888.
[20] R. M. Conrad, R. H. Grubbs, Angew. Chem. Int. Ed. 2009, 48, 8328-8330.
[21] B. D. Fairbanks, P. A. Gunatillake, L. Meagher, Adv. Drug Deliver. Rev. 2015, 91, 141-152.
[22] M. Cieslewicz, J. J. Tang, J. L. Yu, H. Cao, M. Zavaljevski, K. Motoyama, A. Lieber, E. W. Raines, S. H. Pun, Proc. Nat.l. Acad. Sci. USA 2013, 110, 15919-15924.
[23] K. E. B. Doncom, L. D. Blackman, D. B. Wright, M. I. Gibson, R. K. O'Reilly, Chem. Soc. Rev. 2017, 46, 4119-4134.
[24] A. Valdebenito, M. V. Encinas, Polym. Int. 2010, 59, 1246-1251.
[25] L. Agemy, D. Friedmann-Morvinski, V. R. Kotamraju, L. Roth, K. N. Sugahara, O. M. Girard, R. F. Mattrey, I. M. Verma, E. Ruoslahti, Proc. Natl. Acad. Sci. USA 2011, 108, 17450-17455.
[26] V. R. Fantin, M. J. Berardi, H. Babbe, M. V. Michelman, C. M. Manning, P. Leder, Cancer Res. 2005, 65, 6891-6900.

Example 1B: Bioactive Peptide Brush Polymer Via Photoinduced Reversible-Deactivation Radical Polymerization—Supporting Information 1. Materials All amino acids used to prepare peptides by solid phase peptide synthesis (SPPS) were obtained from AAPPTec, Chem-Impex, and NovaBiochem. N,N,N',N",N"-Pentamethyldiethylenetriamine (PMDETA, 99%), eosin Y disodium salt (dye content >85%), N-(3-dimethylaminopropyl)-N'-ethylcarbodiimide hydrochloride (EDC·HCl, 99%), 4-(dimethylamino)pyridine (DMAP, 98%)), 6-Fmoc-amino hexanoic acid (97%), and acetate buffer (0.1 M, pH 5) were purchased from Sigma Aldrich and used without purification. 2-(Dodecylthiocarbonothioylthio)-2-methylpropionic acid (DDMAT) was synthesized according to previous literature.[1] 4-((((2-Carboxyethyl)thio)carbonothioyl)thio)-4-cyanopentanoic acid (water-soluble RAFT agent, 95%) and 4-cyano-4-[(dodecylsulfanylthiocarbonyl)sulfanyl]pentanoic acid (CDTPA, 97%) was purchased from Combi-Blocks and used without further purification. Methacryloxyethyl thiocarbamoyl rhodamine B was purchased from Polysciences, Inc. Thermolysin was purchased from Promega. LED strip light (450 nm) was purchased from Amazon.

2. Methods $^1$H Nuclear Magnetic Resonance (1H NMR): $^1$H NMR spectra were recorded on a Varian Inova spectrometer (500 MHz) in $d_6$-DMSO or $CDCl_3$. Chemical shifts are given in ppm downfield from tetramethylsilane TMS.

Analytical High-Performance Liquid Chromatography (HPLC): Analytical HPLC analysis of peptides was performed on a Jupiter 4μ Proteo 90A Phenomenex column (150×4.60 mm) using a Hitachi-Elite LaChrom L-2130 pump equipped with UV-Vis detector (Hitachi-Elite LaChrom L2420).

Preparative HPLC: Armen Glider CPC preparatory HPLC was used to purify the peptides. The solvent system consists of (A) 0.1% TFA in water and (B) 0.1% TFA in acetonitrile.

Electrospray Ionization Mass Spectrometry (ESI-MS): ESI-MS spectra of peptides were collected using a Bruker Amazon-SL spectrometer configured with an ESI source in both negative and positive ionization mode.

Transmission Electron Microscope (TEM): Twenty microliters of sample were applied onto a 400 mesh carbon grids (Ted Pella, INC.). The grids were observed on a Hitachi HT 7700 microscope operating at 120 kV. The images were recorded with a slow-scan charge-coupled device (CCD) camera (Veleta 2k×2k).

Gel Permeation Chromatography (GPC): GPC measurements were performed on a set of Phenomenex Phenogel 5μ, 1K-75K, 300×7.80 mm in series with a Phenomex Phenogel 5μ, 10K-1000K, 300×7.80 mm columns with HPLC grade solvents as eluents: dimethylformamide (DMF) with 0.05M of LiBr at 60° C. Detection consisted of a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software with dn/dc values determined by assuming 100% mass recovery during GPC analysis.

Dynamic Light Scattering (DLS): DLS analysis was conducted at room temperature on a Zetasizer Nano-ZS (Malvern). The laser for DLS was at a wavelength of 633 nm.

Circular Dichroism Spectrophotometer (CD): CD spectra were measured using a Jasco J-815 spectrometer and each sample was measured from 190 to 260 nm with a slit width of 1 nm, scanning at 1 nm intervals with a 1s integration time. Measurements were taken 3× at 25° C. and then averaged to give the spectra. Notably, the peptide and polymer were dissolved in DIW to a concentration of 100 μM (with respect to peptide concentration).

Atomic Force Microscope (AFM): Samples were prepared by pipetting 50 μl of 10× dilution in water onto 1 $cm^2$ freshly cleaved mica and incubated at room temperature for 1 minute before blot drying by holding the edge of the mica onto lint free tissue. AFM images were acquired using a Bruker Dimension FastScan AFM using Fastscan A tips and analyzed with Nanoscope V1.9 software. Images were acquired with a scan rate of 3.6 Hz at 512 pixels by 512 pixels resolution. Images were plane flattened in XY simultaneously and then flattened using a 0 nm threshold.

Confocal Laser Scanning Microscopy (CLSM): Imaging was accomplished using LEICA SP5 II laser scanning confocal microscope with a 63× oil immersion objective at 1.5× optical zoom. All the images were Z-stack images. Slice thickness was 0.26 μm with a scan size of 1024×1024 pixels and a scan speed of 400 Hz. The cell nuclei (stained with DAPI) was accomplished using a 405 nm laser with a 15% laser power. The cell membrane (stained with Wheat Germ Agglutinin, Alexa Fluor 488 Conjugate) was accomplished using a 488 nm laser with a 12% laser power. Cell imaging for Rhodamine fluorescence was accomplished using a 543 nm laser with an 8% laser power.

Flow Cytometry: The cell uptake study was analyzed via flow cytometry using a BD FacsAria Ilu 4-Laser flow cytometer (Becton Dickinson Inc., USA). Mean fluorescence intensity and PE-A-histogram data was prepared for presentation using FlowJo v10.

3. Experimental 3.1 Preparation of Peptide Monomers Via Solid-Phase Peptide Synthesis (SPPS)

Peptides were synthesized on Rink resin (0.67 mmol/g) using standard FMOC SPPS procedures on an AAPPTec Focus XC automated synthesizer. A typical SPPS procedure included deprotection of the N-terminal Fmoc group with 20% 4-methyl-piperidine in DMF (1×20 min, followed by 1×5 min), and 30 min amide couplings (twice) using 3.0 equiv. of the Fmoc-protected amino acid, 2.9 equiv. of HBTU and 6 equiv. of DIPEA. After that, peptide monomers were prepared by amide coupling to Fmoc-6-aminohexanoic acid, followed by Fmoc deprotection and final amidation with acrylic acid (3 equiv.) in the presence of HBTU (2.9 equiv.), and DIPEA (6 equiv.).

3.2 Photo-Polymerization in DMSO

In a typical organic phase photo-induced polymerization (P1), peptide (GPLGLAGG) (SEQ ID NO:5) acrylamide monomer (30 mg, 50 equiv.) and DMA (3.7 mg, 50 equiv.) were dissolved in 150 μL of DMSO. Then 10 μL (1.0 equiv.) of DDMAT stock solution (2.7 mg in 100 μL of DMSO) was added into the reaction mixture. Following that, 10 μL (0.05 equiv.) of eosin Y disodium salt stock solution (2.6 mg in 1 mL of DMSO) and PMDETA (0.13 mg, 1.0 equiv.) were added. The solution was degassed by $N_2$ flow for 30 min and then placed into the photo-reactor (450 nm, 2.8 $mW/cm^2$) for 24 h. After polymerization, the polymer product was purified by dialysis into DIW, followed by lyophilization.

3.3 Photo-Polymerization in Aqueous Solution

In a typical aqueous photo-induced polymerization (P14), KLA peptide (KLAKLAKKLAKLAK) (SEQ ID NO:3) acrylamide monomer (30 mg, 25 equiv.) and DMA (1.8 mg, 25 equiv.) were dissolved in 150 μL of acetate buffer (0.1 M, pH 5). Then 10 μL (1.0 equiv.) of water-soluble RAFT agent stock solution (2.2 mg in 100 μL of acetate buffer) was added into the reaction mixture. Following that, 10 μL (0.05 equiv.) of eosin Y disodium salt stock solution (2.5 mg in 1 mL of acetate buffer) and PMDETA (0.12 mg, 1.0 equiv.) were added. The solution was degassed by $N_2$ flow for 30 min and then placed into the photo-reactor (450 nm, 2.8 $mW/cm^2$) for 24 h. After polymerization, the polymer product was purified by dialysis into DIW, followed by lyophilization.

3.4 Preparation of Rhodamine-Labeled Polymers

In all the cases of preparing rhodamine-labeled polymers, one equiv. of rhodamine B to RAFT agent was used, ensuring that on average one dye was attached to each polymer chain. In a typical polymerization (rhodamine-labeled P14), KLA peptide (KLAKLAKKLAKLAK) (SEQ ID NO:3) acrylamide monomer (30 mg, 25 equiv.), DMA (1.8 mg, 25 equiv.), and methacryloxyethyl thiocarbamoyl rhodamine B (0.48 mg, 1.0 equiv.) were dissolved in 150 μL of acetate buffer (0.1 M, pH 5). Then 10 μL (1.0 equiv.) of water-soluble RAFT agent stock solution (2.2 mg in 100 μL of acetate buffer) was added into the reaction mixture. Following that, 10 μL (0.05 equiv.) of eosin Y disodium salt stock solution (2.5 mg in 1 mL of acetate buffer) and PMDETA (0.12 mg, 1.0 equiv.) were added. The solution was degassed by $N_2$ flow for 30 min and then placed into the photo-reactor (450 nm, 2.8 $mW/cm^2$) for 24 h. After polymerization, the polymer product was purified by dialysis into DIW, followed by lyophilization.

3.5 N-Acetylation of poly(KLAAm-co-DMA)

In a typical procedure, poly(KLAAm-co-DMA) (1.0 equiv. with respect to free amines) was dissolved in DMF and then treated with 50 equiv. of acetic acid in the presence of 50 equiv. of EDC·HCl and 5 equiv. of 4-DMAP. The reaction mixture was stirred for 12 hours, followed by dialysis into DIW wand lyophilization.

3.6 Thermolysin-Induced Cleavage Experiments

For enzyme-triggered cleavage experiments, the molar ratio of thermolysin to peptide was set to 1:300. Moreover, the temperature was set to 55° C. to achieve the optimal activity of thermolysin. For example, poly($PepAm_{21}$-co-$DMA_{24}$) (P4, 1 mg, 0.87 μmol with respect to peptides, 300 equiv.) was dissolved in 1 ml of DPBS solution. Then thermolysin (0.1 mg, 2.9 nmol, 1 equiv.) was added into the polymer solution which was stirred in a preheated oil bath at 55° C. In the case of control experiments which involved using deactivated thermolysin, EDTA (100 equiv. to thermolysin) was utilized to capture the zinc and calcium ions, resulting in denaturing of thermolysin.

3.7 Cell Culture

Hela cells were purchased from ATCC. Cells were cultured at 37° C. under 5% $CO_2$ in phenol-red containing Dulbecco's Modified Eagle Medium (DMEM; Gibco Life Tech., cat. #11960-044) supplemented with 10% fetal bovine serum (Omega Scientific, cat. #11140-050), sodium pyruvate (Gibco Life Tech., cat. #35050-061), L-glutamine (Gibco Life Tech., cat. #35050-061), and the antibiotics penicillin/streptomycin (Corning Cellgro, cat. #30-002-C1). Cells were grown in T75 culture flasks and subcultured at ~75-80% confluency.

3.8 Cell Viability Assay

The cytotoxicity of materials was assessed using the CellTilter-Blue assay. HeLa cells were plated at a density of 5000 cells per well in a 96 well plate 18 hours prior to treatment. Materials were dissolved in DPBS at the desired concentration and added to the wells along with a 10% DMSO positive control. Cells were incubated for 72 hours at 37° C. Note that the concentration of all the materials is with respect to the peptide concentration to ensure that all peptides and polymers are fairly compared with respect to their therapeutic components. The media was removed and 80 μL of new media without phenol red was added followed by adding 20 μL of CellTilter-Blue reagent. The cells were incubated for 3 hours at 37° C. The fluorescence was measured at 560 nm excitation and 590 nm emission wavelength.

3.9 Confocal Laser Scanning Microscopy for Uptake in HeLa Cells

HeLa cells were plated in a 4-chamber 35 mm round glass-bottom dishes at a density of 50,000 per well. Cells were incubated for 24 hours in a 5% $CO_2$ atmosphere at 37° C. 500 μL of KLA peptide, Poly($KLAAm_{25}$-co-$DMA_{75}$), Poly($KLAAm_{25}$-co-$DMA_{25}$), and Poly($KLAAm_{10}$) (0.25 μM with respect to rhodamine for each material) in 10% FBS DMEM media without phenol red were incubated with the cells for 24 hours, respectively. After washing with DPBS to remove the residual peptides and polymers, 500 μL of Wheat Germ Agglutinin (5 μg/mL) conjugated with Alexa Fluor 488 was added to each well, then fixed with a 4% paraformaldehyde solution for 15 min at room temperature. The cells were washed with DPBS and stained by DAPI for 20 min at room temperature.

3.10 Flow Cytometry for Uptake Ability in HeLa Cells

For cellular uptake measurements, HeLa cells were plated in 12-well plates at a density of 1,000,000 per well and incubated for 24 hours in a 5% $CO_2$ atmosphere at 37° C. 500 μL of 0.25 μM (with respect to rhodamine) KLA peptide, poly($KLAAm_{25}$-co-$DMA_{75}$), poly($KLAAm_{25}$-co-$DMA_{25}$), and poly($KLAAm_{10}$) in 10% FBS DMEM media without phenol red were incubated with the cells for 24 hours respectively. After triple washing with DPBS, 500 μL of 0.25% Trypsin-EDTA was added to each well for 10 min at 37° C. Cells were fixed with a 4% paraformaldehyde solution for 15 min at room temperature.

References Corresponding to Example 1B

1. Xu, J. T.; Shanmugam, S.; Fu, C. K.; Aguey-Zinsou, K. F.; Boyer, C., Selective Photoactivation: From a Single Unit Monomer Insertion Reaction to Controlled Polymer Architectures. *J. Am. Chem. Soc.* 2016, 138 (9), 3094-3106.

Example 2A: Proapoptotic Peptide Brush Polymer Nanoparticles Via Photoinitiated Polymerization-Induced Self-Assembly Abstract: Herein we report photoinitiated polymerization-induced self-assembly (photo-PISA) of spherical micelles consisting of proapoptotic peptide-polymer amphiphiles. The one-pot synthetic approach yielded micellar nanoparticles at high concentrations and at scale (150 mg/mL) with tunable peptide loadings up to 48 wt. %. The size of the micellar nanoparticles was tuned by varying the lengths of hydrophobic and hydrophilic building blocks. Importantly, the peptide-functionalized nanoparticles imbued the peptides, such as proapoptotic "KLA" peptides (amino acid sequence: KLAKLAKKLAKLAK) (SEQ ID NO:3), with two key properties otherwise not inherent to the sequence: 1) proteolytic resistance compared to the oligopeptide alone; 2) significantly enhanced cell uptake permeability by multivalent display of KLA peptide brushes. The result was demonstrated improved apoptosis efficiency in HeLa cells. These results highlight the potential of photo-PISA in the large-scale synthesis of functional, proteolytically resistant peptide-polymer conjugates for intracellular delivery.

Introduction: Synthetic peptides are powerful therapeutics and chemical biology tools because of their biocompatibility, straightforward synthesis, predictable metabolism, and high degree of modularity in molecular design.[1] However, these advantages are typically compromised by natural processes prevalent in cells and tissues that have evolved to degrade them.[2] Traditional approaches for protecting active peptides from enzymatic digestion capitalize on chemical modification of the peptide.[3] These approaches include cyclization,[3a-b] ilipidation,[3c] conjugation of PEG,[3d-e] introduction of unnatural amino acids,[3f] peptide backbone modification (e.g., N-methylation),[3g] and capping of N- or C-terminus,[3h] among others.[3] Consequently, modified peptides are rendered inaccessible to, or unrecognizable by the active site of protease. Nevertheless, the bioactivity or function of modified peptides can be reduced as a result of the alteration of chemical identity and connectivity in amino acids. Moreover, penetration of peptides into cells is typically inefficient unless some special care is taken to engage cell surfaces selectively or through the use of cell penetrating sequences.[4]

Beyond modification of the sequence itself, the three-dimensional spatial arrangement of peptides not only can improve the stability of peptides, but also enhance their biological activities such as cell binding and penetration via multivalent effects.[5] Examples include peptide-coated inorganic nanoparticles,[6] peptide-shell polymer nanoparticles,[7] and peptide brush polymers,[7c, 8] all of which display multiple strands of peptides on a scaffold. However, the synthesis of these materials is not scalable, hindering continued development of these systems to larger animal models and clinical translations.[7d] Standard solvent-switch strategies to access self-assembled nanostructures of peptide-polymer amphiphiles are typically conducted in dilute solution (<1 wt. %).[7c]

Figure 42:
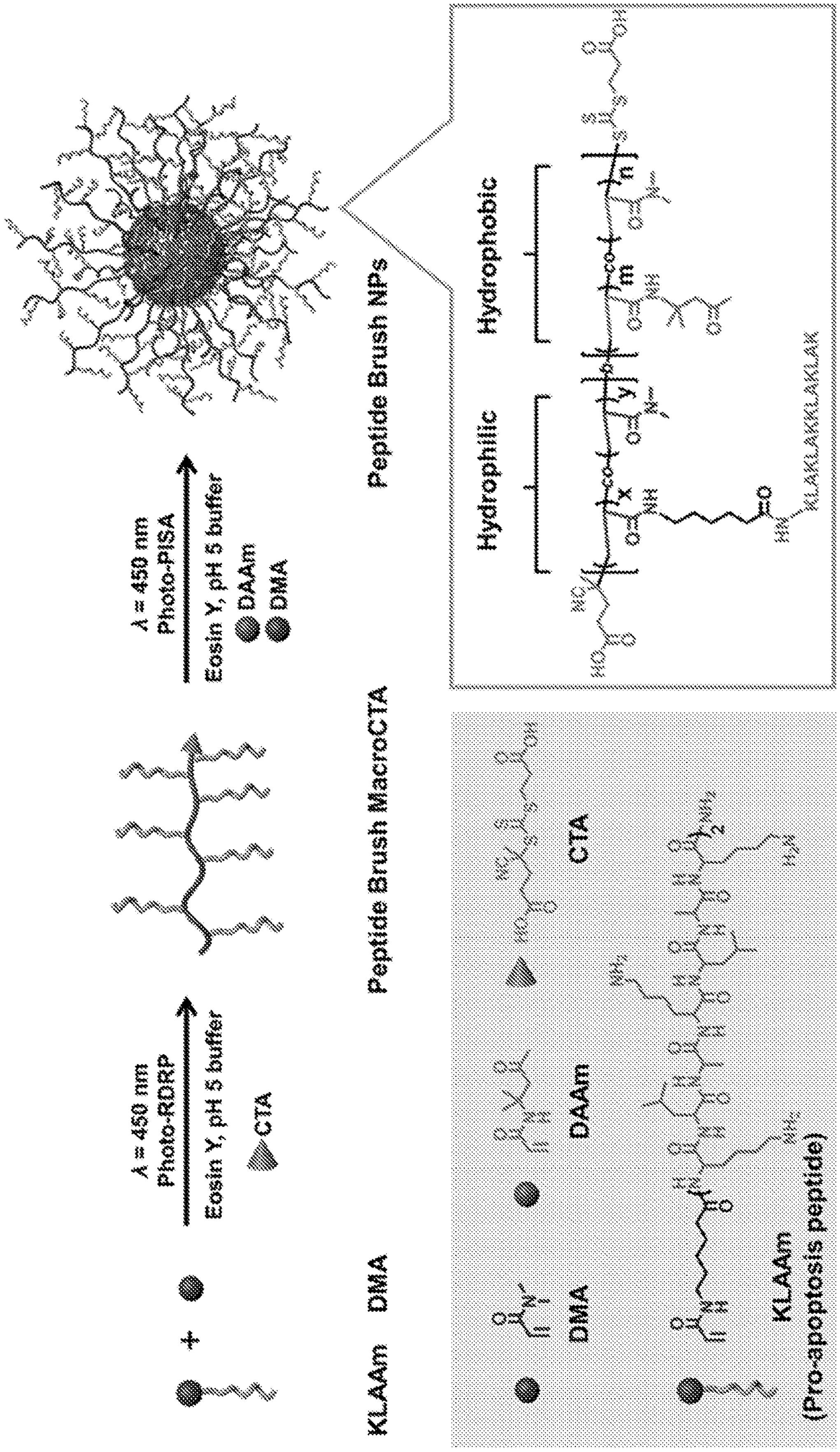
FIG. 42. Schematic illustration of the one-pot photo-PISA approach to proapoptotic peptide brush polymer nanoparticles.

Polymerization-induced self-assembly (PISA) has emerged as a scalable synthetic route to soft nanomaterials at high solids content (up to 50 wt. %).[9] Particularly, photoinitiated PISA (photo-PISA) is promising for the incorporation of biological molecules into nanoparticles, because the reaction can be performed under mild conditions characterized by ambient temperatures, aqueous environments, and metal-free protocols.[10] We reasoned that photo-PISA could be used as a powerful tool for the large-scale synthesis of polymer nanoparticles that exhibit multiple peptides in the hydrophilic shell (FIG. 42). Herein, we present a one-pot photo-PISA approach for the preparation of nanoparticles that carry apoptotic peptides with tunable size (36-105 nm in diameter) and loading of peptides ranging from 20 to 48 wt. %. High concentrations of peptide brush polymer nanoparticles of up to 150 mg/mL were achieved because of the nature of PISA. Importantly, both proteolytical resistance and bioactivity, including cell penetration and apoptotic efficiency, were significantly higher for the peptide brush polymer nanoparticles compared to their linear peptide analogue.

Results and Discussion

Figure 47:
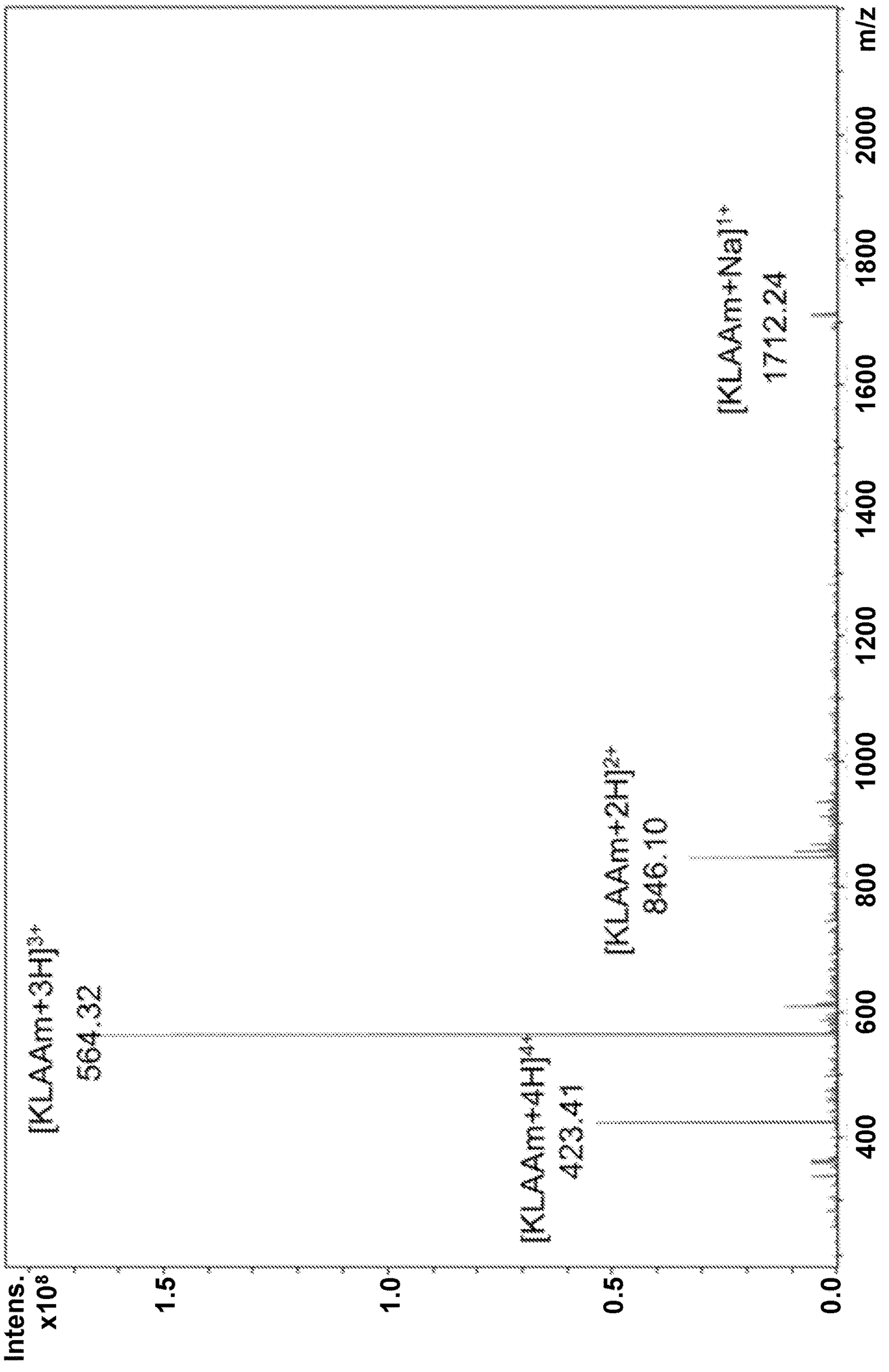
FIG. 47. ESI-MS spectrum of KLAAm.
Figure 48:
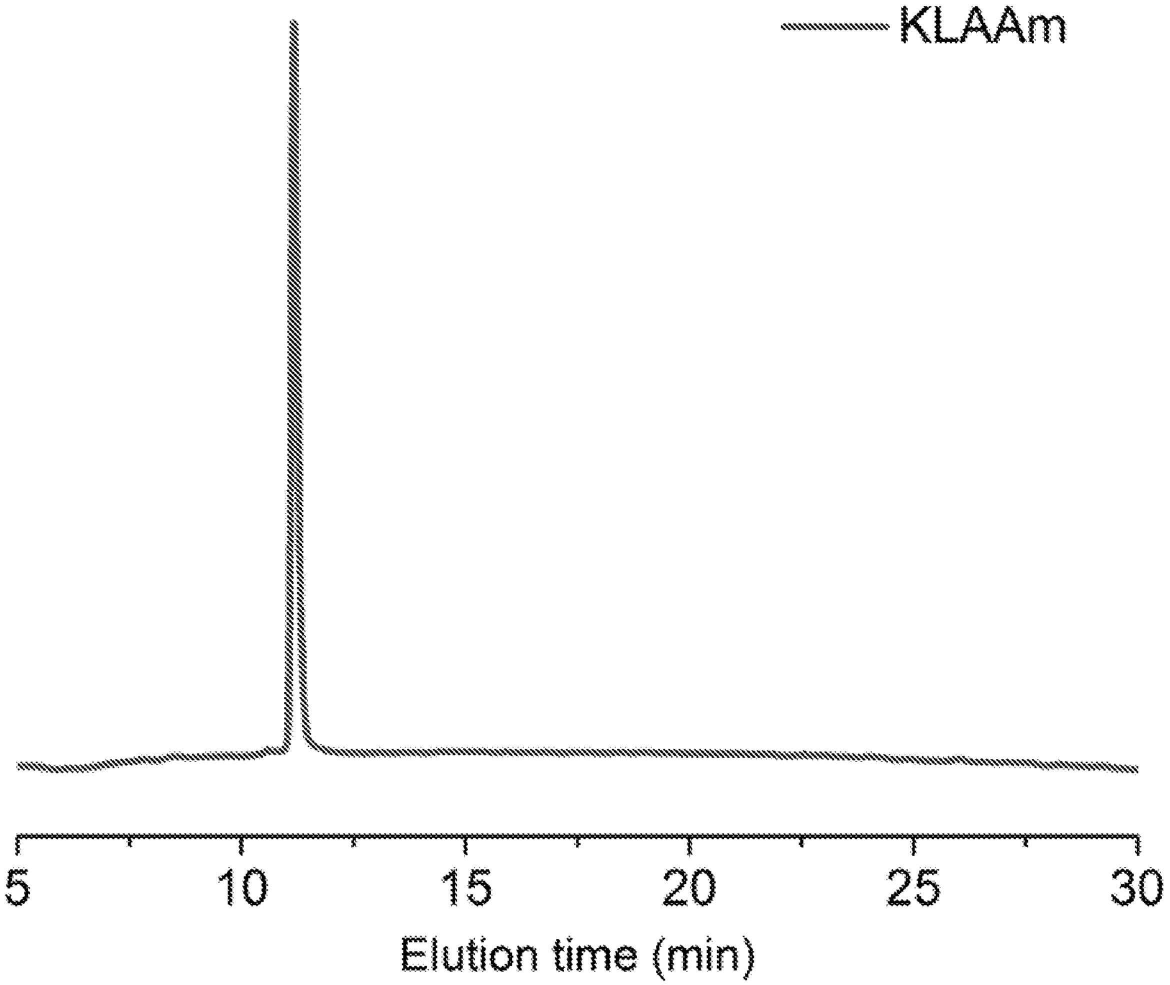
FIG. 48. HPLC trace of KLAAm.
Figure 49:
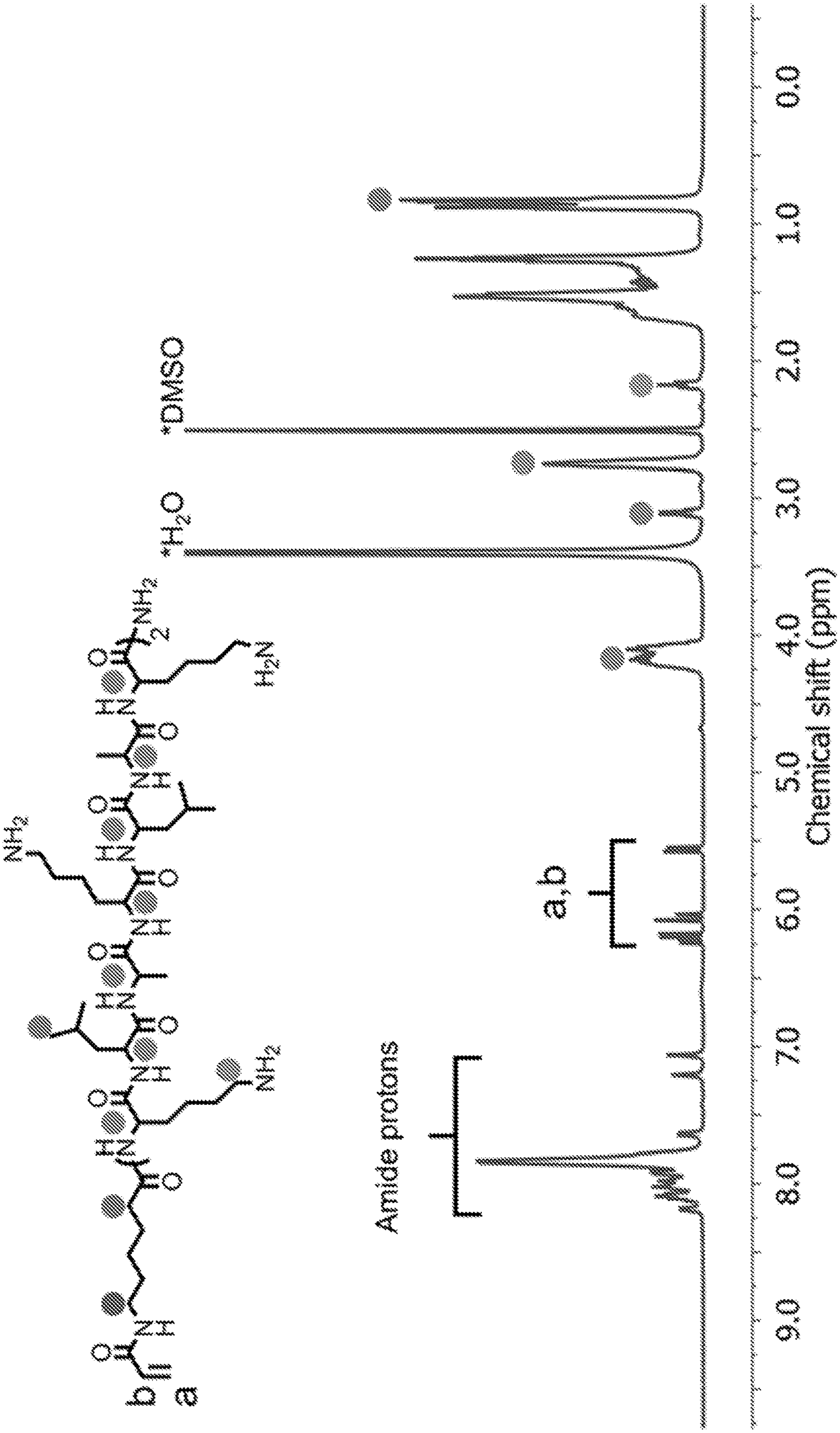
FIG. 49. $^1$H NMR spectrum of KLAAm in DMSO-$d_6$.

With the goal of preparing peptide brush polymer nanoparticles, we began our exploration by designing a peptide acrylamide monomer that features the amino acid sequence of KLAKLAKKLAKLAK (i.e., KLA peptide acrylamide) (SEQ ID NO:3). This peptide sequence is well known for inducing rapid apoptosis of cancer cells via disruption of the mitochondrial membrane.[11] The monomer was prepared via the Fmoc solid-phase peptide synthesis procedure.[7c] High performance liquid chromatography (HPLC), NMR spectroscopy, and electrospray ionization mass spectrometry (ESI-MS) verified the identity and purity of the monomer (FIGS. 47-49).

Figure 50:
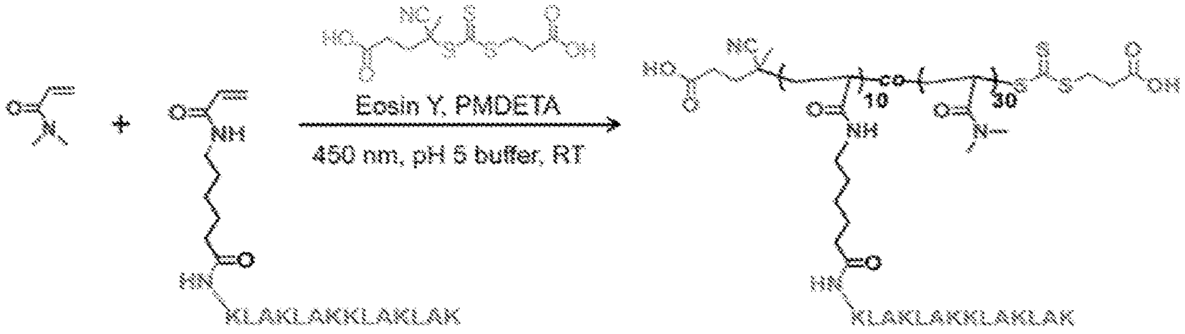
FIG. 50. Synthesis of KLA brush polymer based macroCTA. Full monomer conversion was achieved after photo-polymerization for 12 h, as evidenced by disappearance of vinyl protons from 5.5 to 7.0 ppm. (KLAKLAKKLAKLAK is SEQ ID NO:3.)
Figure 50:
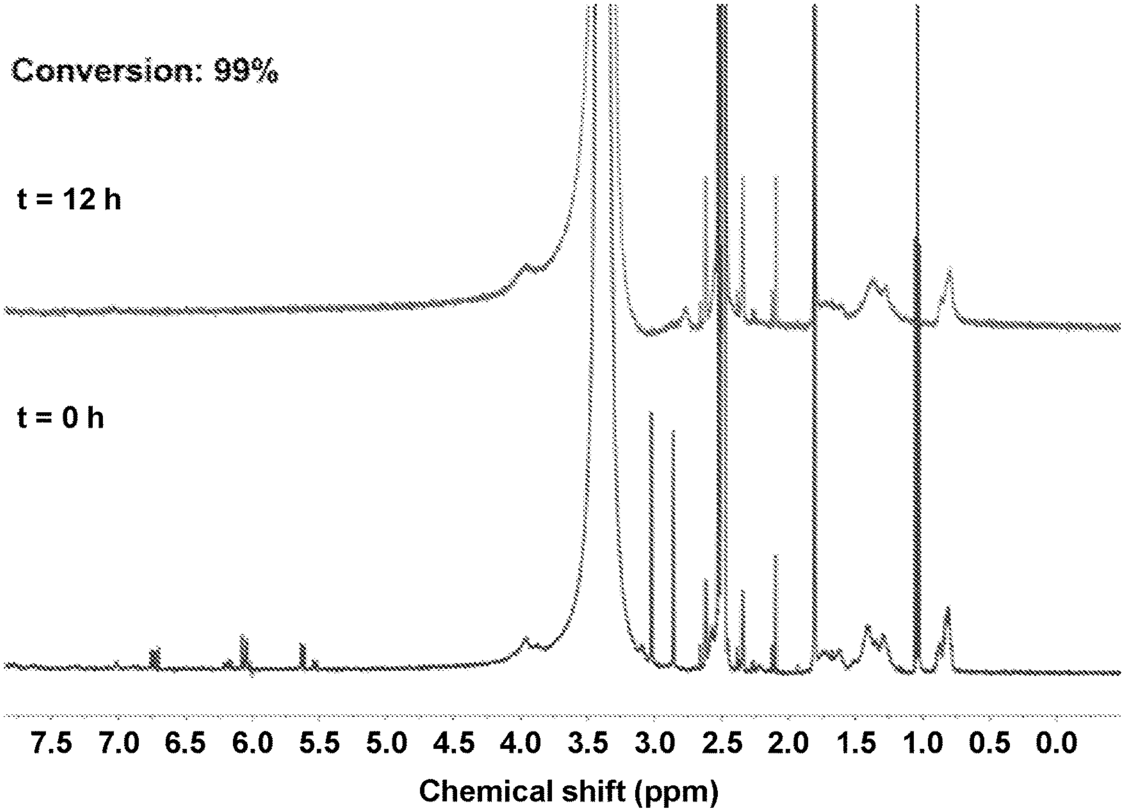
Figure 51:
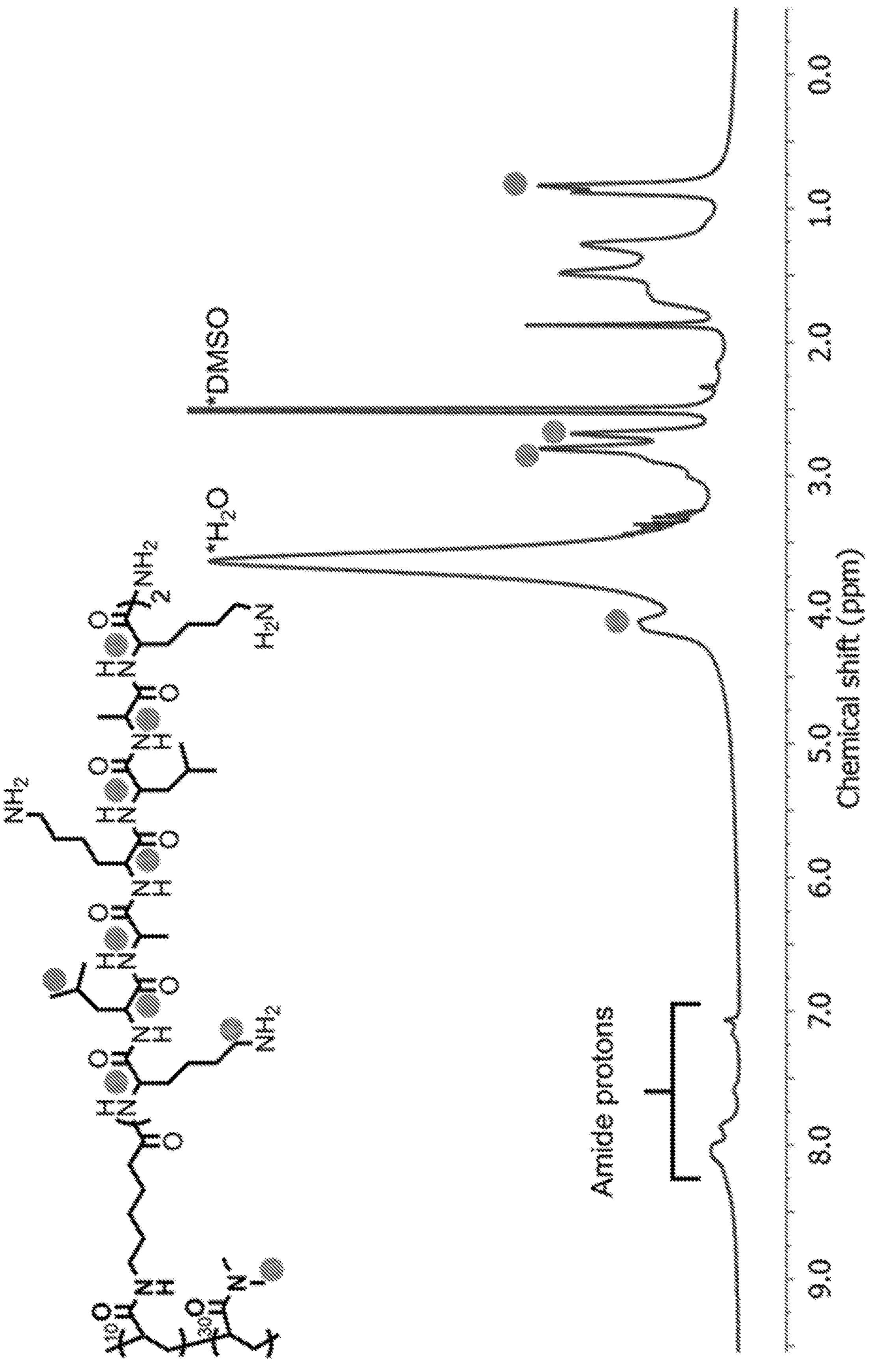
FIG. 51. $^1$H NMR spectrum of poly($KLAAm_{10}$-co-$DMA_{30}$) macroCTA in DMSO-$d_6$.
Figure 52:
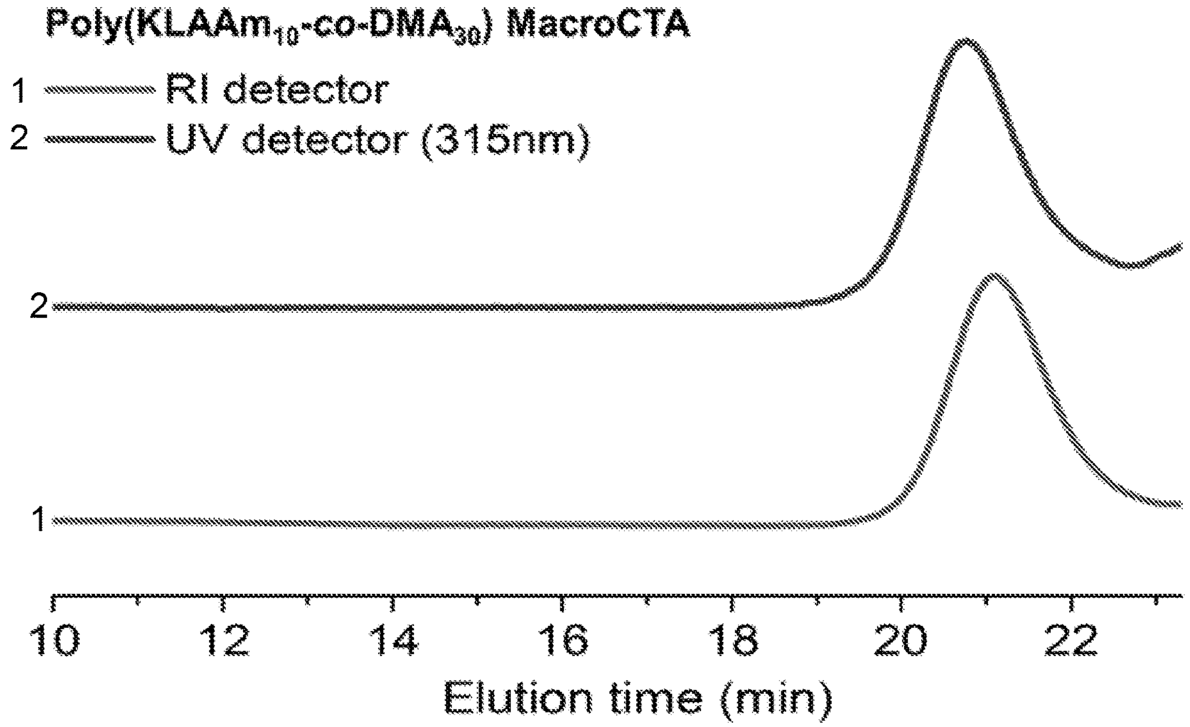
FIG. 52. GPC traces of poly($KLAAm_{10}$-co-$DMA_{30}$) macroCTA monitored with RI and UV detectors.

Photoinduced reversible-deactivation radical polymerization (Photo-RDRP)[10a,12] was used to prepare the macromolecular chain transfer agents (macroCTAs) (FIG. 42). To suppress the nucleophilicity of primary amines that could cause aminolysis of the CTA, an acidic buffer (pH 5.0) was used as the solvent for polymerization. Notably, copolymerization of KLA peptide acrylamide monomer (KLAAm) and a comonomer N, N-dimethylacrylamide (DMA) was conducted in the presence of a biocompatible organic photocatalyst (i.e., eosin Y) at room temperature under visible light irradiation (λ=450 nm). The feed ratio of KLAAm and DMA was varied to tune the loading and graft density of peptides along the hydrophilic polymer chain. The monomers were fully consumed after photo-polymerization for 12 h (FIGS. 50-51). Since the photo-polymerization was conducted at room temperature, we postulated that side reactions such as hydrolysis of terminal trithiocarbonate would be minimized, thus leading to high end-group fidelity.[13] Indeed, gel permeation chromatography (GPC) analysis with integrated UV detection confirmed our hypothesis by revealing that the GPC trace of the macroCTA exhibited the characteristic trithiocarbonate absorption at 315 nm (FIG. 52).

Figure 53A:
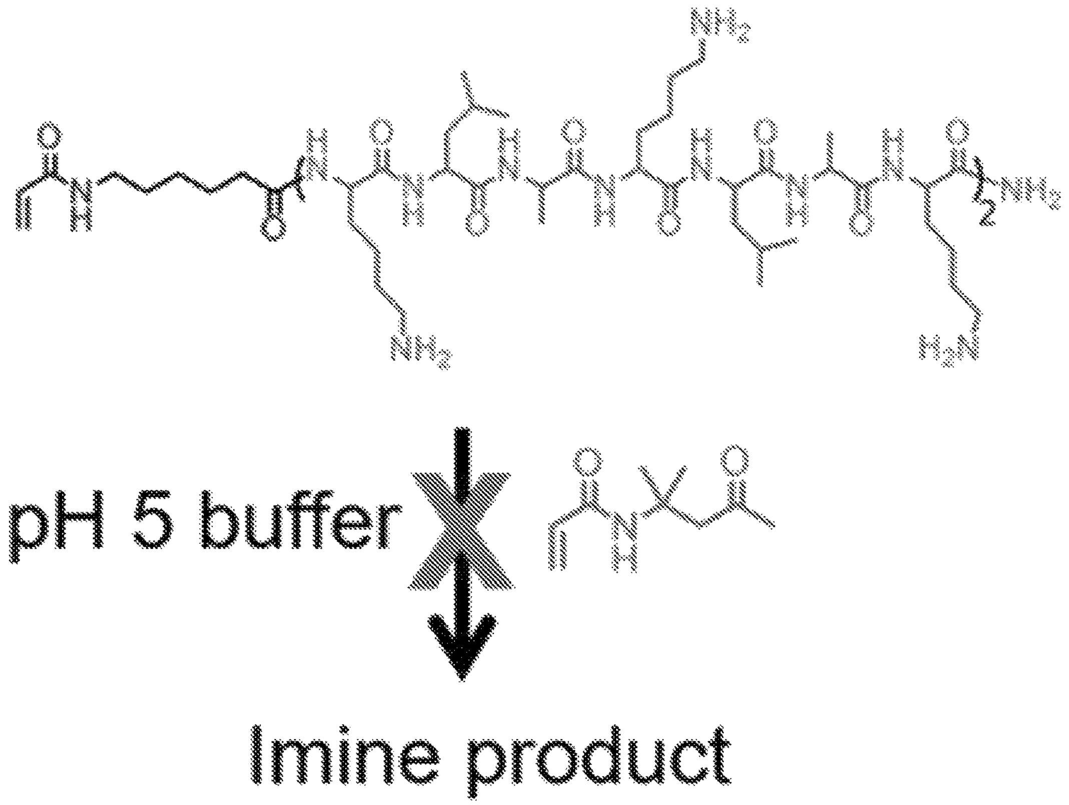
FIGS. 53A-53C. Evaluation of peptidyl functional group tolerance during the PISA process. Both HPLC and ESI-MS analysis verified that free amines of KLAAm did not react with ketone of DAAm under conditions used in photo-PISA, suggesting the compatibility of KLA peptide with photo-PISA protocol. Notably, the equivalent of reactants (i.e., 30 mg of KLAAm, 21 mg of DAAm, and 340 μL of acidic buffer (pH 5.0)) in this control experiment is identical to the condition used in the preparation of NP1 (Experimental section 3.2 and 3.3).
Figure 53B:
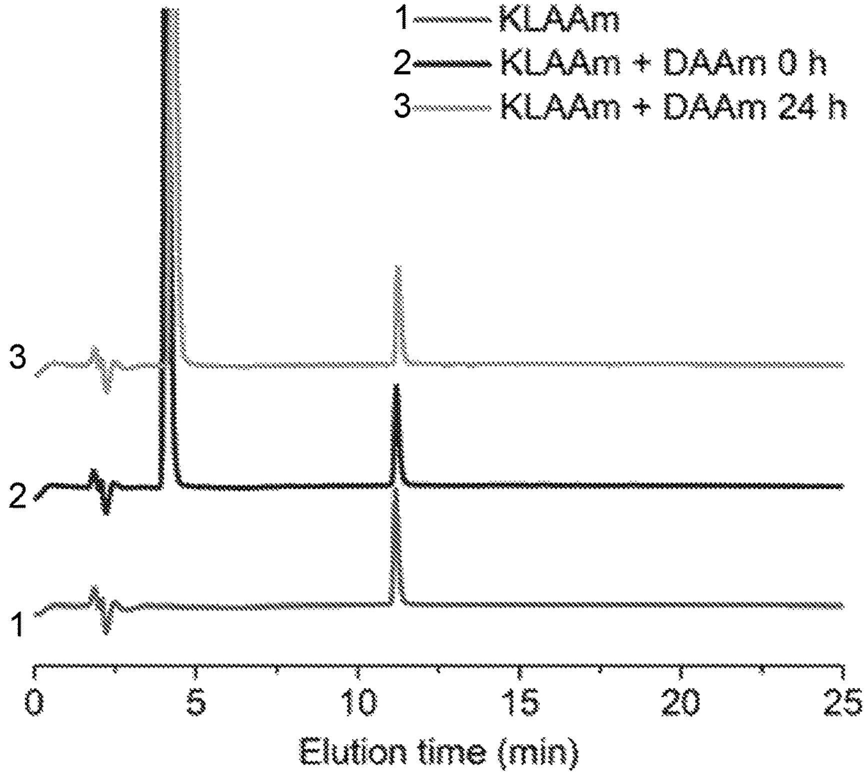
Figure 53C:
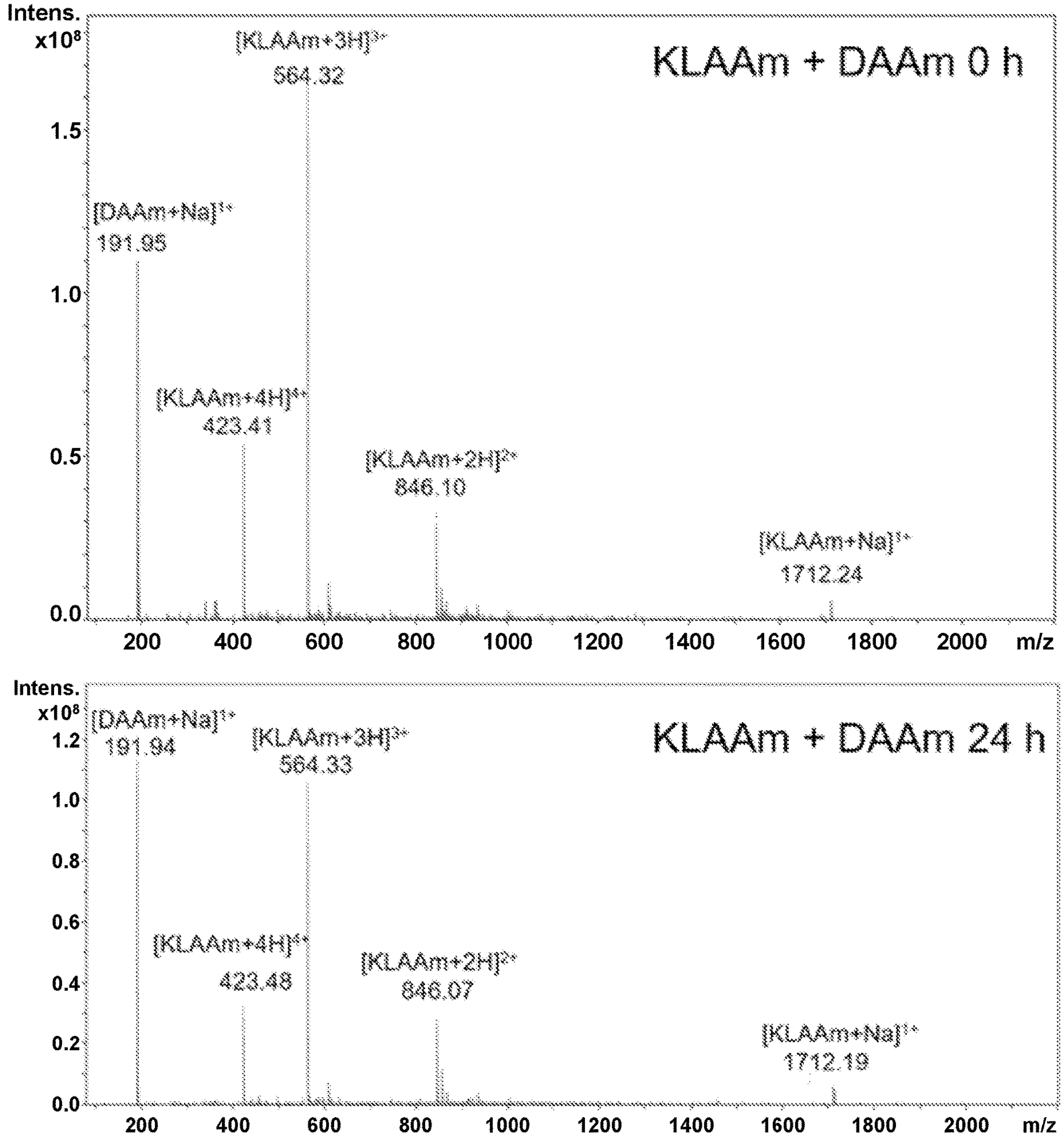

Next, we aimed to perform photo-PISA by chain extension of the macroCTA with a combination of diacetone acrylamide (DAAm) and DMA, which have been shown as readily tunable core-forming monomers in PISA processes (FIGS. 43A-43H). [9f,14] The macroCTA contains primary amines which could potentially form imines with the ketone-containing DAAm. In view of this, we conducted an experiment that involved incubation of KLAAm and DAAm in acidic buffer (pH 5.0). As indicated by HPLC and ESI-MS (FIGS. 53A-53C), no imine products were detected even after 24 h. Therefore, we considered any undesired imine formation during the photo-PISA process would be negligible.

Figure 54A:
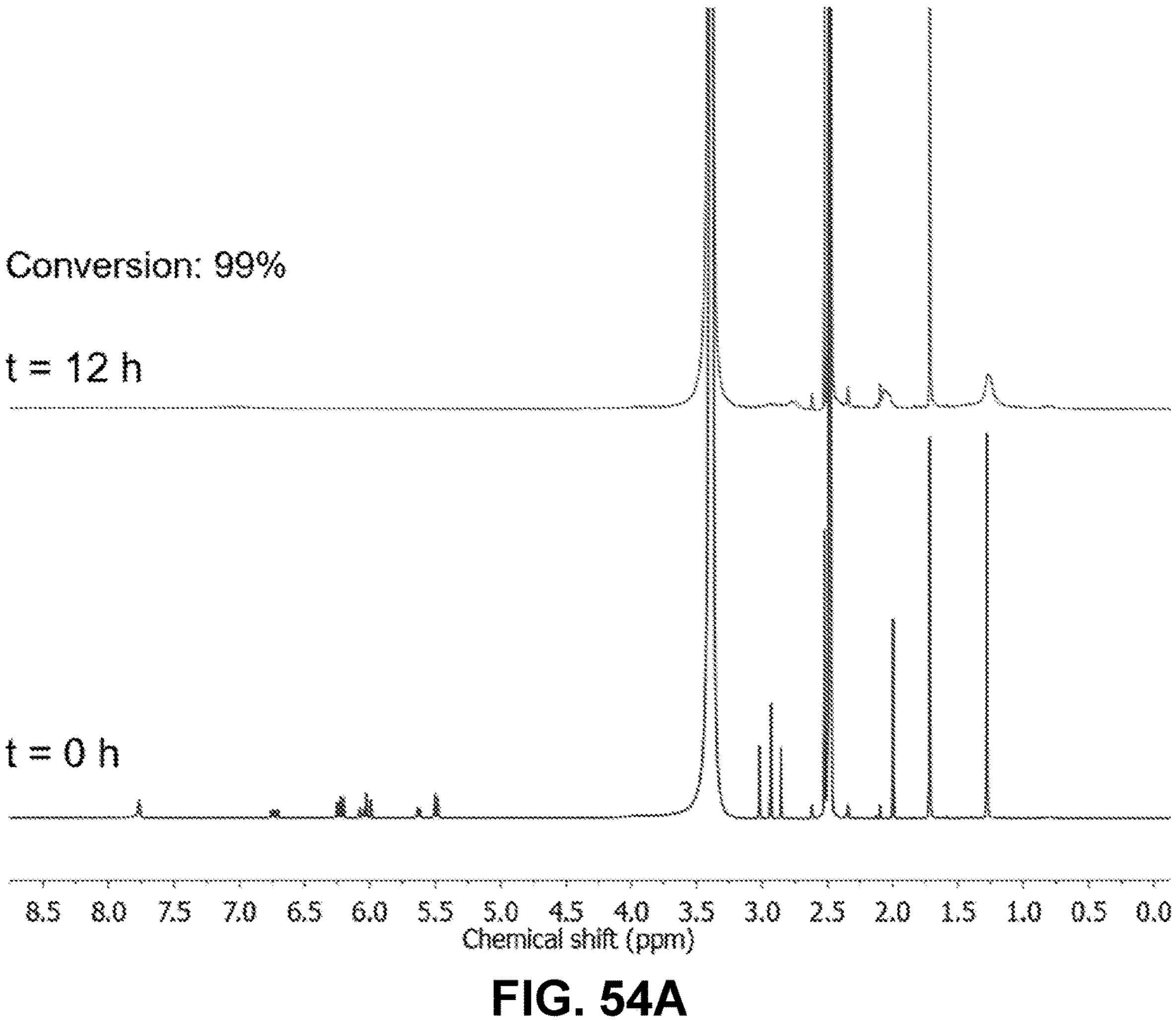
FIG. 54A. Chain extension of poly($KLAAm_{10}$-co-$DMA_{30}$) macroCTA with DAAm and DMA via photo-PISA. $^1$H NMR spectra indicated a full monomer conversion after photo-PISA for 12 h, as evidenced by disappearance of vinyl protons from 5.5 to 7.0 ppm.
Figure 54B:
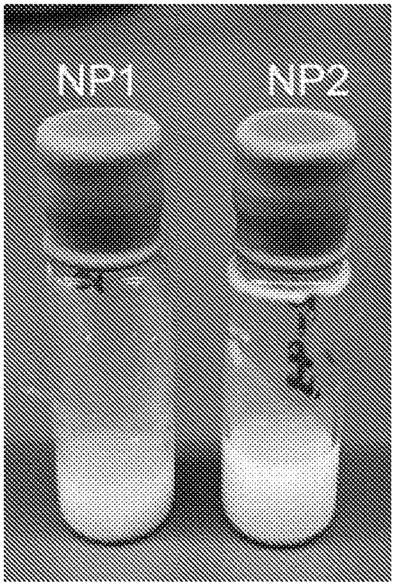
FIG. 54B. Photographs of NPs 1 and 2 (15 wt. %) prepared via one-pot photo-PISA.
Figure 55:
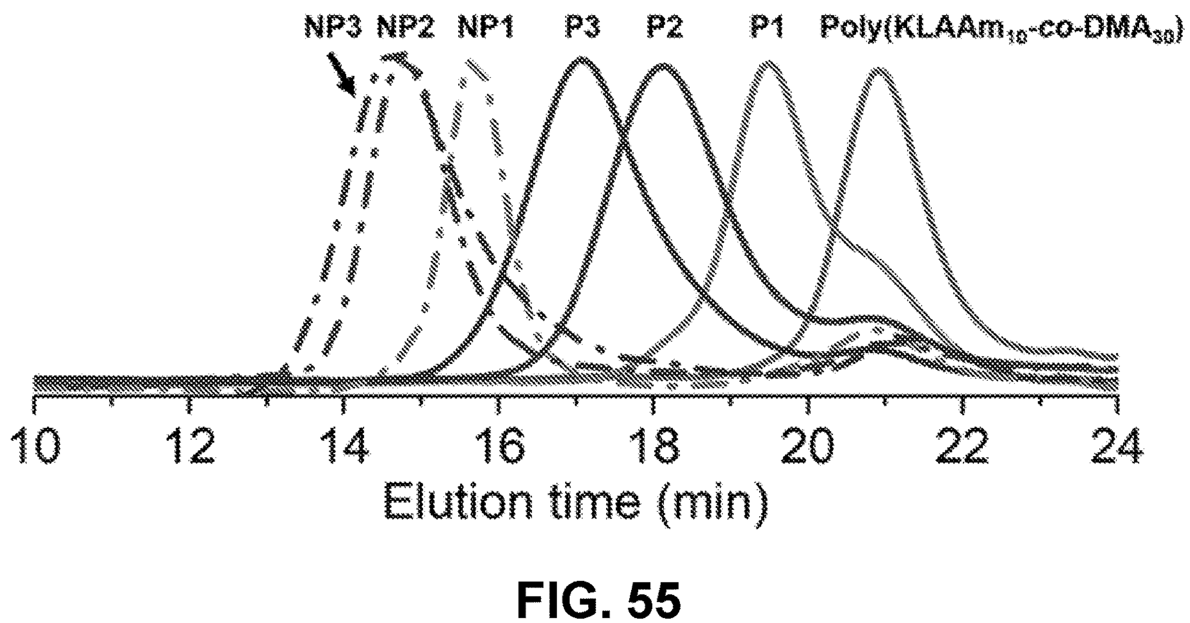
FIG. 55. GPC traces of unimers of P1-P3 and their corresponding core-crosslinked nanoparticles NP1-NP3. The core of NPs was crosslinked with O,O'-1,3-propanediylbishydroxyamine·2HCl (10 mol % with regard to DAAm) prior to the GPC analysis. The condition of crosslinking reaction was adapted according to a previous literature.[1]
Figure 56:
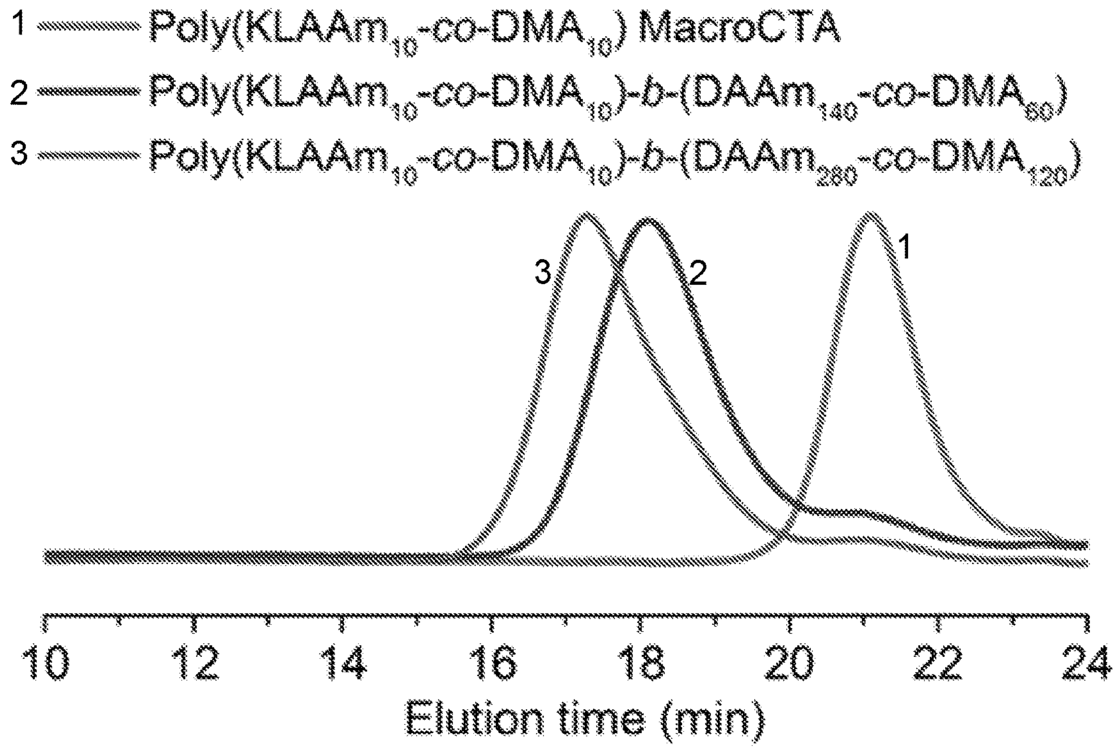
FIG. 56. Chain extension of poly(KLAAm$_{10}$-co-DMA$_{10}$) macroCTA via photo-PISA. GPC traces of block copolymers shifted to shorter elution times after polymerization, indicative of successful chain extension.

Photo-PISA was performed under the identical condition used in the macroCTA synthesis (i.e., eosin Y and acidic buffer). In light of this, the one-pot synthesis of nanoparticles was achieved without isolating the macroCTA from the buffer solution in which it was synthesized. The efficiency of photo-PISA was revealed via NMR spectroscopy analysis that indicated quantitative conversion of monomers after 12 h (FIGS. 54A-54B). Moreover, GPC traces of block copolymers have clearly shifted to higher molecular weight regions with narrow MW distribution, indicative of successful chain extensions (Table 5, Table 6, FIGS. 2A-2B, and FIGS. 55-56). We note that the GPC signal of residual macroCTA remained in all block copolymers (FIG. 2B). However, the extent of residual macroCTA was significantly decreased as the targeted degree of polymerization (DP) increased. The modularity of peptide brush polymer nanoparticles was examined by tuning variables including compositions in hydrophilic macroCTA and hydrophobic polymer core. Hence, five peptide brush polymer nanoparticles with different sizes and loadings of peptide were achieved (Table 5).

TABLE 5

Peptide brush polymer nanoparticles via photo-PISA at solids content of 15 wt. %.

| | Shell-forming | | Core-forming | | Peptide Loading[a] | $M_{n, theo}$[b] | $M_{n, MALS}$[c] | | $D_h$[d] |
|---|---|---|---|---|---|---|---|---|---|
| Entry | KLAAm | DMA | DAAm | DMA | (wt. %) | (g/mol) | (g/mol) | Đ[c] | (nm) |
| NP1 | 10 | 30 | 70 | 30 | 48 | 34 980 | 41 700 | 1.29 | 36 |
| NP2 | 10 | 30 | 140 | 60 | 33 | 51 160 | 57 300 | 1.24 | 62 |
| NP3 | 10 | 30 | 280 | 120 | 21 | 80 640 | 98 600 | 1.17 | 105 |
| NP4 | 10 | 10 | 140 | 60 | 38 | 49 180 | 54 900 | 1.03 | 64 |
| NP5 | 10 | 10 | 280 | 120 | 24 | 78 660 | 92 150 | 1.15 | 92 |

[a]Peptide loading was calculated by feed ratios.

[b]$M_{n, theo}$ = ΣDP of monomers × MW of monomers + MW of CTA.

[c]Number-average molecular weights of polymers were determined by GPC-MALS.

[d]Hydrodynamic diameters of NPs were determined by DLS.

TABLE 6

Characterizations of peptide brush polymer nanoparticles.

| ID | Unimer $M_{n, MALS}$ (kg/mol)[a] | Nanoparticle $M_{n, MALS}$ (kg/mol)[a] | Aggregation number $(N_{agg})$[b] | $R_h$ (nm)[c] | $R_{core}$ (nm)[d] | Surface grafting density (Chains per $nm^2$)[e] | Zeta potential (mV) |
|---|---|---|---|---|---|---|---|
| NP1 | 41.7 | 4874 | 117 | 18 | 13 | 0.055 | 47 |
| NP2 | 57.3 | 49040 | 856 | 31 | 28 | 0.087 | 56 |
| NP3 | 98.6 | 152000 | 1542 | 52 | 46 | 0.058 | 48 |

[a]Molecular weights of unimers and core-crosslinked nanoparticles were determined by GPC-MALS.

[b]$N_{agg} = M_{n, MALS}$ of NP/$M_{n, MALS}$ of unimer.

[c]Hydrodynamic radius ($R_h$) of nanoparticles was determined by DLS.

[d]$R_{core}$ of nanoparticles was estimated by TEM analysis.

[e]Surface grafting density = $N_{agg}/4\pi R_{core}^2$

Figure 43A:
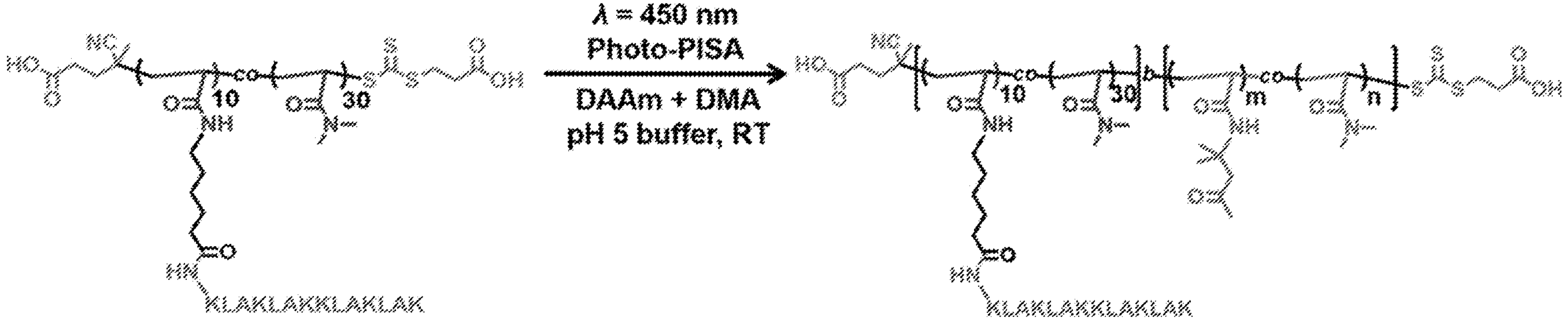
FIGS. 43A-43H. Synthesis and characterization of KLA peptide brush polymer nanoparticles.
Figure 43B:
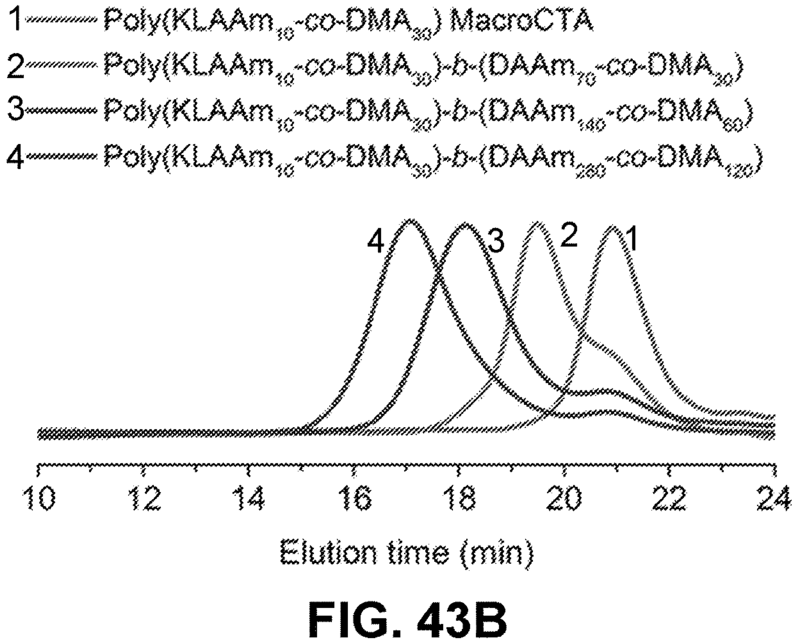
Figure 43C:
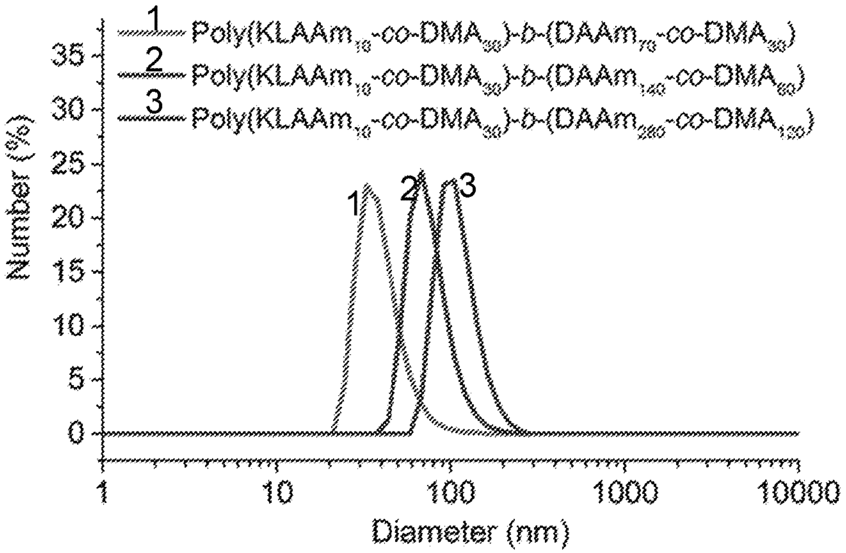
Figure 43D:
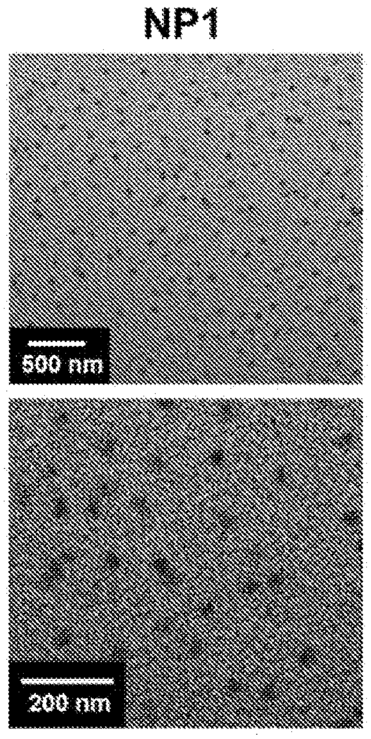
Figure 43E:
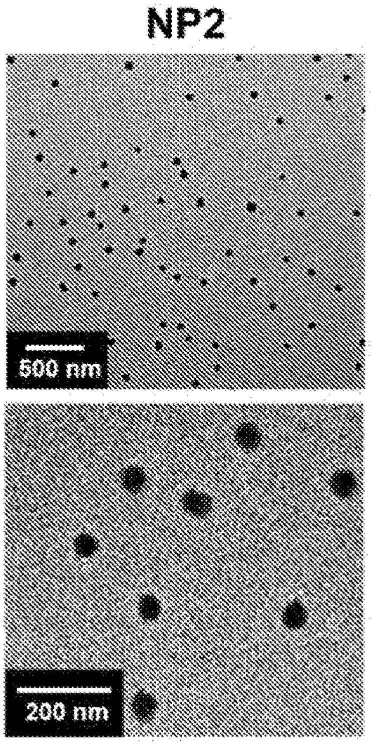
Figure 43F:
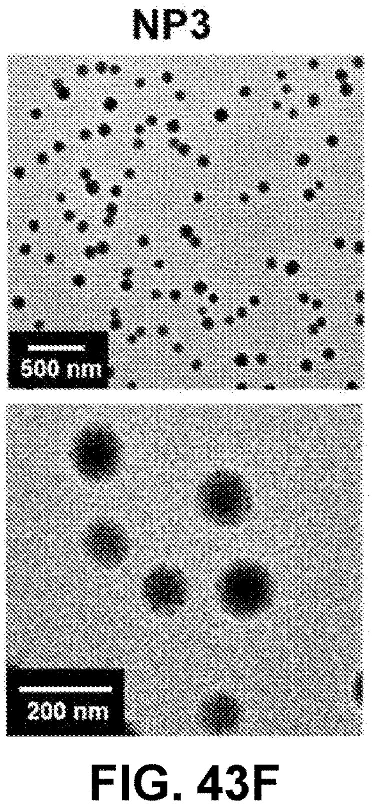
Figure 43G:
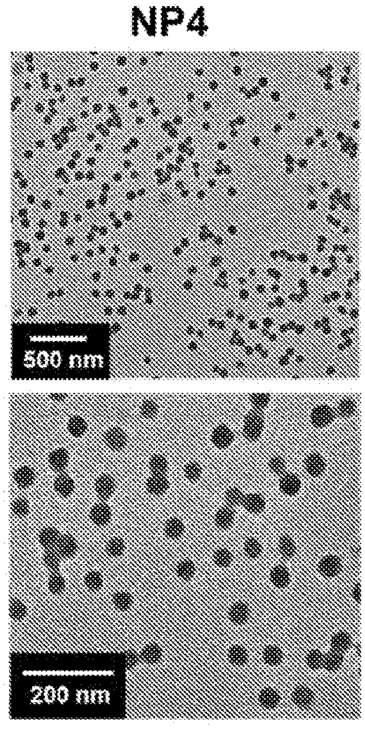
Figure 43H:
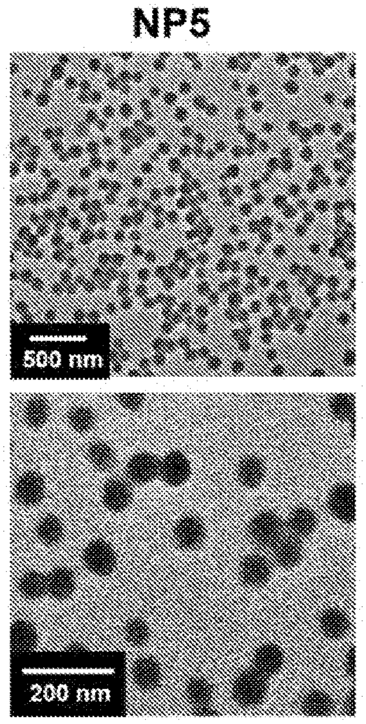
Figure 57:
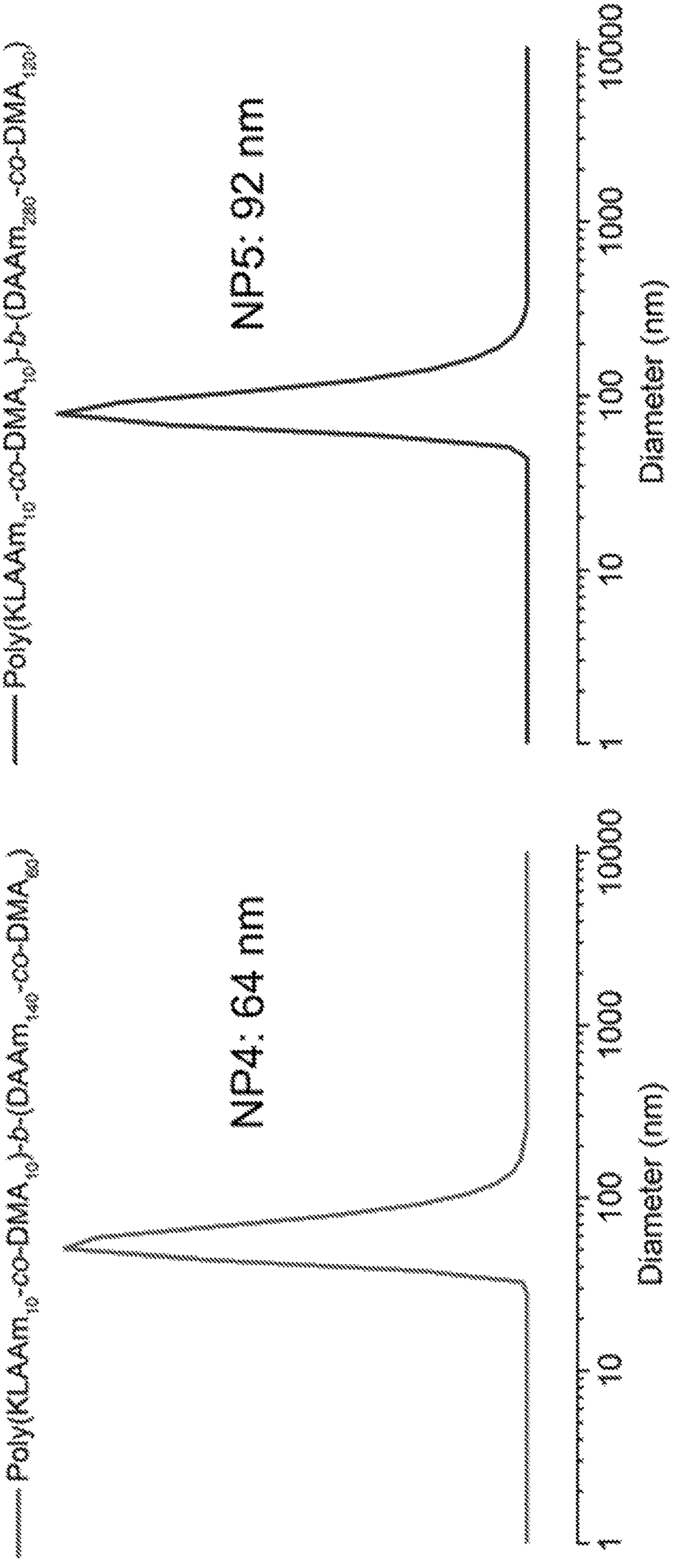
FIG. 57. DLS traces of poly[(KLAAm$_{10}$-co-DMA$_{10}$)-b-(DAAm$_{140}$-co-DMA$_{60}$)](NP4) and poly[(KLAAm$_{10}$-co-DMA$_{10}$)-b-(DAAm$_{280}$-co-DMA$_{120}$)] (NP5).
Figure 58:
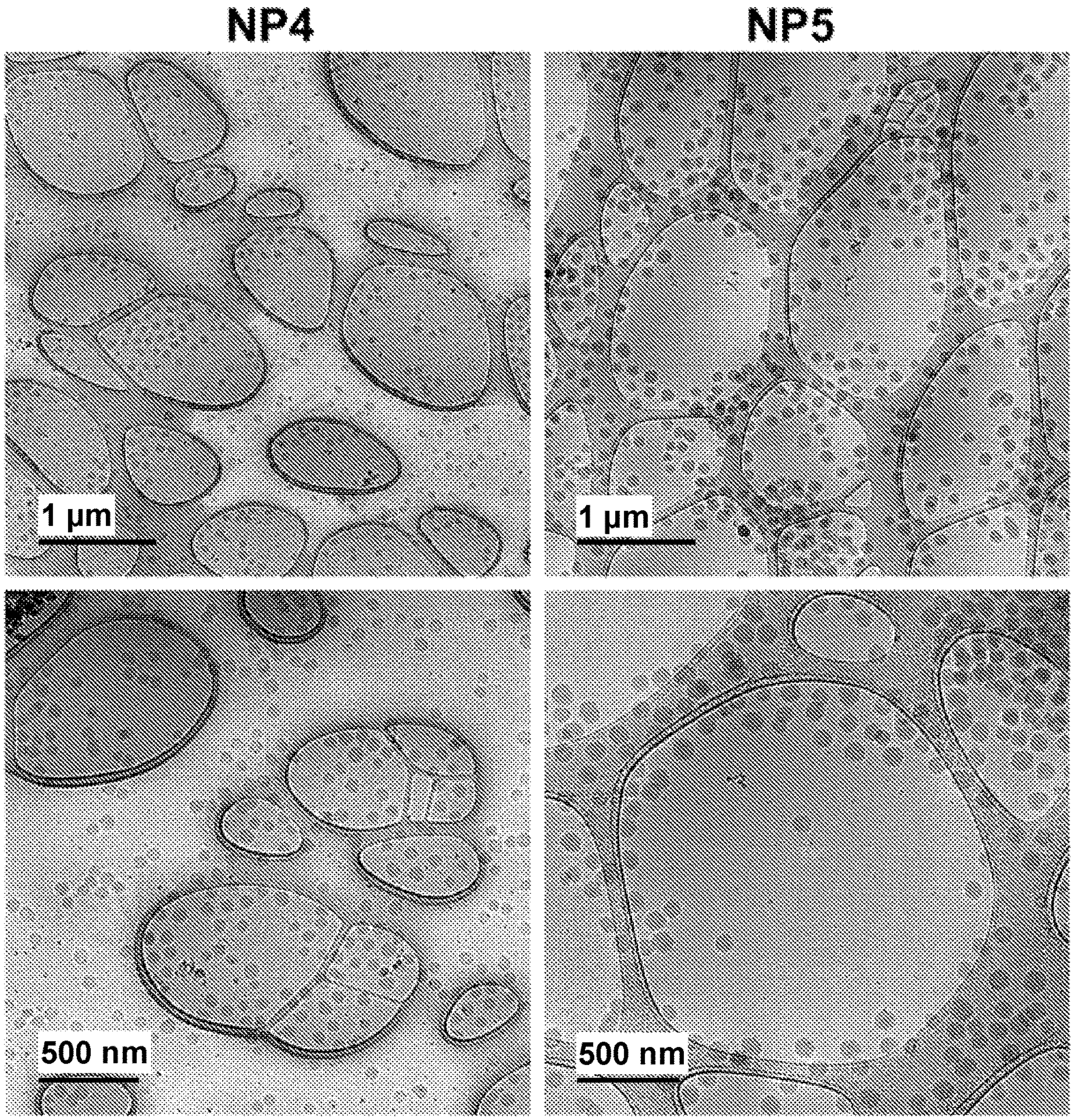
FIG. 58. Representative cryo-TEM images of poly [(KLAAm$_{10}$-co-DMA$_{10}$)-b-(DAAm$_{140}$-co-DMA$_{60}$)] (NP4) and poly[(KLAAm$_{10}$-co-DMA$_{10}$)-b-(DAAm$_{280}$-co-DMA$_{120}$)](NP5). According to images, the size of NP4 (left column) is smaller than that of NP5 (right column). This is in a good agreement with DLS and dry-state TEM results (FIGS. 43A-43H and FIGS. 54A-54B).
Figure 59A:
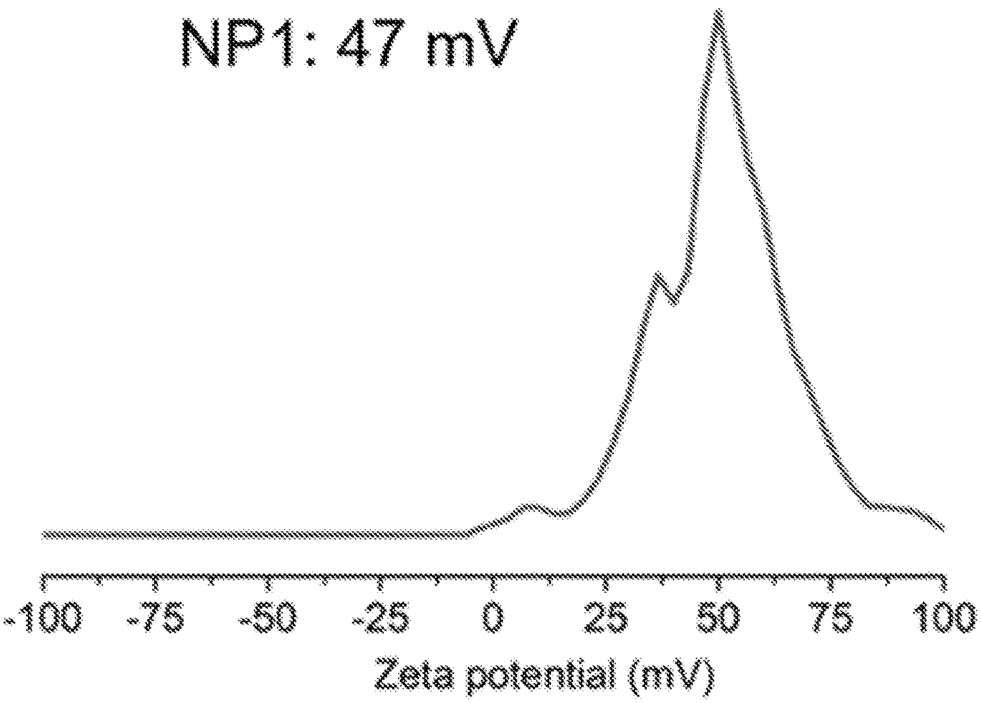
FIGS. 59A-59E. Zeta potentials of NPs 1-5 shown in Table 5.
Figure 59B:
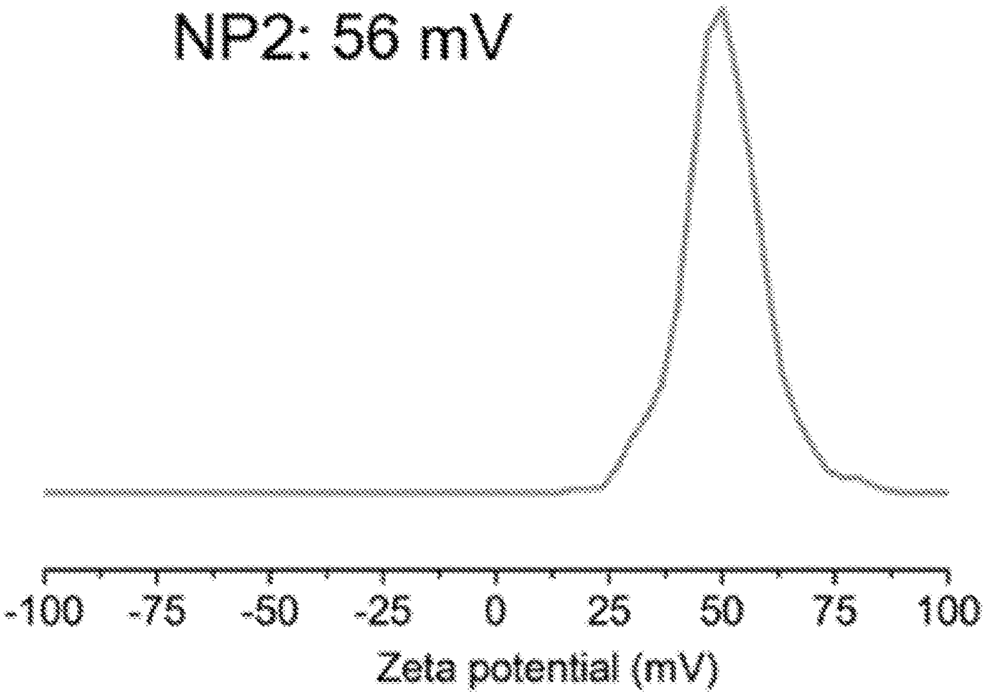
Figure 59C:
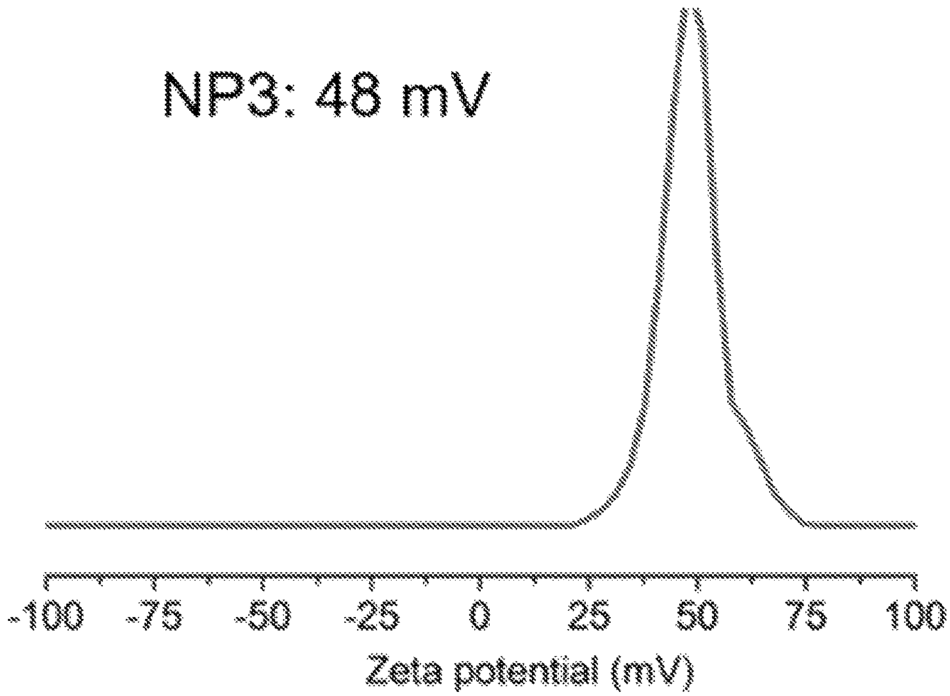
Figure 59D:
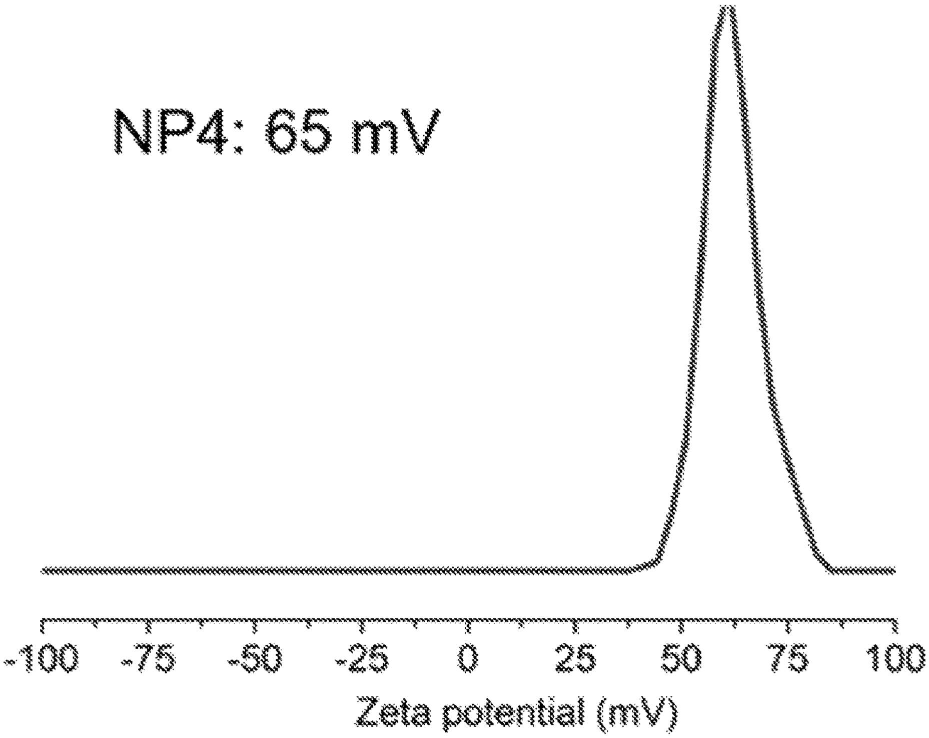
Figure 59E:
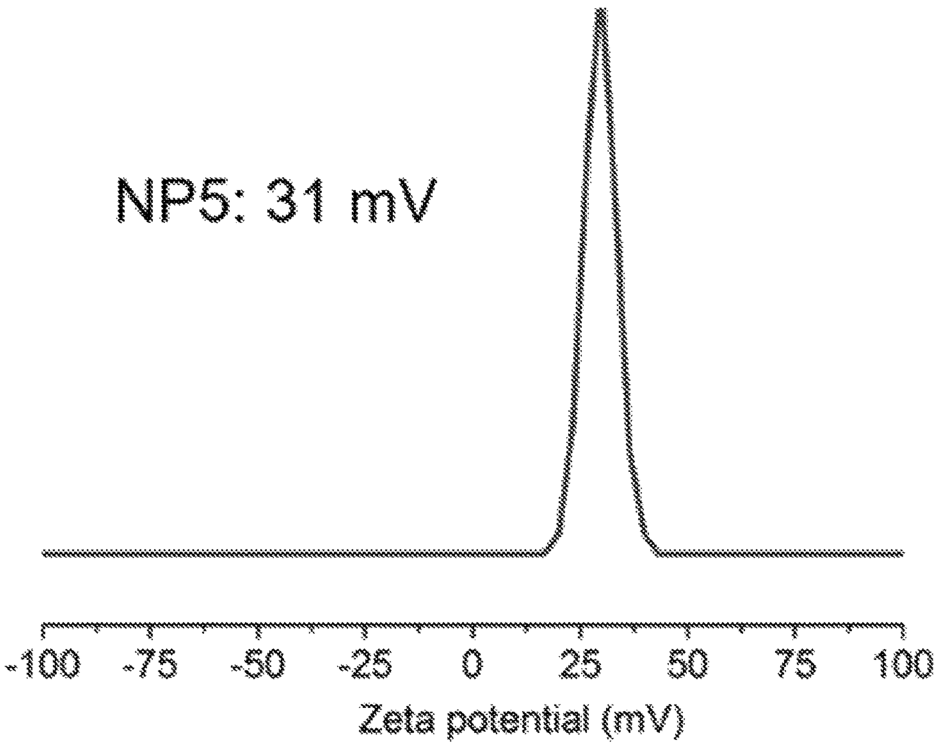
Figure 60:
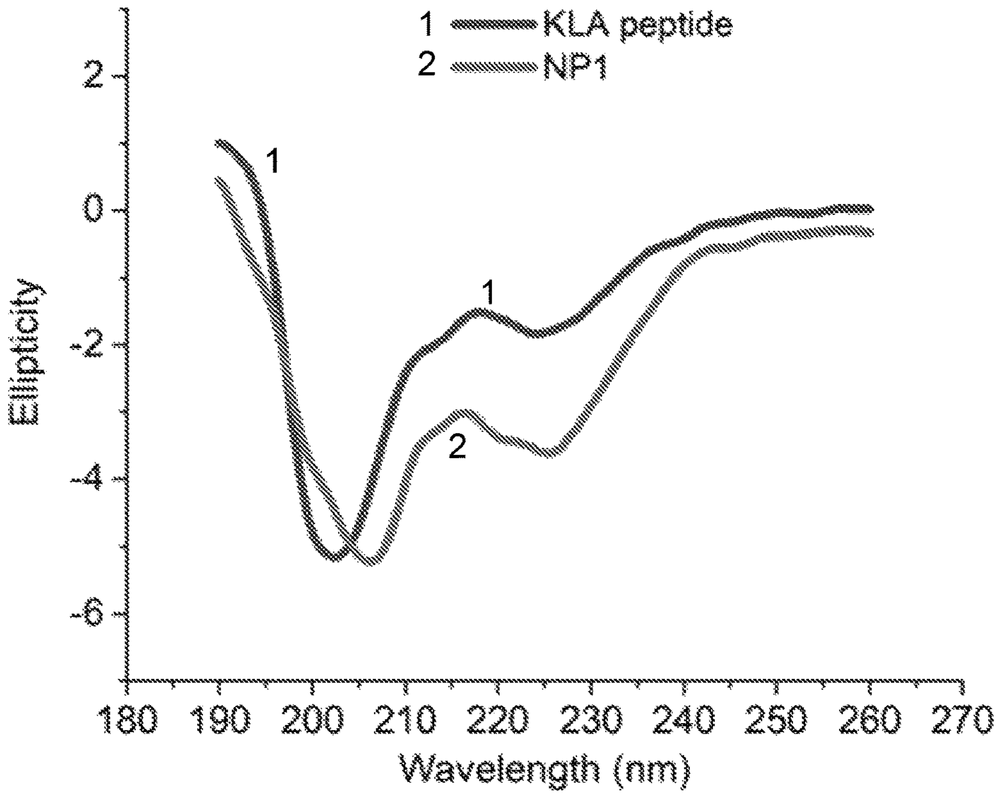
FIG. 60. Circular dichroism spectra of KLA peptide and representative peptide brush polymer nanoparticle (NP1).

The hydrodynamic diameters of peptide brush polymer nanoparticles were determined by dynamic light scattering (DLS), which suggested a trend of increasing size as the length of the hydrophobic chain increased (FIG. 43C and FIG. 57). Transmission electron microscopy (TEM) further revealed the shape and dry-state size of peptide brush polymer nanoparticles (FIGS. 43D-43H). According to the TEM micrographs, all the peptide brush polymer nanoparticles exhibit spherical morphologies and uniform size distributions. In addition, the nanoparticle size increased as the degree of polymerization of the hydrophobic core increased. This is in a good agreement with DLS and cryogenic transmission electron microscopy analysis (FIG. 58). Notably, only spherical morphology of nanoparticles was observed even at high DPs of core-forming monomers. This can be attributed to the high surface curvature which stems from the positively charged peptide brush shell.[15] The net charge of the nanoparticles was further assessed (FIGS. 59A-59E). Zeta potentials of those nanoparticles were positive, ranging from 31 mV to 65 mV because KLA peptide brush polymer nanoparticles have an abundant number of free amines. Furthermore, the secondary structures of KLA peptide and nanoparticles were evaluated by circular dichroism spectroscopy, which exhibited consistent patterns with a mixture of α-helix and random coil conformations (FIG. 60).

Figure 44:
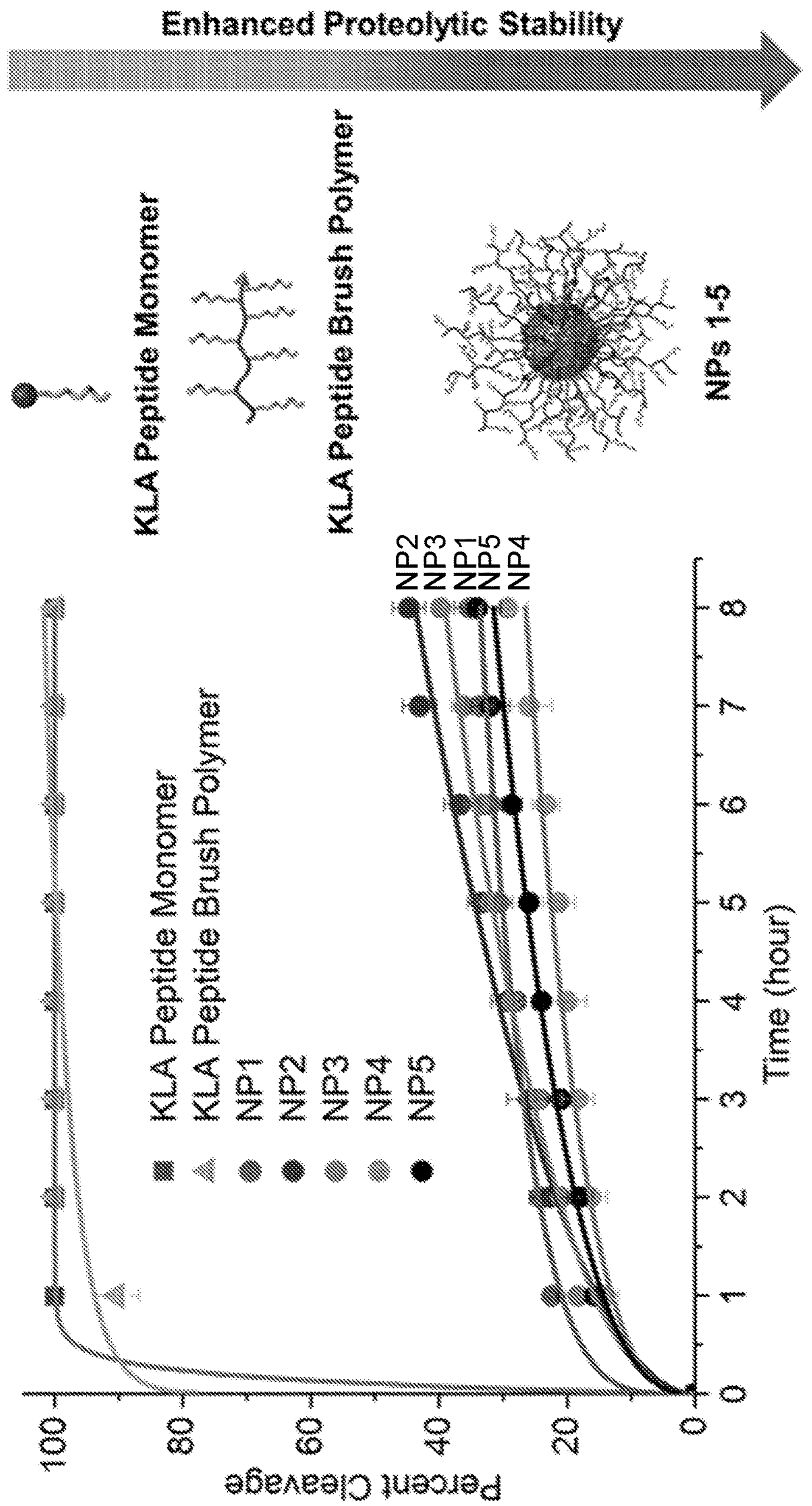
FIG. 44. Proteolytic cleavage of KLA peptide monomer, KLA brush polymer (poly($KLAAm_{10}$-co-$DMA_{10}$)), and KLA peptide brush polymer nanoparticles (NPs 1-5) in the presence of trypsin (0.1 μM) at 37° C. All the peptide containing materials had a concentration of 200 μM with respect to peptide in PBS buffer (pH=7.4). Data displayed as mean±standard deviation of three independent experiments.
Figure 61:
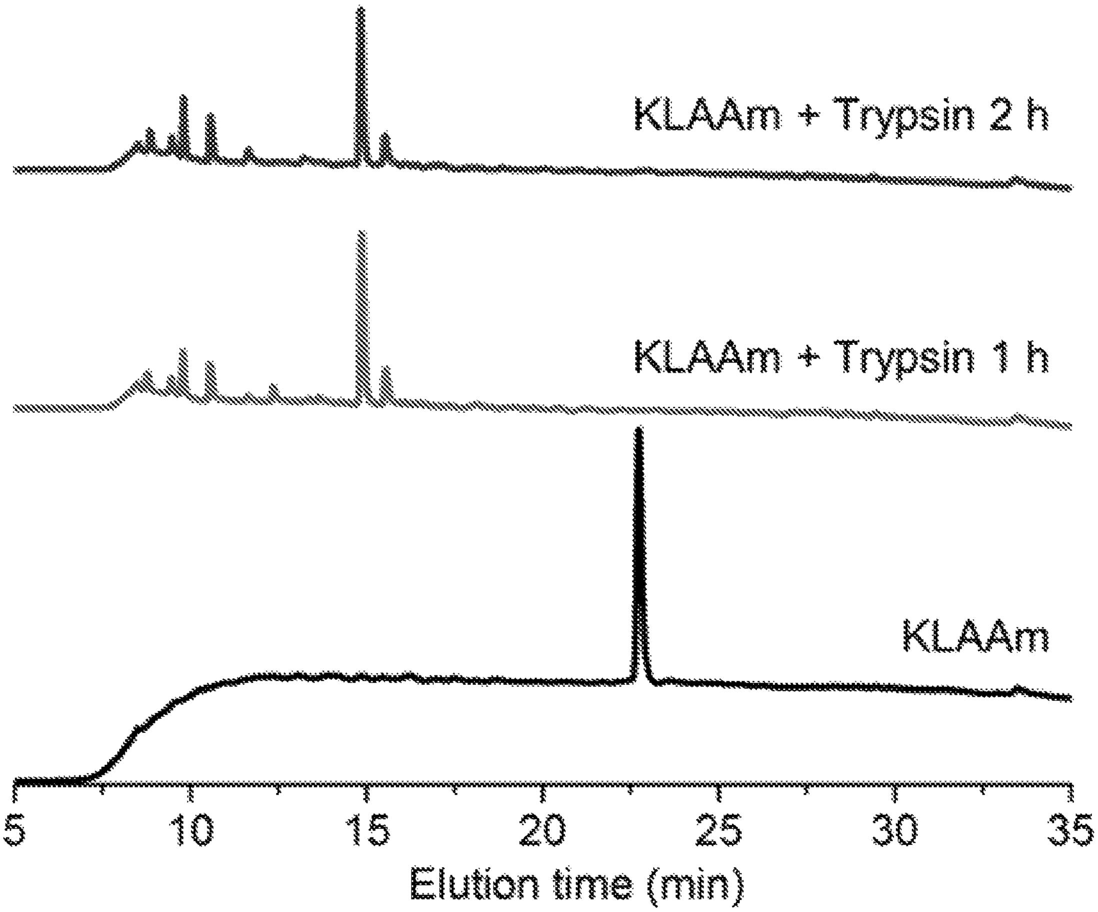
FIG. 61. Trypsin-induced cleavage of KLAAm. The initial peptide concentration was 200 μM in PBS. The ratio of trypsin to peptide is 1:2000. The original HPLC peak of KLAAm fully disappeared within 1 h after incubation with trypsin, indicative of 100% cleavage of the peptide.
Figure 62:
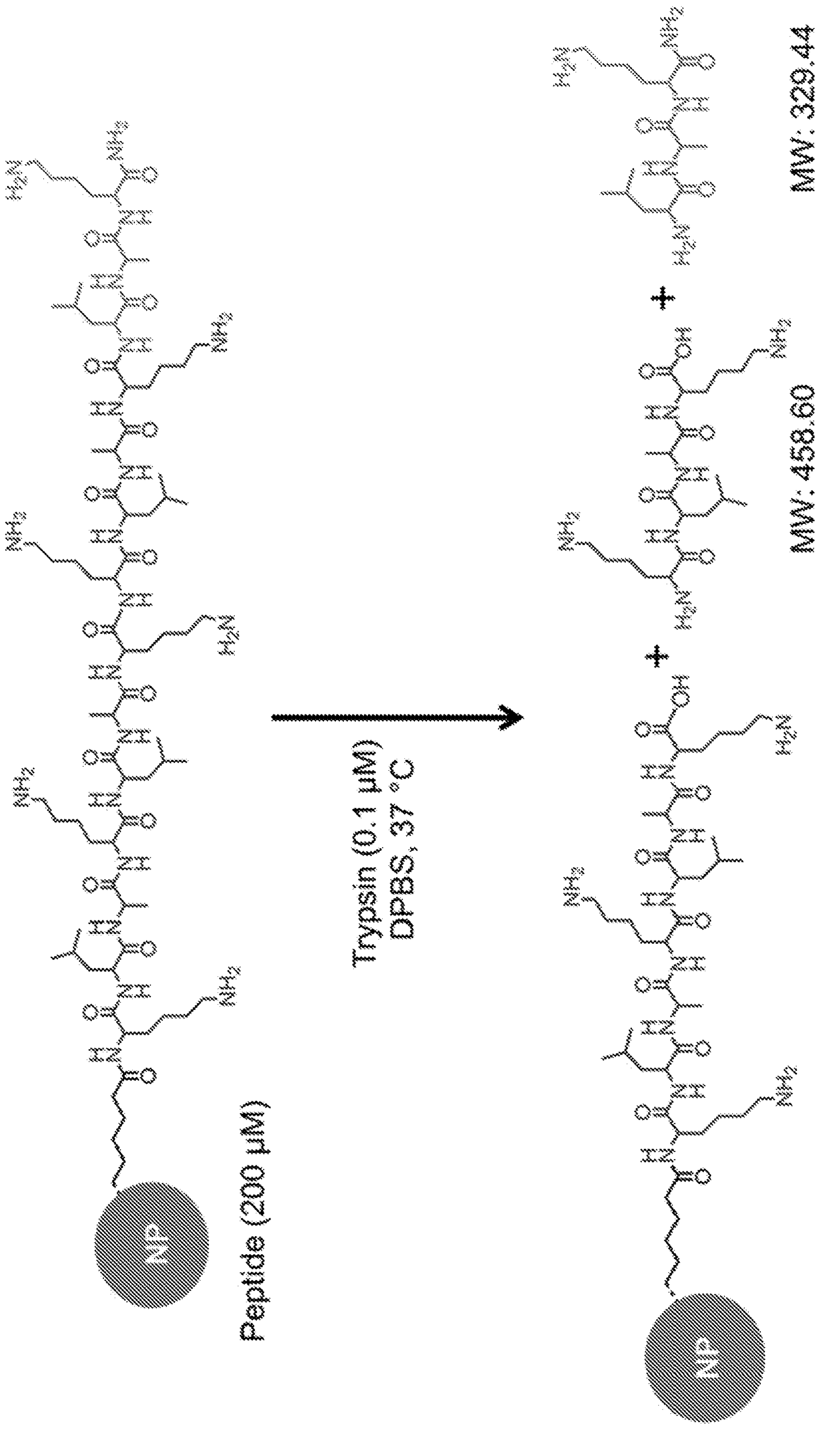
FIG. 62. Confirmed cleavage mechanism of KLA peptide brush nanoparticles in the presence of trypsin.
Figure 63A:
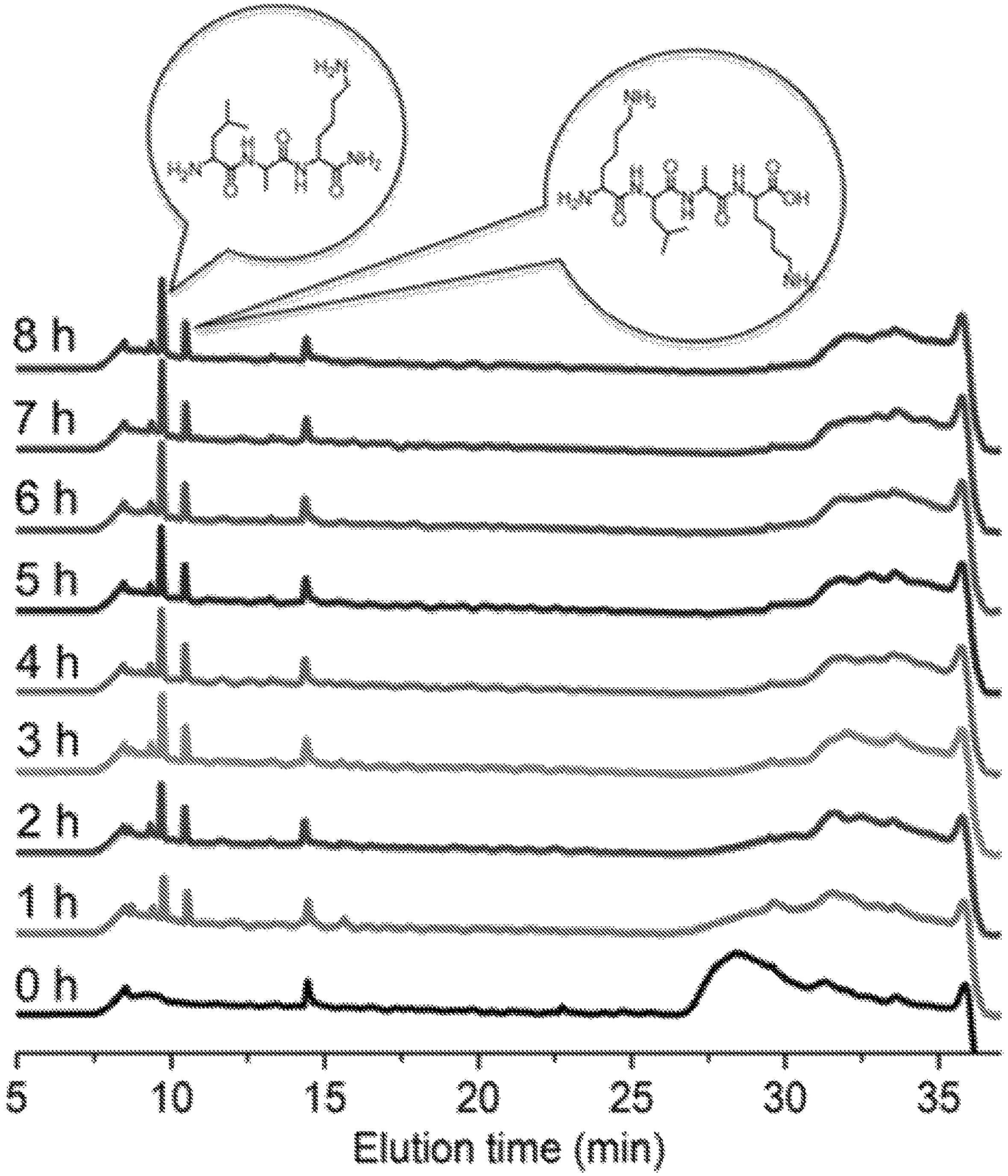
FIGS. 63A-63B. Representative trypsin-induced cleavage kinetics of peptide brush polymer nanoparticles (NP1) is elucidated by analytical RP-HPLC and ESI-MS. The HPLC peak area of peptide fragment (LAK, MW=329.44 g/mol) was used to quantify the percentage of cleaved peptides. A standard curve of synthetic LAK, correlating peak area on RP-HPLC chromatograms was used for the determination of the concentration of cleaved LAK after proteolytic cleavage.
Figure 63B:
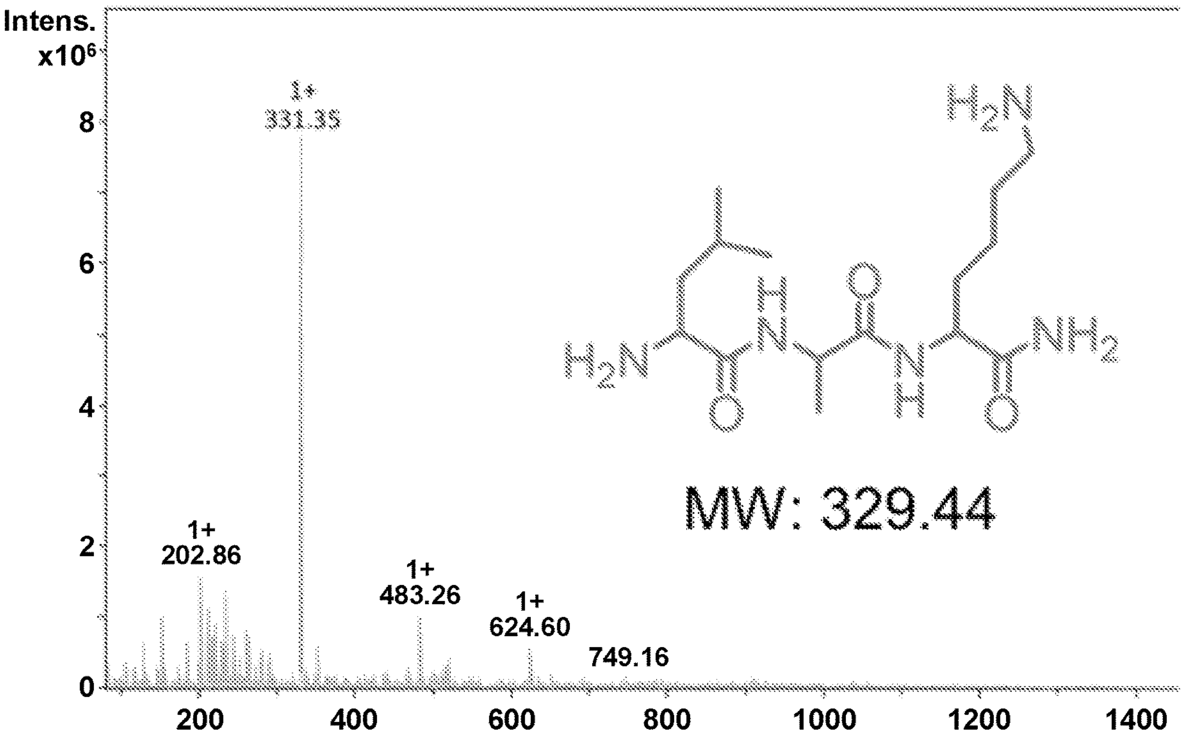
Figure 63B:
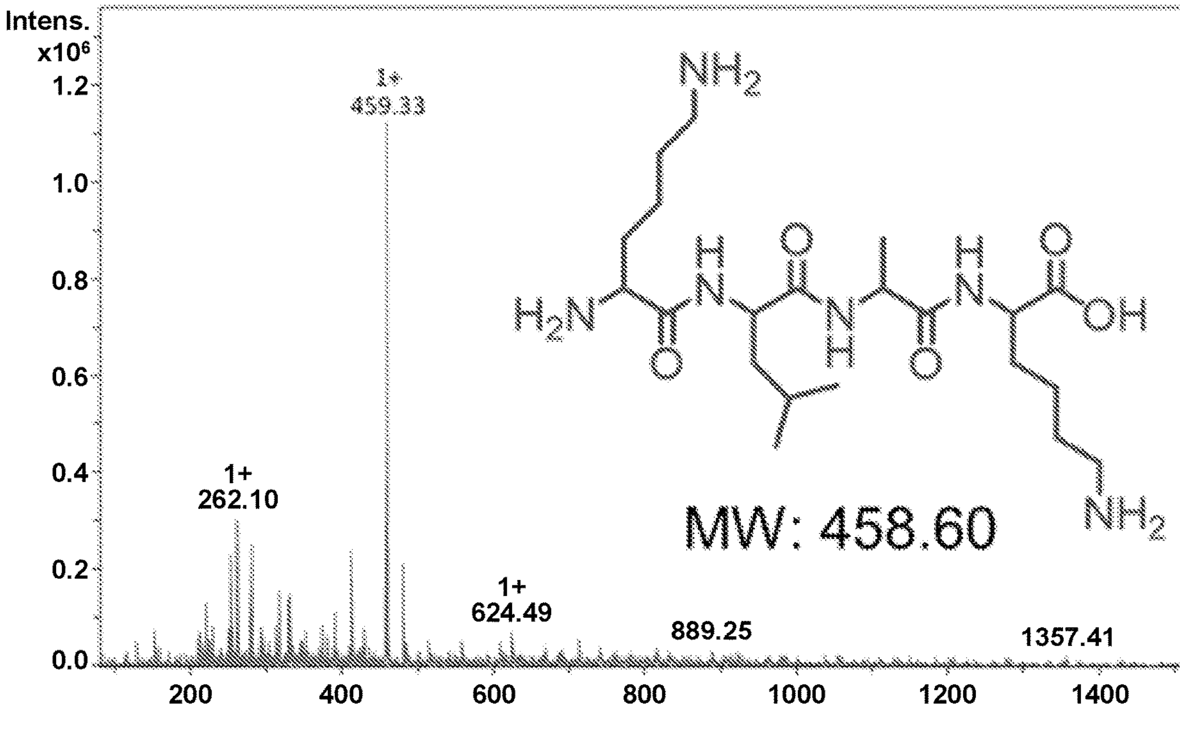

Despite the promise of proapoptotic KLA peptide as anti-cancer therapeutics, the anti-cancer efficacy of free KLA peptide is significantly impeded by its low proteolytic stability as well as poor cell uptake efficiency.[16] Since peptide brush polymer nanoparticles possess a high-density display of KLA peptides on the nanoparticle surface, we reasoned that the stability of the peptides would potentially be enhanced due to steric hindrance limiting access of the peptides to the active sites of proteases.[7c,17] In view of this, we examined the proteolytic resistance of KLA-containing materials of three kinds; 1) peptide, 2) peptide brush polymer, and 3) peptide brush polymer nanoparticles. For this test, trypsin was used as a potent proteinase typically found in the digestive system and freely capable of cleaving the KLA peptide (FIG. 44).[18] The concentration of trypsin was set to 0.1 μM, notably much higher than the level of trypsin in serum.[19] According to HPLC analysis, the KLA peptide underwent fast degradation, reaching 100% cleavage within 1 h (FIG. 61). Similarly, rapid degradation was observed for poly($KLAAm_{10}$-co-$DMA_{10}$), for which more than 90% of the side-chain peptides were cleaved within 1 h. On the other hand, in the case of KLA brush polymer nanoparticles, more than 70% of KLA peptide survived during the first hour of cleavage (FIG. 44, and FIGS. 62-63). This result confirmed that a high-density array of peptides on nanoparticle surface can endow the dangling peptides with enhanced proteolytic stability.

Figure 45:
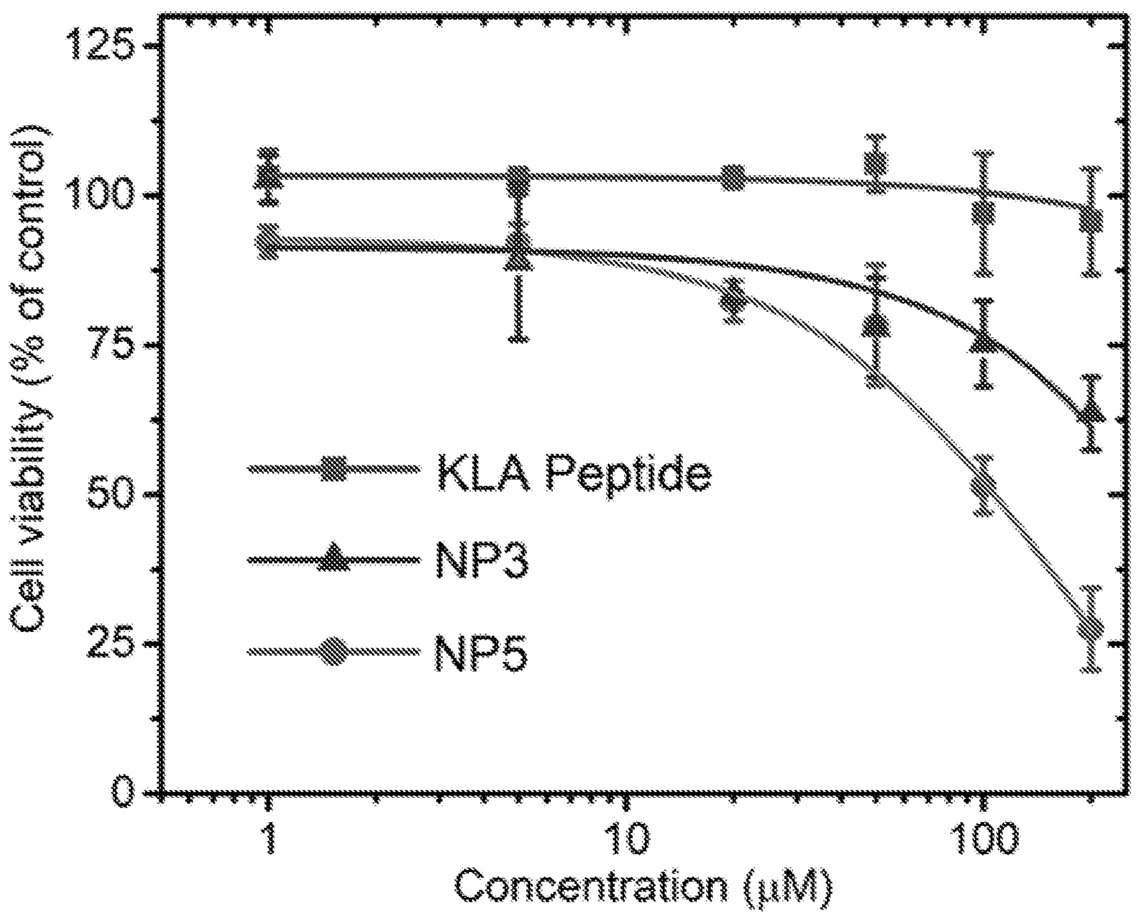
FIG. 45. Cytotoxicity of free KLA peptide, poly[($KLAAm_{10}$-co-$DMA_{30}$)-b-($DAAm_{280}$-co-$DMA_{120}$)] (NP3), and poly[($KLAAm_{10}$-co-$DMA_{10}$)-b-($DAAm_{280}$-co-$DMA_{120}$)](NP5) using a CellTiter-Blue cell viability assay. Concentrations were calculated with respect to the total KLA peptide content. HeLa cells were treated with peptide-containing materials and incubated for 72 h at 37° C. Data displayed as mean±standard deviation of three independent experiments.
Figure 64:
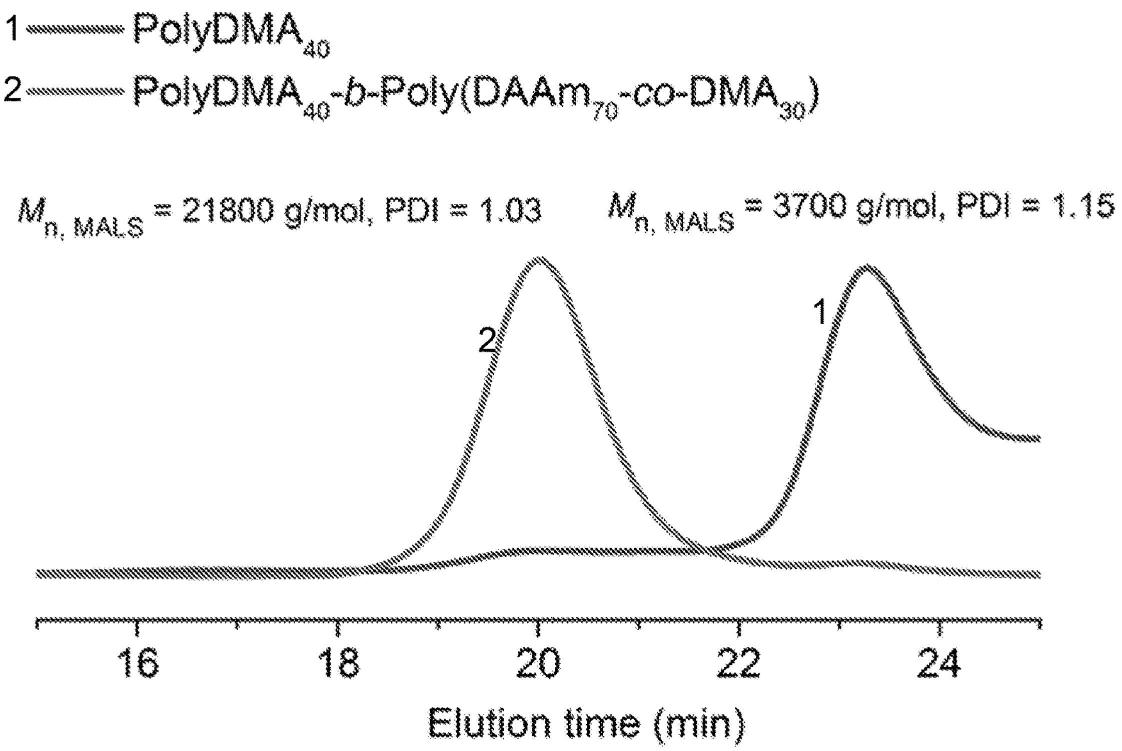
FIG. 64. GPC traces of polyDMA$_{40}$ macroCTA and polyDMA$_{40}$-b-poly(DAAm$_{70}$-co-DMA$_{30}$).
Figure 65:
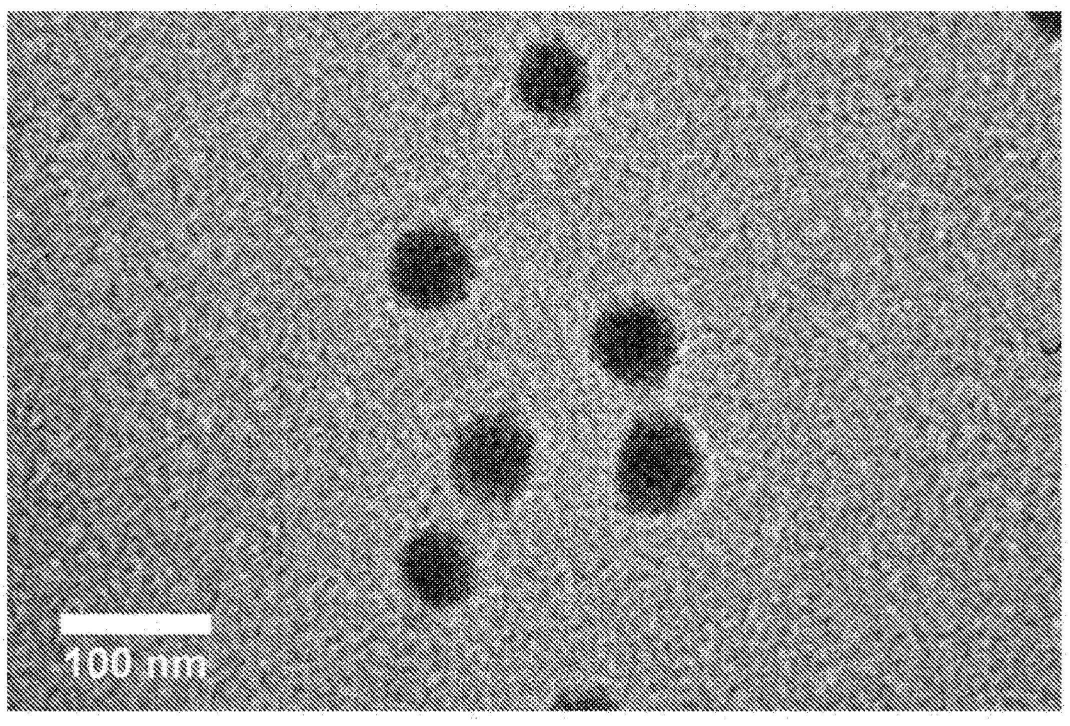
FIG. 65. Dry-state TEM image of polyDMA$_{40}$-b-poly (DAAm$_{70}$-co-DMA$_{30}$) based nanoparticle which was prepared via one-pot photo-PISA at solids content of 15 wt. %. A spherical morphology with an average size of 46 nm was observed.
Figure 66:
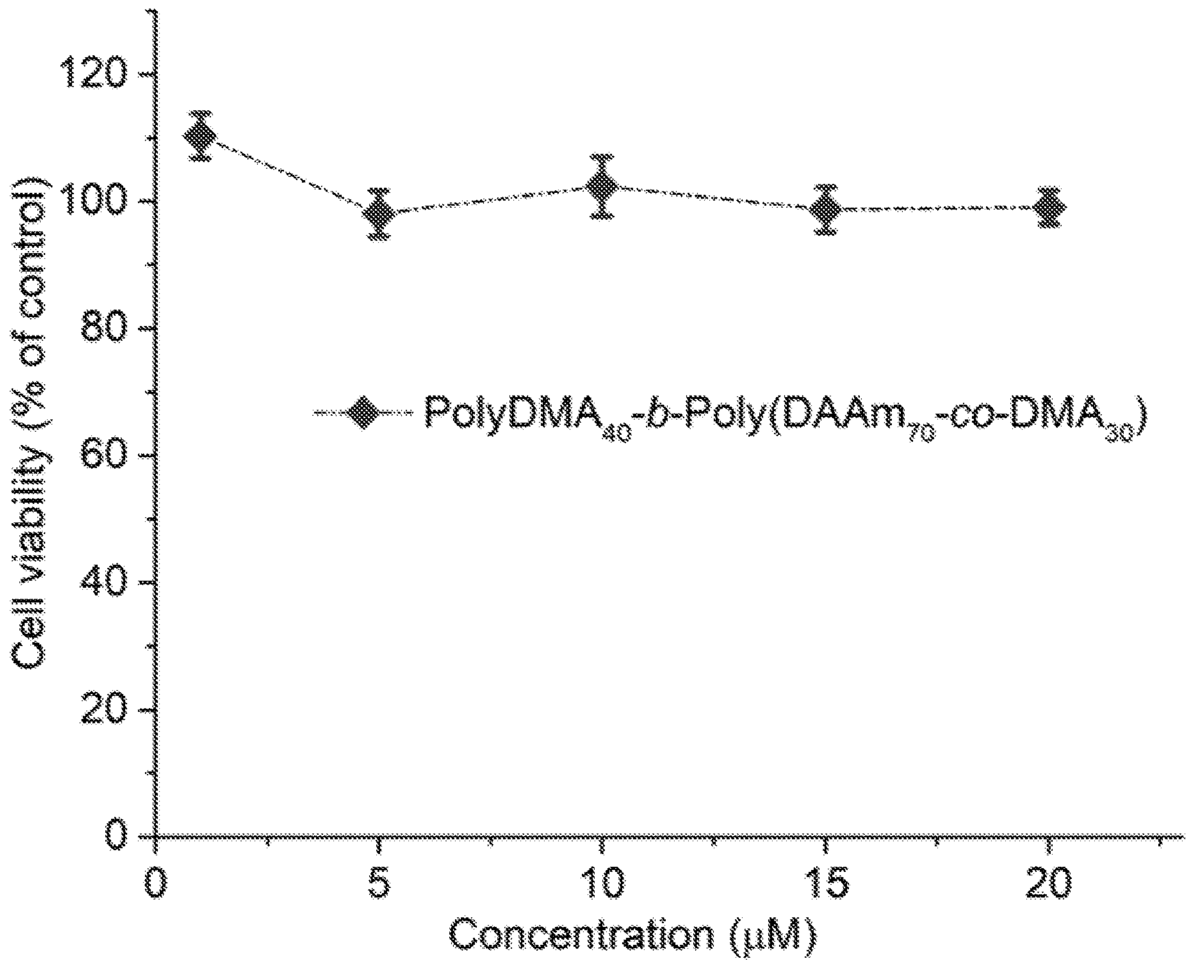
FIG. 66. Cytotoxicity of polyDMA$_{40}$-b-poly(DAAm$_{70}$-co-DMA$_{30}$) based nanoparticle using a CellTiter-Blue cell viability assay. Concentrations were calculated with respect to the polymer or CTA content. HeLa cells were treated with the materials and incubated for 48 h at 37° C. A high cell viability of HeLa cells was observed for this peptide-free polymer nanoparticles even at a high polymer concentration at 20 μM. Data displayed as mean±standard deviation of three independent experiments.
Figure 67A:
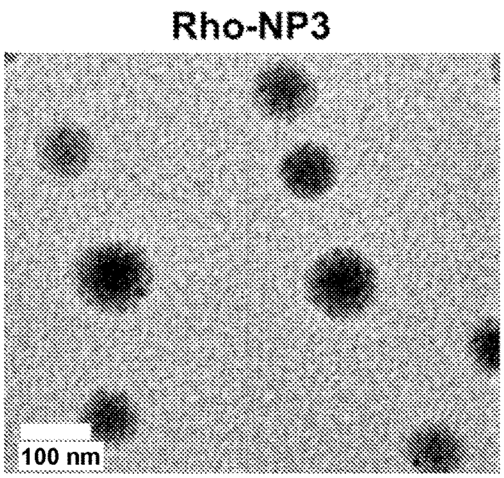
FIGS. 67A-67D. Dry-state TEM images and DLS traces of rhodamine B labeled nanoparticles (i.e., Rho-NP3 and Rho-NP5).
Figure 67B:
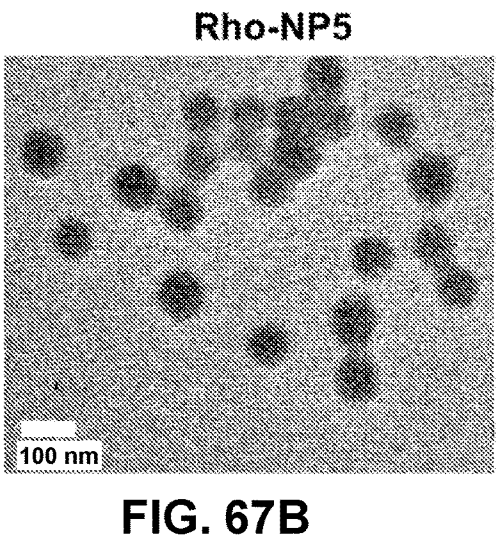
Figure 67C:
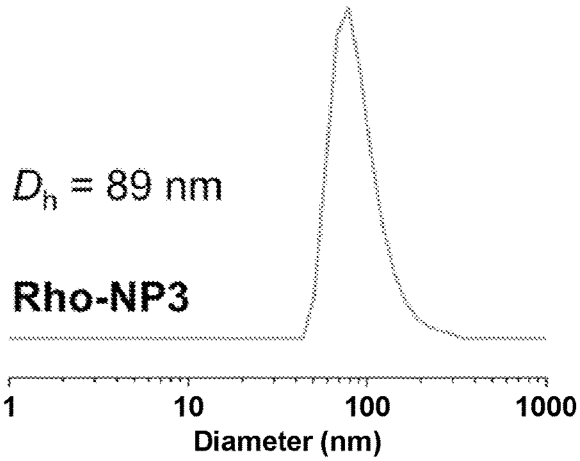
Figure 67D:
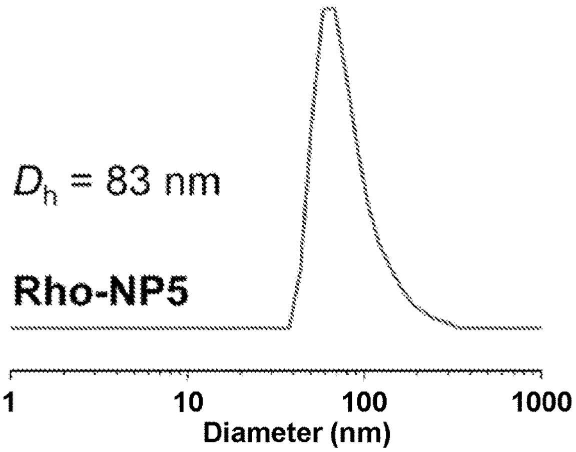

The cytotoxicity of KLA peptide brush nanoparticles and KLA peptide was examined in vitro with human cervical cancer (HeLa) cells (FIG. 45). Two nanoparticles including NP3 and NP5 were chosen to compare in the cell studies because of their similar sizes but different grafting density of peptides on the hydrophilic chain. According to the cell viability assay, NP3 and NP5 demonstrated dose-dependent cytotoxicity in HeLa cells, whereas no toxicity was observed for free KLA peptide even at a high concentration of 200 μM. To unequivocally credit the toxicity of KLA brush nanoparticles to the proapoptotic peptides on the nanoparticles, the cytotoxicity of a spherical polymer nanoparticle without carrying the peptides (i.e., poly$DMA_{40}$-b-poly($DAAm_{70}$-co-$DMA_{30}$)) was further evaluated (FIGS. 64-66). Cell viability assay revealed a high viability (>90%) of HeLa cells in the presence of peptide-free polymer micelles under the investigated concentrations, confirming the cytocompatibility of the polymer nanocarrier.

Figure 68:
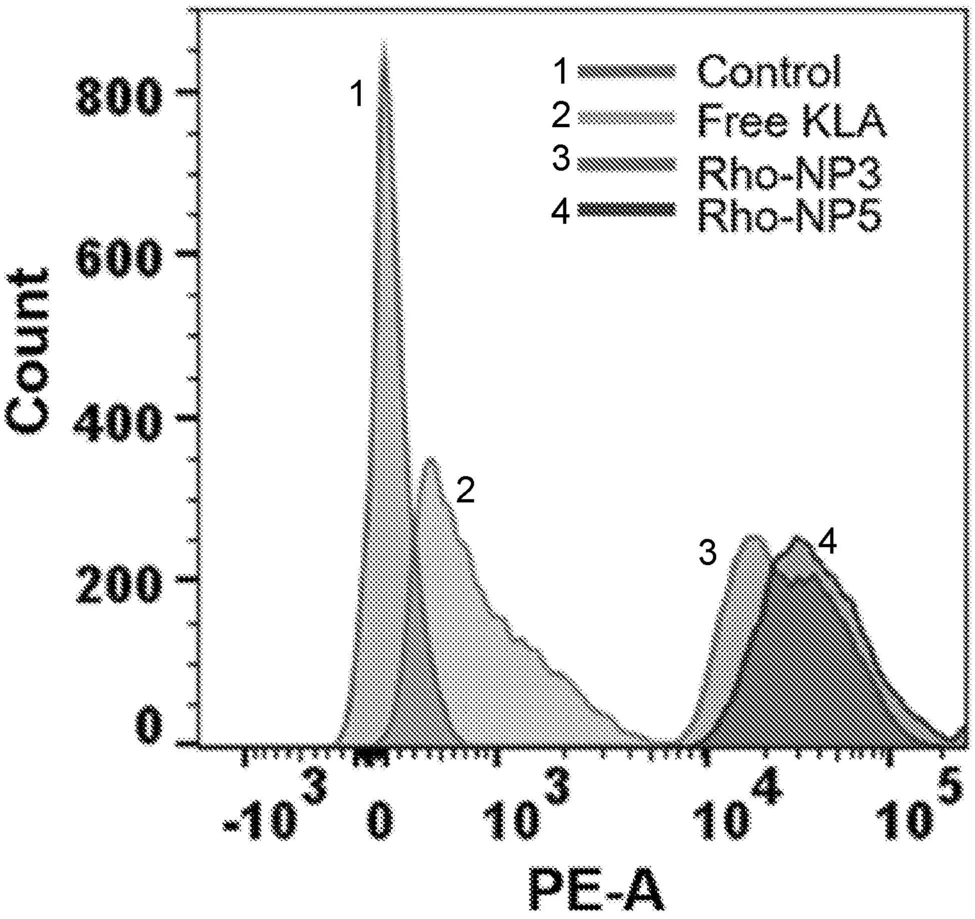
FIG. 68. Flow cytometry analysis ($\lambda_{ex/em}$=548/570 nm) of HeLa cells incubated with Rho-KLA peptide, Rho-NP3, and Rho-NP5 at a concentration of 0.25 μM with respect to Rhodamine.
Figure 69:
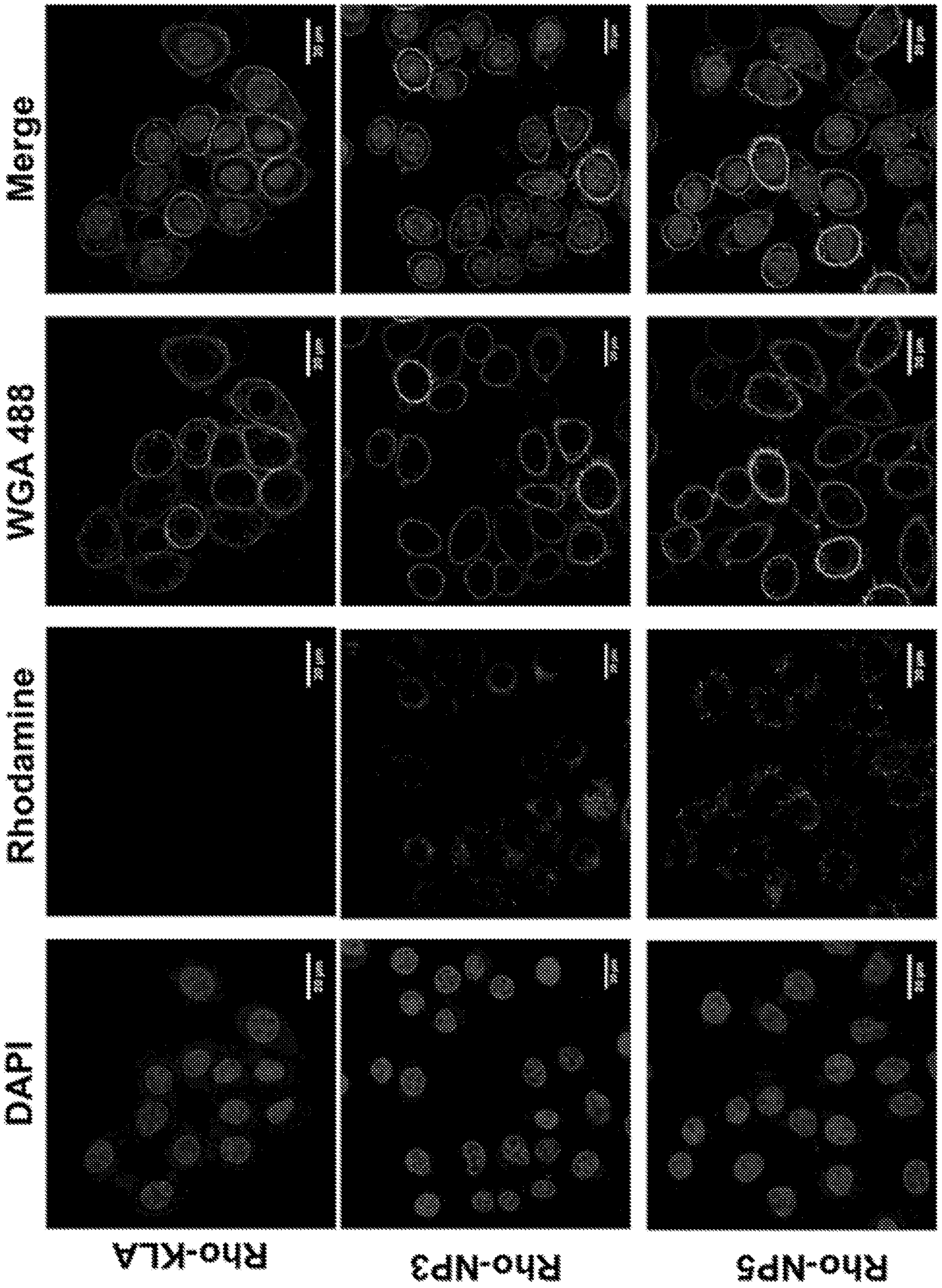
FIG. 69. Confocal microscopy images of HeLa cells incubated with rhodamine-labeled KLA peptide, NP3, and NP5 at a concentration of 0.25 μM with respect to Rhodamine. Cell nuclei were stained with DAPI. Cell membrane was stained with WGA 488. Scale bar: 20 μm.
Figure 70:
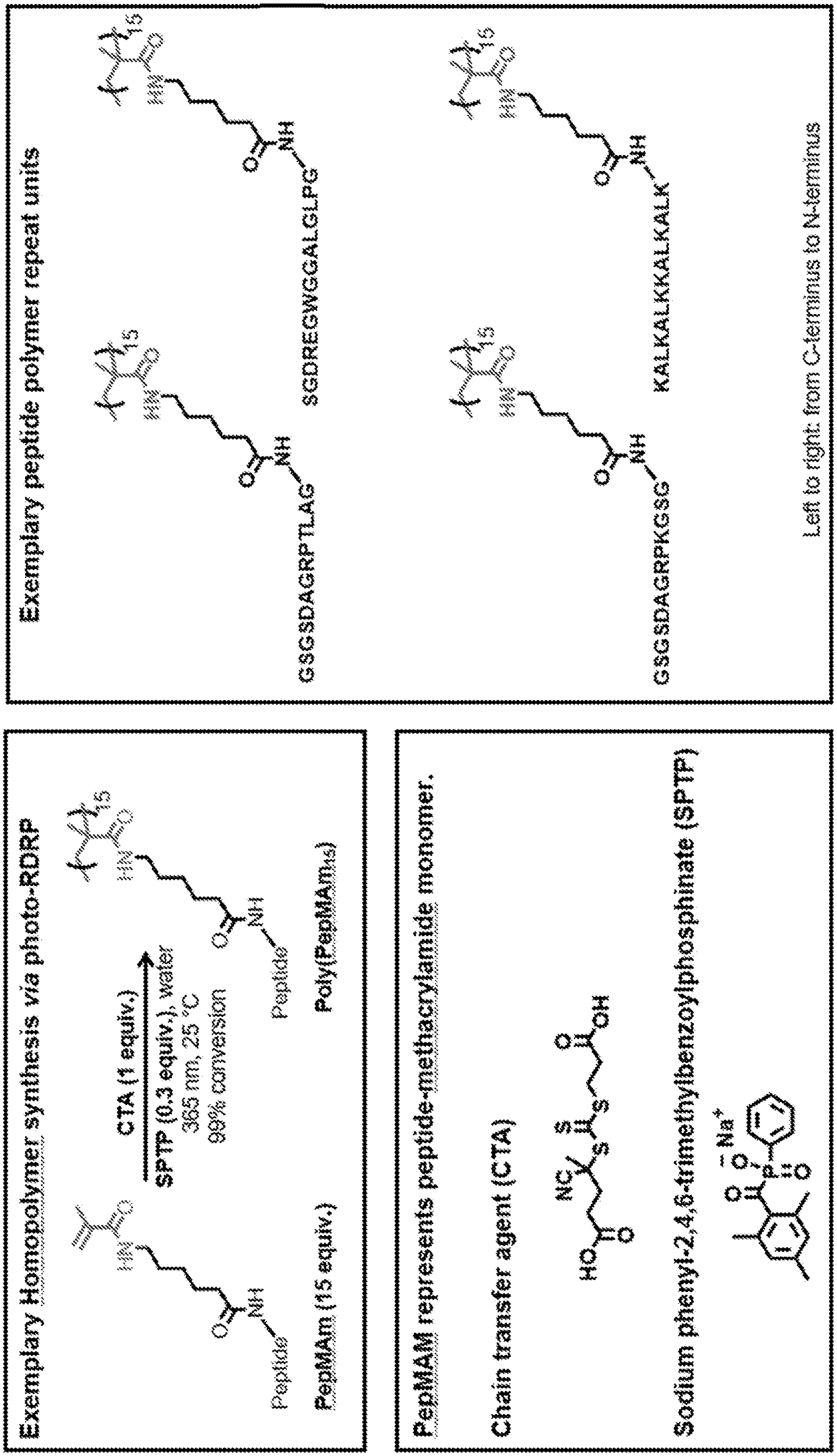
FIG. 70. Summary and formulas of certain embodiments of methods, reagents, and repeating units of polymers disclosed herein. ( ) (GPLGLAGGWGERDGS is SEQ ID NO:1; GALTPRGADSGSG is SEQ ID NO:2; KLAKLAKKLAKLAK is SEQ ID NO:3; GSGKEFGADSGSG is SEQ ID NO:4.)
Figure 71:
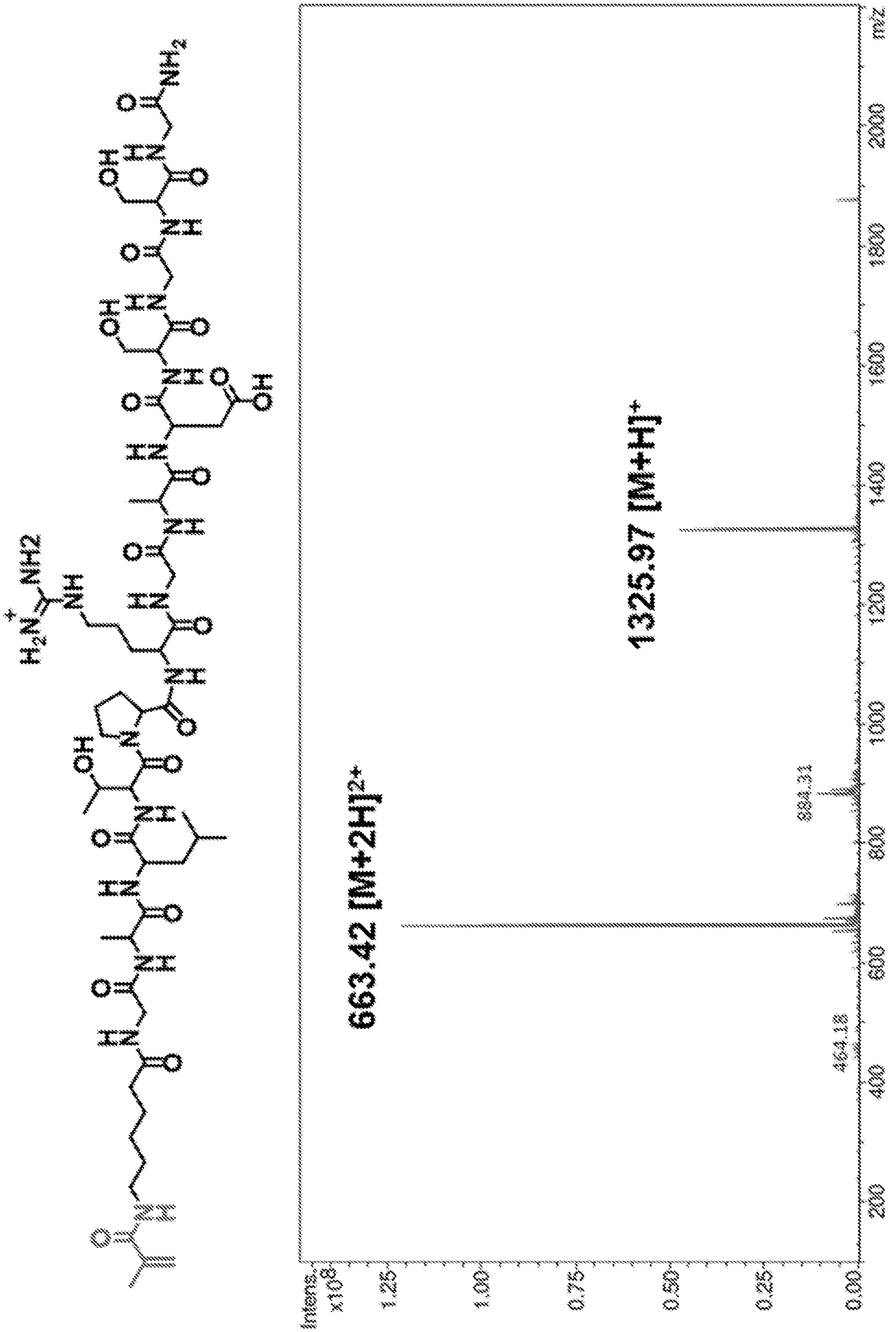
FIG. 71. ESI-MS spectrum of MAm-GALTPRGADSGSG (GALTPRGADSGSG is SEQ ID NO:2).
Figure 72:
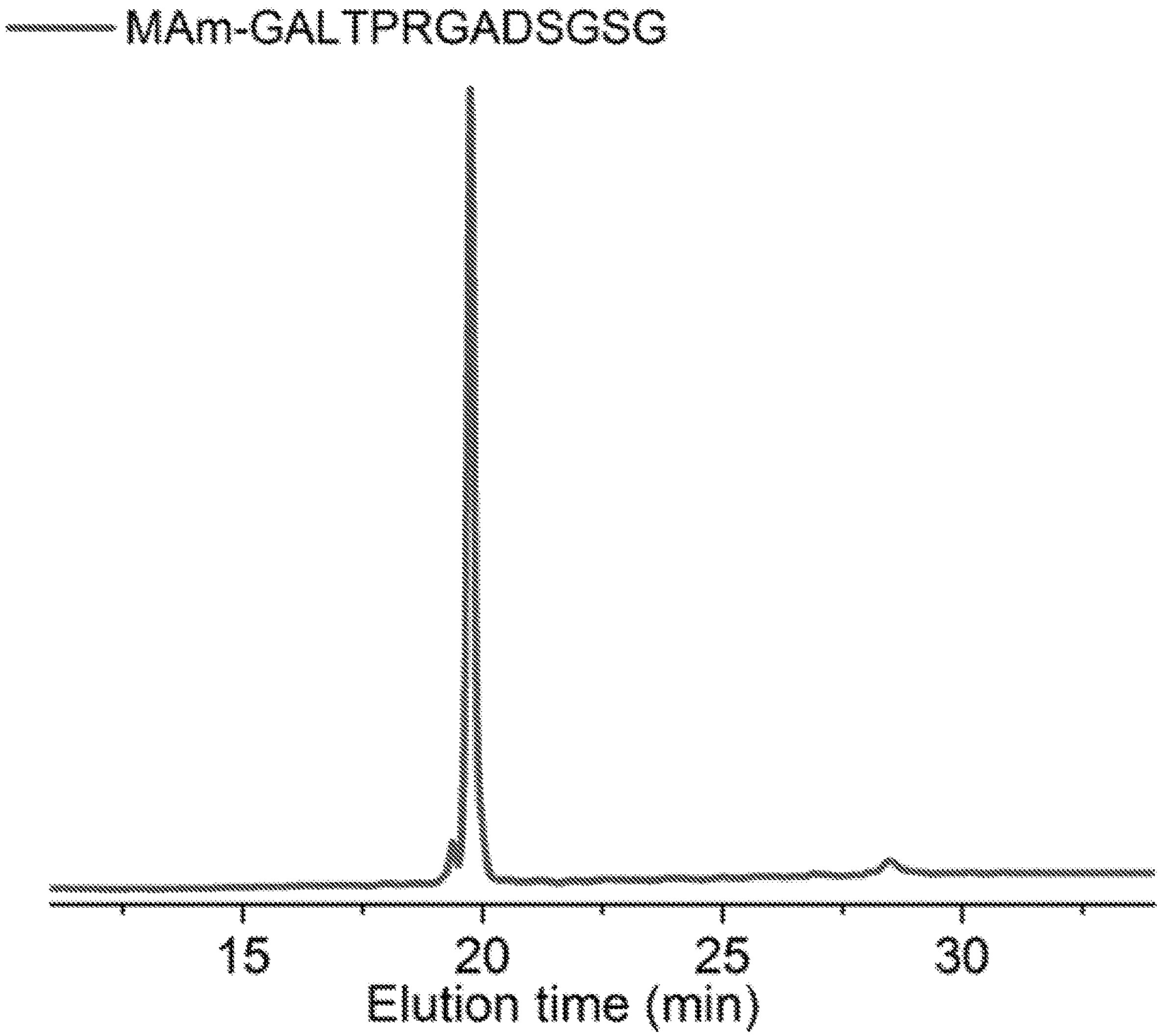
FIG. 72. HPLC trace of MAm-GALTPRGADSGSG (SEQ ID NO:2).
Figure 73:
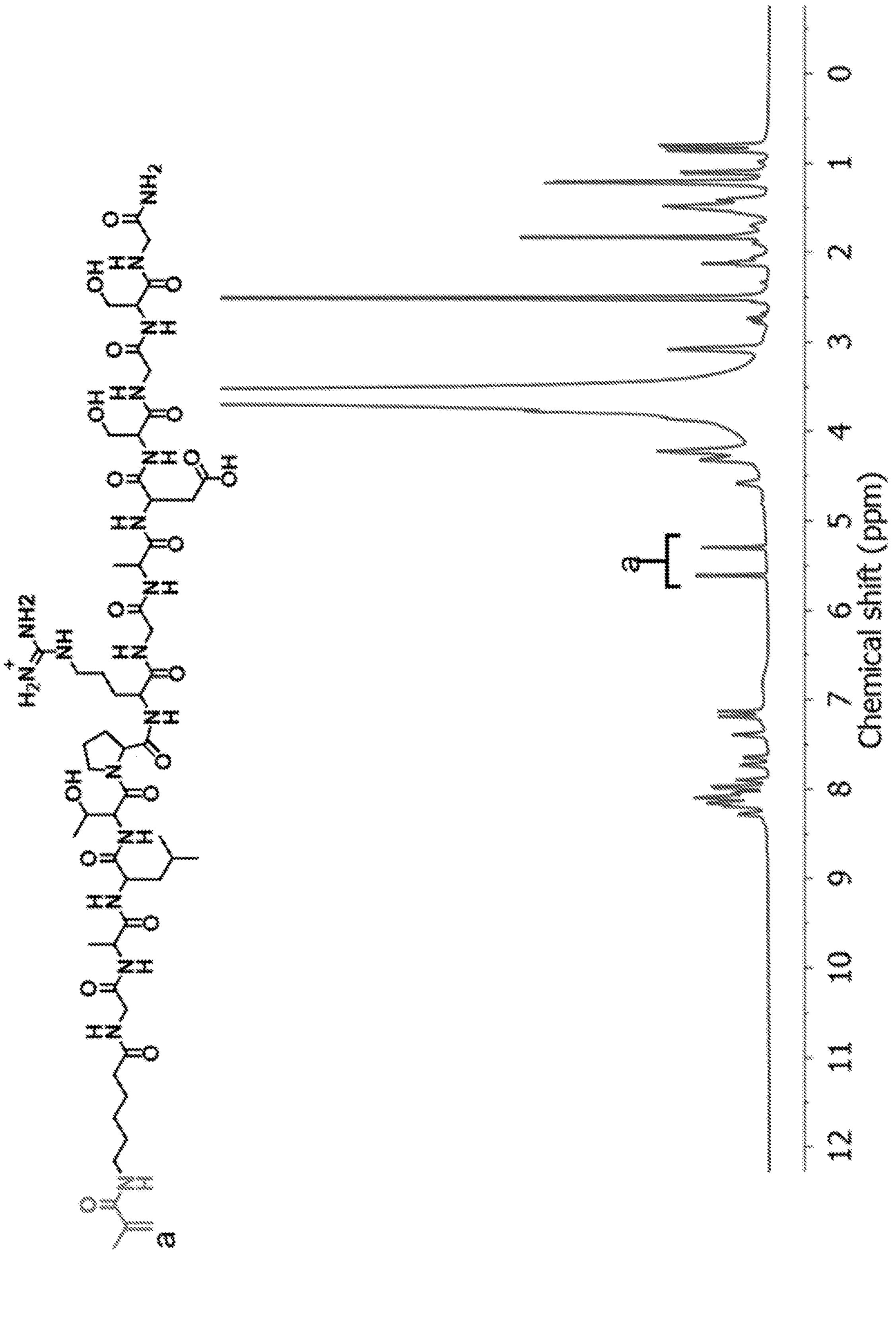
FIG. 73. $^1$H NMR spectrum of MAm-GALTPRGADSGSG (SEQ ID NO:2).
Figure 74:
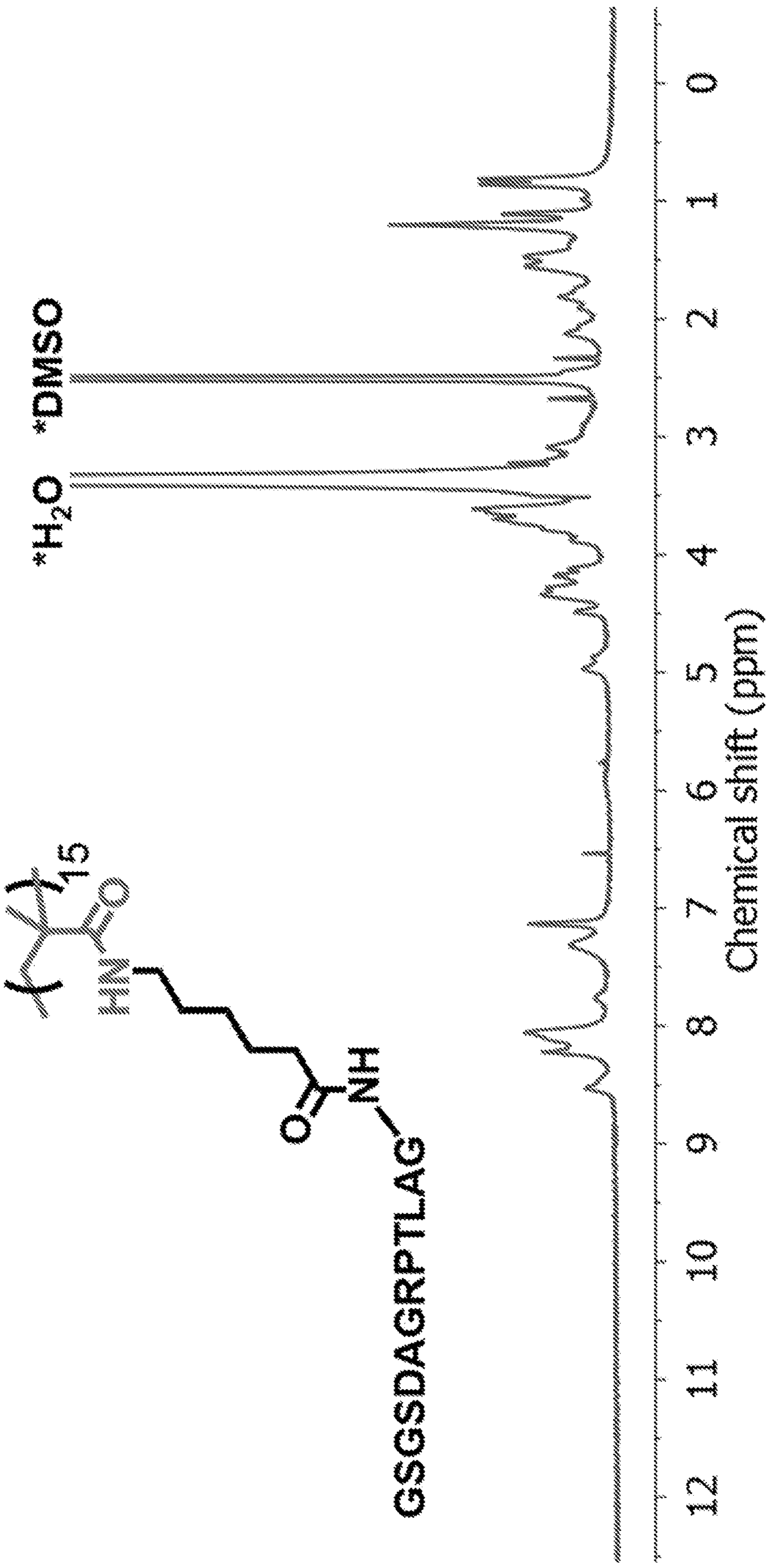
FIG. 74. $^1$H NMR spectrum of poly(MAm-GALTPRGADSGSG) (SEQ ID NO:2) in DMSO-d6.
Figure 75:
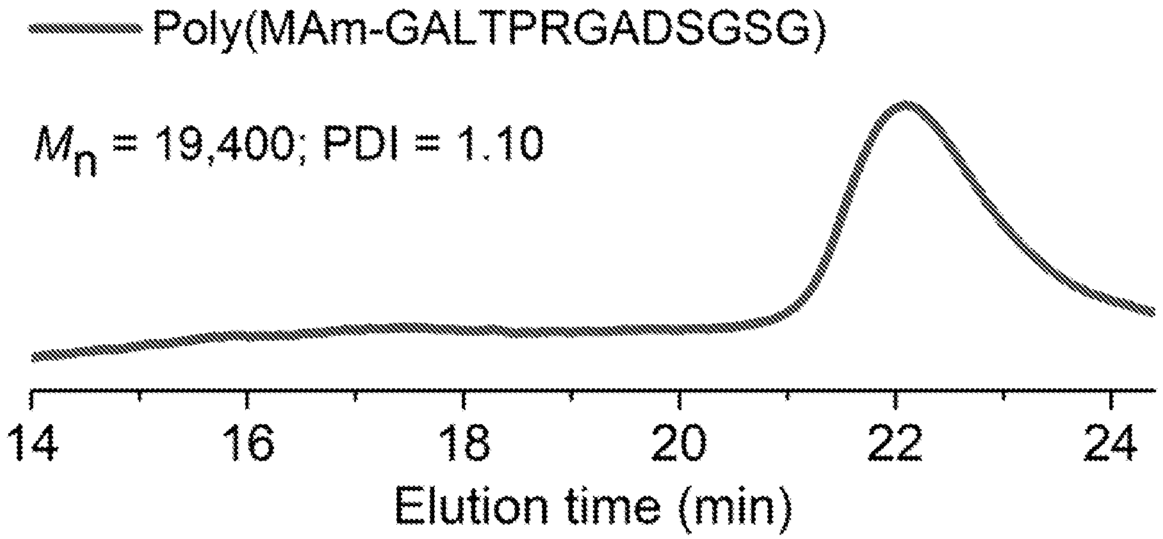
FIG. 75. GPC trace of poly(MAm-GALTPRGADSGSG) (SEQ ID NO:2) in DMF eluent.
Figure 76:
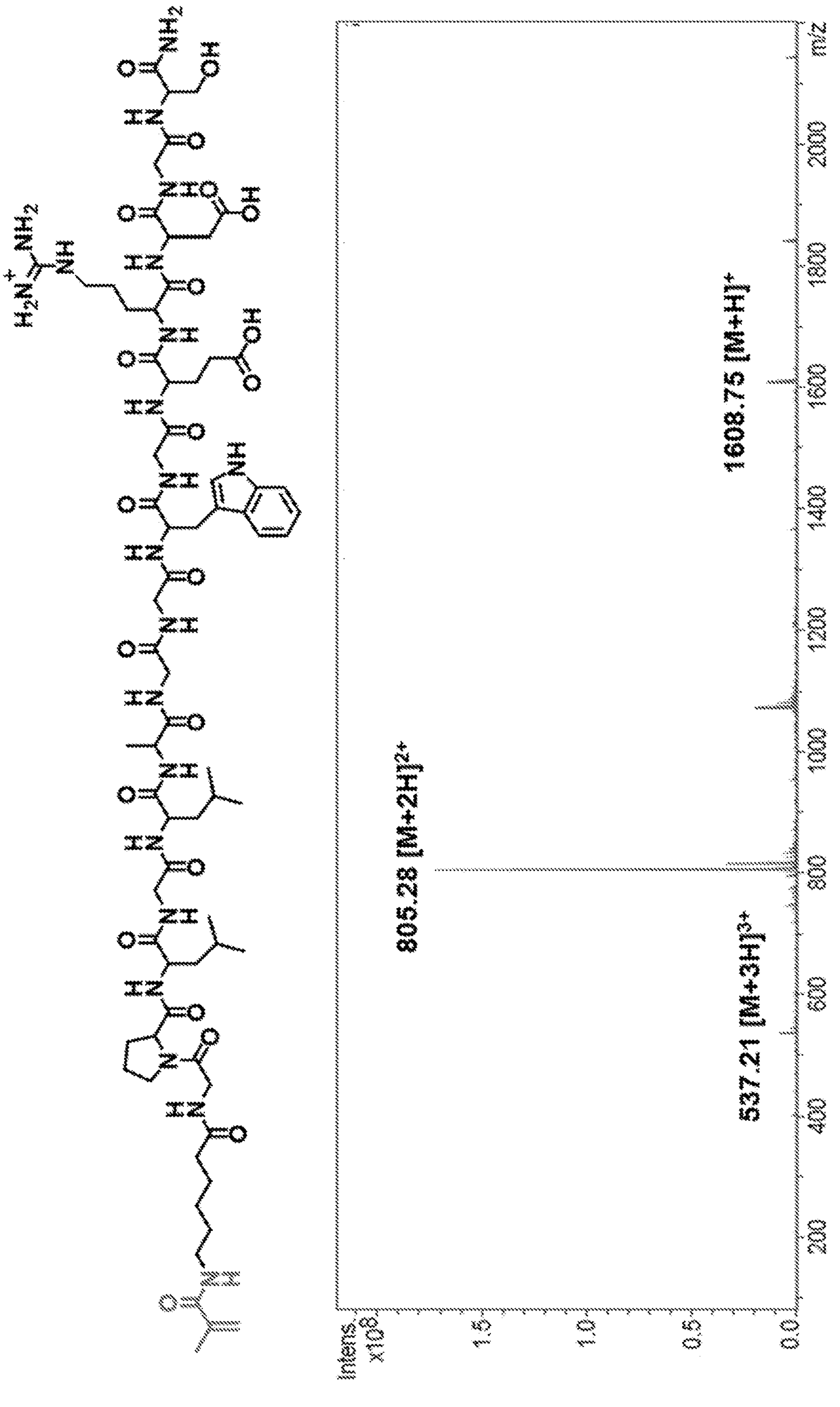
FIG. 76. ESI-MS spectrum of MAm-GPLGLAGGWGERDGS (GPLGLAGGWGERDGS is SEQ ID NO:1).
Figure 77:
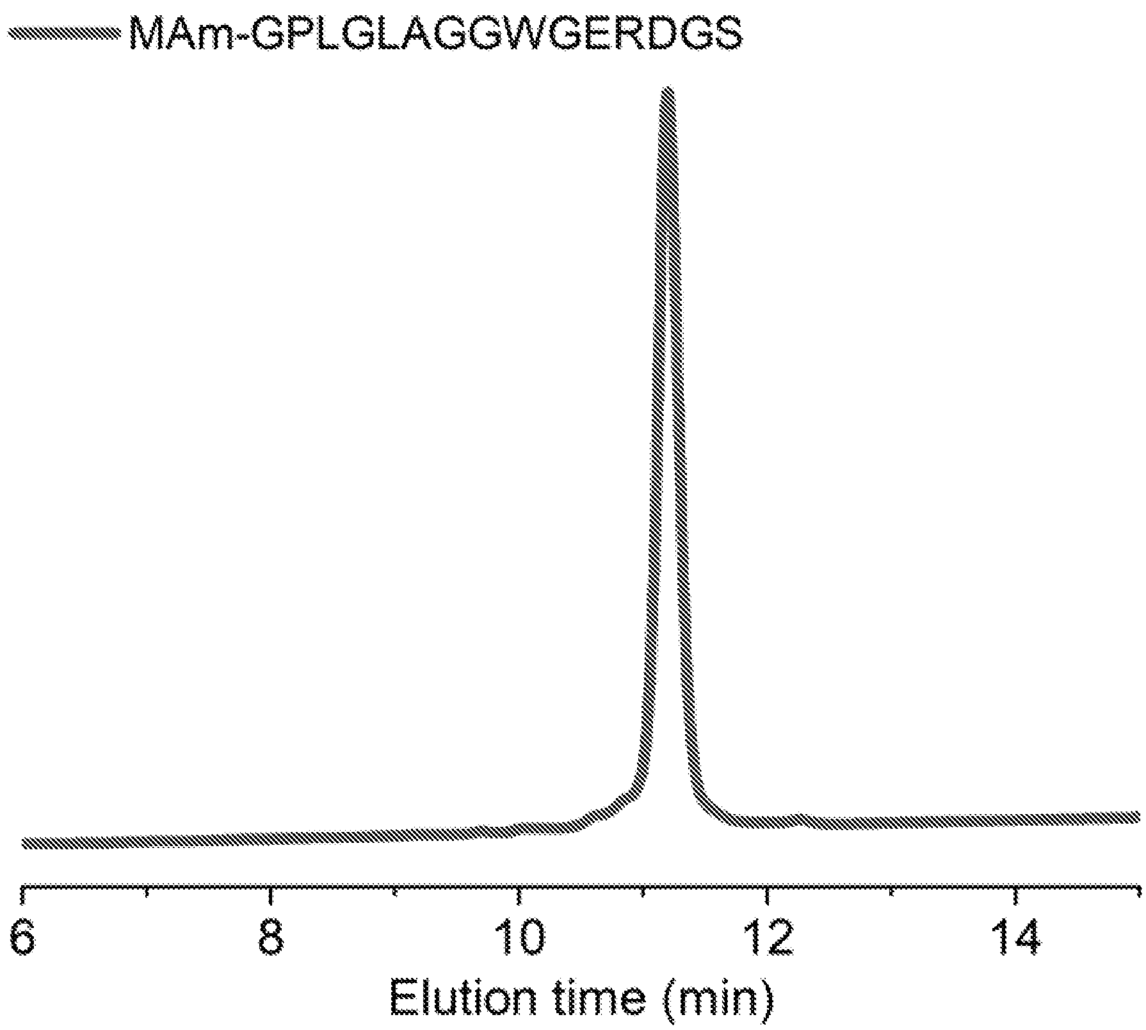
FIG. 77. HPLC trace of MAm-GPLGLAGGWGERDGS (SEQ ID NO:1).
Figure 78:
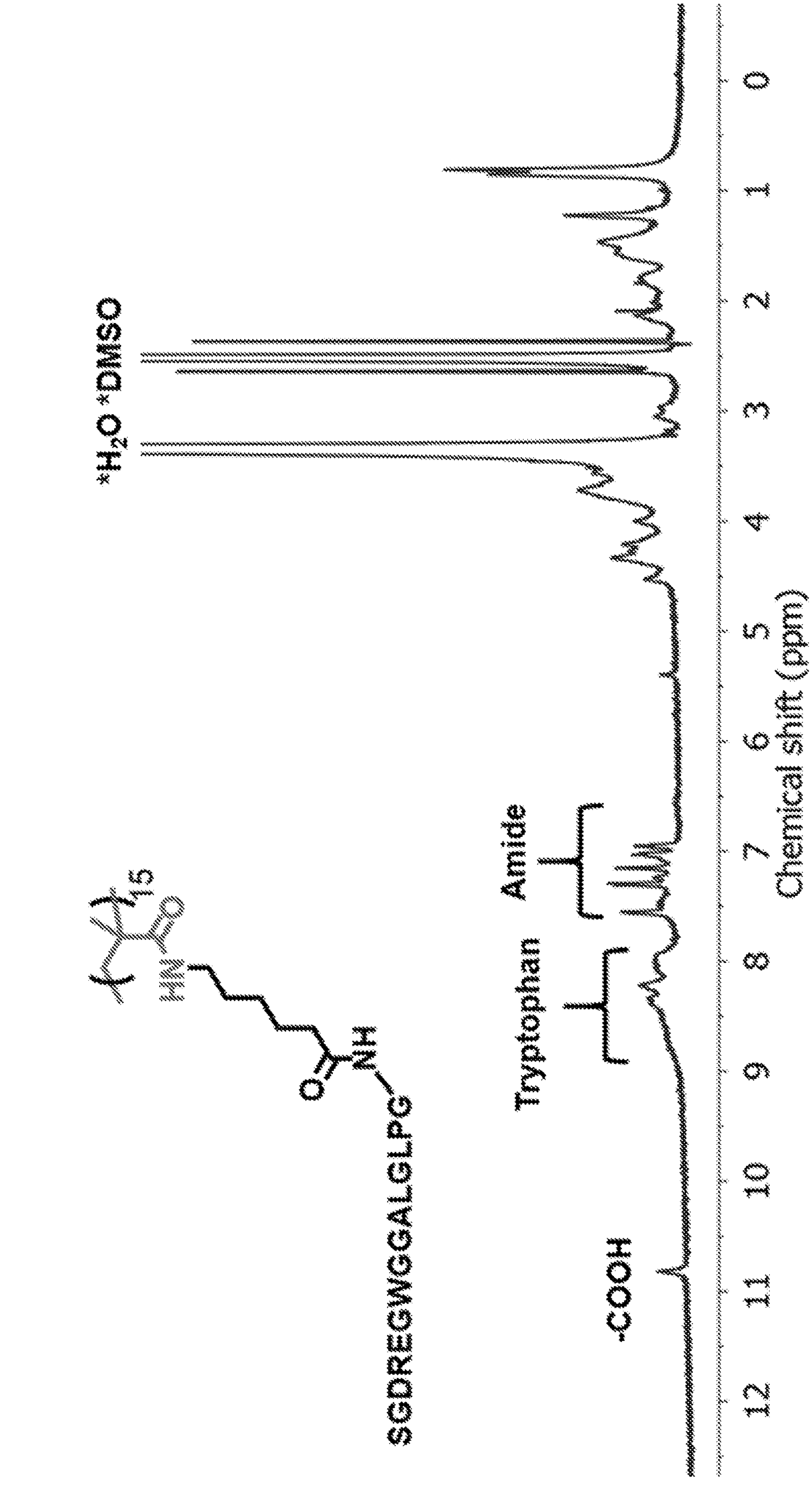
FIG. 78. $^1$H NMR spectrum of poly(MAm-GPLGLAGGWGERDGS) (SEQ ID NO:1) in DMSO-d6.
Figure 79:
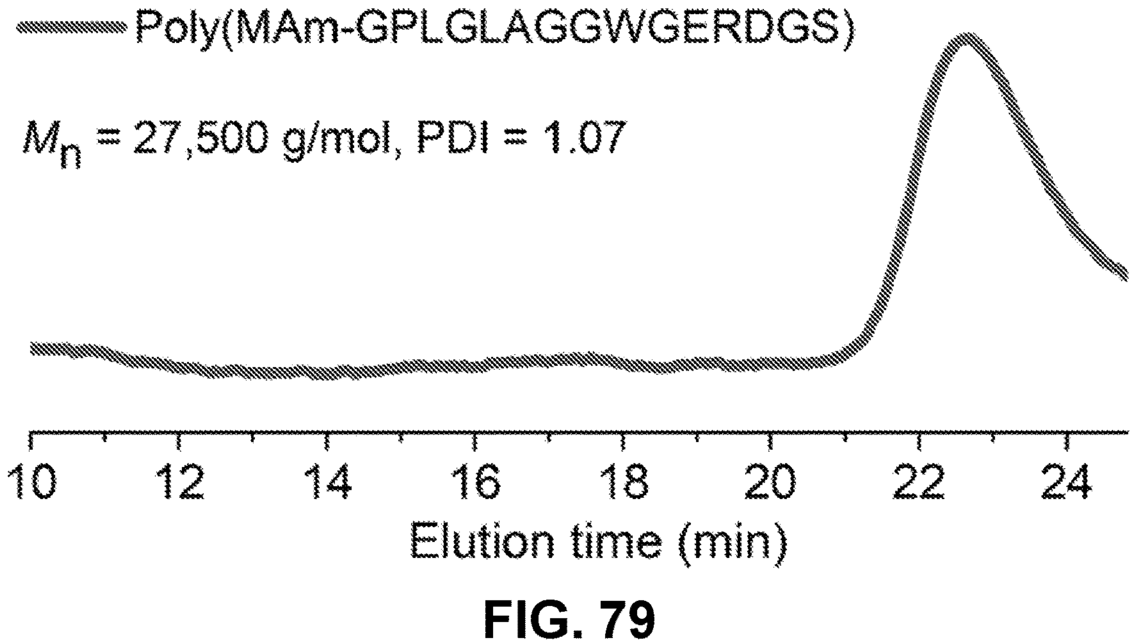
FIG. 79. GPC trace of poly(MAm-GPLGLAGGWGERDGS) (SEQ ID NO:1) in DMF eluent.
Figure 80:
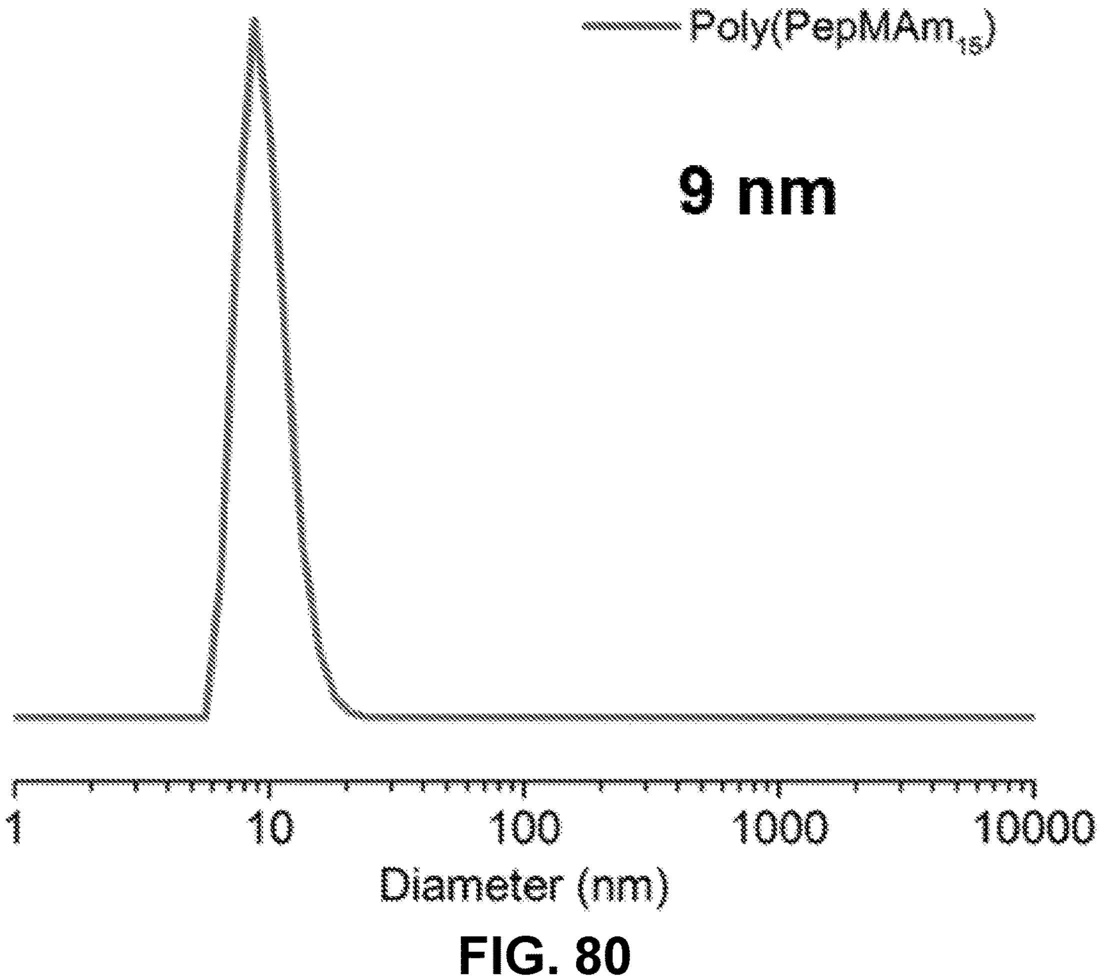
FIG. 80. DLS trace of poly(MAm-GPLGLAGGWGERDGS) (SEQ ID NO:1) in DPBS buffer (pH=7.4).
Figure 81:
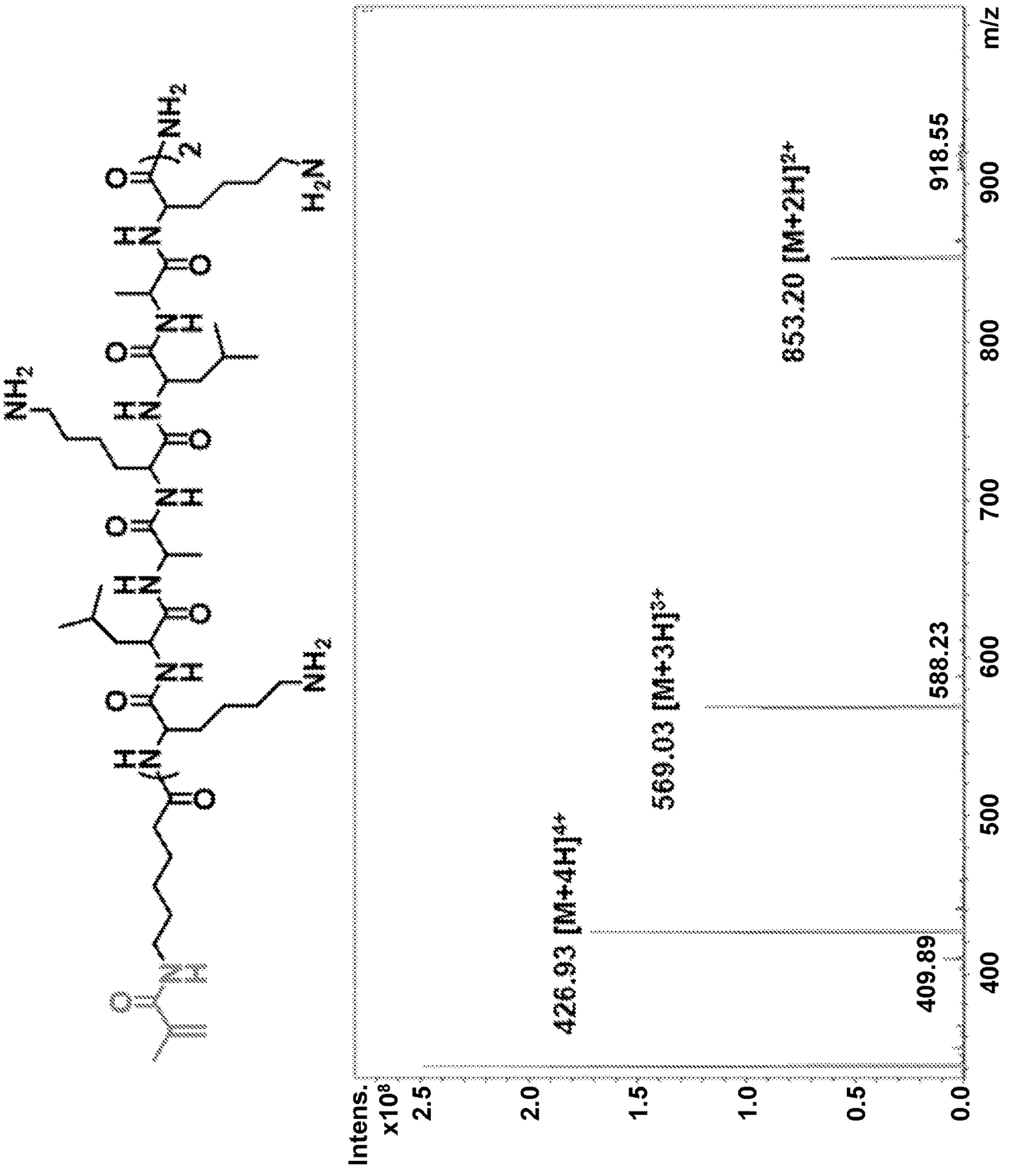
FIG. 81. ESI-MS spectrum of MAm-KLAKLAKKLAKLAK (KLAKLAKKLAKLAK is SEQ ID NO:3).
Figure 82:
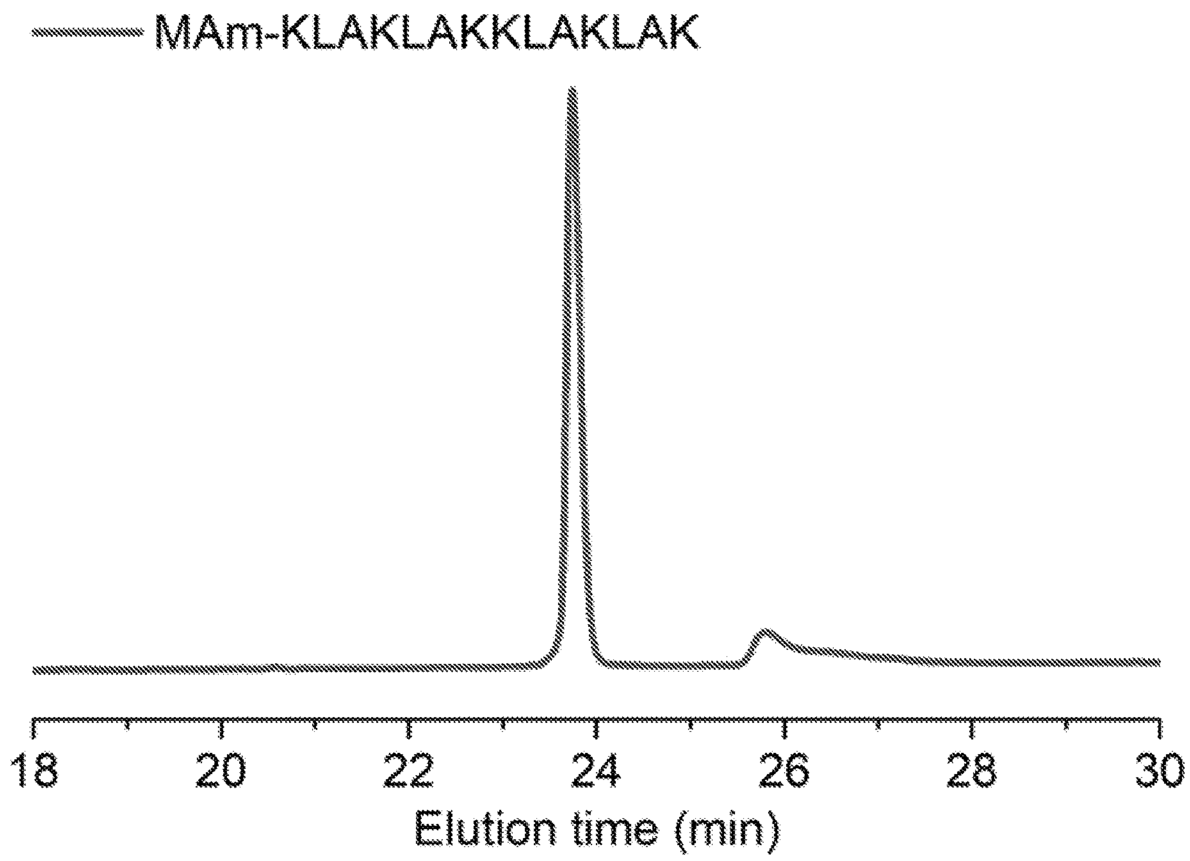
FIG. 82. HPLC trace of MAm-KLAKLAKKLAKLAK (SEQ ID NO:3).
Figure 83:
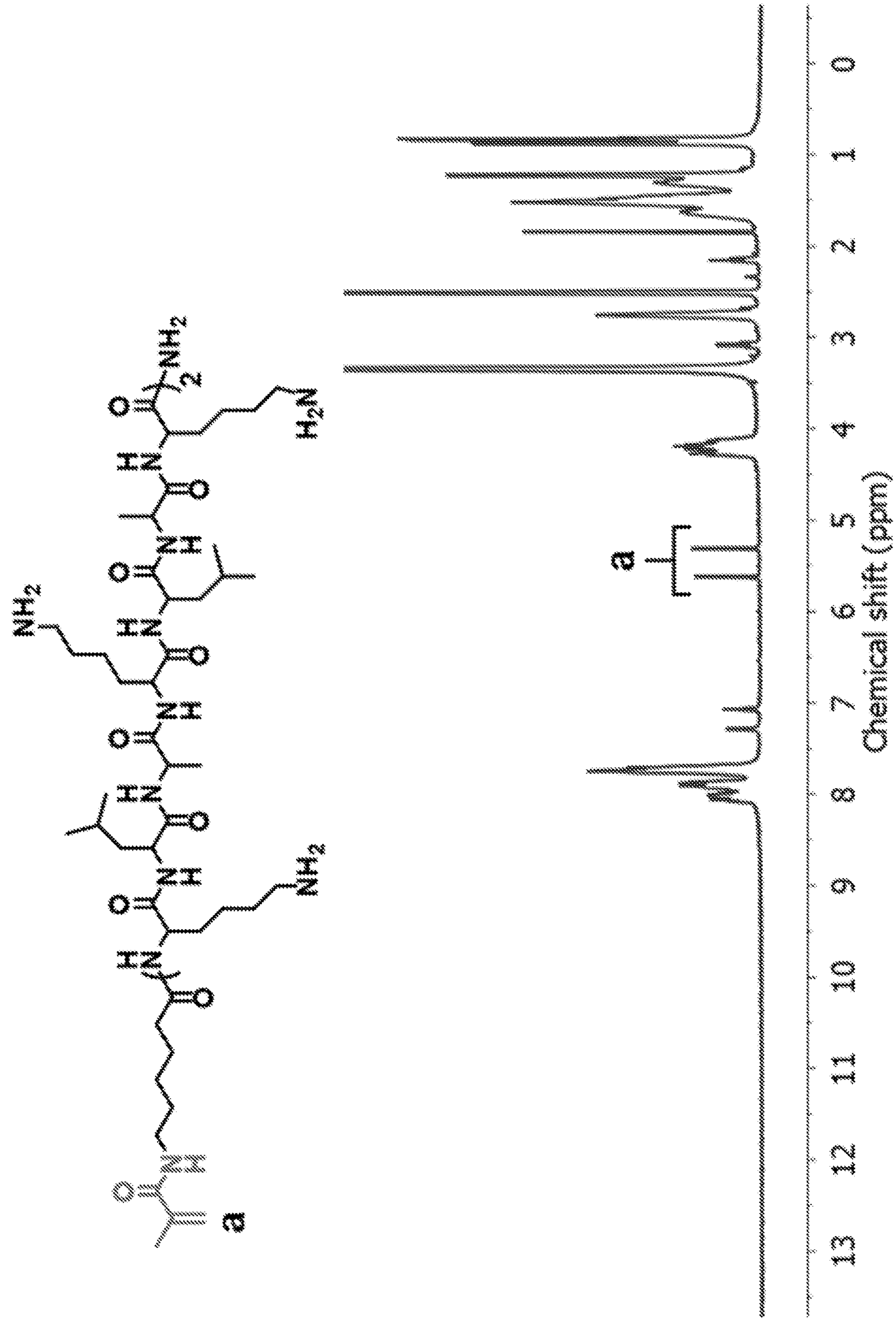
FIG. 83. $^1$H NMR spectrum of MAm-KLAKLAKKLAKLAK (SEQ ID NO:3).
Figure 84:
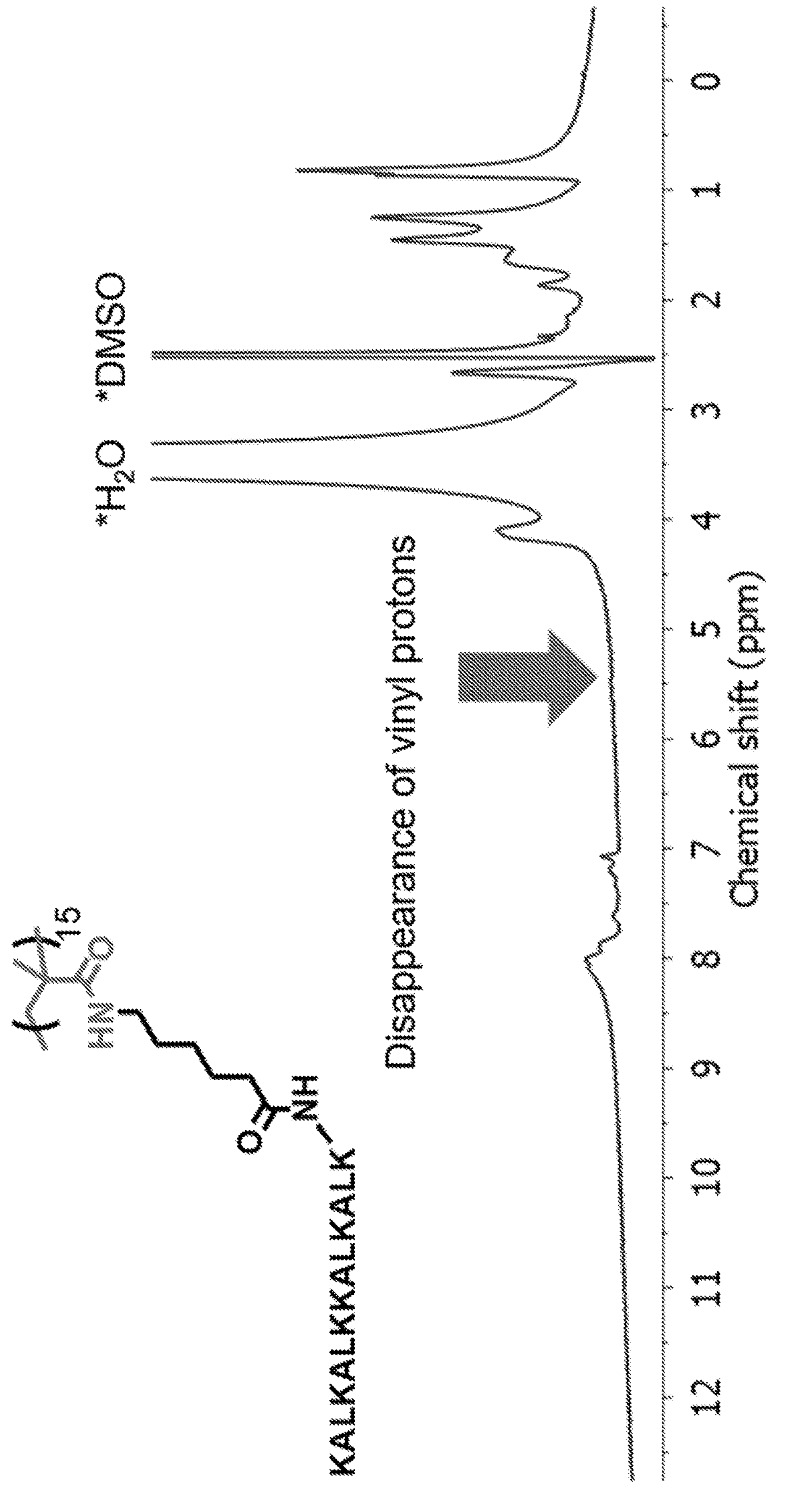
FIG. 84. $^1$H NMR spectrum of poly(MAm-KLAKLAKKLAKLAK) (SEQ ID NO:3) in DMSO-d6.
Figure 85:
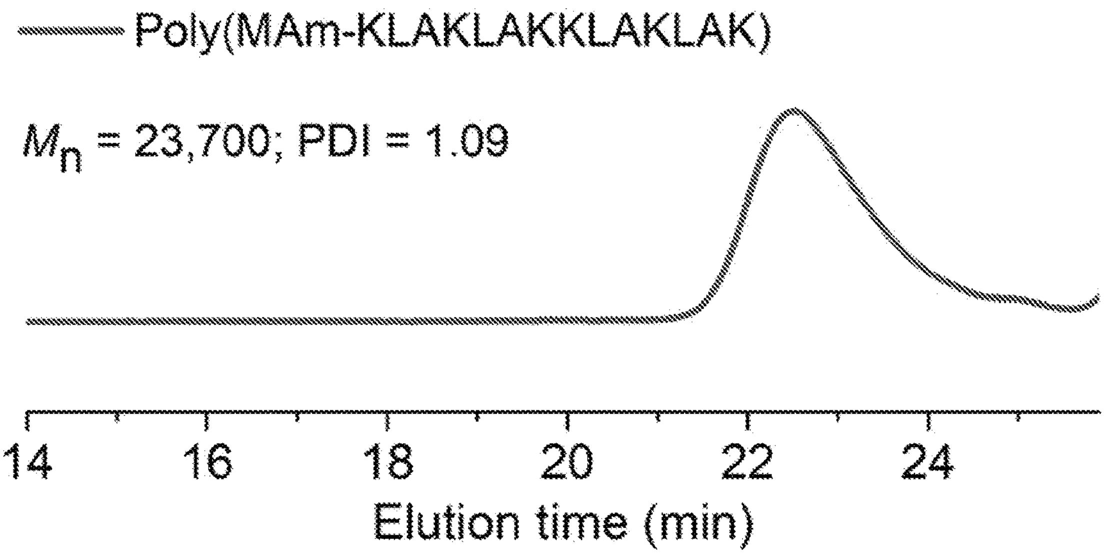
FIG. 85. GPC trace of poly(MAm-KLAKLAKKLAKLAK) (SEQ ID NO:3) in DMF eluent.

Notably, the toxicity of NP5 was significantly higher than NP3, potentially the result of the higher graft density of the KLA peptide in the hydrophilic shell on NP5 leading to enhanced multivalent interactions. In addition, the cell uptake efficiency of rhodamine B-labeled KLA peptide and NPs was investigated (FIGS. 67-69). Flow cytometry and confocal laser scanning microscopy clearly demonstrated the significantly enhanced cell uptake of the NPs over free KLA peptide.

Figure 46:
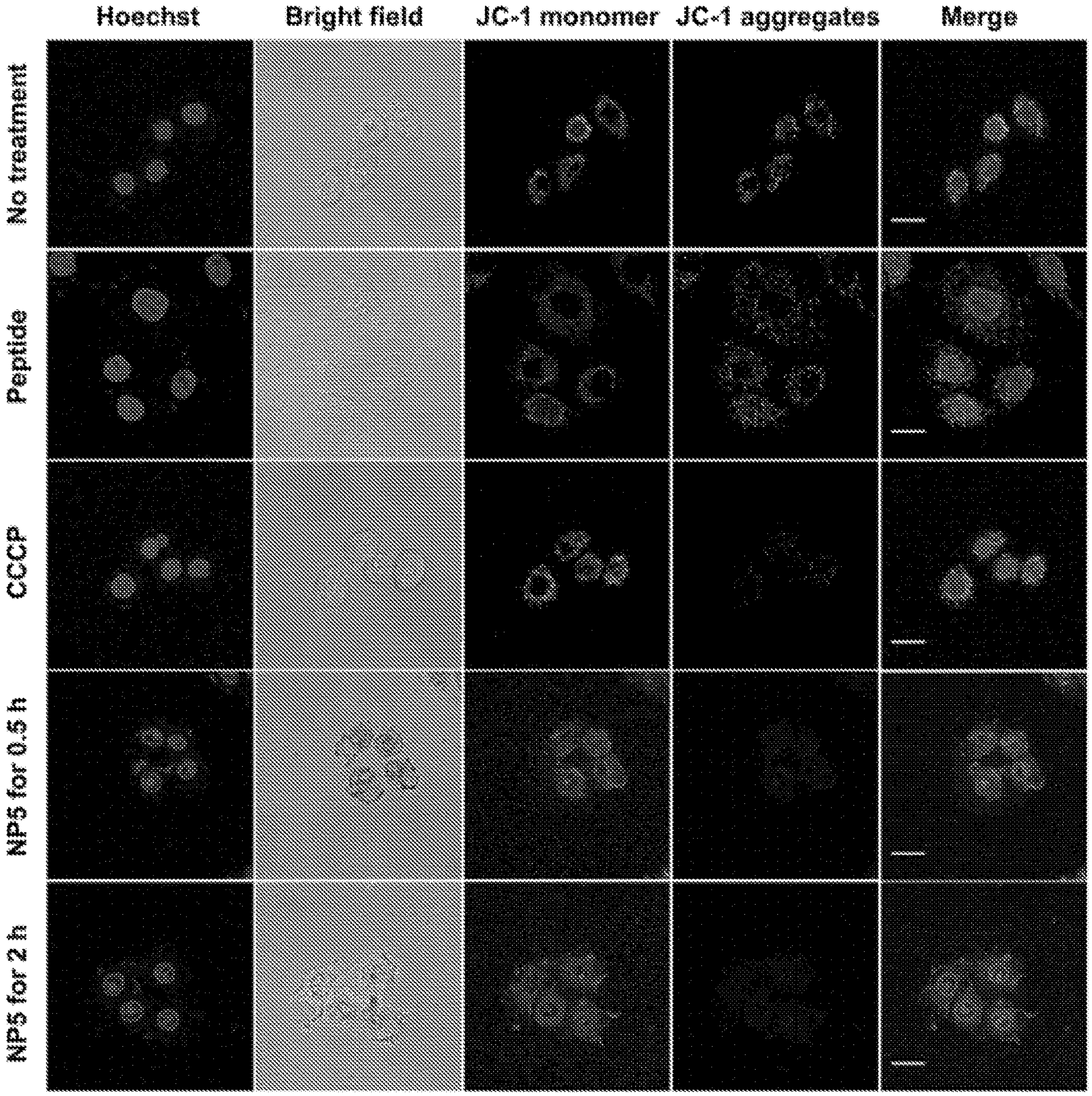
FIG. 46. Assessment of mitochondrial dysfunction induced by the peptide-containing materials using JC-1 probe. Live-cell confocal microscopy images of HeLa cells incubated with KLA peptide, CCCP, NP5 for desired periods of time. Prior to imaging, cells were stained with 2 μM of JC-probe (green, monomer, $\lambda_{ex/em}$=488 nm/510-550 nm; red, J-aggregates, $\lambda_{ex/em}$=488 nm/585-649 nm) and then Hoechst 33342 (blue, $\lambda_{ex/em}$=405 nm/420-480 nm). Scale bars, 20 μm.

Finally, to discern the mechanism of cell death, we studied the mitochondrial membrane potential using the turn-on JC-1 probe. Mitochondria are central regulators of cellular energy and metabolism, and have the essential function of ATP synthesis by maintaining a membrane potential gradient.[20] The JC-1 probe is green-fluorescent carbocyanine that forms red-shifted J-aggregates upon accumulation in mitochondria and has very narrow red fluorescence.[5b,7b] Therefore, confocal laser scanning microscopy was utilized to compare the green and red fluorescence at the same excitation wavelength at 488 nm (FIG. 46). HeLa cells incubated with free KLA peptide showed strong red fluorescence, similar to cells treated only with media, indicative of healthy mitochondria. As a comparison, almost no red emission from JC-1 J-aggregates was observed in cells treated with KLA brush polymer nanoparticles (NP5) even after 30 min incubation, confirming efficient depolarization of the mitochondria. The behavior of NP5 was similar to the commercial mitochondrial membrane potential disruptor, carbonyl cyanide 3-chlorophenylhydrazone (CCCP).

CONCLUSION

In summary, we developed a scalable and highly modular photo-PISA approach to functional peptides displayed as hydrophilic brushes on polymeric amphiphiles packed to form micellar nanoparticles. This is a robust approach to access nanoparticles with a high-density display of peptides, tunable particle size, tunable peptide loading, and at scale (150 mg/mL). This method for packaging peptides was demonstrated with a proof-of-concept proapoptotic peptide. These results clearly demonstrate the promise of exploiting NPs with high peptide grafting densities to achieve enhanced proteolytic stability, cellular internalization, and cytotoxicity in comparison with free apoptotic peptides. We envision that many other functional peptides such as cell-penetrating and therapeutic peptides would be compatible with the photo-PISA approach to polymer brush amphiphile self-assemblies.

References Corresponding to Example 2A

[1] B. Yu, D. Hwang, H. Jeon, H. Kim, Y. Lee, H. Keum, J. Kim, D. Y. Lee, Y. Kim, J. Chung, S. Jon, Angew. Chem. Int. Ed. 2019, 58, 2005-2010.

[2] D. J. Drucker, Nat. Rev. Drug Discov. 2020, 19, 277-289.

[3] a) T. Navaratna, L. Atangcho, M. Mahajan, V. Subramanian, M. Case, A. Min, D. Tresnak, G. M. Thurber, J. Am. Chem. Soc. 2020, 142, 1882-1894; b) M. A. Kasper, M. Glanz, A. Oder, P. Schmieder, J. P. von Kries, C. P. R. Hackenberger, Chem Sci 2019, 10, 6322-6329; c) R. Menacho-Melgar, J. S. Decker, J. N. Hennigan, M. D. Lynch, J. Control Release 2019, 295, 1-12; d) M. J. Roberts, M. D. Bentley, J. M. Harris, Adv. Drug Deliv.

Rev. 2012, 64, 116-127; e) M. J. Webber, E. A. Appel, B. Vinciguerra, A. B. Cortinas, L. S. Thapa, S. Jhunjhunwala, L. Isaacs, R. Langer, D. G. Anderson, Proc. Natl. Acad. Sci. USA 2016, 113, 14189-14194; f) L. Gentilucci, R. De Marco, L. Cerisoli, Curr. Pharm. Design 2010, 16, 3185-3203; g) J. Chatterjee, C. Gilon, A. Hoffman, H. Kessler, Accounts Chem. Res. 2008, 41, 1331-1342; h) H. Itoh, K. Miura, K. Kamiya, T. Yamashita, M. Inoue, Angew. Chem. Int. Ed. 2020, 59, 4564-4571; i) Y. T. Wu, F. Villa, J. Maman, Y. H. Lau, L. Dobnikar, A. C. Simon, K. Labib, D. R. Spring, L. Pellegrini, Angew. Chem. Int. Ed. 2017, 56, 12866-12872.

[4] G. Guidotti, L. Brambilla, D. Rossi, Trends Pharmacol. Sci. 2017, 38, 406-424.

[5] a) J. Pokorski, D. C. Church, Angew. Chem. Int. Ed. 2020; b) A. P. Blum, J. K. Kammeyer, N. C. Gianneschi, Chem. Sci. 2016, 7, 989-994; c) A. P. Blum, J. K. Kammeyer, J. Yin, D. T. Crystal, A. M. Rush, M. K. Gilson, N. C. Gianneschi, J. Am. Chem. Soc. 2014, 136, 15422-15437.

[6] a) T. Suma, J. W. Cui, M. Mullner, S. W. Fu, J. Tran, K. F. Noi, Y. Ju, F. Caruso, J. Am. Chem. Soc. 2017, 139, 4009-4018; b) C. D. Spicer, C. Jumeaux, B. Gupta, M. M. Stevens, Chem. Soc. Rev. 2018, 47, 3574-3620; c) H. L. Chee, C. R. R. Gan, M. Ng, L. Low, D. G. Fernig, K. K. Bhakoo, D. Paramelle, ACS Nano 2018, 12, 6480-649.

[7] a) L. Adamiak, M. A. Touve, C. L. M. LeGuyader, N. C. Gianneschi, ACS Nano 2017, 11, 9877-9888; b) D. B. Cheng, X. H. Zhang, Y. J. Gao, L. Ji, D. Y. Hou, Z. Q. Wang, W. H. Xu, Z. Y. Qiao, H. Wang, J. Am. Chem. Soc. 2019, 141, 7235-7239; c) C. E. Callmann, M. P. Thompson, N. C. Gianneschi, Accounts Chem. Res. 2020, 53, 400-413; d) S. Hua, M. B. C. de Matos, J. M. Metselaar, G. Storm, Front Pharmacol. 2018, 9, 790.

[8] H. Sun, W. Choi, N. Zang, C. Battistella, M. P. Thompson, W. Cao, X. Zhou, C. Forman, N. C. Gianneschi, Angew. Chem. Int. Ed. 2019, 58, 17359-17364.

[9] a) C. Grazon, P. Salas-Ambrosio, E. Ibarboure, A. Buol, E. Garanger, M. W. Grinstaff, S. Lecommandoux, C. Bonduelle, Angew. Chem. Int. Ed. 2020, 59, 622-626; b) J. C. Foster, S. Varlas, L. D. Blackman, L. A. Arkinstall, R. K. O'Reilly, Angew. Chem. Int. Ed. 2018, 57, 10672-10676; c) N. J. W. Penfold, J. Yeow, C. Boyer, S. P. Armes, ACS Macro Lett 2019, 8, 1029-1054; d) S. L. Canning, G. N. Smith, S. P. Armes, Macromolecules 2016, 49, 1985-2001; e) A. M. Oliver, J. Gwyther, C. E. Boott, S. Davis, S. Pearce, I. Manners, J. Am. Chem. Soc. 2018, 140, 18104-18114; f) C. A. Figg, R. N. Carmean, K. C. Bentz, S. Mukherjee, D. A. Savin, B. S. Sumerlin, Macromolecules 2017, 50, 935-943; g) D. B. Wright, M. A. Touve, M. P. Thompson, N. C. Gianneschi, ACS Macro Lett 2018, 7, 401-405; h) M. A. Touve, C. A. Figg, D. B. Wright, C. Park, J. Cantlon, B. S. Sumerlin, N. C. Gianneschi, ACS Central Sci. 2018, 4, 543-547; i) C. A. Figg, A. Simula, K. A. Gebre, B. S. Tucker, D. M. Haddleton, B. S. Sumerlin, Chem. Sci. 2015, 6, 1230-1236; j) D. Le, M. Dilger, V. Pertici, S. Diabate, D. Gigmes, C. Weiss, G. Delaittre, Angew. Chem. In. Ed. 2019, 58, 4725-4731.

[10] a) J. Yeow, C. Boyer, Adv. Sci. 2017, 4, 1700137; b) L. D. Blackman, S. Varlas, M. C. Arno, Z. H. Houston, N. L. Fletcher, K. J. Thurecht, M. Hasan, M. I. Gibson, R. K. O'Reilly, ACS Central Sci. 2018, 4, 718-723; c) J. B. Tan, H. Sun, M. G. Yu, B. S. Sumerlin, L. Zhang, ACS Macro Lett 2015, 4, 1249-1253; d) N. Corrigan, J. Yeow, P. Judzewitsch, J. T. Xu, C. Boyer, Angew. Chem. Int. Ed. 2019, 58, 5170-5189.

[11] M. Cieslewicz, J. J. Tang, J. L. Yu, H. Cao, M. Zavaljevski, K. Motoyama, A. Lieber, E. W. Raines, S. H. Pun, Proc. Natl. Acad. Sci. USA 2013, 110, 15919-15924.

[12] a) J. T. Xu, K. Jung, A. Atme, S. Shanmugam, C. Boyer, J. Am. Chem. Soc. 2014, 136, 5508-5519.; b) M. Chen, M. J. Zhong, J. A. Johnson, Chem. Rev. 2016, 116, 10167-10211.

[13] a) D. B. Thomas, B. S. Sumerlin, A. B. Lowe, C. L. McCormick, Macromolecules 2003, 36, 1436-1439; b) D. B. Thomas, A. J. Convertine, R. D. Hester, A. B. Lowe, C. L. McCormick, Macromolecules 2004, 37, 1735-1741.

[14] a) W. Zhou, Q. W. Qu, Y. Y. Xu, Z. S. An, ACS Macro Lett 2015, 4, 495-499; b) T. Luckerath, K. Koynov, S. Loescher, C. J. Whitfield, L. Nuhn, A. Walther, C. Barner-Kowollik, D. Y. W. Ng, T. Weil, Angew. Chem. Int. Ed. 2020, doi: 10.1002/anie.201916177.

[15] M. P. Chien, A. M. Rush, M. P. Thompson, N. C. Gianneschi, Angew. Chem. Int. Ed. 2010, 49, 5076-5080.

[16] a) J. Lee, E. T. Oh, H. Lee, J. Kim, H. G. Kim, H. J. Park, C. Kim, Bioconjug. Chem. 2020, 31, 43-50; b) D. J. Toft, T. J. Moyer, S. M. Standley, Y. Ruff, A. Ugolkov, S. I. Stupp, V. L. Cryns, ACS Nano 2012, 6, 7956-7965.

[17] a) F. Jia, X. G. Lu, X. Y. Tan, D. L. Wang, X. Y. Cao, K. Zhang, Angew. Chem. Int. Ed. 2017, 56, 1239-1243; b) F. Jia, X. G. Lu, D. L. Wang, X. Y. Cao, X. Y. Tan, H. Lu, K. Zhang, J. Am. Chem. Soc. 2017, 139, 10605-10608.

[18] B. A. Ji, C. D. Logsdon, Gastroenterology 2011, 141, 1972-1975.

[19] J. M. G. Artigas, M. R. A. Faure, M. E. Garcia, A. M. B. Gimeno, Postgrad. Med. J. 1981, 57, 219-222.

[20] M. Giacomello, A. Pyakurel, C. Glytsou, L. Scorrano, Nat. Rev. Mol. Cell Bio. 2020, 21, 202-224.

Example 2B: Proapoptotic Peptide Brush Polymer Nanoparticles Via Photoinitiated Polymerization-Induced Self-Assembly—Supporting Information 1. Materials All amino acids used to prepare peptides by solid phase peptide synthesis (SPPS) were obtained from AAPPTec, Chem-Impex, and NovaBiochem. N,N,N',N",N"-Pentamethyldiethylenetriamine (PMDETA, 99%), eosin Y disodium salt (dye content >85%), 6-Fmoc-amino hexanoic acid (97%), O,O'-1,3-Propanediylbishydroxyamine·2HCl (crosslinker, >99%), and acetate buffer (0.1 M, pH 5) were purchased from Sigma Aldrich and used without purification. Diacetone acrylamide (DAAm, 99%) was purchased from Sigma Aldrich and purified by crystallization twice from ethyl acetate and once from hexane before use.[1] 4-((((2-Carboxyethyl)thio)carbonothioyl)thio)-4-cyanopentanoic acid (water-soluble RAFT agent, 95%) was purchased from Combi-Blocks and used without further purification. Methacryloxyethyl thiocarbamoyl rhodamine B was purchased from Polysciences, Inc. Rhodamine B labeled KLA peptide (Rho-KLA) was synthesized according to our previous report.[2] Trypsin was purchased from Sigma. LED strip light (450 nm) was purchased from Amazon. CellTiter-Blue® was purchased from Promega Corporation. Dulbecco's Phosphate Buffered Saline (without $Ca^{2+}$, $Mg^{2+}$) was purchased from Corning Cellgro. Dulbecco's modified Eagle medium (DMEM), fetal bovine serum (FBS), Hoechst 33342, and JC-1 probe were purchased from ThermoFisher Scientific.

2. Methods $^1H$ Nuclear Magnetic Resonance ($^1H$ NMR): $^1H$ NMR spectra were recorded on a Varian Inova spectrometer (500

MHz) in DMSO-$d_6$. Chemical shifts are given in ppm downfield from tetramethylsilane TMS.

Analytical High-Performance Liquid Chromatography (HPLC): Analytical HPLC analysis of peptides was performed on a Jupiter 4μ Proteo 90A Phenomenex column (150×4.60 mm) using a Hitachi-Elite LaChrom L-2130 pump equipped with UV-Vis detector (Hitachi-Elite LaChrom L2420).

Preparative HPLC: Armen Glider CPC preparatory HPLC was used to purify the peptides. The solvent system consists of (A) 0.1% TFA in water and (B) 0.1% TFA in acetonitrile.

Electrospray Ionization Mass Spectrometry (ESI-MS): ESI-MS spectra of peptides were collected using a Bruker Amazon-SL spectrometer configured with an ESI source in both negative and positive ionization mode.

Dry-State Transmission Electron Microscopy (TEM): Twenty microliters of samples were applied onto a 400 mesh carbon grids (Ted Pella, INC.). The grids were observed on a Hitachi HT 7700 microscope operating at 120 kV. The images were recorded with a slow-scan charge-coupled device (CCD) camera (Veleta 2k×2k).

Cryogenic Transmission Electron Microscopy (Cryo-TEM): Five microliters of sample were applied onto a 200 mesh lacey carbon grid (Ted Pella, INC.) that had been glow discharged for 30 seconds. The samples were manually blotted and vitrified in ethane before imaging on a JEOL 1230 microscope operating at 100 kV. Images were acquired on a One View CCD camera.

Gel Permeation Chromatography (GPC): GPC measurements were performed on a set of Phenomenex Phenogel 5μ, 1 K-75K, 300×7.80 mm in series with a Phenomex Phenogel 5μ, 10K-1000K, 300×7.80 mm columns with HPLC grade solvents as eluents: dimethylformamide (DMF) with 0.05M of LiBr at 60° C. Detection consisted of a Hitachi UV-Vis Detector L-2420, a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software with dn/dc values determined by assuming 100% mass recovery during GPC analysis.

Dynamic Light Scattering (DLS) and Zeta Potential Analysis: DLS and zeta potential analyses were conducted at room temperature on a Zetasizer Nano-ZS (Malvern). The laser for DLS was at a wavelength of 633 nm.

Circular Dichroism Spectrophotometry (CD): CD spectra were measured using a Jasco J815 spectrometer and each sample was measured from 190 to 260 nm with a slit width of 1 nm, scanning at 1 nm intervals with a 1 s integration time. Measurements were taken 3× at 25° C. and then averaged to give the spectra. Notably, the peptide and polymer were dissolved in deionized water to a concentration of 100 μM (with respect to peptide concentration).

Flow Cytometry: The cell uptake study was analyzed via flow cytometry using a BD FacsAria Ilu 4-Laser flow cytometer (Becton Dickinson Inc., USA). Mean fluorescence intensity and PE-A-histogram data was prepared for presentation using FlowJo v10.

Confocal Laser Scanning Microscopy (CLSM): Imaging was accomplished using LEICA SP5 II laser scanning confocal microscope with a 63× oil immersion objective at 1.5× optical zoom. All the images were Z-stack images. Slice thickness was 0.26 μm with a scan size of 1024×1024 pixels and a scan speed of 400 Hz. The cell nuclei (stained with DAPI) was accomplished using a 405 nm laser with a 15% laser power. The cell membrane (stained with Wheat Germ Agglutinin, Alexa Fluor 488 Conjugate) was accomplished using a 488 nm laser with a 12% laser power. Cell imaging for Rhodamine fluorescence was accomplished using a 543 nm laser with an 8% laser power.

Fluorescence Measurement: CellTiter-Blue® fluorescence measurements were recorded using a Perkin Elmer EnSpire multimode Plate Reader.

3. Experimental 3.1 Preparation of KLA Peptide Monomer Via Solid-Phase Peptide Synthesis (SPPS)

KLA peptide acrylamide was synthesized on Rink resin (0.67 mmol/g) using standard FMOC SPPS procedures on an AAPPTec Focus XC automated synthesizer. A typical SPPS procedure included deprotection of the N-terminal Fmoc group with 20% 4-methyl-piperidine in DMF (1×20 min, followed by 1×5 min), and 30 min amide couplings (twice) using 3.0 equiv. of the Fmoc-protected amino acid, 2.9 equiv. of HBTU and 6 equiv. of DIPEA. After that, peptide monomers were prepared by amide coupling to Fmoc-6-aminohexanoic acid, followed by Fmoc deprotection and final amidation with acrylic acid (3 equiv.) in the presence of HBTU (2.9 equiv.), and DIPEA (6 equiv.).

3.2 Synthesis of MacroCTA Via PET-RAFT Polymerization

In a typical aqueous photo-induced RAFT polymerization for making poly($KLAAm_{10}$-co-$DMA_{30}$) macroCTA, KLA peptide acrylamide monomer (30 mg, 10 equiv.) and DMA (4.7 mg, 30 equiv.) were dissolved in 150 μL of acetate buffer (0.1 M, pH 5). Then, water-soluble RAFT agent (0.55 mg, 1.0 equiv.) was added into the reaction mixture. Following that, 10 μL (0.063 mg, 0.05 equiv.) of eosin Y disodium salt stock solution (6.3 mg in 1 mL of acetate buffer) and PMDETA (0.41 mg, 1.0 equiv.) were added. The solution was degassed by $N_2$ flow for 30 min and then placed into the photo-reactor (450 nm, 2.8 $mW/cm^2$) for 12 h. After polymerization, the macroCTA solution was directly used for photo-PISA (vide infra) without purification.

3.3 Photoinitiated Polymerization-Induced Self-Assembly (Photo-PISA)

In a typical photo-PISA protocol for preparing NP1, DAAm (21 mg, 70 equiv.) and DMA (4.7 mg, 30 equiv.) were added into the macroCTA solution which was made in section 3.2 (vide supra). Next, 180 μL of acetate buffer (0.1 M, pH 5) was added to achieve a solids content of 15 wt. %. The solution was degassed by $N_2$ flow for 30 min and then placed into the photo-reactor (450 nm, 2.8 $mW/cm^2$) for 12 h. After PISA, the NPs were further purified via dialysis into deionized water.

3.4 Preparation of Rhodamine B-Labeled NPs

In all the cases of preparing rhodamine-labeled NPs, one equiv. of rhodamine B to RAFT agent was used, ensuring that on average one dye was attached to each polymer chain. In a typical synthesis of rhodamine B-labeled NP3, KLA peptide acrylamide monomer (30 mg, 10 equiv.), DMA (4.7 mg, 30 equiv.), and methacryloxyethyl thiocarbamoyl rhodamine B (1.4 mg, 1.0 equiv.) were dissolved in 150 μL of acetate buffer (0.1 M, pH 5). Then water-soluble RAFT agent (0.55 mg, 1.0 equiv.) was added into the reaction mixture. Following that, 10 μL (0.05 equiv.) of eosin Y disodium salt stock solution (6.3 mg in 1 mL of acetate buffer) and PMDETA (0.41 mg, 1.0 equiv.) were added. The solution was degassed by $N_2$ flow for 30 min and then placed into the photo-reactor (450 nm, 2.8 $mW/cm^2$) for 12 h. After polymerization, the macroCTA solution was directly used in next step (photo-PISA) to prepare rhodamine B-labeled NP3. DAAm (84 mg, 280 equiv.) and DMA (19 mg, 120 equiv.) were added into the macroCTA solution. Next, 630 μL of acetate buffer (0.1 M, pH 5) was added to achieve a solids content of 15 wt. %. The solution was degassed by $N_2$ flow for 30 min and then placed into the photo-reactor (450 nm, 2.8 mW/$cm^2$) for 12 h. After PISA, the rhodamine B labeled NPs were further purified via dialysis in deionized water.

3.5 Synthesis of PolyDMA$_{40}$-b-Poly(DAAm$_{70}$-co-DMA$_{30}$)

DMA (12.6 mg, 40 equiv.) were dissolved in 300 μL of acetate buffer (0.1 M, pH 5). Then, water-soluble RAFT agent (1.1 mg, 1.0 equiv.) was added into the reaction mixture. Following that, 20 μL (0.126 mg, 0.05 equiv.) of eosin Y disodium salt stock solution (6.3 mg in 1 mL of acetate buffer) and PMDETA (0.82 mg, 1.0 equiv.) were added. The solution was degassed by $N_2$ flow for 30 min and then placed into the photo-reactor (450 nm, 2.8 mW/$cm^2$) for 12 h. After polymerization, DAAm (42 mg, 70 equiv.) and DMA (9.4 mg, 30 equiv.) were added into the macroCTA solution. Next, 75 μL of acetate buffer (0.1 M, pH 5) was added to achieve a solids content of 15 wt. %. The solution was degassed by $N_2$ flow for 30 min and then placed into the photo-reactor (450 nm, 2.8 mW/$cm^2$) for 12 h. After PISA, the NPs were further purified via dialysis into deionized water.

3.6 Trypsin-Induced Cleavage Experiments

For protease-triggered cleavage experiments, the molar ratio of trypsin to peptide was set to 1:2000. Moreover, the temperature was set to 37° C. to match the body temperature. For example, poly[(KLAAm$_{10}$-co-DMA$_{30}$)-b-(DAAm$_{70}$-co-DMA$_{30}$)](NP1, 0.9 mg, 0.2 μmol with respect to peptides, 2000 equiv.) was dissolved in 1 ml of DPBS solution. Then trypsin (0.023 mg, 0.1 nmol, 1 equiv.) was added into the polymer solution which was stirred in a preheated oil bath at 37° C. During the cleavage, aliquots were taken for HPLC analysis at predetermined time points.

3.7 Cell Viability Assay

HeLa cells were grown in Dulbecco's modified Eagle medium (DMEM) supplemented with 10% fetal bovine serum (FBS), 1% penicillin-streptomycin. Cells were maintained at 37° C. and 5% $CO_2$ with a relative humidity of 95%. HeLa cells were plated in 96-well plates at a density of 5000 per well and then left to attach for 24 h. Subsequently, the cells were treated with the polymers of various concentrations for the desired time followed by washing 3 times with PBS. Then CellTiter-Blue® at 10% (v/v) in complete media was added to each well and incubated for 2 h to allow the live cells to convert resazurin to fluorescent resorufin. The fluorescent signal (Excitation wavelength: 560 nm; Emission wavelength: 600 nm) was then analyzed by a plate reader. Three replicates were performed for each independent sample. 10% DMSO was used as a positive control and untreated cells in complete medium as a negative control. Viability is reported as a percentage of untreated cells.

3.8 Confocal Laser Scanning Microscopy for Uptake in HeLa Cells

HeLa cells were plated in a 4-chamber 35 mm round glass-bottom dishes at a density of 50,000 per well. Cells were incubated for 24 hours in a 5% $CO_2$ atmosphere at 37° C. 500 μL of Rho-KLA peptide, Rho-NP3, and Rho-NP5 (0.25 μM with respect to rhodamine for each material) in 10% FBS DMEM media without phenol red were incubated with the cells for 24 hours, respectively. After washing with DPBS to remove the residual peptides and nanoparticles, 500 μL of Wheat Germ Agglutinin (5 μg/mL) conjugated with Alexa Fluor 488 was added to each well, then fixed with a 4% paraformaldehyde solution for 15 min at room temperature. The cells were washed with DPBS and stained by DAPI for 20 min at room temperature.

3.9 Flow Cytometry for Uptake Ability in HeLa Cells

For cellular uptake measurements, HeLa cells were plated in 12-well plates at a density of 1,000,000 per well and incubated for 24 hours in a 5% $CO_2$ atmosphere at 37° C. 500 μL of 0.25 μM (with respect to rhodamine) Rho-KLA peptide, Rho-NP3, and Rho-NP5 in 10% FBS DMEM media without phenol red were incubated with the cells for 24 hours respectively. After triple washing with DPBS, 500 μL of 0.25% Trypsin-EDTA was added to each well for 10 min at 37° C. Cells were fixed with a 4% paraformaldehyde solution for 15 min at room temperature.

3.10 Mitochondria Membrane Potential of HeLa Cells

HeLa cells were plated in 4-well, glass bottom dishes at 30,000 cells per well in 500 μL medium. HeLa cells were seeded for 24 h before treatment with nanoparticle suspensions for 24 or 72 h. The cells were stained with 2 μM of JC-1 at 37° C. for 15 minutes, washed with PBS to remove any membrane-bound, non-internalized fluorophores, and returned to complete medium. For the positive control group, the cells were incubated with 50 μM CCCP and 2 μM of JC-1 probe in DPBS solution simultaneously for 15 min. Before the confocal observation, 1 drop of Hoechst 33342 dye was added to stain the nuclei. Confocal microscope was employed to observe the fluorescence of JC-1 monomer, J-aggregates and Hoechst dye.

References Corresponding to Example 2B

1. Figg, C. A.; Carmean, R. N.; Bentz, K. C.; Mukherjee, S.; Savin, D. A.; Sumerlin, B. S., Tuning Hydrophobicity To Program Block Copolymer Assemblies from the Inside Out. Macromolecules 2017, 50 (3), 935-943.
2. Sun, H.; Choi, W.; Zang, N.; Battistella, C.; Thompson, M. P.; Cao, W.; Zhou, X.; Forman, C.; Gianneschi, N. C., Bioactive Peptide Brush Polymers via Photoinduced Reversible-Deactivation Radical Polymerization. Angew. Chem. Int. Ed. 2019, 58 (48), 17359-17364.

Example 3: A Scalable Method for Preparing Peptide-Shell Polymer Nanoparticles Via Photoinitiated Polymerization-Induced Self-Assembly Synthetic oligopeptides represent a class of powerful therapeutics because of their biocompatibility, straightforward synthesis, predictable metabolism, and high degree of modularity in molecular design. However, these advantages are typically compromised by natural processes prevalent in cells and tissues that have evolved to degrade them. Moreover, cell internization of peptides is typically inefficient, often requiring selective cell surface interactions through the use of cell penetrating sequences. These inherent downsides of oligopeptides as drugs have tremendously hampered their translations into clinic use. To tackle these challenges, we herein demonstrate a scalable, one-pot approach to peptide-based brush polymer amphiphile assemblies. For this, we employed one-pot photoinitiated polymerization-induced self-assembly (photo-PISA) to access spheric nanoparticles. The resulting materials are characterized by a high-density display of apoptotic peptides (amino acid sequence: KLAKLAKKLAKLAK) (SEQ ID NO:3) in the hydrophilic shell. Emergent properties include both proteolytical resistance and bioactivity, including cell penetration and apoptotic efficiency. All of these features were significantly higher for the peptide brush polymer nanoparticles compared to their linear peptide analogues. These results demonstrate the promise of exploiting polymer nanoparticles with high peptide grafting densities to achieve enhanced proteolytic stability and cytotoxicity in comparison with free apoptotic peptides.

Applications include peptide delivery systems for treating human diseases, high performance adhesive materials, and anti-fouling coatings.

Advantages: In tradition, solvent-switch strategies are used to access self-assembled nanostructures of peptide-polymer amphiphiles. However, the scale or the concentration of the products is limited to less than 20 mg/mL by these classic methods. In our invention, we solved this problem by using polymerization-induced self-assembly approach, which led to the at scale production of high concentrations of peptide brush polymer nanoparticles up to 150 mg/mL. This scale is very important for the translation of these promising nanomedicine into large animal models and eventually clinic trial. Oligopeptides are very unstable in the presence of protease which are everywhere in vivo. In our invention, peptide brush polymer nanoparticles adopt the three-dimensional spatial arrangement of peptides. This not only can improve the proteolytic stability of peptides, but also can enhance their biological activities such as cell binding and penetration via multivalent effects.

Herein we report photoinitiated polymerization-induced self-assembly (photo-PISA) of spherical micelles consisting of proapoptotic peptide-polymer amphiphiles. The one-pot synthetic approach yielded micellar nanoparticles at high concentrations and at scale (150 mg/mL) with tunable peptide loadings up to 48 wt. %. The size of the micellar nanoparticles was tuned by varying the lengths of hydrophobic and hydrophilic building blocks. Importantly, the peptide-functionalized nanoparticles imbued peptides, such as the proapoptotic "KLA" peptides (amino acid sequence: KLAKLAKKLAKLAK) (SEQ ID NO:3), with two key properties otherwise not inherent to the sequence: 1) proteolytic resistance compared to the oligopeptide alone; 2) significantly enhanced cell uptake permeability by multivalent display of KLA peptide brushes. The result was demonstrated improved apoptosis efficiency in HeLa cells. These results highlight the potential of photo-PISA in the large-scale synthesis of functional, proteolytically resistant peptide-polymer conjugates for intracellular delivery. We envision that many other functional peptides such as cell-penetrating, anti-fouling, and therapeutic peptides would be compatible with the photo-PISA approach to polymer brush amphiphile self-assemblies.

Included herein is a new peptide delivery system which can significantly enhance the life-time (stability), cell penetration, and efficacy of peptide therapeutics. Currently, pharmaceutical industry can achieve enhanced stability of peptides by using strategies such as PEGlyzation, lipidation, and cyclization, among others. However, these methods compromise the bioactivity or function of modified peptides as a result of the alteration of chemical identity and connectivity in amino acids.

References Corresponding to Example 3

1. Wright, D. B.; Proetto, M. T.; Touve, M. A.; Gianneschi, N. C., Ring-opening metathesis polymerization-induced self-assembly (ROMPISA) of a cisplatin analogue for high drug-loaded nanoparticles. Polym. Chem. 2019, 10 (23), 2996-3000.
2. Blackman, L. D.; Varlas, S.; Arno, M. C.; Houston, Z. H.; Fletcher, N. L.; Thurecht, K. J.; Hasan, M.; Gibson, M. I.; O'Reilly, R. K., Confinement of Therapeutic Enzymes in Selectively Permeable Polymer Vesicles by Polymerization-Induced Self-Assembly (PISA) Reduces Antibody Binding and Proteolytic Susceptibility. ACS Cent. Sci. 2018, 4 (6), 718-723.
3. Liu, X.; Sun, M.; Sun, J.; Hu, J.; Wang, Z.; Guo, J.; Gao, W., Polymerization Induced Self-Assembly of a Site-Specific Interferon α-Block Copolymer Conjugate into Micelles with Remarkably Enhanced Pharmacology. J. Am. Chem. Soc. 2018, 140(33), 10435-10438.
4. Le, D.; Wagner, F.; Takamiya, M.; Hsiao, I.; Gil Alvaradejo, G.; Strahle, U.; Weiss, C.; Delaittre, G., Straightforward access to biocompatible poly(2-oxazoline)-coated nanomaterials by polymerization-induced self-assembly. Chem. Commun, 2019, 55, 3741-3744.

Example 4: Exemplary Methods and Descriptions of Homopolymers Via Photo-RDRP

Typical protocol of making peptide brush homopolymers via photo-RDRP: Synthesis of poly(MAm-KLAK-LAKKLAKLAK) (SEQ ID NO:3): In a typical protocol, the peptide methacrylamide monomer MAm-KLAK-LAKKLAKLAK (SEQ ID NO:3) (31 mg, 15 equiv.) was dissolved in 180 μL of sodium acetate buffer (0.1 M, pH=5). Thereafter, 10 μL (1.0 equiv.) of water-soluble CTA stock solution (3.8 mg in 100 μL of DMSO) was added into the reaction mixture. Following that, the photoinitiator sodium phenyl-2,4,6-trimethylbenzoylphosphinate (SPTP, 0.12 mg, 0.3 equiv.) was added into the solution by injecting 10 μL of SPTP stock solution (1.2 mg in 0.1 mL of acetate buffer) were added. The solution was degassed by $N_2$ flow for 20 min and then placed into the photo-reactor (365 nm) for 18 h. After the polymerization, the polymer product was purified by dialysis into DIW, followed by lyophilization.

In some literature, peptide brush homopolymers made by traditional or thermally-initiated RDRP methods are limited to short and simple peptides such as MARGD and VPGVG which consist of only five amino acids.[1-2] The RDRP based synthesis of peptide brush homopolymers with long and complex peptide sequence still remain unexplored. Leveraging photo-RDRP, we have now invented a synthetic approach to peptide brush homopolymers consisting of long peptide sequences (e.g., up to 15 amino acids). This approach is versatile to a library of long and complicated peptide sequences, including but not limited to GPLGLAGGWGER (SEQ ID NO:12), GALTPR-GADSGSG (SEQ ID NO:2), GSGKEFGADSGSG (SEQ ID NO:4), and KLAKLAKKLAKLAK (SEQ ID NO:3). In addition, the monomer conversions were quantitative (>99%) in all cases, indicative of robustness of this approach.

References Corresponding to Example 4

1. Thang et al. Polym. Chem., 2018, 9, 1780-1786.
2. Cameron et al. Macromolecules 2007, 40, 17, 6094-6099.

Example 5: Photo-RDRP Versus Thermally Initiated RAFT for Peptide Brush Polymers "Graft through" reversible deactivation radical polymerization (RDRP) of methacrylic macromonomers such as long and bulky peptide methacrylamide is synthetically challenging because the repulsion between bulky side chains would lead to a reduced enthalpy of polymerization (ΔH) due to C—C bond stretching and bond-angle deformation in the vinyl polymer backbone.[1] The decreased ΔH would result in a smaller gain in free energy of polymerization (ΔG) and thus generate competition between polymerization and depolymerization. In view of this, graft through RDRP of peptide macromonomers would suffer from a rather high equilibrium monomer concentration ($[M]_{eq}$) at which the polymerization rate is equal to depolymerization rate.[2] To mitigate the issue of high equilibrium concentration and achieve a high monomer conversion, we contemplate strategies including (i) increase the initial monomer concentration; (ii) increase the pressure; (iii) use a poor solvent for the side chain; and (iv) lower the reaction temperature.[1,3]

Traditional or thermally initiated reversible addition-fragmentation transfer (RAFT) polymerizations are typically performed at temperatures above 50° C. and have been proven successful for controlled polymerization of commercially available monomers such as methyl methacrylate and dimethylacrylamides which have small molecular weights.[4] While the high temperatures would lead to high equilibrium monomer concentrations, one can still achieve high monomer conversions of those small molecular monomers by increasing the initial monomer concentrations. However, this strategy cannot be applied for the RAFT polymerization of vinyl macromonomer such as long and complex peptide monomers (e.g., having 5 amino acid groups, having 6 amino acid groups, having 7 amino acid groups, having 8 amino acid groups, having 9 amino acid groups, having 10 amino acid groups, having 11 amino acid groups, or having 12 amino acid groups) because of the upper solubility limit of the bulky peptide macromonomer. For example, the maximum concentration of KLA peptide acrylamide monomer (amino acid sequence: KLAKLAKKLAKLAK) (SEQ ID NO:3) is about 100 mM in water.[5] This is tremendously lower than the upper solubility limits of small molecular monomers (e.g., dimethylacrylamide: 9700 mM in bulk).

In the photo-RAFT methods we develop and disclose throughout this application for the synthesis of peptide brush homopolymers, room temperature can be used and thus significantly decrease the equilibrium monomer concentration (Van't hoff equation, see below), favoring the polymerization. Therefore, in methods disclosed herein, a large fraction of monomers can be polymerized before reaching the equilibrium, leading to a high monomer conversion. This is inaccessible by thermally-initiated RAFT polymerizations.

Van't hoff Equation:

$$\ln[M]_{eq} = \frac{\Delta H}{RT} - \frac{S^0}{R}$$

References Corresponding to Example 5

1. Matyjaszewski et al. ACS Macro Lett. 2020, 9, 1303-1309.
2. Gramlich et al. Polym. Chem. 2018, 9, 2328-2335.
3. (a) Janata et al. Macromolecules 2014, 47 (21), 7311-7320; (b) Ivin et al. J. Polym. Sci., Part A: Polym. Chem. 2000, 38 (12), 2137-2146.
4. Perrier et al. Macromolecules 2017, 50, 19, 7433-7447.
5. Gianneschi et al. Angew. Chem. Int. Ed. 2019, 58, 17359-17364.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every polymer, composition, formulation, and method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for synthesizing a peptide brush polymer, the method comprising:

exposing a mixture comprising peptide-containing monomers, one or more photoinitiators, and one or more chain transfer agents to a light sufficient to induce photopolymerization, and photopolymerizing the peptide-containing monomers in the mixture;

wherein:

the resulting peptide brush polymer comprises at least one peptide-containing polymer block;

the at least one peptide-containing polymer block is characterized by a degree of polymerization of at least 10 and a peptide graft density of 50% to 100%; and at least one peptide moiety of the at least one peptide-containing polymer block has 5 or more amino acid groups.

2. The method of claim 1, wherein the one or more photoinitiators comprise eosin Y disodium, pentamethyldiethylenetriamine, sodium phenyl-2,4,6-trimethylbenzoylphosphinate, lithium phenyl-2,4,6-trimethylbenzoylphosphinate, Zn(II) meso-Tetra(4-sulfonatophenyl) porphine, or a combination of these.

3. The method of claim 1, wherein the one or more chain transfer agents comprises a chain transfer agent characterized by formula FX13:

(FX13)

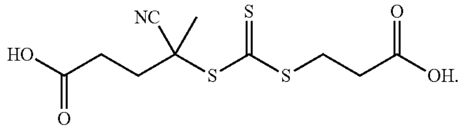

4. The method of claim 1, the method comprising metal-free photoinduced reversible-deactivation radical polymerization and/or photo-electron transfer reversible addition-fragmentation transfer polymerization.

5. The method of claim 1, wherein each peptide-containing monomer is independently characterized by formula FX1:

$$Z\text{-}(A\text{-}Pep)_x \quad \text{(FX1); wherein:}$$

Z is a polymer backbone precursor group;
A is a covalent anchor group;
Pep is a peptide moiety; and
x is an integer selected from the range of 1 to 2.

6. The method of claim 5, wherein each Pep comprises a sequence having at least 80% sequence homology with SEQ ID NO:1 (GPLGLAGGWGERDGS), SEQ ID NO:2 (GALTPRGADSGSG), SEQ ID NO:3 (KLAKLAKKLAKLAK), SEQ ID NO:4 (GSGKEFGADSGSG), SEQ ID NO:5 (GPLGLAGG), SEQ ID NO:6 (HVLVMSATKKKK), SEQ ID NO:7 (GGGCYFQNCPKG) (Terlipressin), SEQ ID NO:8 (DRVYIHPF) (Angiotensin 2), SEQ ID NO:9 (AQYQDKLAR) (DA1), SEQ ID NO:10 (GVi (allo) SQIRP) (ABT898), SEQ ID NO:11 (KVPRNQDWL) (gp100), SEQ ID NO:12 (GPLGLAGGWGER), or a combination of these.

7. The method of claim 1, wherein the peptide brush polymer is characterized by formula FX6A or FX6B:

$$Q^1\text{-}[B^1]_m\text{-}Q^2 \quad \text{(FX6A); or}$$

$$Q^1\text{-}[B^1]_m\text{—/—}[B^2]_n\text{-}Q^2 \quad \text{(FX6B); wherein:}$$

each $B^1$ is independently a peptide-containing polymer block;
each $B^2$ is independently a peptide-free polymer block;
each of m and n is independently an integer greater than or equal to 1;
the symbol "/" indicates that the units separated thereby are covalently linked randomly or in any order; and
each of $Q^1$ and $Q^2$ is independently a polymer terminating group.

8. The method of claim 7, wherein each $B^1$ is characterized by the formula (FX7):

(FX7)

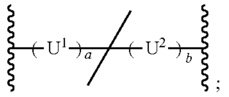

wherein:
each $U^1$ is independently a peptide-containing repeating unit;
each $U^2$ is independently a peptide-free repeating unit;
a is an integer selected from the range of 2 to 100;
b is 0 or an integer selected from the range of 2 to 100; and
the symbol "/" indicates that the units separated thereby are covalently linked randomly or in any order.

9. The method of claim 8, wherein each $U^1$ is independently characterized by the formula FX8A or FX8B and each $U^2$, if present, is independently characterized by the formula FX9A or FX9B:

(FX8A)

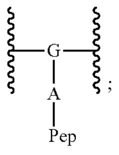

-continued (FX8B)

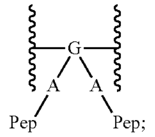

(FX9A)

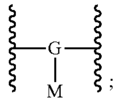

(FX9B)

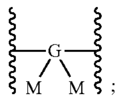

wherein:
each G is independently a polymer backbone group;
each A is independently a covalent anchor group;
each Pep is independently a peptide moiety; and
each M is independently an alkyl group, an alkenylene group, an arylene group, an alkoxy group, an acyl group, a carboxyl group, an aliphatic group, an amide group, an aryl group, an amine group, an ether group, a ketone group, an ester group, or combinations thereof.

10. The method of claim 9, wherein the peptide brush polymer is characterized by formula FX11A or FX11B:

(FX11A)

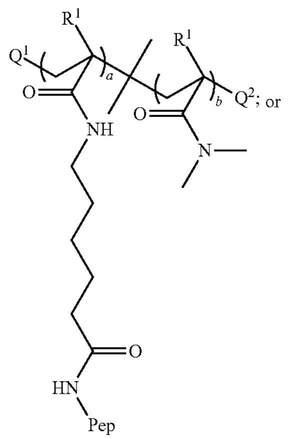

(FX11B)

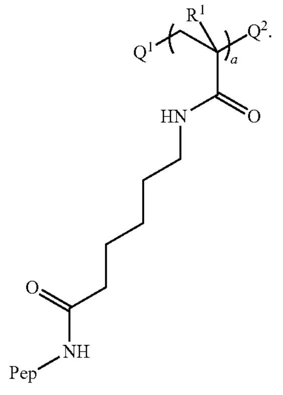

11. The method of claim 9, wherein the peptide brush polymer is characterized by formula FX12:
(FX12)
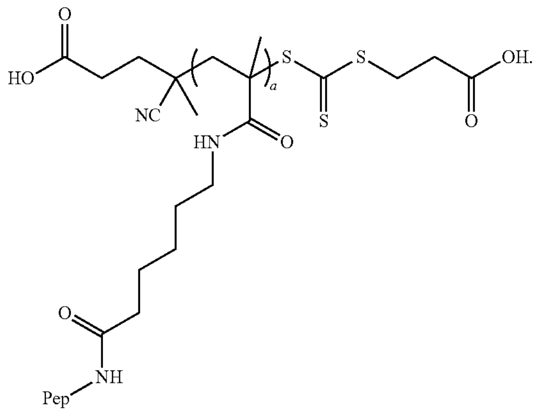
* * * * *